(12) United States Patent
Hayashi et al.

(10) Patent No.: US 7,291,617 B2
(45) Date of Patent: Nov. 6, 2007

(54) ARYLAMIDINE DERIVATIVE OR SALT THEREOF

(75) Inventors: Kazuya Hayashi, Uozu (JP); Katsuji Ojima, Toyama (JP); Kozo Hori, Kosugi-machi (JP); Noriyuki Okujo, Kishiwada (JP); Junichi Mitsuyama, Kamiichi-machi (JP); Kazuto Kunitani, Kosugi-machi (JP); Keisuke Tohdo, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 358 days.

(21) Appl. No.: 10/506,422

(22) PCT Filed: Mar. 4, 2003

(86) PCT No.: PCT/JP03/02506

§ 371 (c)(1),
(2), (4) Date: Sep. 2, 2004

(87) PCT Pub. No.: WO03/074476

PCT Pub. Date: Sep. 12, 2003

(65) Prior Publication Data

US 2005/0113424 A1     May 26, 2005

(51) Int. Cl.
*C07D 211/00*     (2006.01)
*A61K 31/445*     (2006.01)
*A61K 31/497*     (2006.01)

(52) U.S. Cl. .................. 514/252.1; 514/317; 544/336; 546/192

(58) Field of Classification Search ............... 514/318, 514/345, 357, 317, 252.1; 546/193, 290, 546/304, 192; 544/336
See application file for complete search history.

(56) References Cited

FOREIGN PATENT DOCUMENTS

| | | |
|---|---|---|
| EP | 0 805 149 A1 | 11/1997 |
| EP | 1 178 038 A1 | 2/2002 |
| GB | 868552 | 5/1967 |

OTHER PUBLICATIONS

Loeffler et al, Journal of Medicinal Chemistry, vol. 18, No. 3, pp. 287-292, 1975.*
Tidwell, R.R. et al., Analogs of 1,5-bis(4-amidinophenoxy) pentane (pentamidine) in the treatment of experimental Pneumocystis carinii pneumonia, Journal of Medicinal Chemistry, vol. 33 No. 4, pp. 1252-1257 1990.
Rinsho to Biseibutsu, Clinics and Microorganism, vol. 17 No. 3, p. 265, ISSN 0910-7029 1990.
Rinsho to Bieseibutsu, Clinics and Microorganism, vol. 21 No. 3, p. 277 1994.
Rinsho to Biseibutsu, vol. 28 No. 1, p. 51-58 2001.
Akito Tanaka, et al., "Design, Synthesis, and Evaluation of Orally Active Fibrinogen Inhibitors" Bioorganic and Medicinal Chemistry Letters, vol. 7, No. 5, XP-004136058, Mar. 4, 1997, pp. 521-526.

* cited by examiner

*Primary Examiner*—Zinna N. Davis
(74) *Attorney, Agent, or Firm*—Oblon, Spivak, McClelland, Maier & Neustadt, P.C.

(57) ABSTRACT

An arylamidine derivative represented by a general formula described below or a salt thereof has an excellent antifungal action and high safety, and it is useful as an antifungal agent with good pharmacokinetics and pharmacodynamic properties

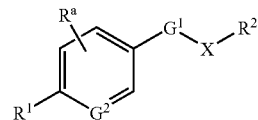

wherein X represents an unsubstituted or substituted lower alkylene or alkenylene group; $G^1$ represents an oxygen atom, a sulfur atom, or an imino group; $G^2$ represents a carbon atom or a nitrogen atom; $R^a$ represents at least one group selected from the group consisting of a hydrogen atom, a halogen atom, and unsubstituted or substituted alkyl, cycloalkyl and alkoxy groups; $R^1$ represents an unprotected or protected or unsubstituted or substituted amidino group; and $R^2$ represents a substituted amino or substituted cyclic amino group, or the like.

10 Claims, No Drawings

ARYLAMIDINE DERIVATIVE OR SALT THEREOF

TECHNICAL FIELD

The present invention relates to a novel arylamidine derivative having an antifungal activity, or a salt thereof. In addition, it relates to an antifungal agent containing the arylamidine derivative as active ingredients.

BACKGROUND ART

Serious deep mycosis such as invasive candidiasis often becomes a fatal disease. Originally, it has been considered that a principal protective mechanism on the side of a host organism to Mycomycetes such as *Candida* would be non-specific immunization by neutrophils. When this protective mechanism normally functions, there is a little risk of becoming infected with Mycomycetes. However, in recent years, a risk of developing deep mycosis has been increased because of increase in the number of patients with underlying diseases decreasing the immunological function of an organism, such as malignant tumors (in particular, hemopoietic malignant tumors such as acute leukemia or malignant lymphoma) or AIDS, heavy use of anticancer agents or immunosuppressive agents, heavy use of antibacterial antibiotics or steroid hormone, long-term use of central venous hyperalimentation or venous catheterization, and so on (*Rinsho to Biseibutsu* (Clinics and Microorganisms), vol. 17, p. 265, 1990).

The number of agents applied to a treatment for such deep mycosis is much smaller than that of antibacterial agents. There are only 6 types of agents, such as amphotericin B, flucytosine, miconazole, fluconazole, itraconazole, and micafungin.

Amphotericin B has an extremely strong fungicidal action to Mycomycetes. However, at the same time, it has a problem regarding strong side effects such as nephrotoxicity, and therefore, to use the agent in a clinical situation is limited. In addition, flucytosine has a problem that the agent causes rapid development of resistance when it is chronically used. Accordingly, at present, this agent is seldom used singly. Micafungin has a low activity to the *Cryptococcus* species. Other agents are generically called azole antifungal agents in terms of their structural characteristics. There is a general tendency that the fungicidal action of these agents to Mycomycetes is poorer than that of amphotericin B. However, considering both effectiveness and safety, azole antifungal agents are most frequently used at present ((*Rinsho to Biseibutsu* (Clinics and Microorganisms), vol. 21, p. 277, 1994).

Currently, fluconazole-resistant *Candida albicans* (*C. albicans*) has been detected with a high frequency of 30% or more in oropharyngeal candidiasis lesion of AIDS patients to whom fluconazole had been repeatedly administered. Moreover, most of the resistant strains show cross resistance to itraconazole and other azole agents. Furthermore, separation of the resistant strains has also been reported regarding non-AIDS patients who developed chronic mucocutaneous candidiasis or deep candidiasis (*Rinsho to Biseibutsu* (Clinics and Microorganisms), vol. 28, p. 57, 2001).

Thus, if a limited number of agents have a problem regarding resistance, it will inevitably affect the management of patients with deep mycosis, the number of which is being increased (*Rinsho to Biseibutsu* (Clinics and Microorganisms), vol. 28, p. 51, 2001).

Accordingly, it is strongly desired that an antifungal agent will be developed, whose action mechanism differs from those of the existing agents and which has effects on Mycomycetes resistant to azole agents, while having a little side effects.

DISCLOSURE OF THE INVENTION

Under such circumstances, the present inventors have intensively studied. As a result, they have found that an arylamidine derivative formed by introducing an amidino group into an aryl ring, represented by general formula [1]described below, or a salt thereof, has an excellent antifungal activity, thereby completing the present invention:

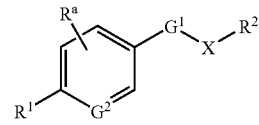

[1]

wherein X represents an unsubstituted or substituted lower alkylene or alkenylene group; $G^1$ represents an oxygen atom, a sulfur atom, or an imino group; $G^2$ represents a carbon atom or a nitrogen atom; $R^a$ represents at least one group selected from the group consisting of a hydrogen atom, a halogen atom, and an unsubstituted or substituted alkyl, cycloalkyl and alkoxy group; $R^1$ represents an unprotected or protected or unsubstituted or substituted amidino group; and $R^2$ represents a group represented by the following formula (1), (2) or (3):

(1)

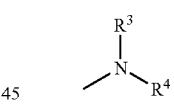

wherein $R^3$ represents a hydrogen atom, an amino protecting group, or an unsubstituted or substituted cycloalkyl or alkenyl group, or group represented by the following formula:

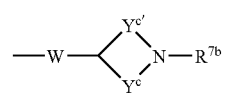

wherein W represents an unsubstituted or substituted lower alkylene group or a direct bond; $Y^c$ represents an unsubstituted or substituted $C_{2-4}$ lower alkylene group; $Y^{c'}$ represents an unsubstituted or substituted $C_{1-4}$ lower alkylene group; and $R^{7b}$ represents a hydrogen atom, an amino protecting group, or an unsubstituted or substituted alkyl, cycloalkyl or alkenyl group, or group represented by the following formula:

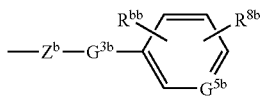

wherein $Z^b$ represents an unsubstituted or substituted lower alkylene or alkenylene group; $G^{3b}$ represents an oxygen atom, a sulfur atom, an imino group, or a direct bond; $G^{5b}$ represents a carbon atom or a nitrogen atom; $R^{bb}$ represents at least one group selected from the group consisting of a hydrogen atom, a halogen atom, and an unsubstituted or substituted alkyl, cycloalkyl and alkoxy group; and $R^{8b}$ represents an unprotected or protected or unsubstituted or substituted amidino group, which is bonded at the para or meta position of the position connected to $G^{3b}$;

$R^4$ represents a hydrogen atom, an amino protecting group, or an unsubstituted or substituted alkyl, cycloalkyl or alkenyl group;

(2)

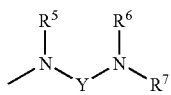

wherein Y represents an unsubstituted or substituted $C_{2-6}$ lower alkylene or $C_{3-6}$ alkenylene group; each of $R^5$ and $R^6$, which may be the same or different, represents a hydrogen atom, an amino protecting group, or an unsubstituted or substituted alkyl, cycloalkyl or alkenyl group; and $R^7$ represents a hydrogen atom, an amino protecting group, or an unsubstituted or substituted alkyl, cycloalkyl or alkenyl group, or a group represented by the following formula:

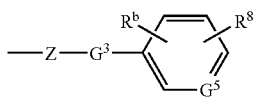

wherein Z represents an unsubstituted or substituted lower alkylene or alkenylene group; $G^3$ represents an oxygen atom, a sulfur atom, an imino group, or a direct bond; $G^5$ represents a carbon atom or a nitrogen atom; $R^b$ represents at least one group selected from the group consisting of a hydrogen atom, a halogen atom and an unsubstituted or substituted alkyl, cycloalkyl and alkoxy group; and $R^8$ represents an unprotected or protected or unsubstituted or substituted amidino group, which is bonded at the para or meta position of the position connected to $G^3$; or (3)

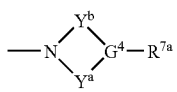

wherein $Y^a$ represents an unsubstituted or substituted $C_{2-4}$ lower alkylene group; $Y^b$ represents an unsubstituted or substituted $C_{1-4}$ lower alkylene group; $G^4$ represents a carbon atom or a nitrogen atom; $R^{7a}$ represents an alkyl group substituted by at least one group selected from the group consisting of a cyano group, a nitro group, a halogen atom, a sulfo group, a phosphoryl group, an unprotected or protected hydroxyl group, an unprotected or protected amino group, an unprotected or protected carbamoyl group, an unprotected or protected hydroxycarbamoyl group, an unprotected or protected aminosulfonyl group, an unprotected or protected cyclic amino group, an unprotected or protected lower alkylamino group, a lower alkenyl group, a lower alkoxy group, a heterocyclic group, a cycloalkyl group, a lower alkylidene group, a mercapto group, an amidinophenylaryloxy group, an aryloxy group, a lower alkylthio group, a lower alkylsulfinyl group, a lower alkylsulfonyl group, a lower alkylcarbamoyl group, a lower alkylsulfonylamino group, a lower alkylaminosulfonyl group, a carboxyl lower alkenyl group, a hydroxyl heterocyclic group, a lower alkyl heterocyclic group, a lower alkoxy-lower alkoxy group, and a lower alkoxyimino group, or an unsubstituted or substituted phenyl, cycloalkyl or alkenyl group, or group represented by the following formula:

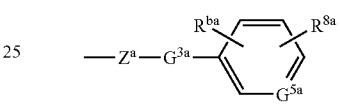

wherein $Z^a$ represents an unsubstituted or substituted lower alkylene or alkenylene group; $G^{3a}$ represents an oxygen atom, a sulfur atom, an imino group, or a direct bond; $G^{5a}$ represents a carbon atom or a nitrogen atom; $R^{ba}$ represents at least one group selected from the group consisting of a hydrogen atom, a halogen atom, and an unsubstituted or substituted alkyl, cycloalkyl and alkoxy groups; and $R^{8a}$ represents an unprotected or protected or unsubstituted or substituted amidino group, which is bonded at the para or meta position of the position connected to $G^{3a}$ (provided that where $G^1$ represents an imino group, X represents an unsubstituted or substituted $C_{3-6}$ lower alkylene group, or an unsubstituted or substituted alkenylene group).

Moreover, these compounds or salts thereof are highly safe and exhibit excellent pharmacokinetics and pharmacodynamic properties. Accordingly, these are useful as excellent antifungal agents.

The compound of the present invention will be described in detail below.

In the present invention, unless otherwise specified, the term "halogen atom" is used to mean a fluorine atom, a chlorine atom, a bromine atom, and an iodine atom; the term "alkyl group" is used to mean a linear or branched $C_{1-12}$ alkyl group such as methyl, ethyl, n-propyl, isopropyl, n-butyl, sec-butyl, isobutyl, tert-butyl, pentyl, isopentyl, hexyl, heptyl, or octyl; the term "lower alkyl group" is used to mean a linear or branched $C_{1-6}$ alkyl group such as methyl, ethyl, n-propyl, isopropyl, n-butyl, sec-butyl, isobutyl, tert-butyl, pentyl, or isopentyl; the term "halogeno lower alkyl group" is used to mean a linear or branched halogeno-$C_{1-6}$ alkyl group such as fluoromethyl, chloromethyl, bromomethyl, dichloromethyl, trifluoromethyl, trichloromethyl, chloroethyl, dichloroethyl, trichloroethyl, or chloropropyl; the term "lower alkoxy-lower alkyl group" is used to mean a linear or branched $C_{1-6}$ alkoxy-$C_{1-6}$ alkyl group such as methoxymethyl, ethoxymethyl, n-propoxymethyl, methoxyethyl, or ethoxyethyl; the term "hydroxy lower alkyl group" is used to mean a linear or branched hydroxy-$C_{1-6}$ alkyl group such as hydroxymethyl, hydroxyethyl, or hydroxypropyl; the term "amino lower alkyl group" is used to mean a linear or branched amino-$C_{1-6}$ alkyl group such as aminomethyl, aminoethyl, or aminopropyl; the term "carboxyl lower alkyl group" is used to mean a linear or branched $C_{1-6}$ alkyl group, which is substituted by a carboxyl group; the term "alkenyl group" is used to mean a linear or branched $C_{2-12}$ alkenyl group such as vinyl, allyl, propenyl, isopropenyl, butenyl, isobutenyl, pentenyl, hexenyl, heptenyl, or octenyl; the term "lower alkenyl group" is used to mean a linear or branched $C_{2-6}$ alkenyl group such as vinyl, allyl, propenyl, isopropenyl, butenyl, isobutenyl, or pentenyl; the term "cycloalkyl group" is used to mean a $C_{3-7}$ cycloalkyl group such as cyclopropyl, cyclobutyl, cyclopentyl, cyclohexyl, or cycloheptyl; the term "lower alkylene group" is used to mean a linear or branched $C_{1-6}$ alkylene group such as methylene, ethylene, propylene, butylene, amylene, or hexylene; the term "alkenylene group" is used to mean a linear or branched $C_{2-6}$ alkenylene group such as vinylene, propenylene, 2-butenylene, 1-butenylene, or isopropenylene; the term "aryl group" is used to mean a group such as phenyl, tolyl, or naphthyl; the term "aralkyl group" is used to mean an ar $C_{1-12}$ alkyl group such as benzyl, diphenylmethyl, trityl, phenethyl, 4-methylbenzyl, or naphthylmethyl; the term "aryloxy group" is used to mean a group such as phenoxy or naphthoxy; the term "aryloxycarbonyl group" is used to mean a group such as phenoxycarbonyl or naphthoxycarbonyl; the term "amidinophenylaryloxy group" is used to mean an aryloxy group substituted by an amidinophenyl group, such as 4-(4-amidinophenyl) phenyloxy, 4-(4-amidinophenyl)-2-fluoro-phenyloxy, or 4-(3-amidinophenyl)phenyloxy; the term "alkoxy group" is used to mean a linear or branched $C_{1-12}$ alkoxy group such as methoxy, ethoxy, n-propoxy, isopropoxy, n-butoxy, isobutoxy, sec-butoxy, tert-butoxy, pentyloxy, isopentyloxy, hexyloxy, heptyloxy, or octyloxy; the term "lower alkoxy group" is used to mean a linear or branched $C_{1-6}$ alkoxy group such as methoxy, ethoxy, n-propoxy, isopropoxy, n-butoxy, isobutoxy, sec-butoxy, tert-butoxy, pentyloxy, or isopentyloxy; the term "lower alkoxycarbonyl group" is used to mean a linear or branched $C_{1-6}$ alkyloxycarbonyl group such as methoxycarbonyl, ethoxycarbonyl, isopropoxycarbonyl, or n-propoxycarbonyl; the term "lower alkoxycarbonyl-lower alkyl group" is used to mean a linear or branched $C_{1-6}$ alkoxycarbonyl-$C_{1-6}$ alkyl group such as methoxycarbonylmethyl, ethoxycarbonylmethyl, n-propoxycarbonylmethyl, methoxycarbonylethyl, or ethoxycarbonylethyl; the term "lower alkoxyimino group" is used to mean a linear or branched $C_{1-6}$ alkoxyimino group such as methoxyimino or ethoxyimino; the term "lower alkylamino group" is used to mean a linear or branched mono- or di-$C_{1-6}$ alkylamino group such as methylamino, ethylamino, isopropylamino, n-propylamino, dimethylamino, diethylamino, or methylethylamino; the term "lower alkylamino-lower alkyl group" is used to mean a mono- or di-$C_{1-6}$ alkylamino-$C_{1-6}$ alkyl group such as methylaminomethyl, methylaminoethyl, ethylaminomethyl, methylaminopropyl, isopropylaminoethyl, n-propylaminoethyl, dimethylaminomethyl, diethylaminomethyl, diethylaminoethyl, or dimethylaminopropyl; the term "lower alkylidene group" is used to mean a $C_{1-6}$ alkylidene group such as methylene, ethylidene, propylidene, or isopropylidene; the term "nitrogen-containing heterocyclic group" is used to mean a 5- or 6-membered ring, condensed ring, or bridge ring heterocyclic group, which contains at least one nitrogen atom as a heterocyclic atom forming the above described heterocyclic ring of a group such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, quinazolyl, thiazolyl, tetrazolyl, thiadiazolyl, pyrrolinyl, imidazolinyl, imidazolidinyl, pyrazolinyl, pyrazolidinyl, purinyl, or indazolyl, and which may further contain at least one oxygen or sulfur atom; the term "heterocyclic group" is used to include the above described nitrogen-containing heterocyclic group, and a 5- or 6-membered ring, condensed ring, or bridge ring heterocyclic group, which contains at least one heterocyclic atom selected from the group consisting of nitrogen, oxygen, and sulfur atoms, and which may further contain at least one oxygen or sulfur atom as a heterocyclic atom forming the above described heterocyclic ring of a group such as furyl, thienyl, benzothienyl, pyranyl, isobenzofuranyl, oxazolyl, benzofuranyl, indolyl, benzimidazolyl, benzoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, thiadiazolyl, oxadiazolyl, pyridazinyl, isoindolyl, or isoquinolyl; the term "acyl group" is used to mean, for example, a formyl group, a linear or branched $C_{2-12}$ alkanoyl group such as acetyl, isovaleryl, or propionyl, an aralkylcarbonyl group such as benzylcarbonyl, an aroyl group such as benzoyl or naphthoyl, and a heterocyclic carbonyl group such as a nicotinoyl, thenoyl, pyrrolidinocarbonyl or furoyl group; the term "cyclic amino group" is used to mean, for example, either a saturated or unsaturated cyclic amino group, which may contain one or more heterocyclic atom such as a nitrogen, oxygen, or sulfur atom, and carbonyl carbon, and which may be monocyclic, bicyclic, or tricyclic. Specific examples of such a cyclic amino group may include: saturated or unsaturated monocyclic 3- to 7-membered cyclic amino groups containing one nitrogen atom, such as aziridin-1-yl, azetidin-1-yl, azetidin-2-yl, pyrrolidin-1-yl, pyrrolidin-2-yl, pyrrolidin-3-yl, 1-methylpyrrolidin-2-yl, 1-methylpyrrolidin-3-yl, pyrolin-1-yl, pyrrol-1-yl, dihydropyridin-1-yl, piperidin-1-yl, piperidin-2-yl, piperidin-3-yl, piperidin-4-yl, 1-methylpiperidin-2-yl, 1-methylpiperidin-3-yl, 1-methylpiperidin-4-yl, dihydroazepin-1-yl, or perhydroazepin-1-yl; saturated or unsaturated monocyclic 3- to 7-membered cyclic amino groups containing two nitrogen atoms, such as imidazol-1-yl, imidazolidin-1-yl, imidazolin-1-yl, pyrazolidin-1-yl, piperazin-1-yl, 4-methylpiperazin-1-yl, 1,4-dihydropyrazin-1-yl, 1,2-dihydropyrimidin-1-yl, 4-methylhomopiperazin-1-yl, perhydropyrazin-1-yl, or homopiperazin-1-yl; saturated or unsaturated monocyclic 3- to 7-membered cyclic amino groups containing 3 or more nitrogen atoms, such as 1,2,4-triazol-1-yl, 1,2,3-triazol-1-yl, 1,2-dihydro-1,2,4-triazin-1-yl, or perhydro-S-triazin-1-yl; saturated or unsaturated monocyclic 3- to 7-membered cyclic amino groups containing 1 to 4 hetero atoms selected from the group consisting of oxygen and sulfur atoms, as well as nitrogen atoms, such as oxazolidin-3-yl, isoxazolidin-2-yl, morpholino, thiazolidin-3-yl, isothiazolidin-2-yl, thiomorpholino, homothiomorpholin-4-yl, or 1,2,4-thiadiazolin-2-yl; saturated or unsaturated bicyclic or tricyclic amino groups such as isoindolin-2-yl, indolin-1-yl, 1H-indazol-1-yl, purin-7-yl, or tetrahydroquinolin-1-yl; and spiro or bridged saturated or unsaturated 5- to 12-membered cyclic amino groups such as quinuclidin-1-yl, 5-azaspiro [2.4]heptan-5-yl, 2,8-diazabicyclo [4.3.0]nonan-8-yl, 3-azabicyclo [3.1.0]hexan-3-yl, 2-oxa-5,8-diazabicyclo [4.3.0]nonan-8-yl, 2,8-diazaspiro [4.4]nonan-2-yl, or 7-azabicyclo [2.2.1]heptan-7-yl. The term "lower alkylthio group" is used to mean a linear or branched $C_{1-6}$ alkylthio group such as methylthio, ethylthio, n-propylthio, isopropylthio, n-butylthio, isobutylthio, sec-butylthio, tert-butylthio, pentylthio, or isopentylthio; the term "alkylsulfonyl group" is used to mean a linear or branched $C_{1-12}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, isopentylsulfonyl, hexylsulfonyl, heptylsulfonyl, or octylsulfonyl; the term "arylsulfonyl group" is used to mean an aryl-$SO_2$-group such as phenylsulfonyl or naphthylsulfonyl; the term "lower alkylsulfinyl group" is used to mean a linear or branched $C_{1-6}$ alkylsulfinyl group such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, or hexylsulfinyl; the term "lower alkylsulfonyl group" is used to mean a linear or branched $C_{1-6}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, or pentylsulfonyl; the term "lower alkylcarbamoyl group" is used to mean a mono- or di-$C_{1-6}$ alkylcarbamoyl group such as methylcarbamoyl, ethylcarbamoyl, n-propylcarbamoyl, isopropylcarbamoyl, dimethylcarbamoyl, diethylcarbamoyl, or methylethylcarbamoyl; the term "lower alkylsulfonylamino group" is used to mean a linear or branched $C_{1-6}$ alkylsulfonylamino group such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, or pentylsulfonylamino; the term "lower alkylsulfonylcarbamoyl group" is used to mean a linear or branched $C_{1-6}$ alkylsulfonylcarbamoyl group such as methylsulfonylcarbamoyl, ethylsulfonylcarbamoyl, n-propylsulfonylcarbamoyl, isopropylsulfonylcarbamoyl, n-butylsulfonylcarbamoyl, isobutylsulfonylcarbamoyl, sec-butylsulfonylcarbamoyl, tert-butylsulfonylcarbamoyl, or pentylsulfonylcarbamoyl; the term "lower alkylaminosulfonyl group" is used to mean a mono- or di-$C_{1-6}$ alkylaminosulfonyl group such as methylaminosulfonyl, ethylaminosulfonyl, n-propylaminosulfonyl, isopropylaminosulfonyl, dimethylaminosulfonyl, diethylaminosulfonyl, or methylethylaminosulfonyl; the term "carboxyl lower alkenyl group" is used to mean, for example, a linear or branched $C_{2-6}$ alkenyl group substituted by a carboxyl group; the term "hydroxy heterocyclic group" is used to mean, for example, a heterocyclic group substituted by a hydroxyl group; the term "lower alkyl heterocyclic group" is used to mean, for example, a heterocyclic group substituted by a linear or branched lower alkyl; the term "lower alkoxy-lower alkoxy group" is used to mean a linear or branched $C_{1-6}$ alkoxy group substituted by lower alkoxy; the term "leaving group" is used to include halogen atoms such as a fluorine atom, chlorine atom, bromine atom, or iodine atom, alkylsulfonyloxy groups such as methanesulfonyloxy or trifluoromethanesulfonyloxy, arylsulfonyloxy groups such as para-toluenesulfonyloxy or benzenesulfonyloxy, and acyloxy groups such as acetyloxy or trifluoroacetyloxy.

Any protecting group can be used as a protecting group of a carboxyl group, as long as it can be used as an ordinary carboxylprotecting group. Examples of such a protecting group may include: alkyl groups such as methyl, ethyl, n-propyl, isopropyl, 1,1-dimethylpropyl, n-butyl, or tert-butyl; aryl groups such as phenyl or naphthyl; aralkyl groups such as benzyl, diphenylmethyl, trityl, p-nitrobenzyl, p-methoxybenzyl, or bis (p-methoxyphenyl)methyl; acylalkyl groups such as acetylmethyl, benzoylmethyl, p-nitrobenzoylmethyl, p-bromobenzoylmethyl, or p-methanesulfonylbenzoylmethyl; oxygen-containing heterocyclic groups such as 2-tetrahydropyranyl or 2-tetrahydrofuranyl; halogenoalkyl groups such as 2,2,2-trichloroethyl; alkylsilylalkyl groups such as 2-(trimethylsilyl)ethyl; acyloxyalkyl groups such as acetoxymethyl, propionyloxymethyl, or pivaloyloxymethyl; nitrogen-containing heterocyclic alkyl groups such as phthalimidomethyl or succinimidomethyl; cycloalkyl groups such as cyclohexyl; alkoxyalkyl groups such as methoxymethyl, methoxyethoxymethyl, or 2-(trimethylsilyl) ethoxymethyl; aralkoxyalkyl groups such as benzyloxymethyl; lower alkylthioalkyl groups such as methylthiomethyl or 2-methylthioethyl; arylthioalkyl groups such as phenylthiomethyl; alkenyl groups such as 1,1-dimethyl-2-propenyl, 3-methyl-3-butenyl, or allyl; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, or tert-butylmethoxyphenylsilyl. Preferred examples may include alkyl groups, aralkyl groups, and substituted silyl groups.

Any protecting group can be used as a protecting group of an amino group, as long as it can be used as an ordinary amino protecting group. Examples of such a protecting group may include: acyl groups such as (mono-, di-, or tri-)chloroacetyl, trifluoroacetyl, phenylacetyl, formyl, acetyl, benzoyl, phthaloyl, succinyl, or an amino acid residue with an unprotected or protected N-terminus (examples of amino acid may include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, and hydroxyproline); alkyloxycarbonyl groups such as methoxycarbonyl, diphenylmethoxycarbonyl, ethoxycarbonyl, trichloroethoxycarbonyl, tribromoethoxycarbonyl, 1,1-dimethylpropoxycarbonyl, isopropoxycarbonyl, 2-ethylhexyloxycarbonyl, tert-pentyloxycarbonyl, tert-butoxycarbonyl, or 1-adamantyloxycarbonyl; aralkyloxycarbonyl groups such as benzyloxycarbonyl, p-nitrobenzyloxycarbonyl, o-bromobenzyloxycarbonyl, p-methoxybenzyloxycarbonyl, 3,4-dimethoxybenzyloxycarbonyl, or 4-(phenylazo)benzyloxycarbonyl; aryloxycarbonyl groups such as phenyloxycarbonyl, 4-fluorophenyloxycarbonyl, 4-methoxyphenyloxycarbonyl, 8-quinolyloxycarbonyl, or 2-furfuryloxycarbonyl; aralkyl groups such as benzyl, diphenylmethyl, or trityl; alkoxyalkyl groups such as methoxymethyl, benzyloxymethyl, 2-methoxyethoxymethyl, 2,2,2-trichloroethoxymethyl, 2-(trimethylsilyl) ethoxymethyl, or 1-ethoxyethyl; arylthio groups such as 2-nitrophenylthio or 2,4-dinitrophenylthio; alkylsulfonyl or arylsulfonyl groups such as methanesulfonyl or p-toluenesulfonyl; dialkylaminoalkylidene groups such as N,N-dimethylaminomethylene; aralkylidene groups such as benzylidene, 2-hydroxybenzylidene, 2-hydroxy-5-chlorobenzylidene, or 2-hydroxy-1-naphthylmethylene; nitrogen-containing heterocyclic alkylidene groups such as 3-hydroxy-4-pyridylmethylene; cycloalkylidene groups such as cyclohexylidene, 2-ethoxycarbonylcyclohexylidene, 2-ethoxycarbonylcyclopentylidene, 2-acetylcyclohexylidene, or 3,3-dimethyl-5-oxycyclohexylidene; diaryl- or diaralkylphosphoryl groups such as diphenylphosphoryl or dibenzylphosphoryl; oxygen-containing heterocyclic alkyl groups such as 5-methyl-2-oxo-2H-1,3-dioxol-4-yl-methyl; and substituted silyl groups such as trimethylsilyl.

Any protecting group can be used as a protecting group of a hydroxyl group, as long as it can be used as an ordinary hydroxylprotecting group. Examples of such a protecting group may include: acyl groups such as benzyloxycarbonyl, 4-nitrobenzyloxycarbonyl, 4-bromobenzyloxycarbonyl, 4-methoxybenzyloxycarbonyl, 0,3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, or benzoyl; alkyl groups such as methyl, isopropyl, isobutyl, tert-butyl, 2,2,2-trichloroethyl, or 2-trimethylsilylethyl; alkenyl groups such as allyl; aralkyl groups such as benzyl, p-methoxybenzyl, 3,4-dimethoxybenzyl, diphenylmethyl, or trityl; oxygen- or sulfur-containing heterocyclic groups such as tetrahydrofuryl, tetrahydropyranyl, or tetrahydrothiopyranyl; alkoxyalkyl groups such as methoxymethyl, benzyloxymethyl, 2-methoxyethoxymethyl, 2,2,2-trichloroethoxymethyl, 2-(trimethylsilyl)ethoxymethyl, or 1-ethoxyethyl; alkylsulfonyl or arylsulfonyl groups such as methanesulfonyl or p-toluenesulfonyl; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, or tert-butylmethoxyphenylsilyl.

Any protecting group can be used as a protecting group of an aldehyde group, as long as it can be used as an ordinary aldehyde protecting group. Examples of such a protecting group may include dialkylacetals such as dimethylacetal, and 5- or 6-membered cyclic acetals such as 1,3-dioxolane or 1,3-dioxane.

Any protecting group can be used as a protecting group of an amidino group as long as it can be used as an ordinary amidino protecting group. Examples of such a protecting group may include: acyl groups such as (mono-, di-, or tri-)chloroacetyl, trifluoroacetyl, phenylacetyl, formyl, acetyl, benzoyl, phthaloyl, succinyl, or an amino acid residue with an unprotected or protected N-terminus (examples of amino acid may include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, and hydroxyproline); alkyloxycarbonyl groups such as methoxycarbonyl, ethoxycarbonyl, propyloxycarbonyl, butyloxycarbonyl, pentyloxycarbonyl, hexyloxycarbonyl, heptyloxycarbonyl, morpholinoethoxycarbonyl, trichloroethoxycarbonyl, tribromoethoxycarbonyl, 1-acetoxyethoxycarbonyl, 5-methyl-2-oxo-1,3-dioxol-4-yl-methoxycarbonyl, tert-pentyloxycarbonyl, tert-butoxycarbonyl, diphenylmethoxycarbonyl, 1,1-dimethylpropoxycarbonyl, isopropoxycarbonyl, or 1-adamantyloxycarbonyl; cycloalkyloxycarbonyl groups such as cyclopentyloxy or cyclohexyloxy; aralkyloxycarbonyl groups such as benzyloxycarbonyl, o-bromobenzyloxycarbonyl, p-nitrobenzyloxycarbonyl, p-methoxybenzyloxycarbonyl, or 3,4-dimethoxybenzyloxycarbonyl; aryloxycarbonyl groups such as phenyloxycarbonyl, 4-fluorophenyloxycarbonyl, 4-methoxyphenyloxycarbonyl, or 8-quinolyloxycarbonyl; alkylthiocarbonyl groups such as ethylthiocarbonyl; aralkyl groups such as benzyl, diphenylmethyl, or trityl; alkoxyalkyl groups such as methoxymethyl, benzyloxymethyl, 2-methoxyethoxymethyl, 2,2,2-trichloroethoxymethyl, 2-(trimethylsilyl)ethoxymethyl, or 1-ethoxyethyl; arylthio groups such as 2-nitrophenylthio or 2,4-dinitrophenylthio; alkylsulfonyl or arylsulfonyl groups such as methanesulfonyl or p-toluenesulfonyl; dialkylaminoalkylidene groups such as N,N-dimethylaminomethylene; aralkylidene groups such as benzylidene, 2-hydroxybenzylidene, 2-hydroxy-5-chlorobenzylidene, or 2-hydroxy-1-naphthylmethylene; nitrogen-containing heterocyclic alkylidene groups such as 3-hydroxy-4-pyridylmethylene; cycloalkylidene groups such as cyclohexylidene, 2-ethoxycarbonylcyclohexylidene, 2-ethoxycarbonylcyclopentylidene, 2-acetylcyclohexylidene, or 3,3-dimethyl-5-oxycyclohexylidene; oxygen-containing heterocyclic alkyl groups such as 5-methyl-2-oxo-2H-1,3-dioxol-4-yl-methyl; and substituted silyl groups such as trimethylsilyl.

With regard to the compound represented by general formula [1] or a salt thereof, examples of such a salt of the compound may include publicly known salts of basic groups such as an amino group, or of acidic groups such as a hydroxyl or carboxyl group. Examples of such a salt of a basic group may include: salts produced with mineral acids such as hydrochloric acid, hydrobromic acid, or sulfuric acid; salts produced with organic carboxylic acids such as tartaric acid, formic acid, acetic acid, citric acid, trichloroacetic acid, or trifluoroacetic acid; and salts produced with sulfonic acids such as methanesulfonic acid, benzenesulfonic acid, p-toluenesulfonic acid, mesitylenesulfonic acid, or naphthalenesulfonic acid. Examples of such a salt of an acidic group may include: salts produced with alkaline metals such as sodium or potassium; salts produced with alkaline earth metals such as calcium or magnesium; ammonium salts; and salts produced with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, or N,N'-dibenzylethylenediamine. Among the above described salts, preferred salts of the compound represented by general formula [1] may include pharmacologically acceptable salts.

The substituents of the present invention, $R^3$, $R^{3c}$, $R^{3f}$, $R^{4c}$, $R^{4f}$, $R^5$, $R^{5d}$, $R^{5g}$, $R^6$, $R^{6d}$, $R^{6g}$, $R^7$, $R^{7a}$, $R^{7b}$, $R^{7d}$, $R^{7g}$, $R^a$, $R^b$, $R^{ba}$, and $R^{bb}$, may further be substituted by at least one group selected from the group consisting of a cyano group, a nitro group, a halogen atom, a sulfo group, a phosphoryl group, unprotected or protected carboxyl, hydroxyl, amino, carbamoyl, hydroxycarbamoyl, aminosulfonyl, hydroxyl lower alkyl, amino lower alkyl, cyclic amino, lower alkylamino and lower alkylamino-lower alkyl groups, a lower alkyl group, a lower alkenyl group, a lower alkoxy group, a lower alkoxycarbonyl group, an acyl group, an aryl group, a heterocyclic group, a cycloalkyl group, an aralkyl group, a lower alkylidene group, a mercapto group, a lower alkylthio group, a lower alkylsulfinyl group, a lower alkylsulfonyl group, a lower alkylcarbamoyl group, a lower alkylsulfonylamino group, a lower alkylaminosulfonyl group, a carboxyl lower alkyl group, a carboxyl lower alkenyl group, a hydroxyl heterocyclic group, a lower alkyl heterocyclic group, a lower alkoxy-lower alkoxy group, a halogeno lower alkyl group, a lower alkoxy-lower alkyl group, a lower alkoxycarbonyl-lower alkyl group, and a lower alkoxyimino group.

Substituents, $R^1$, $R^8$, $R^a$, $R^{8b}$, $R^{8d}$, $R^{8e}$, $R^{8g}$, and $R^{8h}$, may further be substituted by at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group, and an aralkyl group.

Substituents, X, Y, $Y^a$, $Y^c$, $Y^d$, $Y^e$, $Y^g$, $Y^h$, $Z^a$, $Z^b$, $Z^d$, $Z^e$, $Z^g$, $Z^h$, and W, may further be substituted by at least one group selected from the group consisting of a cyano group, a nitro group, a halogen atom, an unprotected or protected amino, hydroxyl, carboxyl, carbamoyl, hydroxycarbamoyl and lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group, and a lower alkoxycarbonyl group.

Substituents, $Y^b$, $Y^{c'}$, $Y^{e'}$, and $Y^{h'}$, may further be substituted by at least one group selected from the group consisting of a cyano group, a nitro group, a halogen atom, an unprotected or protected amino, carboxyl, carbamoyl, hydroxycarbamoyl, hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group, and a keto group.

The above described substituents may further be substituted by groups exemplified as substituents for each substituent.

Moreover, a heterocyclic group and a cyclic amino group as the above substituents for each substituent may also be substituted by keto groups.

The following compounds can preferably be used as compounds of the present invention:

A compound wherein $R^1$ is an unprotected or protected amidino group is preferable. A compound wherein $R^1$ is an amidino group is more preferable.

A compound wherein X is an unsubstituted or substituted lower alkylene group is preferable. A compound wherein X is a lower alkylene group is more preferable, and a compound wherein X is a $C_{2-4}$ lower alkylene group is further more preferable.

A compound wherein $G^1$ is an oxygen atom is preferable.
A compound wherein $G^2$ is a carbon atom is preferable.
A compound wherein $R^a$ is at least one group selected from a hydrogen atom or a halogen atom is preferable, and a compound wherein $R^a$ is a hydrogen atom is more preferable.

In a preferred compound, $R^2$ preferably represents a group represented by the following formula (1), (2) or (3):

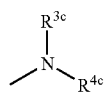

(1)

wherein $R^{3c}$ represents a hydrogen atom, an amino protecting group, or an unsubstituted or substituted cycloalkyl or an alkenyl group; and $R^{4c}$ represents a hydrogen atom, an amino protecting group, or an unsubstituted or substituted alkyl, cycloalkyl or alkenyl group,

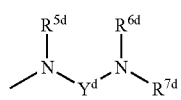

(2)

wherein $Y^d$ represents an unsubstituted or substituted $C_{2-6}$ lower alkylene or $C_{3-6}$ alkenylene group; each of $R^{5d}$ and $R^{6d}$, which may be the same or different, represents a hydrogen atom, an amino protecting group, or an unsubstituted or substituted alkyl, cycloalkyl or alkenyl group; and $R^{7d}$ represents a hydrogen atom, an amino protecting group, or an unsubstituted or substituted alkyl, cycloalkyl or alkenyl group, or a group represented by the following formula:

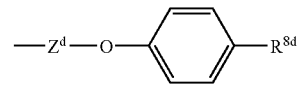

wherein $Z^d$ represents an unsubstituted or substituted lower alkylene or alkenylene group, $R^{8d}$ represents an unprotected or protected or unsubstituted or substituted amidino group, or

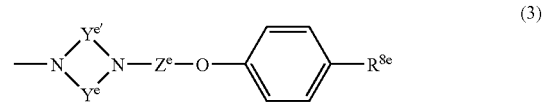

(3)

wherein each of $Y^e$ and $Y^{e'}$, which may be the same or different, represents an unsubstituted or substituted $C_{2-4}$ lower alkylene group; $Z^e$ represents an unsubstituted or substituted lower alkylene or alkenylene group; and $R^{8e}$ represents an unprotected or protected or unsubstituted or substituted amidino group. In a more preferred compound, $R^2$ more preferably represents a group represented by the following formula:

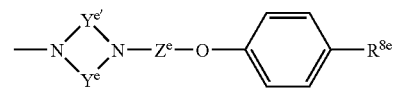

wherein each of $Y^e$ and $Y^{e'}$, which may be the same or different, represents an unsubstituted or substituted $C_{2-4}$ lower alkylene group; $Z^e$ represents an unsubstituted or substituted lower alkylene or alkenylene group; and $R^{8e}$ represents an unprotected or protected or unsubstituted or substituted amidino group.

Moreover, in a preferred compound, $R^2$ preferably represents a group represented by the following formula (1), (2) or (3):

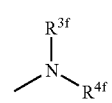

(1)

wherein $R^3$ represents a hydrogen atom, an amino protecting group, or an unsubstituted or substituted cycloalkyl or alkenyl group; and $R^{4f}$ represents a hydrogen atom, an amino protecting group, or an unsubstituted or substituted alkyl, cycloalkyl or alkenyl group,

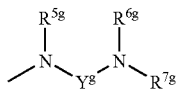

(2)

wherein $Y^g$ represents an unsubstituted or substituted $C_{2-6}$ lower alkylene or $C_{3-6}$ alkenylene group; each of $R^{5g}$ and $R^{6g}$, which may be the same or different, represents a hydrogen atom, an amino protecting group, an unsubstituted or substituted alkyl, cycloalkyl or alkenyl group; and $R^{7g}$ represents a hydrogen atom, an amino protecting group, or an unsubstituted or substituted alkyl, cycloalkyl or alkenyl group, or group represented by the following formula:

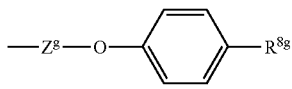

wherein $Z^g$ represents an unsubstituted or substituted lower alkylene or alkenylene group, $R^{8g}$ represents an unprotected or protected or unsubstituted or substituted amidino group, or

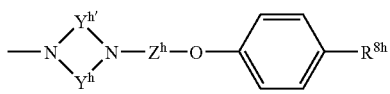

(3)

wherein each of $Y^h$ and $Y^{h\prime}$, which may be the same or different, represents an unsubstituted or substituted $C_{2-4}$ lower alkylene group; $Z^h$ represents an unsubstituted or substituted lower alkylene or alkenylene group; and $R^{8h}$ represents an unprotected or protected or unsubstituted or substituted amidino group. Furthermore, in a more preferred compound, $R^2$ more preferably represents a group represented by the following formula:

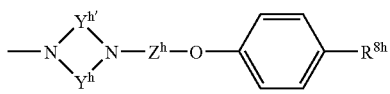

wherein each of $Y^h$ and $Y^{h\prime}$, which may be the same or different, represents an unsubstituted or substituted $C_{2-4}$ lower alkylene group; $Z^h$ represents an unsubstituted or substituted lower alkylene or alkenylene group; and $R^{8h}$ represents an unprotected or protected or unsubstituted or substituted amidino group.

In a preferred compound, $R^{3c}$, a preferred substituent of $R^2$, is a hydrogen atom, an amino protecting group, or an unsubstituted or substituted cycloalkyl group. In a more preferred compound, $R^{3c}$, a preferred substituent of $R^2$, is a hydrogen atom or an amino protecting group.

Moreover, in a preferred compound, $R^{4c}$, a preferred substituent of $R^2$, is a hydrogen atom, an amino protecting group, or an unsubstituted or substituted alkyl or cycloalkyl group. In a more preferred compound, $R^{4c}$, a preferred substituent of $R^2$, is a hydrogen atom, an amino protecting group, or an unsubstituted or substituted alkyl group. In a further more preferred compound, $R^{4c}$, a preferred substituent of $R^2$, is a hydrogen atom, an amino protecting group, or an alkyl group that may be substituted by a carboxyl group.

Furthermore, in a preferred compound, $R^{5d}$, a preferred substituent of $R^2$, is a hydrogen atom, an amino protecting group, or an unsubstituted or substituted alkyl or cycloalkyl group. In a more preferred compound, $R^{5d}$, a preferred substituent of $R^2$, is a hydrogen atom, an amino protecting group, or an unsubstituted or substituted alkyl group. In a further more preferred compound, $R^{5d}$, a preferred substituent of $R^2$, is a hydrogen atom or an amino protecting group.

Still further, in a preferred compound, $R^{6d}$, a preferred substituent of $R^2$, is a hydrogen atom, an amino protecting group, or an unsubstituted or substituted alkyl or cycloalkyl group. In a more preferred compound, $R^{6d}$, a preferred substituent of $R^2$, is a hydrogen atom, an amino protecting group, or an unsubstituted or substituted alkyl group. In a further more preferred compound, $R^{6d}$, a preferred substituent of $R^2$, is a hydrogen atom or an amino protecting group.

Still further, in a preferred compound, $R^{7d}$, a preferred substituent of $R^2$, is a hydrogen atom, an amino protecting group, or an unsubstituted or substituted alkyl or cycloalkyl group. In a more preferred compound, $R^{7d}$, a preferred substituent of $R^2$, is a hydrogen atom, an amino protecting group, or an unsubstituted or substituted alkyl group. In a further more preferred compound, $R^{7d}$, a preferred substituent of $R^2$, is a hydrogen atom, an amino protecting group, or an alkyl group that may be substituted by a lower alkoxycarbonyl or carboxyl group.

Still further, in a preferred compound, $R^{8d}$, a preferred substituent of $R^2$, is an unprotected or protected amidino group. In a more preferred compound, $R^{8d}$, a preferred substituent of $R^2$, is an amidino group.

Still further, in a preferred compound, $Y^d$, a preferred substituent of $R^2$, is an unsubstituted or substituted $C_{2-6}$ lower alkylene group. In a more preferred compound, $yd$, a preferred substituent of $R^2$, is a $C_{2-6}$ lower alkylene group. In a further more preferred compound, $yd$, a preferred substituent of $R^2$, is a $C_{2-3}$ lower alkylene group.

Still further, in a preferred compound, $Z^d$, a preferred substituent of $R^2$, is an unsubstituted or substituted lower alkylene group. In a more preferred compound, $Z^d$, a preferred substituent of $R^2$, is a lower alkylene group. In a further more preferred compound, $Z^d$, a preferred substituent of $R^2$, is a $C_{2-4}$ lower alkylene group.

Still further, in a preferred compound, $Y^e$, a preferred substituent of $R^2$, is a $C_{2-4}$ lower alkylene group. In a more preferred compound, $Y^e$, a preferred substituent of $R^2$, is a $C_{2-3}$ lower alkylene group.

Still further, in a preferred compound, $Y^{e\prime}$, a preferred substituent of $R^2$, is a $C_{2-4}$ lower alkylene group. In a more preferred compound, $Y^{e\prime}$, a preferred substituent of $R^2$, is a $C_{2-3}$ lower alkylene group.

Still further, in a preferred compound, $Z^e$, a preferred substituent of $R^2$, is an unsubstituted or substituted lower alkylene group. In a more preferred compound, $Z^e$, a preferred substituent of $R^2$, is a lower alkylene group. In a further more preferred compound, $Z^e$, a preferred substituent of $R^2$, is a $C_{2-4}$ lower alkylene group.

Still further, in a preferred compound, $R^{8e}$, a preferred substituent of $R^2$, is an unprotected or protected amidino group. In a more preferred compound, $R^{8e}$, a preferred substituent of $R^2$, is an amidino group.

Still further, in a preferred compound, $R^{8g}$, a preferred substituent of $R^2$, is an unprotected or protected amidino group. In a more preferred compound, $R^{8g}$, a preferred substituent of $R^2$, is an amidino group.

Still further, in a preferred compound, $Y^g$, a preferred substituent of $R^2$, is an unsubstituted or substituted $C_{2-6}$ lower alkylene group. In a more preferred compound, $Y^g$, a preferred substituent of $R^2$, is a $C_{2-6}$ lower alkylene group. In a further more preferred compound, $Y^g$, a preferred substituent of $R^2$, is a $C_{2-3}$ lower alkylene group.

Still further, in a preferred compound, $Y^h$, a preferred substituent of $R^2$, is a $C_{2-4}$ lower alkylene group. In a more preferred compound, $Y^h$, a preferred substituent of $R^2$, is a $C_{2-3}$ lower alkylene group.

Still further, in a preferred compound, $Y^{h'}$, a preferred substituent of $R^2$, is a $C_{2-4}$ lower alkylene group. In a more preferred compound, $Y^{h'}$, a preferred substituent of $R^2$, is a $C_{2-3}$ lower alkylene group.

Still further, in a preferred compound, $Z^g$, a preferred substituent of $R^2$, is an unsubstituted or substituted lower alkylene group. In a more preferred compound, $Z^g$, a preferred substituent of $R^2$, is a lower alkylene group. In a further more preferred compound, $Z^g$, a preferred substituent of $R^2$, is a $C_{2-4}$ lower alkylene group.

Still further, in a preferred compound, $Z^h$, a preferred substituent of $R^2$, is an unsubstituted or substituted lower alkylene group. In a more preferred compound, $Z^h$, a preferred substituent of $R^2$, is a lower alkylene group. In a further more preferred compound, $Z^h$, a preferred substituent of $R^2$, is a $C_{2-4}$ lower alkylene group.

Still further, in a preferred compound, $R^{8h}$, a preferred substituent of $R^2$, is an unprotected or protected amidino group. In a more preferred compound, $R^{8h}$, a preferred substituent of $R^2$, is an amidino group.

In the present invention, examples of a preferred amino protecting group may include an acyl group, an alkyloxycarbonyl group, an aryloxycarbonyl group, an aralkyloxycarbonyl group, an aralkyl group, an alkoxyalkyl group, an arylthio group, an alkylsulfonyl group, an arylsulfonyl group, a dialkylaminoalkylidene group, an aralkylidene group, a nitrogen-containing heterocyclic aralkylidene group, a cycloalkylidene group, an oxygen-containing heterocyclic alkyl group, and a substituted silyl group. Examples of a more preferred amino protecting group may include an acyl group, an alkyloxycarbonyl group, an aryloxycarbonyl group, an aralkyloxycarbonyl group, an aralkyl group, and an alkoxyalkyl group.

In the present invention, examples of a preferred amidino protecting group may include an acyl group, an alkyloxycarbonyl group, an aryloxycarbonyl group, an aralkyloxycarbonyl group, aralkyl group, an alkoxyalkyl group, an arylthio group, an alkylsulfonyl group, an arylsulfonyl group, an oxygen-containing heterocyclic alkyl group, and a substituted silyl group. Examples of a more preferred example may include an acyl group, an aralkyl group, and an alkoxyalkyl group.

Compounds shown in Tables 1 to 13 below are representative compounds of the present invention. In the tables, Me represents methyl; Et represents ethyl; Pr represents propyl; Bu represents butyl; Bn represents benzyl; c-Pr represents cyclopropyl; Cbz represents benzyloxycarbonyl; Ac represents acetyl; Ph represents phenyl; Boc represents tert-butoxycarbonyl; and Phe represents a phenylalanine residue.

TABLE 1

| $R^1$ | X | $R^3$ | $R^4$ |
|---|---|---|---|
| Amidino | —CH₂CH₂CH₂— | H | H |
| Amidino | —CH₂CH₂CH₂— | H | Acetyl |
| Amidino | —CH₂CH₂CH₂— | H | Me |
| Amidino | —CH₂CH₂CH₂— | H | n-Pr |
| Amidino | —CH₂CH₂CH₂— | H | n-Bu |
| Amidino | —CH₂CH₂CH₂— | H | n-hexyl |
| Amidino | —CH₂CH₂CH₂— | H | Allyl |
| Amidino | —CH₂CH₂CH₂— | H | c-Pr |
| Amidino | —CH₂CH₂CH₂— | H | —CH₂COOH |
| Amidino | —CH₂CH₂CH₂— | H | —CH₂CH₂COOH |
| Amidino | —CH₂CH₂CH₂— | H | —(CH₂)₃COOH |
| Amidino | —CH₂CH₂CH₂— | H | —(CH₂)₄COOH |
| Amidino | —CH₂CH₂CH₂— | H | —(CH₂)₅COOH |
| Amidino | —CH₂CH₂CH₂— | H | —CH₂CH₂OH |
| Amidino | —CH₂CH₂CH₂— | Allyl | Allyl |
| Amidino | —CH₂CH₂CH₂— | c-Pr | c-Pr |
| Amidino | —CH₂CH₂— | H | H |
| Amidino | —CH₂(CH₂)₂CH₂— | H | H |
| Amidino | —CH₂(CH₂)₂CH₂— | H | —(CH₂)₅COOH |
| Amidino | —CH₂(CH₂)₃CH₂— | H | H |
| Amidino | —CH₂(CH₂)₄CH₂— | H | H |
| Amidino | —CH₂CH(CH₃)CH₂— | H | H |
| Amidino | —CH(CH₃)CH₂— | H | H |
| Amidino | —CH₂CH=CHCH₂— | H | H |
| N'-hydroxyamidino | —CH₂CH₂CH₂— | H | H |
| N-methylamidino | —CH₂CH₂CH₂— | H | H |
| N-Cbz-amidino | —CH₂CH₂CH₂— | H | H |

TABLE 2

| $R^1$ | X | Y | $R^5$ | $R^6$ | $R^7$ |
|---|---|---|---|---|---|
| Amidino | —(CH₂)₃— | —(CH₂)₂— | H | H | H |
| Amidino | —(CH₂)₃— | —(CH₂)₂— | H | H | Acetyl |
| Amidino | —(CH₂)₃— | —(CH₂)₂— | H | H | Me |

TABLE 2-continued

| R¹ | X | Y | R⁵ | R⁶ | R⁷ |
|---|---|---|---|---|---|
| Amidino | —(CH₂)₃— | —(CH₂)₂— | H | H | Et |
| Amidino | —(CH₂)₃— | —(CH₂)₂— | H | H | n-Pr |
| Amidino | —(CH₂)₃— | —(CH₂)₂— | H | H | n-Bu |
| Amidino | —(CH₂)₃— | —(CH₂)₂— | H | H | n-pentyl |
| Amidino | —(CH₂)₃— | —(CH₂)₂— | H | H | n-hexyl |
| Amidino | —(CH₂)₃— | —(CH₂)₂— | H | H | Allyl |
| Amidino | —(CH₂)₃— | —(CH₂)₂— | H | H | c-Pr |
| Amidino | —(CH₂)₃— | —(CH₂)₂— | H | H | —CH₂COOH |
| Amidino | —(CH₂)₃— | —(CH₂)₂— | H | H | —CH₂CH₂COOH |
| Amidino | —(CH₂)₃— | —(CH₂)₂— | H | H | —(CH₂)₃COOH |
| Amidino | —(CH₂)₃— | —(CH₂)₂— | H | H | —(CH₂)₄COOH |
| Amidino | —(CH₂)₃— | —(CH₂)₂— | H | H | —(CH₂)₅COOH |
| Amidino | —(CH₂)₃— | —(CH₂)₂— | H | H | —CH₂CH₂CH₂OH |
| Amidino | —(CH₂)₃— | —(CH₂)₂— | H | H | Aminoethyl |
| Amidino | —(CH₂)₃— | —(CH₂)₂— | Me | Me | H |
| Amidino | —(CH₂)₃— | —(CH₂)₃— | H | H | H |
| Amidino | —(CH₂)₂— | —(CH₂)₂— | H | H | H |
| Amidino | —(CH₂)₄— | —(CH₂)₂— | H | H | H |
| Amidino | —(CH₂)₄— | —(CH₂)₂— | H | H | n-hexyl |
| Amidino | —(CH₂)₄— | —(CH₂)₂— | H | H | —(CH₂)₅COOH |
| Amidino | —CH₂CH(CH₃)CH₂— | —(CH₂)₂— | H | H | H |
| Amidino | —CH₂CH=CHCH₂— | —(CH₂)₂— | H | H | H |
| N'-hydroxyamidino | —(CH₂)₃— | —(CH₂)₂— | H | H | H |
| N-methylamidino | —(CH₂)₃— | —(CH₂)₂— | H | H | H |
| N-Cbz-amidino | —(CH₂)₃— | —(CH₂)₂— | H | H | H |

TABLE 3

| R¹ | X | Y | Z | R⁵ | R⁶ | R⁸ |
|---|---|---|---|---|---|---|
| Amidino | —(CH₂)₃— | —(CH₂)₂— | —(CH₂)₃— | H | H | Amidino |
| Amidino | —(CH₂)₃— | —(CH₂)₂— | —(CH₂)₃— | Boc | Boc | Amidino |
| Amidino | —(CH₂)₃— | —(CH₂)₂— | —(CH₂)₃— | Me | Me | Amidino |
| Amidino | —(CH₂)₃— | —(CH₂)₂— | —(CH₂)₃— | Allyl | Allyl | Amidino |
| Amidino | —(CH₂)₃— | —(CH₂)₂— | —(CH₂)₃— | c-Pr | c-Pr | Amidino |
| Amidino | —(CH₂)₃— | —(CH₂)₂— | —(CH₂)₂— | H | H | Amidino |
| Amidino | —(CH₂)₄— | —(CH₂)₂— | —(CH₂)₄— | H | H | Amidino |
| Amidino | —(CH₂)₃— | —(CH₂)₃— | —(CH₂)₃— | H | H | Amidino |
| Amidino | —(CH₂)₂— | —(CH₂)₂— | —(CH₂)₂— | H | H | Amidino |
| Amidino | —(CH₂)₅— | —(CH₂)₂— | —(CH₂)₅— | H | H | Amidino |
| Amidino | —(CH₂)₆— | —(CH₂)₂— | —(CH₂)₆— | H | H | Amidino |
| Amidino | —CH(CH₃)CH₂— | —(CH₂)₂— | —CH(CH₃)CH₂— | H | H | Amidino |
| Amidino | —CH₂CH(CH₃)CH₂— | —(CH₂)₂— | —CH₂CH(CH₃)CH₂— | H | H | Amidino |
| Amidino | —CH₂CH=CHCH₂— | —(CH₂)₂— | —CH₂CH=CHCH₂— | H | H | Amidino |
| N'-hydroxyamidino | —(CH₂)₃— | —(CH₂)₂— | —(CH₂)₃— | H | H | Amidino |
| N-methylamidino | —(CH₂)₃— | —(CH₂)₂— | —(CH₂)₃— | H | H | Amidino |
| N-Cbz-amidino | —(CH₂)₃— | —(CH₂)₂— | —(CH₂)₃— | H | H | Amidino |

TABLE 4

![structure: R¹-phenyl-O-X-N(Yᵃ,Yᵇ)N-Zᵃ-O-phenyl-R⁸ᵃ]

| R¹ | X | Yᵃ | Yᵇ | Zᵃ | R⁸ᵃ |
|---|---|---|---|---|---|
| Amidino | —(CH₂)₃— | —(CH₂)₂— | Oxalyl | —(CH₂)₃— | Amidino |
| Amidino | —(CH₂)₃— | —(CH₂)₂— | Oxalyl | —(CH₂)₂— | Amidino |
| Amidino | —(CH₂)₃— | —(CH₂)₃— | Oxalyl | —(CH₂)₃— | Amidino |
| Amidino | —(CH₂)₂— | —(CH₂)₂— | Oxalyl | —(CH₂)₂— | Amidino |
| Amidino | —(CH₂)₄— | —(CH₂)₂— | Oxalyl | —(CH₂)₄— | Amidino |
| Amidino | —(CH₂)₆— | —(CH₂)₂— | Oxalyl | —(CH₂)₆— | Amidino |
| Amidino | —(CH₂)₃— | —(CH₂)₂— | Carbonyl | —(CH₂)₃— | Amidino |
| Amidino | —CH₂CH=CHCH₂— | —(CH₂)₂— | Oxalyl | —(CH₂)₃— | Amidino |

TABLE 5

![structure: R¹-phenyl-G¹-X-N(H)-R⁴]

| R¹ | G¹ | X | R⁴ |
|---|---|---|---|
| Amidino | O | —(CH₂)₂— | H |
| Amidino | O | —(CH₂)₄— | H |
| Amidino | NH | —(CH₂)₃— | H |
| Amidino | S | —(CH₂)₃— | H |
| Amidino | O | —(CH₂)₃— | Et |
| Amidino | O | —(CH₂)₃— | n-pentyl |
| N-Ac-amidino | O | —(CH₂)₃— | H |
| Amidino | O | —(CH₂)₂— | 2-(4-amidinophenoxy)ethyl |
| Amidino | O | —(CH₂)₃— | 3-(4-amidinophenoxy)propyl |
| Amidino | O | —(CH₂)₃— | 4-(4-amidinophenoxy)butyl |
| Amidino | O | —(CH₂)₃— | 5-(4-amidinophenoxy)pentyl |
| Amidino | O | —(CH₂)₃— | 6-(4-amidinophenoxy)hexyl |
| Amidino | O | —(CH₂)₃— | 4-(4-amidinophenoxy)butyl |
| Amidino | O | —(CH₂)₄— | 4-(4-amidinophenoxy)butyl |
| Amidino | O | —(CH₂)₅— | 5-(4-amidinophenoxy)pentyl |
| Amidino | O | —(CH₂)₆— | 6-(4-amidinophenoxy)hexyl |
| N-methylamidino | O | —(CH₂)₃— | —(CH₂)₃—O—C₆H₄—C(=NH)NH—Me |
| N-Ac-amidino | O | —(CH₂)₃— | —(CH₂)₃—O—C₆H₄—C(=NH)NH—Ac |
| N'-hydroxyamidino | O | —(CH₂)₃— | —(CH₂)₃—O—C₆H₄—C(NH₂)=N—CH |
| N-Cbz-amidino | O | —(CH₂)₃— | —(CH₂)₃—O—C₆H₄—C(=NH)NH—C(=O)O—CH₂—Ph |

TABLE 6

| $R^1$ | X | $R^4$ | $Y^c$ | $Y^{c'}$ | $Z^b$ | $G^{3b}$ | $R^{8b}$ |
|---|---|---|---|---|---|---|---|
| Amidino | —(CH$_2$)$_2$— | H | —(CH$_2$)$_2$— | —(CH$_2$)$_2$— | —(CH$_2$)$_2$— | O | Amidino |
| Amidino | —(CH$_2$)$_2$— | H | —(CH$_2$)$_2$— | —(CH$_2$)$_2$— | —(CH$_2$)$_3$— | O | Amidino |
| Amidino | —(CH$_2$)$_3$— | H | —(CH$_2$)$_2$— | —(CH$_2$)$_2$— | —(CH$_2$)$_3$— | O | Amidino |
| Amidino | —(CH$_2$)$_4$— | H | —(CH$_2$)$_2$— | —(CH$_2$)$_2$— | —(CH$_2$)$_3$— | O | Amidino |
| Amidino | —(CH$_2$)$_5$— | H | —(CH$_2$)$_2$— | —(CH$_2$)$_2$— | —(CH$_2$)$_3$— | O | Amidino |
| Amidino | —(CH$_2$)$_6$— | H | —(CH$_2$)$_2$— | —(CH$_2$)$_2$— | —(CH$_2$)$_3$— | O | Amidino |
| Amidino | —(CH$_2$)$_3$— | H | —(CH$_2$)$_2$— | —(CH$_2$)$_2$— | —CH$_2$— | — | Amidino |
| Amidino | —(CH$_2$)$_3$— | H | —(CH$_2$)$_2$— | —(CH$_2$)$_2$— | —(CH$_2$)$_2$— | — | Amidino |
| Amidino | —(CH$_2$)$_3$— | H | —(CH$_2$)$_2$— | —(CH$_2$)$_2$— | —(CH$_2$)$_2$— | O | Amidino |
| Amidino | —(CH$_2$)$_3$— | H | —(CH$_2$)$_2$— | —(CH$_2$)$_2$— | —(CH$_2$)$_4$— | O | Amidino |
| Amidino | —(CH$_2$)$_3$— | H | —(CH$_2$)$_2$— | —(CH$_2$)$_2$— | —(CH$_2$)$_5$— | O | Amidino |
| Amidino | —(CH$_2$)$_3$— | H | —(CH$_2$)$_2$— | —(CH$_2$)$_2$— | —(CH$_2$)$_6$— | O | Amidino |
| Amidino | —(CH$_2$)$_3$— | H | —(CH$_2$)$_2$— | —CH$_2$— | —(CH$_2$)$_3$— | O | Amidino |
| Amidino | —(CH$_2$)$_3$— | H | —(CH$_2$)$_2$— | —CH$_2$— | —(CH$_2$)$_6$— | O | Amidino |
| Amidino | —(CH$_2$)$_3$— | H | —(CH$_2$)$_3$— | —(CH$_2$)$_2$— | —(CH$_2$)$_3$— | O | Amidino |
| Amidino | —(CH$_2$)$_3$— | H | —(CH$_2$)$_3$— | —(CH$_2$)$_2$— | —(CH$_2$)$_6$— | O | Amidino |
| Amidino | —(CH$_2$)$_3$— | CH$_3$ | —(CH$_2$)$_2$— | —CH$_2$— | —(CH$_2$)$_3$— | O | Amidino |
| N-methylamidino | —(CH$_2$)$_3$— | H | —(CH$_2$)$_2$— | —(CH$_2$)$_2$— | —(CH$_2$)$_3$— | O | N-methylamidino |
| N-Ac-amidino | —(CH$_2$)$_3$— | H | —(CH$_2$)$_2$— | —(CH$_2$)$_2$— | —(CH$_2$)$_3$— | O | N-Ac-amidino |
| N'-hydroxyamidino | —(CH$_2$)$_3$— | H | —(CH$_2$)$_2$— | —(CH$_2$)$_2$— | —(CH$_2$)$_3$— | O | N'-hydroxyamidino |
| N-Cbz-amidino | —(CH$_2$)$_3$— | H | —(CH$_2$)$_2$— | —(CH$_2$)$_2$— | —(CH$_2$)$_3$— | O | N-Cbz-amidino |

TABLE 7

| $R^1$ | Y | $R^5$ | $R^6$ | $R^7$ |
|---|---|---|---|---|
| Amidino | —(CH$_2$)$_2$— | H | H | 5-methyl-3-hydroxyisoxazole (CH$_2$-linked) |
| N-Boc-amidino | —(CH$_2$)$_2$— | H | H | 5-methylisoxazol-3-yl phenylsulfonate (CH$_2$-linked) |
| Amidino | —(CH$_2$)$_2$— | Me | Me | Me |
| Amidino | —(CH$_2$)$_4$— | H | H | H |
| Amidino | —(CH$_2$)$_2$— | H | H | —(CH$_2$)$_4$-piperidin-4-yl |
| N-Ac-amidino | —(CH$_2$)$_2$— | H | H | H |

TABLE 8

| R¹ | G¹ | X | Y | Z | R⁵ | R⁶ | G³ | R⁸ |
|---|---|---|---|---|---|---|---|---|
| Amidino | O | —(CH₂)₃— | —(CH₂)₄— | —(CH₂)₃— | H | H | O | 4-amidino |
| Amidino | O | —(CH₂)₃— | —(CH₂)₅— | —(CH₂)₃— | H | H | O | 4-amidino |
| Amidino | O | —(CH₂)₃— | —(CH₂)₆— | —(CH₂)₃— | H | H | O | 4-amidino |
| Amidino | O | —(CH₂)₃— | —(CH₂)₃— | —(CH₂)₂— | H | H | O | 4-amidino |
| Amidino | O | —(CH₂)₃— | —(CH₂)₂— | —(CH₂)₆— | H | H | O | 4-amidino |
| Amidino | O | —CH₂CH(OH)CH₂— | —(CH₂)₂— | —CH₂CH(OH)CH₂— | H | H | O | 4-amidino |
| Amidino | O | —(CH₂)₃— | —(CH₂)₂— | —(CH₂)₃— | H | H | N | 4-amidino |
| Amidino | NH | —(CH₂)₃— | —(CH₂)₂— | —(CH₂)₃— | H | H | N | 4-amidino |
| Amidino | O | —(CH₂)₃— | —(CH₂)₂— | —(CH₂)₃— | Ac | Ac | O | 4-amidino |
| Amidino | O | —(CH₂)₃— | —(CH₂)₂— | —(CH₂)₃— | H | H | O | 3-amidino |
| N-methylamidino | O | —(CH₂)₃— | —(CH₂)₂— | —(CH₂)₃— | H | H | O | N-methylamidino(4-yl) |
| N-Ac-amidino | O | —(CH₂)₃— | —(CH₂)₂— | —(CH₂)₃— | H | H | O | N-Ac-amidino(4-yl) |
| N'-hydroxyamidino | O | —(CH₂)₃— | —(CH₂)₂— | —(CH₂)₃— | H | H | O | N'-hydroxyamidino(4-yl) |
| N-Cbz-amidino | O | —(CH₂)₃— | —(CH₂)₂— | —(CH₂)₃— | H | H | O | N-Cbz-amidino(4-yl) |

TABLE 9

| R¹ | X | R⁷ᵃ |
|---|---|---|
| Amidino | —(CH₂)₃— | —(CH₂)₂—NH₂ |
| Amidino | —(CH₂)₃— | —(CH₂)₃—NH₂ |
| Amidino | —(CH₂)₃— | —(CH₂)₄—NH₂ |
| Amidino | —(CH₂)₃— | —(CH₂)₅—NH₂ |
| Amidino | —(CH₂)₃— | —(CH₂)₆—NH₂ |
| Amidino | —(CH₂)₃— | —(CH₂)₆—NHAc |
| Amidino | —(CH₂)₃— | —CH₂—C₆H₄—C(=NH)NH₂ |
| Amidino | —(CH₂)₂— | —C₆H₄—C(=NH)NH₂ |
| Amidino | —(CH₂)₃— | —C₆H₄—C(=NH)NH₂ |
| Amidino | —(CH₂)₄— | —C₆H₄—C(=NH)NH₂ |
| Amidino | —(CH₂)₅— | —C₆H₄—C(=NH)NH₂ |
| Amidino | —(CH₂)₃— | —C₆H₄—C(=NH)NH₂ |
| Amidino | —(CH₂)₂— | —(biphenyl)—C(=NH)NH₂ |
| Amidino | —(CH₂)₃— | —(biphenyl)—C(=NH)NH₂ |
| Amidino | —(CH₂)₄— | —(biphenyl)—C(=NH)NH₂ |
| Amidino | —(CH₂)₃— | —(CH₂)₆—N(piperazine)NH |
| Amidino | —(CH₂)₃— | —(CH₂)₄—(N-Me piperidine) |
| Amidino | —(CH₂)₃— | —(CH₂)₄—(piperidine-NH) |

TABLE 9-continued

| R¹ | X | R⁷ᵃ |
|---|---|---|
| N-methylamidino | —(CH₂)₃— | 4-(NHMe)(C=NH)-phenyl |
| N-Ac-amidino | —(CH₂)₃— | 4-(NHAc)(C=NH)-phenyl |
| N'-hydroxyamidino | —(CH₂)₃— | 4-(N-OH)(C=NH)-phenyl |
| N-Cbz-amidino | —(CH₂)₃— | 4-(NHCbz)(C=NH)-phenyl |

TABLE 10

| R¹ | G¹ | X | Yᵇ | Zᵃ | G³ᵃ | R⁸ᵃ |
|---|---|---|---|---|---|---|
| Amidino | O | —(CH₂)₃— | Oxalyl | —(CH₂)₆— | O | 4'-amidino |
| Amidino | O | —(CH₂)₃— | Oxalyl | —CH₂CH:CHCH₂— | O | 4'-amidino |
| Amidino | O | —(CH₂)₃— | Oxalyl | —(CH₂)₃— | O | 3'-amidino |
| Amidino | O | —(CH₂)₃— | Carbonyl | —(CH₂)₃— | O | 3'-amidino |
| Amidino | O | —CH₂CH(OBn)CH₂— | —(CH₂)₂— | —CH₂CH(OBn)CH₂— | O | 4'-amidino |
| Amidino | O | —(CH₂)₃— | Oxalyl | —(CH₂)₃— | NH | 4'-amidino |
| Amidino | NH | —(CH₂)₃— | Oxalyl | —(CH₂)₃— | NH | 4'-amidino |
| Amidino | O | —(CH₂)₂— | —(CH₂)₂— | —(CH₂)₂— | O | 4'-amidino |
| Amidino | O | —(CH₂)₂— | —(CH₂)₂— | —(CH₂)₃— | O | 4'-amidino |
| Amidino | O | —(CH₂)₃— | —(CH₂)₂— | —(CH₂)₃— | O | 4'-amidino |
| Amidino | O | —(CH₂)₄— | —(CH₂)₂— | —(CH₂)₄— | O | 4'-amidino |
| Amidino | O | —(CH₂)₅— | —(CH₂)₂— | —(CH₂)₅— | O | 4'-amidino |
| Amidino | O | —(CH₂)₆— | —(CH₂)₂— | —(CH₂)₆— | O | 4'-amidino |
| Amidino | O | —(CH₂)₃— | —(CH₂)₃— | —(CH₂)₃— | O | 4'-amidino |
| Amidino | O | —(CH₂)₃— | —(CH₂)₄— | —(CH₂)₃— | O | 4'-amidino |
| Amidino | O | —(CH₂)₃— | —CH₂CH(CH₃)— | —(CH₂)₃— | O | 4'-amidino |
| Amidino | O | —CH₂CH:CHCH₂— | —(CH₂)₂— | —CH₂CH:CHCH₂— | O | 4'-amidino |
| Amidino | O | —CH₂CH(CH₃)CH₂— | —(CH₂)₂— | —CH₂CH(CH₃)CH₂— | O | 4'-amidino |
| Amidino | O | —CH₂CH(CH₃)CH₂— | —(CH₂)₂— | —(CH₂)₃— | O | 4'-amidino |
| Amidino | O | —CH₂CH(OH)CH₂— | —(CH₂)₂— | —CH₂CH(OH)CH₂— | O | 4'-amidino |
| Amidino | O | —CH₂CH(CH₃)CH₂— | —(CH₂)₂— | —(CH₂)₃— | O | 4'-amidino |
| Amidino | O | —(CH₂)₃— | —(CH₂)₂— | —(CH₂)₃— | O | 3'-amidino |
| Amidino | O | —(CH₂)₃— | —CH₂CH(CO₂H)— | —(CH₂)₃— | O | 4'-amidino |
| Amidino | O | —(CH₂)₃— | —CH₂CH₂C(O)— | —(CH₂)₃— | O | 4'-amidino |

TABLE 11

| R¹ | Rᵃ | G² | G⁵ᵃ | Rᵇᵃ | Rᴮᵃ |
|---|---|---|---|---|---|
| Amidino | 2-F | C | C | 2'-F | 4'-amidino |
| Amidino | 3-F | C | C | 3'-F | 4'-amidino |
| Amidino | 2-Me | C | C | 2'-Me | 4'-amidino |
| Amidino | 2-OMe | C | C | 2'-OMe | 4'-amidino |
| Amidino | H | 2-N | 2'-N | H | 4'-amidino |
| N-methylamidino | H | C | C | H | N-methylamidino(4'-yl) |
| HN=C(-)-N(H)-CH₂-CH=O (H₂O=) | H | C | C | H | NH=C(-)-N(H)-CH=CH₂ (4'-yl) |
| N'-hydroxyamidino | H | C | C | H | N'-hydroxyamidino(4'-yl) |
| N'-methoxyamidino | H | C | C | H | N'-methoxyamidino(4'-yl) |
| N-Ac-amidino | H | C | C | H | N-Ac-amidino(4'-yl) |
| N-Ac-Phe-amidino | H | C | C | H | N-Ac-Phe-amidino(4'-yl) |
| N'-hydroxyamidino | H | 2-N | 2'-N | H | N'-hydroxyamidino(4'-yl) |

TABLE 12

| R¹ | X | Yᵇ | Zᵃ | R⁸ᵃ |
|---|---|---|---|---|
| Amidino | –(CH₂)₃– | –(CH₂)₂– | –(CH₂)₂– | 4'-amidino |
| Amidino | –(CH₂)₃– | –(CH₂)₂– | –(CH₂)₃– | 4'-amidino |
| Amidino | –(CH₂)₃– | –(CH₂)₂– | –(CH₂)₄– | 4'-amidino |
| Amidino | –(CH₂)₂– | –(CH₂)₂– | –(CH₂)₂– | 4'-amidino |
| Amidino | –(CH₂)₂– | –(CH₂)₂– | –(CH₂)₃– | 4'-amidino |
| Amidino | –(CH₂)₂– | –(CH₂)₂– | –(CH₂)₂– | 4'-amidino |
| Amidino | –(CH₂)₂– | –CH₂– | –(CH₂)₃– | 4'-amidino |
| Amidino | –(CH₂)₄– | –CH₂– | –(CH₂)₂– | 4'-amidino |
| N-methylamidino | –(CH₂)₃– | –(CH₂)₂– | –(CH₂)₂– | N-methylamidino |
| N-Ac-amidino | –(CH₂)₃– | –(CH₂)₂– | –(CH₂)₂– | N-Ac-amidino |
| N'-hydroxyamidino | –(CH₂)₃– | –(CH₂)₂– | –(CH₂)₂– | N'-hydroxyamidino |
| N-Cbz-amidino | –(CH₂)₃– | –(CH₂)₂– | –(CH₂)₂– | N-Cbz-amidino |

TABLE 13

Structural formula

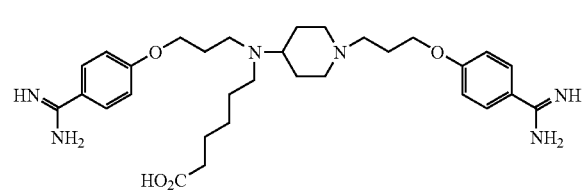

When an isomer (e.g., optical isomer, geometric isomer, tautomer, etc.) exists in the compound represented by general formula [1] or a salt thereof, these isomers are included in the present invention. In addition, a solvate, a hydrate, and various forms of crystals are also included in the present invention.

Next, a method for producing the compound of the present invention will be described.

The compound of the present invention is produced by combined use of known methods. For example, it can be produced by the following schemes.

[Scheme 1]

A compound represented by general formula [1a] can be produced, for example, by the following scheme:

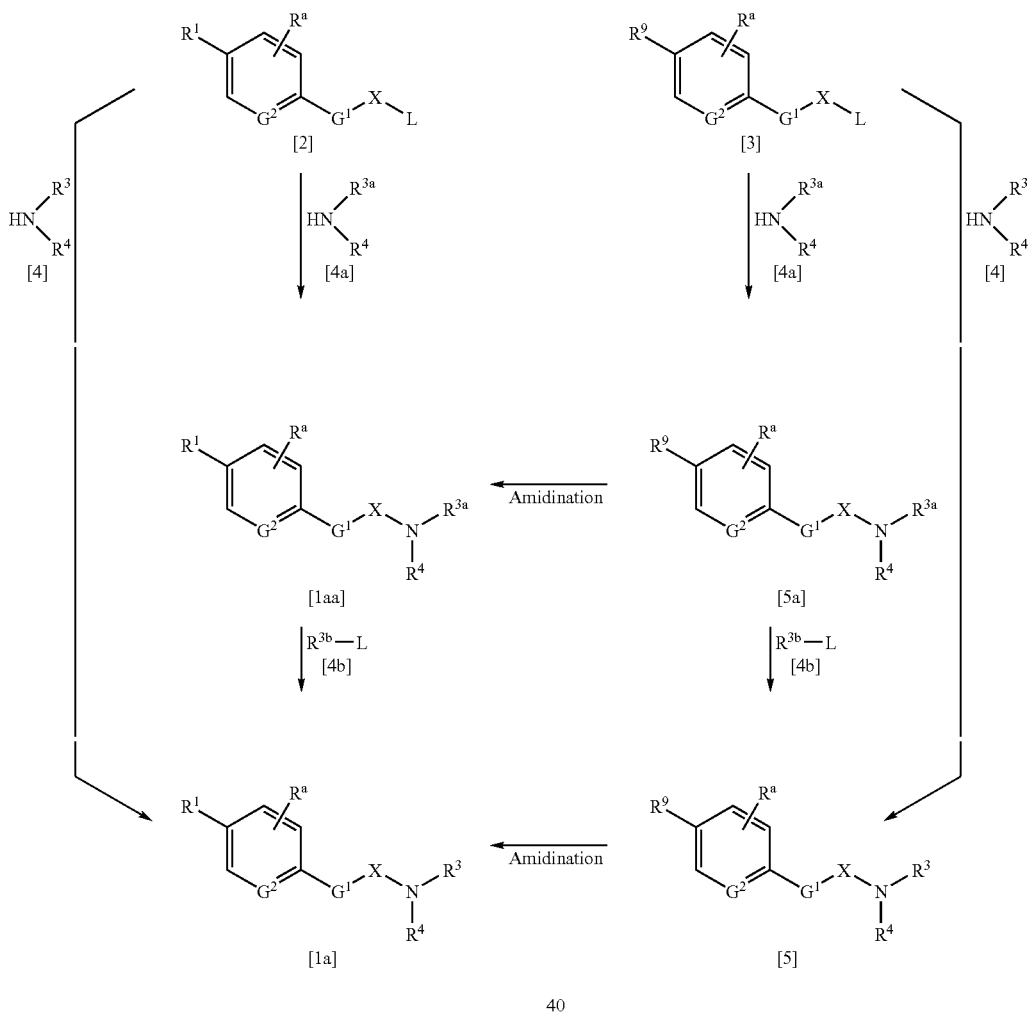

wherein $R^{3a}$ represents a hydrogen atom, $R^{3b}$ represents the same substituent as for $R^3$, except for a hydrogen atom; $R^9$ represents a cyano group or an amide group; L represents a leaving group; each of X, $R^1$, $R^3$, $R^4$, $R^a$, $G^1$, and $G^2$ has the same meaning as described above.

The compounds represented by general formulas [2] and [3] can be produced by a method described in International Publication WO96/16947, or methods equivalent thereto.

(1-a)

The compounds represented by general formulas [1a] and [1aa] can be produced by reacting the compound represented by general formula [2] with the compounds represented by general formulas [4] and [4a], respectively, in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compound represented by general formula [2] at a molar ratio of 1:1 or greater, and preferably at a molar ratio of 1:1 to 3:1.

In this reaction, the compounds represented by general formulas [4] and [4a] may be used with respect to the compound represented by general formula [2] at a molar ratio of 1:1 or greater, and preferably at a molar ratio of 1:1 to 5:1.

This reaction may be carried out at 0° C. to 200° C., preferably at 0° C. to 150° C., for 1 minute to 24 hours.

(1-b)

The compound represented by general formula [1a] can be produced by reacting the compound represented by general formula [1aa] with the compound represented by general formula [4b] in the presence or absence of a base.

This reaction may be carried out in the same manner as the reaction described in the scheme 1-a.

In this reaction, the compound represented by general formula [4b] may be used with respect to the compound represented by general formula [1aa] at a molar ratio of 1:1 or greater, and preferably at a molar ratio of 1:1 to 5:1.

This reaction may be carried out at 0° C. to 200° C., preferably at 0° C. to 150° C., for 1 minute to 24 hours.

(1-c)

Each of the compounds represented by general formulas [5] and [5a] can be produced by reacting the compound represented by general formula [3] with each of the compounds represented by general formulas [4], [4a] and [4b] according to the schemes 1-a and 1-b.

(1-d)

The compounds [1a] and [1aa] can be produced by amidinating the compounds [5] and [5a], respectively.

When $R^9$ is a cyano group, amidination may be carried out according to the methods described in International Publication WO96/16947; the Journal of Medicinal Chemistry (J. Med. Chem.), vol. 36, pp. 1811 to 1819, 1993; the Journal of Organic Chemistry (J. Org. Chem.), vol. 64, pp. 12 to 13, 1999; and the Journal of American Chemical Society (J. Am. Chem. Soc.), vol. 107, pp. 2,743 to 2,748, 1985, or methods equivalent thereto.

Otherwise, when amidination is carried out by way of amidoxime or an analog thereof, the reaction may be carried out according to the methods described in Tetrahedron, vol. 51, pp. 12,047 to 12,068, 1995; Synthetic Communication, vol. 26, pp. 4,351 to 4,367, 1996; the Journal of Medicinal Chemistry (J. Med. Chem.), vol. 43, pp. 4,063 to 4,070, 2000; the same publication, vol. 44, pp. 1,217 to 1,230, 2001; and the Chemical and Pharmaceutical Bulletin (Chem. Pharm. Bull.), vol. 49, pp. 268 to 277, 2001, or methods equivalent thereto.

More specifically, the reaction may be carried out by the method described as "scheme 2."

When $R^9$ is an amide group, amidination may be carried out according to the methods described in the Journal of Organic Chemistry (J. Org. Chem.), vol. 33, pp. 1,679 to 1,681, 1968, or methods equivalent thereto.

(1-e)

A compound from which an amino protecting group is eliminated can be produced, as appropriate, from the compounds represented by general formulas [1aa] and [5a] wherein, in the compounds represented by general formulas [1a] and [5], both $R^3$ and $R^4$ are amino protecting groups, or either one of $R^3$ and $R^4$ is an amino protecting group.

[Scheme 2]

A compound represented by general formula [1a] can be produced, for example, by the following scheme:

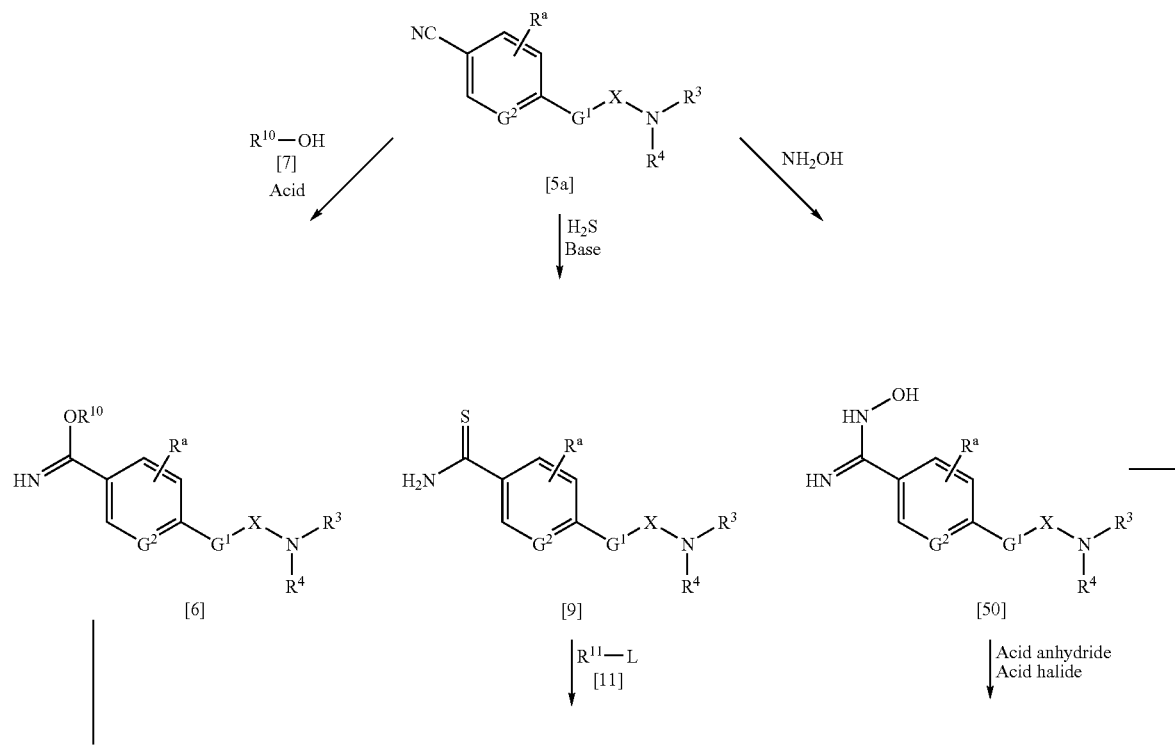

-continued

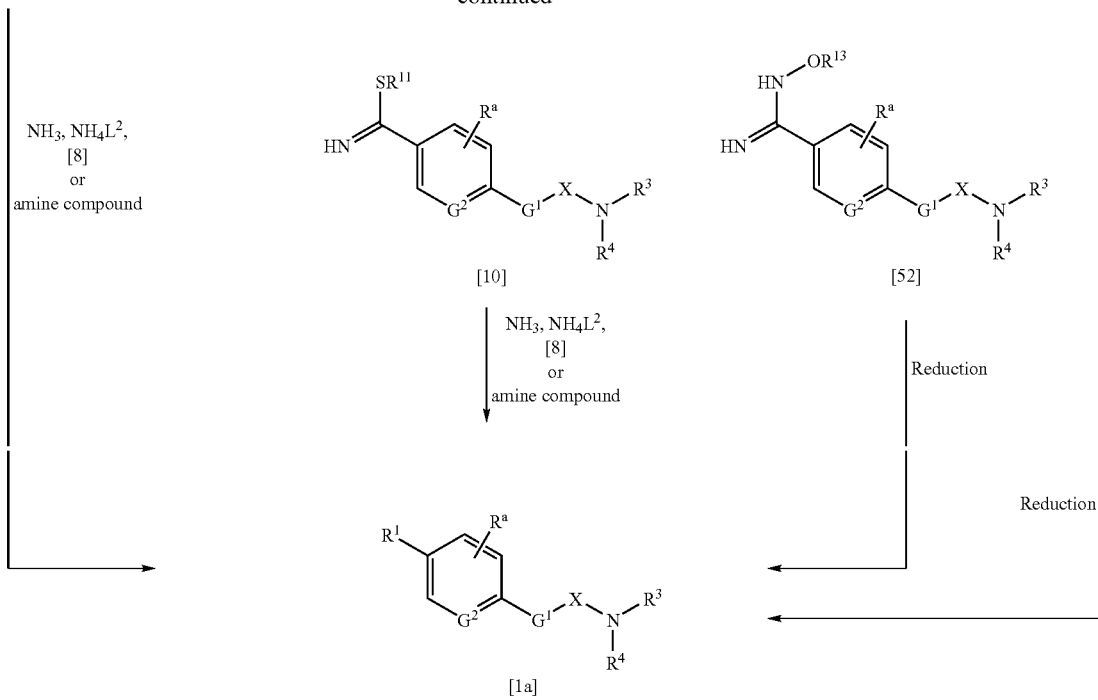

wherein each of X, $R^a$, $R^1$, $R^3$, $R^4$, $G^1$, $G^2$, and L has the same meaning as described above; each of $R^{10}$ and $R^{11}$ represents an alkyl group; $L^2$ represents a halogen atom or an acyloxy group; and $R^{13}$ represents a hydrogen atom, or an unsubstituted or substituted acyl group.

(2-a)

The compound represented by general formula [6] can be produced by reacting the compound represented by general formula [5a] with the compound represented by general formula [7] in the presence of acid.

As a solvent used in this reaction, the compound represented by general formula [7] may be used as the solvent, or any other solvents may be used as long as they do not affect the reaction. Examples of a solvent may include: ethers such as dioxane, tetrahydrofuran, anisole, or diethylene glycol diethyl ether; ketones such as acetone or 2-butanone; and halogenated hydrocarbons such as methylene chloride, chloroform, or 1,2-dichloroethane. These solvents may be used in combination.

Examples of acid used in this reaction may include hydrogen chloride, hydrobromic acid, perchloric acid, p-toluenesulfonic acid, and methanesulfonic acid. Such acid may be used with respect to the compound represented by general formula [5a] at a molar ratio of 1:1 to 200:1, and preferably at a molar ratio of 5:1 to 100:1.

In this reaction, the compound represented by general formula [7] may be used with respect to the compound represented by general formula [5a] at a molar ratio of 1:1 to 1,000:1, and preferably at a molar ratio of 10:1 to 100:1.

This reaction may be carried out at −30° C. to 150° C., and preferably at 10° C. to 50° C., for 30 minutes to 24 hours.

The compound represented by general formula [1a] can be produced by reacting the compound represented by general formula [6] with ammonia, the compound represented by general formula [8], or an amine compound or a salt thereof, in the presence or absence of a base.

Any solvent may be used in this reaction, as long as it does not affect the reaction. Examples of a solvent may include: alcohols such as methanol, ethanol, isopropanol, or tert-butanol; ethers such as dioxane, tetrahydrofuran, anisole, diethylene glycol diethyl ether, or ethylene glycol monomethyl ether; amides such as N,N-dimethylformamide or N,N-dimethylacetamide; and sulfoxides such as dimethyl sulfoxide. These solvents may also be used in combination.

Examples of the compound represented by general formula [8] may include ammonium salts such as ammonium chloride, ammonium bromide, or ammonium acetate.

Examples of an amine compound may include aliphatic amines such as methylamine, ethylamine, allylamine, or methoxyamine; and hydroxylamine. Such an amine compound may be used with respect to the compound represented by general formula [6] or a salt thereof at a molar ratio of 1:1 to 100:1, and preferably 1:1 to 10:1.

This reaction may be carried out usually at 0° C. to 150° C., and preferably at 20° C. to 120° C., for 1 minute to 24 hours.

(2-b)

The compound represented by general formula [9] can be produced by reacting the compound represented by general formula [5a] with hydrogen sulfide in the presence of a base.

Examples of a base used in this reaction may include ammonia, pyridine, triethylamine, and diisopropylethylamine.

A solvent used in this reaction is not particularly limited, as long as it does not affect the reaction. Examples of a solvent may include: alcohols such as methanol, ethanol, isopropanol, or tert-butanol; ethers such as tetrahydrofuran or dioxane; ketones such as acetone or 2-butanone; and heteroaromatics such as pyridine. These solvents may be used in combination.

Hydrogen sulfide and a base may be used with respect to the compound represented by general formula [5a] at a molar ratio of 1:1 to 500:1 and 1:1 to 100:1, respectively.

This reaction may be carried out usually at 0° C. to 150° C., and preferably at 10° C. to 100° C., for 1 minute to 24 hours.

The compound represented by general formula [10] can be produced by reacting the compound represented by general formula [9] with the compound represented by general formula [11].

A solvent used in this reaction is not particularly limited, as long as it does not affect the reaction. Examples of a solvent may include: alcohols such as methanol, ethanol, isopropanol, or tert-butanol; ethers such as dioxane, tetrahydrofuran, anisole, diethylene glycol diethyl ether, or ethylene glycol monomethyl ether; sulfoxides such as dimethyl sulfoxide; amides such as N,N-dimethylformamide or N,N-dimethylacetamide; ketones such as acetone or 2-butanone; and esters such as ethyl acetate. These solvents may be used in combination.

The compound represented by general formula [11] may be used with respect to the compound represented by general formula [9] at a molar ratio of 1:1 to 100:1, and preferably at a molar ratio of 1:1 to 10:1.

This reaction may be carried out usually at −10° C. to 150° C., and preferably at 20° C. to 120° C., for 1 minute to 24 hours.

The compound represented by general formula [1a] can be produced by reacting the compound represented by general formula [10] with ammonia, the compound represented by general formula [8], or an amine compound or a salt thereof, in the presence or absence of a base.

A solvent used in this reaction is not particularly limited, as long as it does not affect the reaction. Examples of a solvent may include: alcohols such as methanol, ethanol, isopropanol, or tert-butanol; ethers such as dioxane, tetrahydrofuran, anisole, diethylene glycol diethyl ether, or ethylene glycol monomethyl ether; amides such as N,N-dimethylformamide or N,N-dimethylacetamide; and sulfoxides such as dimethyl sulfoxide. These solvents may be used in combination.

As in the case described above, examples of the compound represented by general formula [8] may include ammonium salts such as ammonium chloride, ammonium bromide, or ammonium acetate. Examples of an amine compound may include aliphatic amines such as methylamine, ethylamine, allylamine, or methoxyamine; and hydroxylamine. Such an amine compound may be used with respect to the compound represented by general formula [10] at a molar ratio of 1:1 to 100:1, and preferably 1:1 to 10:1.

This reaction may be carried out usually at 0° C. to 150° C., and preferably at 20° C. to 120° C., for 1 minute to 24 hours.

(2-c)

The compound represented by general formula [50] can be produced by reacting the compound represented by general formula [5a] with hydroxylamine or a salt thereof in the presence or absence of a base.

Any solvent may be used in this reaction, as long as it does not affect the reaction. Examples of a solvent may include: alcohols such as methanol, ethanol, isopropanol, or tert-butanol; ethers such as dioxane, tetrahydrofuran, anisole, diethylene glycol diethyl ether, or ethylene glycol monomethyl ether; amides such as N,N-dimethylformamide or N,N-dimethylacetamide; sulfoxides such as dimethyl sulfoxide; and heteroaromatics such as pyridine. These solvents may also be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine.

Hydroxylamine or a salt thereof may be used with respect to the compound represented by general formula [5a] at a molar ratio of 1:1 or greater, and preferably at a molar ratio of 1:1 to 3:1.

This reaction may be carried out at 0° C. to 150° C., and preferably at 50° C. to 150° C., for 1 minute to 24 hours.

The compound represented by general formula [52] can be produced by reacting the compound represented by general formula [50] with an acid anhydride or acid halide in the presence or absence of a base.

A solvent used in this reaction is not particularly limited, as long as it does not affect the reaction. Examples of a solvent may include: amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; esters such as ethyl acetate; carboxylic acids such as acetic acid; ketones such as acetone or 2-butanone; and nitriles such as acetonitrile. These solvents may be used in combination.

Examples of an acid anhydride may include formic acetic anhydride, acetic anhydride, trichloroacetic anhydride, and trifluoroacetic anhydride. Such an acid anhydride may be used with 2.0 respect to the compound represented by general formula [50] at a molar ratio of 1:1 or greater, and preferably at a molar ratio of 1:1 to 5:1.

Examples of an acid halide may include acetyl chloride, trichloroacetyl chloride, and trifluoroacetyl chloride.

Examples of a base that is used in this reaction as desired may include sodium methoxide, sodium ethoxide, potassium tert-butoxide, sodium tert-butoxide, sodium hydroxide, potassium hydroxide, sodium bicarbonate, sodium carbonate, potassium carbonate, sodium hydride, potassium hydride, triethylamine, and pyridine.

Each of such an acid anhydride, an acid halide, and a base may be used with respect to the compound represented by general formula [50] at a molar ratio of 1:1 or greater, and preferably at a molar ratio of 1:1 to 3:1.

This reaction may be carried out at −20° C. to 100° C., and preferably at 0° C. to 50° C., for 1 minute to 24 hours.

The compound represented by general formula [1a] can be produced by subjecting the compounds represented by general formulas [50] and [52] to a reduction reaction.

Examples of a reduction reaction used herein may include catalytic hydrogenation, reduction with metal or metal salts, reduction with a metal hydrogen compound, reduction with a metal hydrogen complex compound, and reduction with hydrazine.

More specifically, when the compound represented by general formula [52] is subject to catalytic hydrogenation using a metal catalyst, a solvent used herein is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; esters such as ethyl acetate; carboxylic acids such as acetic acid; mineral acids such as hydrochloric acid; and nitrites such as acetonitrile. These solvents may be used in combination.

Examples of a metal catalyst may include palladium oxide, platinum oxide, and palladium-carbon. A metal catalyst may be used with respect to the compounds represented by general formulas [50] and [52] at a weight ratio (W/W) of 0.001:1 to 1:1, and preferably at a weight ratio (W/W) of 0.01:1 to 0.5:1.

Examples of a reducing agent may include zinc, formic acid, hydrazine, as well as hydrogen. The reducing agent may be used with respect to the compounds represented by general formulas [50] and [52] at a molar ratio of 1:1 to 100:1, and preferably 1:1 to 10:1.

This reaction may be carried out at 0° C. to 200° C., and preferably at 0° C. to 100° C., for 1 minute to 24 hours.

[Scheme 3]

A compound represented by general formula [1ab] can be produced, for example, by the following scheme:

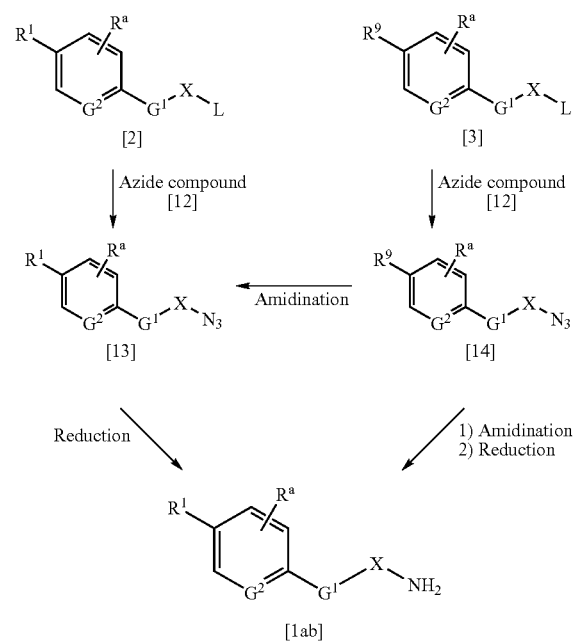

wherein each of X, $R^a$, $R^1$, $R^9$, $G^1$, $G^2$, and L has the same meaning as described above.

(3-a)

The compound represented by general formula [13] can be produced by reacting the compound represented by general formula [2] with the compound represented by general formula [12].

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitriles such as acetonitrile; ketones such as acetone or 2-butanone; and sulfoxides such as dimethyl sulfoxide. These solvents may be used in combination.

Examples of the compound represented by general formula [12] used in this reaction may include sodium azide, lithium azide, barium azide, cesium azide, and trimethylsilyl azide. The compound represented by general formula [12] may be used with respect to the compound represented by general formula [2] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

The compound represented by general formula [13] can also be produced by amidinating the compound represented by general formula [14] according to the scheme 1-b or scheme 2.

(3-b)

The compound represented by general formula [1ab] can be produced by subjecting the compound represented by general formula [13] to known reduction reactions listed below.

Examples of a reduction reaction may include (1) catalytic hydrogenation using a metal catalyst, (2) a reaction with triphenylphosphine, and the subsequent hydrolysis reaction (Tetrahedron Letters, vol. 24, pp. 763 to 764, 1983, etc.), (3) a reaction with sodium borohydride (Synthesis, pp. 48 to 49, 1987, etc.), and (4) a reaction with inorganic and organic mercaptans (the Journal of Organic Chemistry (J. Org. Chem.), vol. 44, pp. 4,712 to 4,713, 1979 etc.).

More specifically, when catalytic hydrogenation using a metal catalyst is applied, a solvent used in the reaction is not particularly limited as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycoldiethyl ether, or ethylene glycol monomethyl ether; ketones such as acetone or 2-butanone; and nitrites such as acetonitrile. These solvents may be used in combination.

Examples of a metal catalyst may include palladium oxide, platinum oxide, and palladium-carbon. A metal catalyst may be used with respect to the compound represented by general formula [13] at a weight ratio (W/W) of 0.001:1 to 1:1, and preferably at a weight ratio (W/W) of 0.01:1 to 0.5:1.

Examples of a reducing agent may include hydrogen and formic acid. A reducing agent may be used with respect to the compound represented by general formula [13] at a molar ratio of 1:1 to 100:1, and preferably 1:1 to 10:1.

This reaction may be carried out at 0° C. to 200° C., and preferably at 0° C. to 100° C., for 1 minute to 24 hours.

(3-c)

The compound represented by general formula [14] can be produced by reacting the compound represented by general formula [3] with the compound represented by general formula [12] according to the scheme 3-a.

(3-d)

The compound represented by general formula [1ab] can be produced by amidinating the compound represented by general formula [14] according to the scheme 1-b or scheme 2, and then subjecting the resultant product to a reduction reaction according to the scheme 3-b.

The compound represented by general formula [1ab] is reacted, for example, with $R^{3a}$-L (wherein $R^{3a}$ represents a group for $R^3$, other than a hydrogen atom; and L represents a leaving group), so as to produce another compound represented by general formula [1a]. Moreover, the compound represented by general formula [14] is reduced, and then the resultant product is reacted, for example, with $R^{3a}$-L (wherein $R^{3a}$ represents a group for $R^3$, other than a hydrogen atom; and L represents a leaving group), followed by amidination, so as to produce a compound of interest of the invention of the present application.

[Scheme 4]

A compound represented by general formula [1b] can be produced, for example, by the following scheme:

ride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; ketones such as acetone or 2-butanone; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compound represented

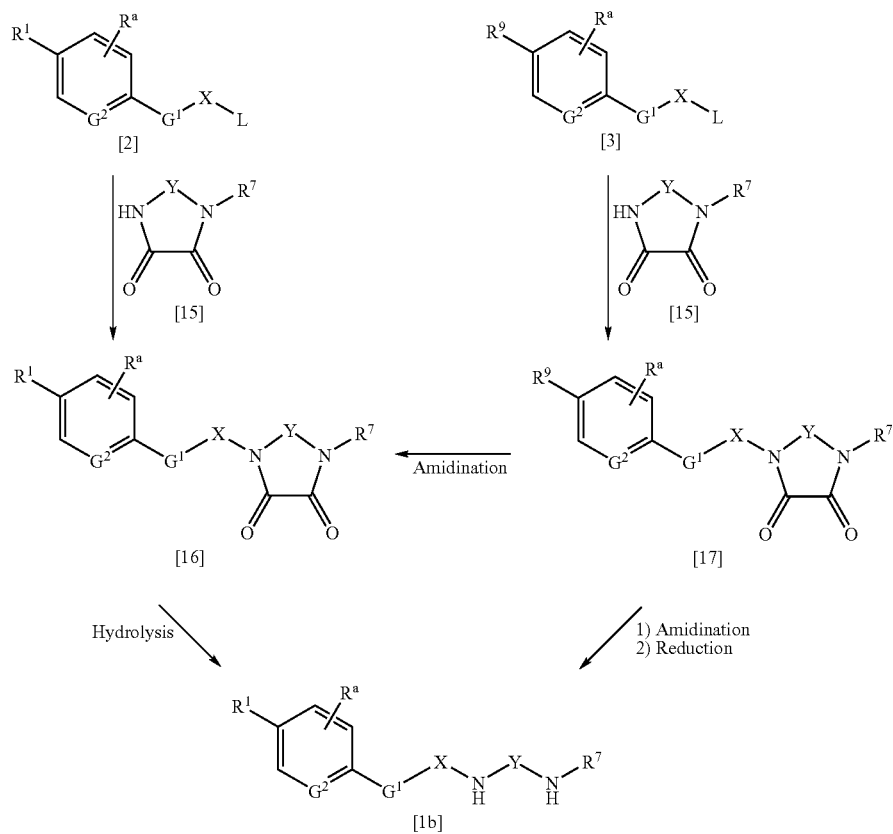

wherein each of X, Y, $R^a$, $R^1$, L, $R^7$, $R^9$, $G^1$, and $G^2$ has the same meaning as described above.

(4-a)

The compound represented by general formula [16] can be produced by reacting the compound represented by general formula [2] with the compound represented by general formula [15] in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloby general formula [2] at a molar ratio of 1:1 or greater, and preferably at a molar ratio of 1:1 to 3:1.

In this reaction, the compound represented by general formula [15] may be used with respect to the compound represented by general formula [2] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

In addition, the compound represented by general formula [16] can also be produced by amidinating the compound represented by general formula [17] according to the scheme 1-b or scheme 2.

(4-b)

The compound represented by general formula [1b] can be produced by hydrolysis of the compound represented by general formula [16] using acid or a base.

A solvent used in this reaction is not particularly limited, as long as it does not affect the reaction. Examples of a solvent may include: alcohols such as methanol, ethanol, isopropanol, or tert-butanol; ethers such as tetrahydrofuran, ethyl ether, dioxane, or anisole; dimethyl sulfoxide; ketones such as acetone or 2-butanone; and sulfoxides such as water. These solvents may be used in combination.

Examples of acid used in this reaction may include mineral acids such as hydrochloric acid, hydrobromic acid, or sulfuric acid. Such acid may be used with respect to the compound represented by general formula [16] at a molar ratio of 1:1 to 1,000:1, and preferably at a molar ratio of 1:1 to 100:1.

Examples of a base used in this reaction may include hydroxides of alkaline metals or alkaline-earth metals, such as sodium hydroxide, potassium hydroxide, or barium hydroxide. Such a base may be used with respect to the compound represented by general formula [16] at a molar ratio of 1:1 to 1,000:1, and preferably at a molar ratio of 1:1 to 10:1.

This reaction may be carried out at 0° C. to 150° C., and preferably at 0° C. to 100° C., for 10 minutes to 24 hours.

(4-c)

The compound represented by general formula [17] can be produced by reacting the compound represented by general formula [3] with the compound represented by general formula [15] in the presence or absence of a base according to the scheme 4-a.

(4-d)

Moreover, the compound represented by general formula [1b] can be produced by amidinating the compound represented by general formula [17] according to the scheme 1-b or scheme 2, and then subjecting the resultant product to a hydrolysis reaction according to the scheme 4-b.

[Scheme 5]

A compound represented by general formula [1b] can be produced, for example, by the following scheme:

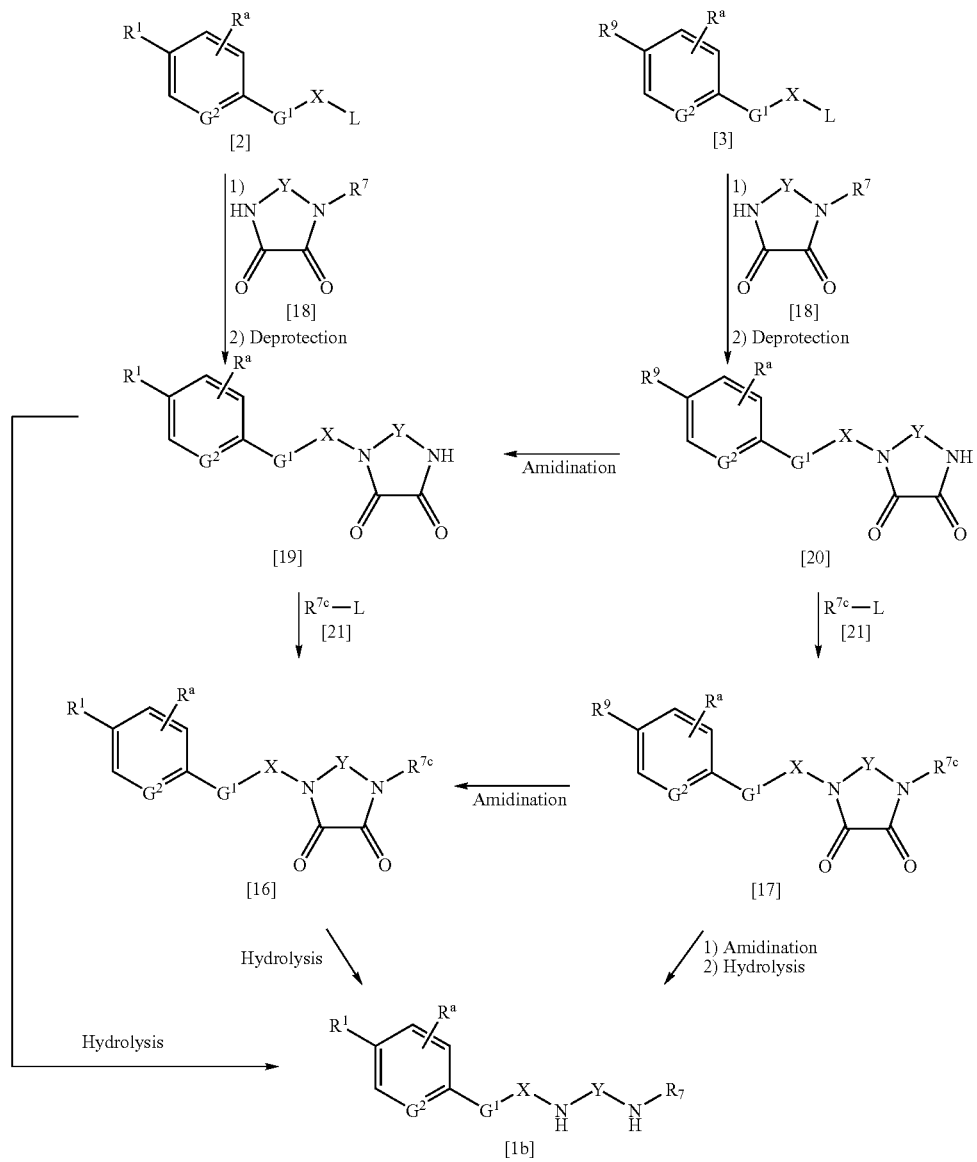

wherein $R^{7c}$ represents any one of the same substituents as $R^7$, except for a hydrogen atom; each of X, Y, $R^a$, $R^1$, $R^7$, L, $R^9$, $G^1$, and $G^2$ has the same meaning as described above; and R represents an amino protecting group.

The compound represented by general formula [18] can be produced according to the method described in Yakugaku Zasshi (Journal of the Pharmaceutical Society of Japan, vol. 99, pp. 929 to 935, 1979) etc., or methods equivalent thereto.

Each of the compounds represented by general formulas [19] and [20] can be produced by reacting each of the compounds represented by general formulas [2] and [3] with the compound represented by general formula [18], and then deprotecting an amino protecting group according to, for example, the method described in International Publication WO96/16947, or methods equivalent thereto.

In addition, the compound represented by general formula [19] can also be produced by amidinating the compound represented by general formula [20] according to the scheme 1-b or scheme 2.

(5-a)

The compound represented by general formula [16] can be produced by reacting the compound represented by general formula [19] with the compound represented by general formula [21] in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; ketones such as acetone or 2-butanone; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compound represented by general formula [19] at a molar ratio of 1:1 or greater, and preferably at a molar ratio of 1:1 to 3:1.

In this reaction, the compound represented by general formula [21] may be used with respect to the compound represented by general formula [19] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

The compound represented by general formula [16] can also be produced by amidinating the compound represented by general formula [17] according to the scheme 1-b or scheme 2.

(5-b)

The compound represented by general formula [1b] can be produced by hydrolysis of the compound represented by general formula [16] or compound represented by general formula [19] according to the scheme 4-b.

Moreover, the compound represented by general formula [1b] can be produced by amidinating the compound represented by general formula [17] according to the scheme 1-b or scheme 2, and then subjecting the resultant product to a hydrolysis reaction according to the scheme 4-b.

(5-c)

The compound represented by general formula [17] can be produced by reacting the compound represented by general formula [20] with the compound represented by general formula [21] in the presence or absence of a base according to the scheme 5-a.

[Scheme 6]

A compound represented by general formula [1c] can be produced, for example, by the following scheme:

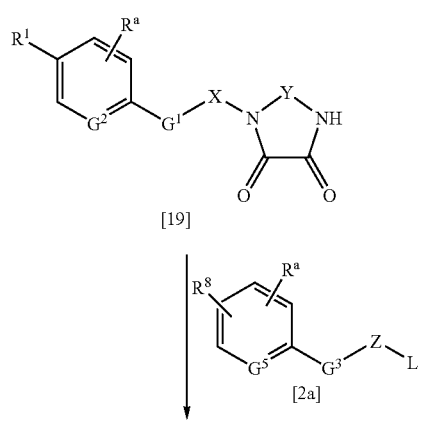

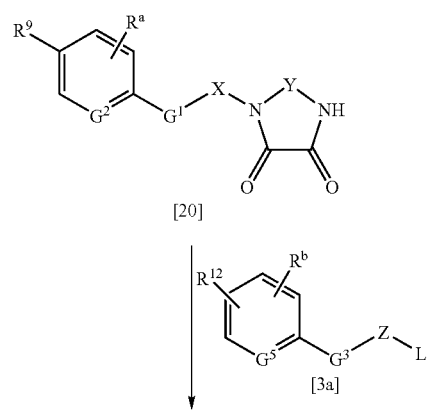

-continued

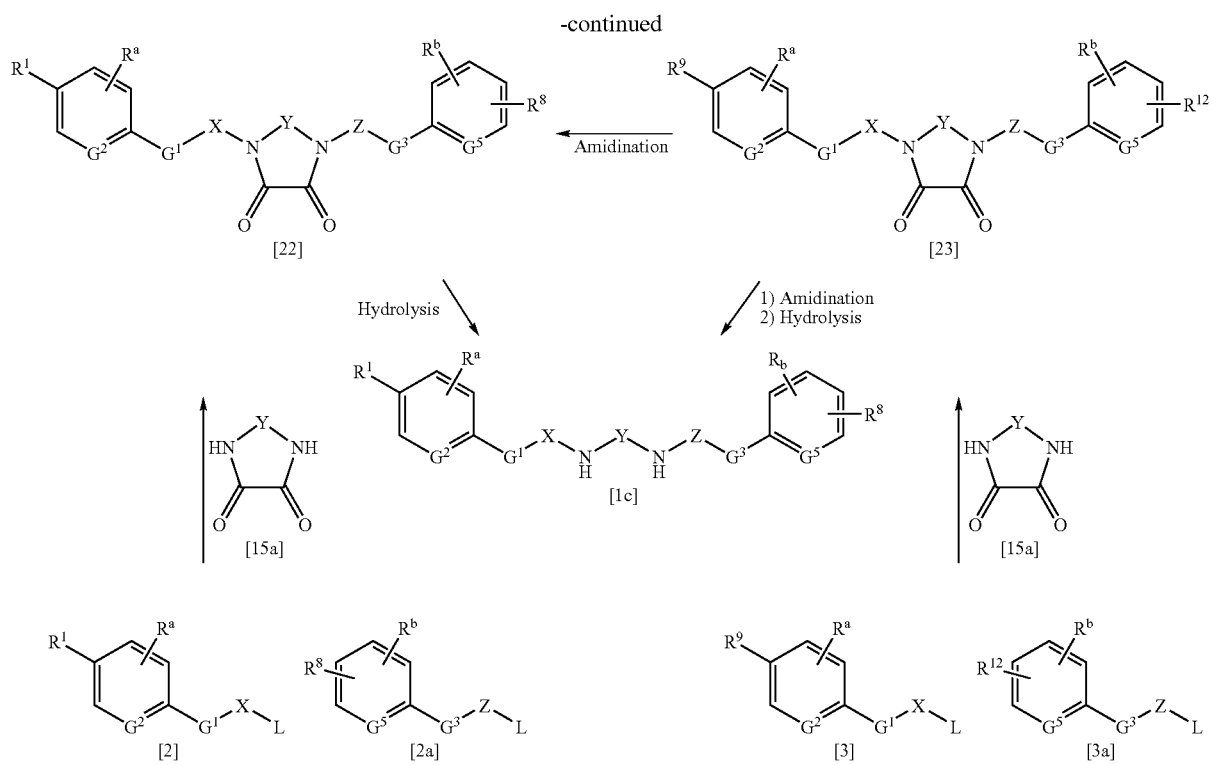

wherein $R^{12}$ represents a cyano group, amide group, or unprotected or protected or unsubstituted or substituted amidino group, which binds with the binding site of $G^3$ at its para or meta position; and each of X, Y, Z, $R^a$, $R^b$, $R^1$, $R^1$, $R^9$, L, $G^1$, $G^2$, $G^3$, and $G^5$ has the same meaning as described above.

(6-a)

The compound represented by general formula [22] can be produced by reacting the compound represented by general formula [19] with the compound represented by general formula [2a], or by reacting the compound represented by general formula [2] with the compound represented by general formula [15a], in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; ketones such as acetone or 2-butanone; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compound represented by general formula [19] at a molar ratio of 1:1 or greater, and preferably at a molar ratio of 1:1 to 3:1.

In this reaction, the compound represented by general formula [2a] may be used with respect to the compound represented by general formula [19] at a molar ratio of 1:1 or greater, and preferably at a molar ratio of 1:1 to 5:1.

Moreover, the compound represented by general formula [15a] may be used with respect to the compound represented by general formula [2] at a molar ratio of 0.5:1 or greater.

This reaction may be carried out at 0° C. to 200° C., and preferably at 0° C. to 150° C., for 1 minute to 24 hours.

(6-b)

The compound represented by general formula [22] can also be produced by amidinating the compound represented by general formula [23] according to the scheme 1-b or scheme 2.

(6-c)

The compound represented by general formula [23] can be produced by reacting the compound represented by general formula [20] with the compound represented by general formula [3a], or by reacting the compound represented by general formula [3] with the compound represented by general formula [15a], in the presence or absence of a base according to the scheme 6-a.

(6-d)

The compound represented by general formula [1c] can be produced by hydrolysis of the compound represented by general formula [22] according to the scheme 4-b.

In addition, the compound represented by general formula [1c] can be produced by amidinating the compound represented by general formula [23] according to the scheme 1-b or scheme 2, and then subjecting the resultant product to a hydrolysis reaction according to the scheme 4-b.

[Scheme 7]

A compound represented by general formula [1d] can be produced, for example, by the following scheme:

wherein each of $R^1$, $R^5$, $R^7$, $R^9$, $R^a$, X, Y, $G^1$, $G^2$, and L has the same meaning as described above; and $R^c$ represents a protected aldehyde group; $R^{15}$ represents a hydrogen atom or hydroxylprotecting group; $Y^1$ represents an unsubstituted or substituted $C_{1-5}$ lower alkylene or $C_{2-5}$ alkenylene group.

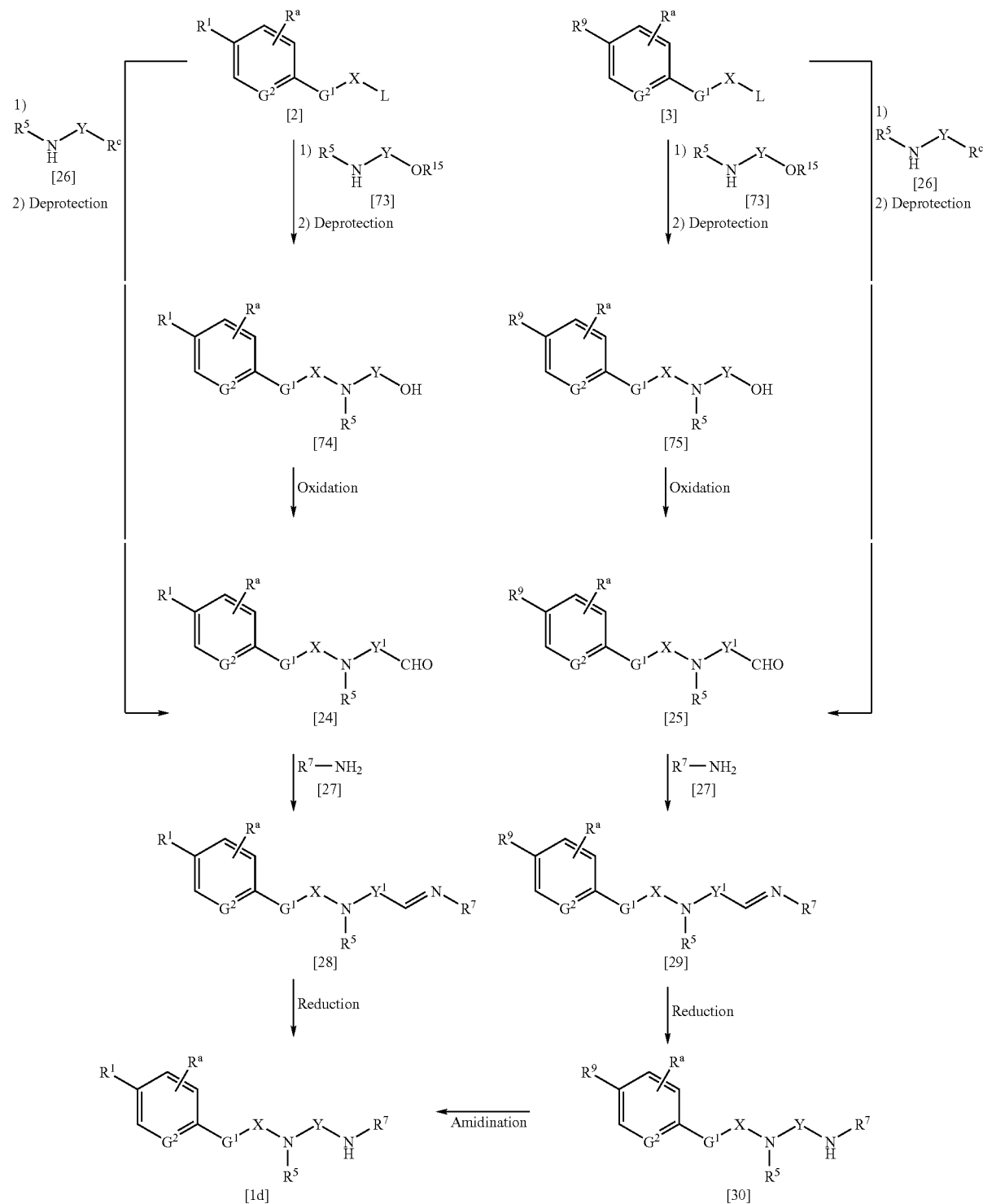

(7-a)

The compound represented by general formula [24] can be produced by reacting the compound represented by general formula [2] with the compound represented by general formula [26] according to the scheme 1-a, and then deprotecting an aldehyde protecting group.

In addition, the compound represented by general formula [24] can also be produced by reacting the compound represented by general formula [2] with the compound represented by general formula [73] according to the scheme 1-a, and eliminating $R^{15}$, as desired, to obtain a compound represented by general formula [74], and then subjecting the compound represented by general formula [74] to an oxidative reaction.

The oxidative reaction of the compound represented by general formula [74] may be carried out according to the method described in, for example, "Yukikagakujikken no Tebiki [3]—Gosei Hanno [I]—" ("Guide for Organic Chemistry Experiments [3], Synthetic Reaction [I]", Kagaku Dojin, pp. 1 to 5.)

A solvent used in this reaction is not particularly limited, as long as it does not affect the reaction. Examples of a solvent may include: amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; sulfoxides such as dimethyl sulfoxide; and ketones such as acetone or 2-butanone. These solvents may be used in combination.

Examples of an oxidizing agent or oxidizing method used in this reaction may include: chromic acids such as the Collins reagent (chromium oxide (IV)-pyridine), pyridinium chlorochromate (PCC), or pyridinium dichromate (PDC); a method of performing the reaction by way of alkoxysulfonium salts (DMSO oxidization); and the Dess-Martin reagent described in the Journal of Organic Chemistry (J. Org. Chem.), vol. 48, pp. 4,155 to 4,156, 1983.

The use amount of an oxidizing agent is different depending on the type of the oxidizing agent. For example, such an oxidizing agent may be used with respect to the compound represented by general formula [74] at a molar ratio of 1:1 or greater. More preferably, where the oxidizing agent is chromic acid, it may be used in an amount much greater than the compound represented by general formula [74], and where the oxidizing agent is one other than chromic acids, it may be used with respect to the above compound at a molar ratio of 1:1 to 5:1.

(7-b)

The compound represented by general formula [28] can be produced by subjecting the compound represented by general formula [24] and the compound represented by general formula [27] to a dehydration reaction in the presence or absence of a dehydrating agent.

A solvent used in this reaction is not particularly limited, as long as it does not affect the reaction. Examples of a solvent may include: alcohols such as methanol, ethanol, n-propanol, isopropanol, n-butanol, isobutanol, tert-butanol, n-hexanol, cyclopentanol, or cyclohexanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitriles such as acetonitrile; and sulfoxides such as dimethyl sulfoxide. These solvents may be used in combination.

Examples of a dehydrating agent that is used in this reaction as desired may include anhydrous magnesium sulfate, sodium sulfate, calcium chloride, Zeolum, and molecular sieves. Such a dehydrating agent may be used with respect to the compound represented by general formula [24] at a weight ratio (W/W) of 1:1 to 50:1, and preferably at a weight ratio (W/W) of 1:1 to 10:1.

In this reaction, the compound represented by general formula [27] may be used with respect to the compound represented by general formula [24] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

(7-c)

The compound represented by general formula [1d] can be produced by subjecting the compound represented by general formula [28] to a reduction reaction.

A solvent used in this reaction is not particularly limited, as long as it does not affect the reaction. Examples of a solvent may include: alcohols such as methanol, ethanol, n-propanol, isopropanol, n-butanol, isobutanol, tert-butanol, n-hexanol, cyclopentanol, or cyclohexanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; nitriles such as acetonitrile; and ethers such as dioxane, tetrahydrofuran, anisole, diethylene glycol diethyl ether, or ethylene glycol monomethyl ether. These solvents may be used in combination.

Examples of a reducing agent used in this reaction may include: metal hydrides such as triacetoxy sodium borohydride, diisobutyl aluminum hydride, a tin hydride compound, borane, dialkylborane, or hydrosilane; boron hydride complex compounds such as sodium borohydride, lithium borohydride, potassium borohydride, or calcium borohydride; and aluminum hydride complex compounds such as lithium aluminum hydride. The use amount of a reducing agent is different depending on the type of the reducing agent. For example, in the case of a boron hydride complex compound, it may be used with respect to the compound represented by general formula [28] at a molar ratio of 0.25:1 or greater, and preferably at a molar ratio of 1:1 to 5:1.

In addition, catalytic hydrogenation using a metal catalyst may be applied as a reduction reaction. Examples of a metal catalyst used therein may include palladium oxide, platinum oxide, and palladium-carbon. A metal catalyst may be used with respect to the compounds represented by general formulas [28] and [29] at a weight ratio (W/W) of 0.001:1 to 1:1, and preferably at a weight ratio (W/W) of 0.01:1 to 0.5:1.

This reaction may be carried out at −50° C. to 120° C., and preferably at 0° C. to 80° C., for 10 minutes to 24 hours.

(7-d)

The compound represented by general formula [1d] can be produced by subjecting the compound represented by general formula [24] and the compound represented by general formula [27] to a reductive amination reaction without isolating the compound represented by general formula [28].

A solvent used in this reaction is not particularly limited, as long as it does not affect the reaction. Examples of a solvent may include: alcohols such as methanol, ethanol, n-propanol, isopropanol, n-butanol, isobutanol, tert-butanol, n-hexanol, cyclopentanol, or cyclohexanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; nitriles such as acetonitrile; and ethers such as dioxane, tetrahydrofuran, anisole, diethylene glycol diethyl ether, or ethylene glycol monomethyl ether. These solvents may be used in combination.

Examples of a reducing agent used in this reaction may include: metal hydrides such as triacetoxy sodium borohydride, diisobutyl aluminum hydride, a tin hydride compound, a borane-tetrahydrofuran complex, diborane, dialkylborane, or hydrosilane; boron hydride complex compounds such as sodium borohydride, lithium borohydride, potassium borohydride, calcium borohydride, or triacetoxy sodium borohydride; and aluminum hydride complex compounds such as lithium aluminum hydride, which are described in the Journal of Medicinal Chemistry (J. Med. Chem.), vol. 43, pp. 27 to 58, 2000. The use amount of a reducing agent is different depending on the type of the reducing agent. For example, in the case of triacetoxy sodium borohydride, it may be used with respect to the compound represented by general formula [24] at a molar ratio of 1:1 or greater, and preferably at a molar ratio of 1:1 to 5:1.

In addition, catalytic hydrogenation using a metal catalyst may be applied as a reduction reaction. Examples of a metal catalyst used herein may include palladium oxide, platinum oxide, and palladium-carbon. A metal catalyst may be used with respect to the compounds represented by general formulas [24] and [25] at a weight ratio (W/W) of 0.001:1 to 1:1, and preferably at a weight ratio (W/W) of 0.01:1 to 0.5:1.

This reaction may be carried out at −50° C. to 120° C., and preferably at 0° C. to 80° C., for 10 minutes to 24 hours.

(7-e)

The compound represented by general formula [25] can be produced by reacting the compound represented by general formula [3] with the compound represented by general formula [26] according to the scheme 1-a, and then deprotecting an aldehyde protecting group.

In addition, the compound represented by general formula [25] can also be produced by reacting the compound represented by general formula [3] with the compound represented by general formula [73] according to the scheme 1-a, and eliminating $R^{15}$, as desired, to obtain a compound represented by general formula [75], and then subjecting the compound represented by general formula [75] to an oxidative reaction according to the scheme 7-a.

The compound represented by general formula [29] can be produced by subjecting the compound represented by general formula [25] and the compound represented by general formula [27] to a dehydration reaction in the presence or absence of a dehydrating agent according to the scheme 7-b.

The compound represented by general formula [30] can be produced by reducing the compound represented by general formula [29] according to the scheme 7-c.

In addition, the compound represented by general formula [30] can also be produced by subjecting the compound represented by general formula [24] and the compound represented by general formula [27] to a reductive amination reaction according to the scheme 7-d.

The compound represented by general formula [1d] can be produced by amidinating the compound represented by general formula [30] according to the scheme 1-b or scheme 2.

[Scheme 8]

A compound represented by general formula [1e] can be produced, for example, by the following scheme:

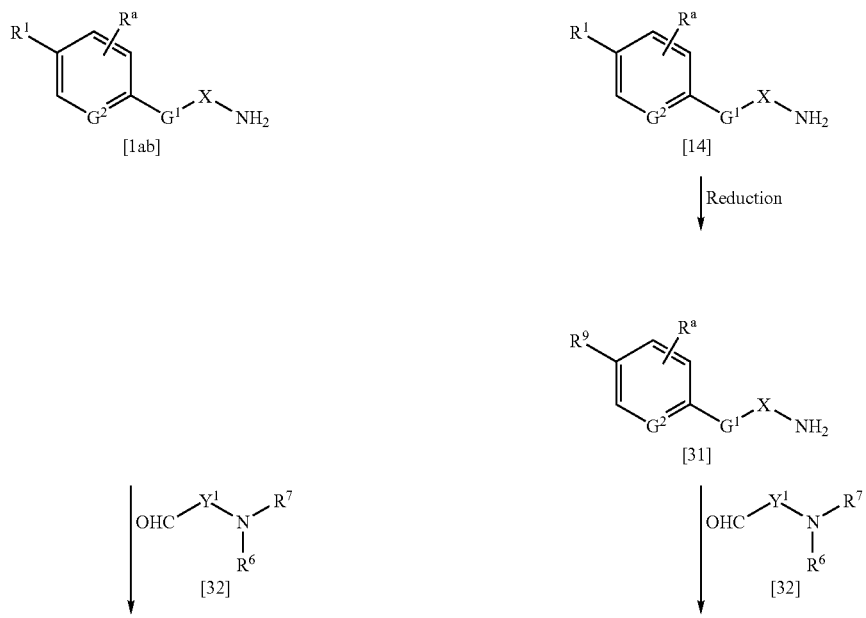

-continued

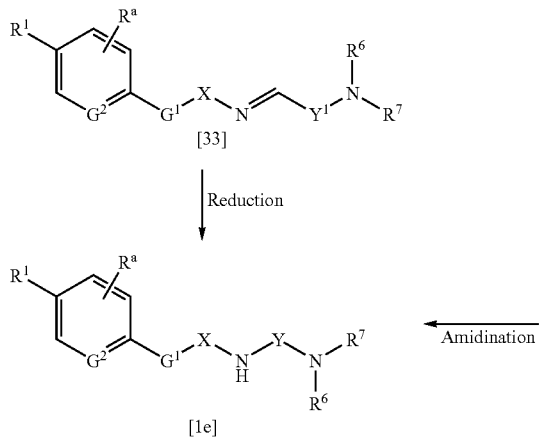

[33]

|Reduction

[1e]

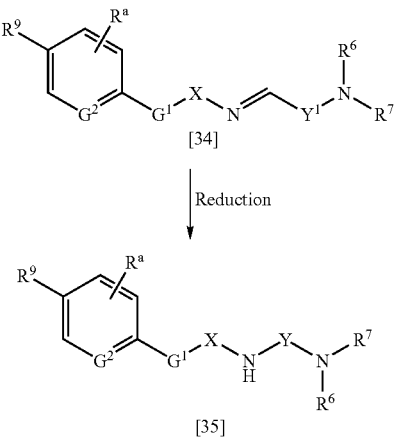

[34]

|Reduction

[35]

← Amidination wherein each of $R^1$, $R^6$, $R^7$, $R^9$, $R^a$, X, Y, $Y^1$, $G^1$, and $G^2$ has the same meaning as described above.

(8-a)

The compound represented by general formula [33] can be produced by subjecting the compound represented by general formula [1ab] and the compound represented by general formula [32] to a dehydration reaction in the presence or absence of a dehydrating agent.

A solvent used in this reaction is not particularly limited, as long as it does not affect the reaction. Examples of a solvent may include: amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; and sulfoxides such as dimethyl sulfoxide. These solvents may be used in combination.

Examples of a dehydrating agent that is used in this reaction as desired may include anhydrous magnesium sulfate, molecular sieves, sodium sulfate, Zeolum, and calcium chloride. Such a dehydrating agent may be used with respect to the compound represented by general formula [1ab] at a weight ratio (W/W) of 1:1 to 50:1, and preferably at a weight ratio (W/W) of 1:1 to 10:1.

In this reaction, the compound represented by general formula [32] may be used with respect to the compound represented by general formula [1ab] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

(8-b)

The compound represented by general formula [1e] can be produced by subjecting the compound represented by general formula [33] to a reduction reaction.

A solvent used in this reaction is not particularly limited, as long as it does not affect the reaction. Examples of a solvent may include: alcohols such as methanol, ethanol, n-propanol, isopropanol, n-butanol, isobutanol, tert-butanol, n-hexanol, cyclopentanol, or cyclohexanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; nitriles such as acetonitrile; and ethers such as dioxane, tetrahydrofuran, anisole, diethylene glycol diethyl ether, or ethylene glycol monomethyl ether. These solvents may be used in combination.

Examples of a reducing agent used in this reaction may include: metal hydrides such as diisobutyl aluminum hydride, a tin hydride compound, borane, dialkylborane, or hydrosilane; boron hydride complex compounds such as sodium borohydride, lithium borohydride, potassium borohydride, or calcium borohydride; and aluminum hydride complex compounds such as lithium aluminum hydride.

The use amount of a reducing agent is different depending on the type of the reducing agent. For example, in the case of a boron hydride complex compound, it may be used with respect to the compound represented by general formula [33] at a molar ratio of 0.25:1 or greater, and preferably at a molar ratio of 1:1 to 5:1.

This reduction reaction may be carried out at −50° C. to 120° C., and preferably at 0° C. to 80° C., for 10 minutes to 24 hours.

In addition, the compound represented by general formula [1e] can also be produced by amidinating the compound represented by general formula [35] according to the scheme 1-b or scheme 2.

(8-c)

The compound represented by general formula [31] can be produced by reducing the compound represented by general formula [14] according to a method similar to the scheme 3-a.

The compound represented by general formula [34] can be produced by subjecting the compound represented by general formula [31] and the compound represented by general formula [32] to a dehydration reaction in the presence or absence of a dehydrating agent according to a method similar to the scheme 7-b.

The compound represented by general formula [35] can be produced by reducing the compound represented by general formula [34] according to the scheme 8-a.

[Scheme 9]

A compound represented by general formula [1ba] can be produced, for example, by the following scheme:

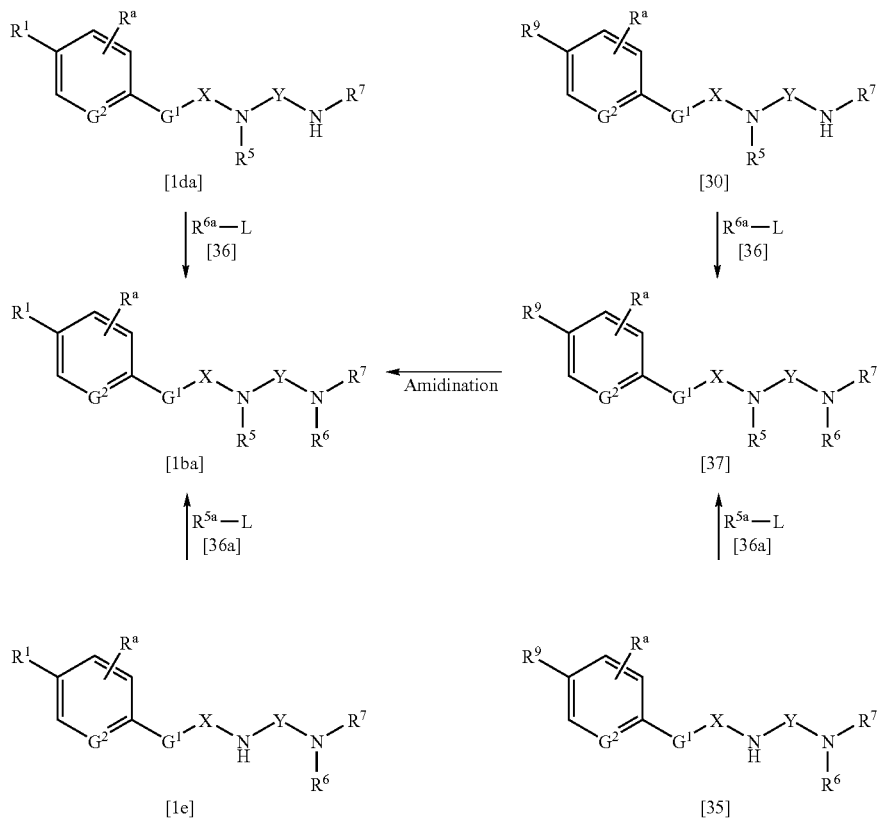

wherein each of $R^1$, $R^5$, $R^6$, $R^7$, $R^9$, $R^a$, X, Y, $G^1$, $G^2$ and L has the same meaning as described above; and each of $R^{5a}$ and $R^{6a}$ identically or differently represents an amino protecting group, or an unsubstituted or substituted alkyl, cycloalkyl or alkenyl group.

(9-a)

The compound represented by general formula [1ba] can be produced by reacting the compound represented by general formula [1da] with the compound represented by general formula [36], or by reacting the compound represented by general formula [1e] with the compound represented by general formula [36a], in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitriles such as acetonitrile; ketones such as acetone or 2-butanone; and sulfoxides such as dimethyl sulfoxide. These solvents may be used in combination.

Examples of a base that is used in this reaction as desired may include sodium methoxide, sodium ethoxide, potassium tert-butoxide, sodium tert-butoxide, sodium hydroxide, potassium hydroxide, sodium bicarbonate, sodium carbonate, potassium carbonate, sodium hydride, potassium hydride, triethylamine, and pyridine. Such a base may be used with respect to the compound represented by general formula [1da] or compound represented by general formula [1e] at a molar ratio of 1:1 or greater, and preferably at a molar ratio of 1:1 to 3:1.

In this reaction, the compound represented by general formula [36] or compound represented by general formula [36a] may be used with respect to the compound represented by general formula [1da] or compound represented by general formula [1e] at a molar ratio of 1:1 or greater, and preferably at a molar ratio of 1:1 to 3:1.

This reaction may be carried out at 0° C. to 200° C., and preferably at 0° C. to 150° C., for 1 minute to 24 hours.

(9-b)

The compound represented by general formula [37] can be produced by reacting the compound represented by general formula [30] with the compound represented by general formula [36], or by reacting the compound represented by general formula [35] with the compound represented by general formula [36a], in the presence or absence of a base according to the scheme 9-a.

In addition, the compound represented by general formula [1ba] can also be produced by amidinating the compound represented by general formula [37] according to the scheme 1-b or scheme 2.

[Scheme 10]

A compound represented by general formula [1f] can be produced, for example, by the following scheme:

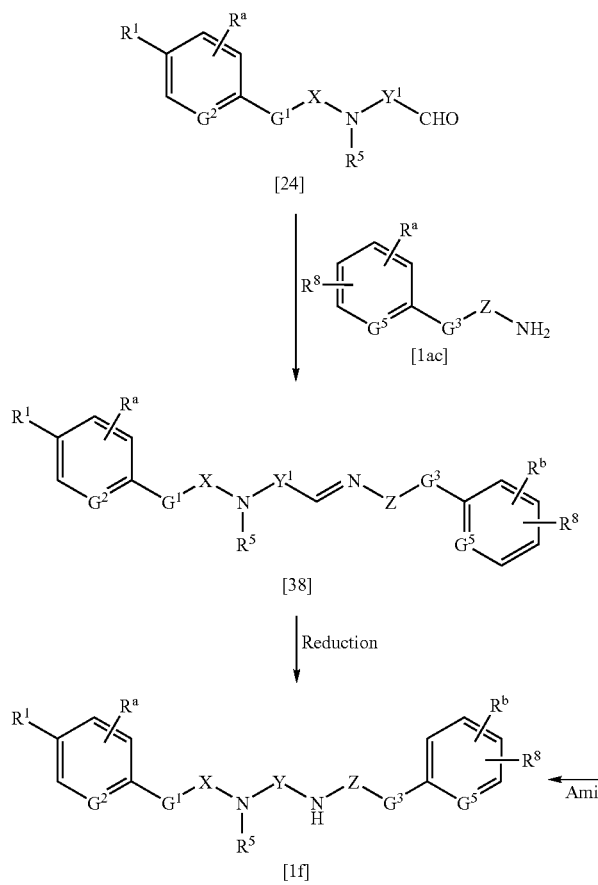

[24] → [1ac] → [38] → Reduction → [1f]

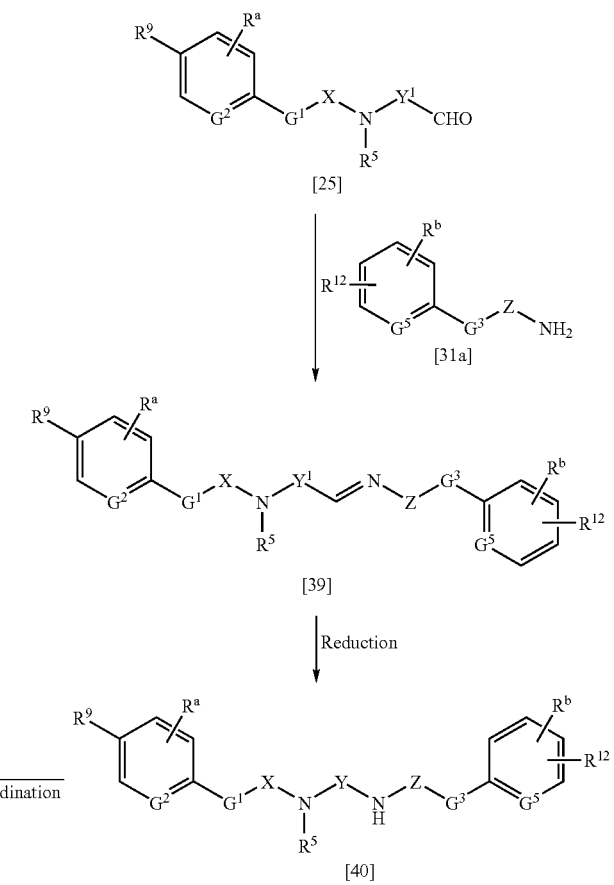

[25] → [31a] → [39] → Reduction → [40] → Amidination → [1f]

wherein each of $R^1$, $R^5$, $R^8$, $R^9$, $R^{12}$, $R^a$, $R^b$, X, Y, $Y^1$, Z, $G^1$, $G^2$, $G^3$, and $G^5$ has the same meaning as described above.

(10-a)

The compound represented by general formula [38] can be produced by subjecting the compound represented by general formula [24] and the compound represented by general formula [1ac] to a dehydration reaction in the presence or absence of a dehydrating agent according to the scheme 7-b.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; and sulfoxides such as dimethyl sulfoxide. These solvents may be used in combination.

Examples of a dehydrating agent that is used in this reaction as desired may include anhydrous magnesium sulfate, molecular sieves, sodium sulfate, Zeolum, and calcium chloride. Such a dehydrating agent may be used with respect to the compound represented by general formula [24] at a weight ratio (W/W) of 1:1 to 50:1, and preferably at a weight ratio (W/W) of 1:1 to 10:1.

In this reaction, the compound represented by general formula [1ac] may be used with respect to the compound represented by general formula [24] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

(10-b)

The compound represented by general formula [1f] can be produced by subjecting the compound represented by general formula [38] to a reduction reaction according to the scheme 7-a.

A solvent used in this reaction is not particularly limited, as long as it does not affect the reaction. Examples of a solvent may include: alcohols such as methanol, ethanol, n-propanol, isopropanol, n-butanol, isobutanol, tert-butanol, n-hexanol, cyclopentanol, or cyclohexanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; nitrites such as acetonitrile; and ethers such as dioxane, tetrahydrofuran, anisole, diethylene glycol diethyl ether, or ethylene glycol monomethyl ether. These solvents may be used in combination.

Examples of a reducing agent used in this reaction may include: metal hydrides such as triacetoxy sodium borohydride, diisobutyl aluminum hydride, a tin hydride compound, a borane-tetrahydrofuran complex compound, diborane, dialkylborane, or hydrosilane; boron hydride complex compounds such as sodium borohydride, lithium borohydride, potassium borohydride, or calcium borohydride; and aluminum hydride complex compounds such as lithium aluminum hydride.

The use amount of a reducing agent is different depending on the type of the reducing agent. For example, in the case of a boron hydride complex compound, it may be used with respect to the compound represented by general formula [38] at a molar ratio of 0.25:1 or greater, and preferably at a molar ratio of 1:1 to 5:1.

This reaction may be carried out generally at −50° C. to 120° C., and preferably at 0° C. to 80° C., for 10 minutes to 24 hours.

In addition, the compound represented by general formula [1f] can also be produced by amidinating the compound represented by general formula [40] according to the scheme 1-b or scheme 2.

(10-c)

The compound represented by general formula [39] can be produced by subjecting the compound represented by general formula [25] and the compound represented by general formula [31a] to a dehydration reaction in the presence or absence of a dehydrating agent according to the scheme 7-b.

The compound represented by general formula [40] can be produced by reducing the compound represented by general formula [39] according to the scheme 7-c.

[Scheme 11]

A compound represented by general formula [1ca] can be produced, for example, by the following scheme:

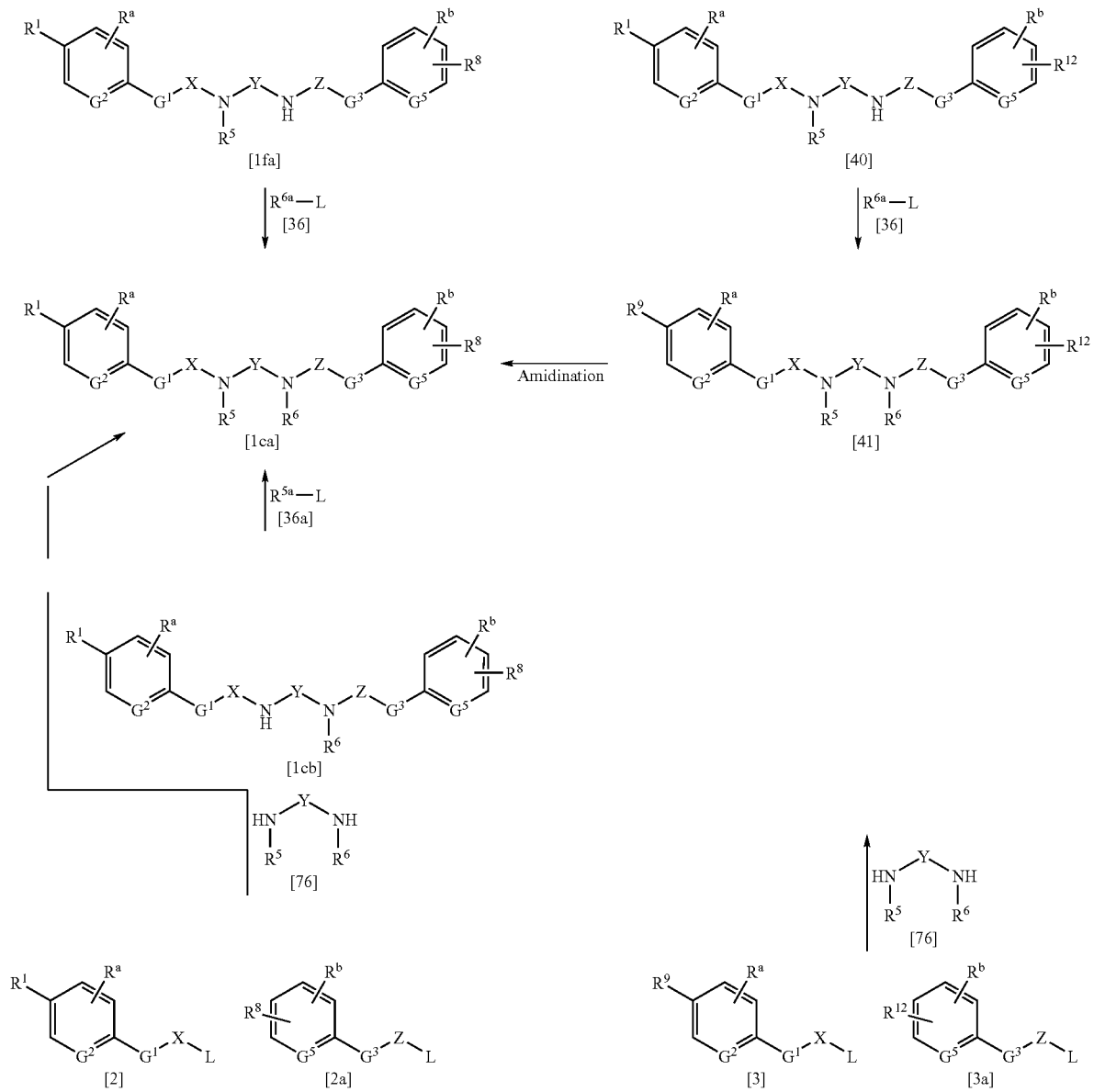

wherein each of $R^1$, $R^5$, $R^{5a}$, $R^6$, $R^{6a}$, $R^8$, $R^9$, $R^{12}$, $R^a$, $R^b$, X Y, Z, $G^1$, $G^2$, $G^3$, $G^5$, and L has the same meaning as described above.

(11-a)

The compound represented by general formula [1ca] can be produced by reacting the compound represented by general formula [1fa] with the compound represented by general formula [36], or by reacting the compound represented by general formula [1cb] with the compound represented by general formula [36a], in the presence or absence of a base.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; ketones such as acetone or 2-butanone; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compounds represented by general formulas [1fa] and [1cb] at a molar ratio of 1:1 or greater, and preferably at a molar ratio of 1:1 to 3:1.

In this reaction, the compounds represented by general formulas [36] and [36a] may be used with respect to the compounds represented by general formulas [1fa] and [1cb] at a molar ratio of 1:1 or greater, and preferably at a molar ratio of 1:1 to 3:1, respectively.

This reaction may be carried out at 0° C. to 200° C., and preferably at 0° C. to 150° C., for 1 minute to 24 hours.

In addition, the compound represented by general formula [1ca] can also be produced by reacting the compound represented by general formula [2] or [2a] with the compound represented by general formula [76] according to the scheme 6-a.

Moreover, the compound represented by general formula [1ca] can also be produced by amidinating the compound represented by general formula [41] according to the scheme 1-b or scheme 2.

(11-b)

The compound represented by general formula [41] can be produced by reacting the compound represented by general formula [40] with the compound represented by general formula [36] according to the scheme 11-a in the presence or absence of a base.

In addition, the compound represented by general formula [41] can also be produced by reacting the compound represented by general formula [3] or [3a] with the compound represented by general formula [76] according to the scheme 6-a.

[Scheme 12]

A compound represented by general formula [1g] can be produced, for example, by the following scheme:

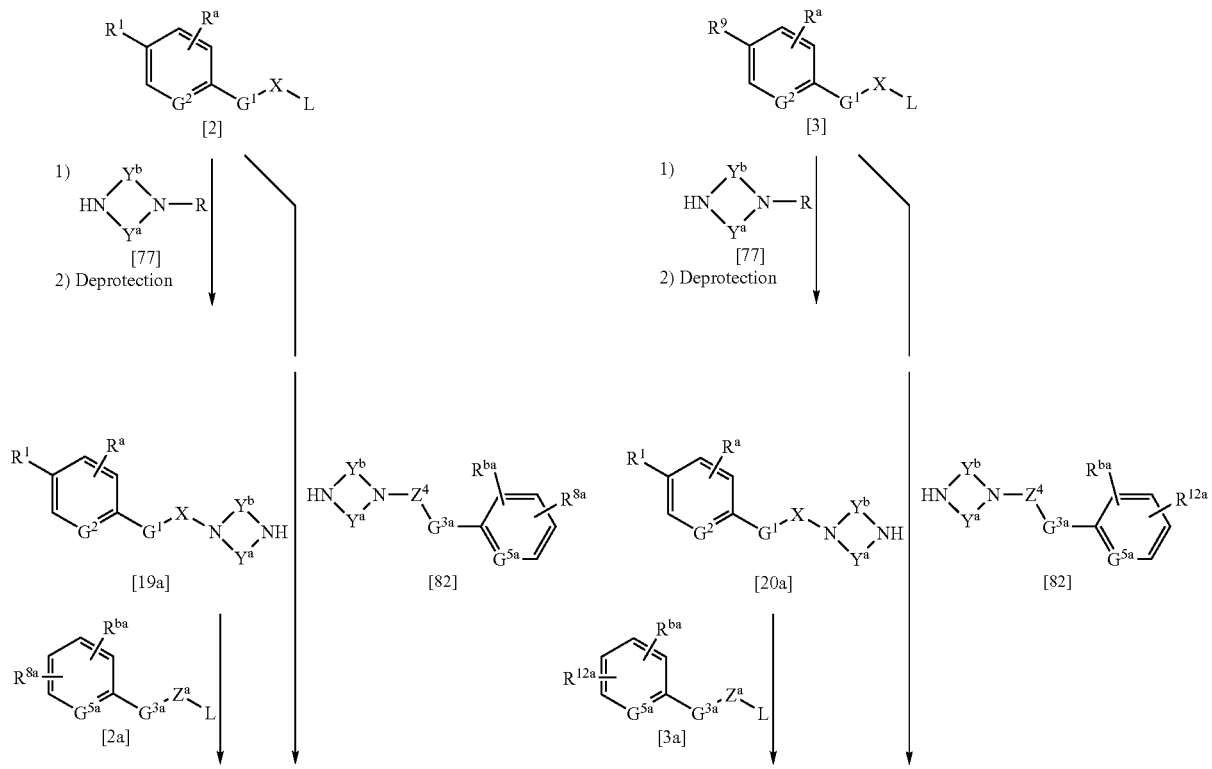

-continued

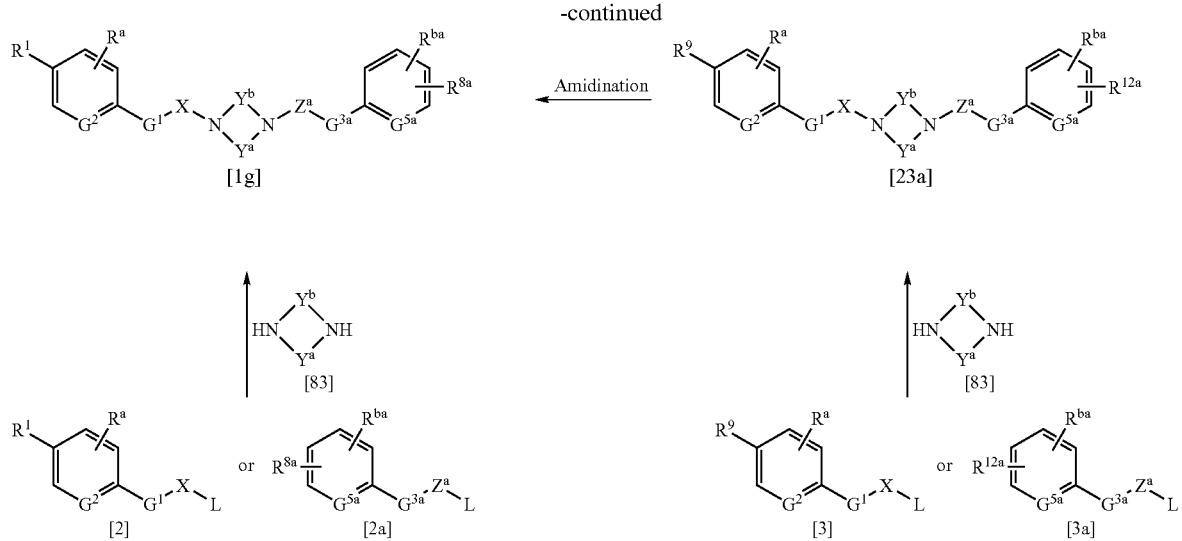

wherein $R^{12a}$ represents a cyano group, amide group, or unprotected or protected or unsubstituted or substituted amidino group; and each of R, $R^1$, $R^{8a}$, $R^9$, $R^a$, $R^{ba}$, X, $Y^b$, $Z^a$, $G^1$, $G^2$, $G^{3a}$, $G^{5a}$, and L has the same meaning as described above.

The compounds represented by general formulas [19a] and [20a] can be produced by reacting the compounds represented by general formulas [2] and [3] with the compound represented by general formula [77], respectively, according to the method described in, for example, International Publication WO96/16947, or method equivalent thereto, and then removing secondary amino protecting groups according to conventional methods.

(12-a)

The compound represented by general formula [19] can be produced by reacting the compound represented by general formula [19a] with the compound represented by general formula [2a], or by reacting the compound represented by general formula [2] with the compound represented by general formula [82], according to the scheme 6-a.

In addition, the compound represented by general formula [1g] can also be produced by reacting the compound represented by general formula [2] or [2a] with the compound represented by general formula [83] according to the scheme 6-a.

(12-b)

The compound represented by general formula [23a] can be produced by reacting the compound represented by general formula [20a] with the compound represented by general formula [3a], or by reacting the compound represented by general formula [3] with the compound represented by general formula [82], according to the scheme 6-a.

In addition, the compound represented by general formula [23a] can also be produced by reacting the compound represented by general formula [3] or [3a] with the compound represented by general formula [83] according to the scheme 6-a.

Further, the compound represented by general formula [1g] can also be produced by amidinating the compound represented by general formula [23a] according to the scheme 1-b or scheme 2.

[Scheme 13]

A compound represented by general formula [1g] can be produced, for example, by the following scheme:

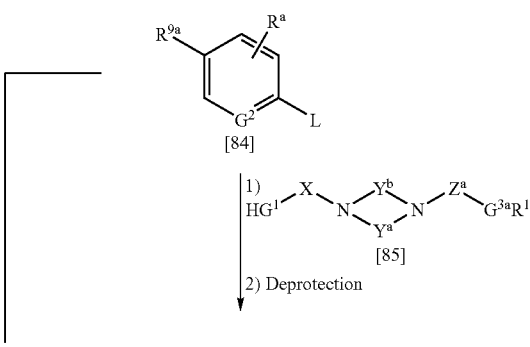

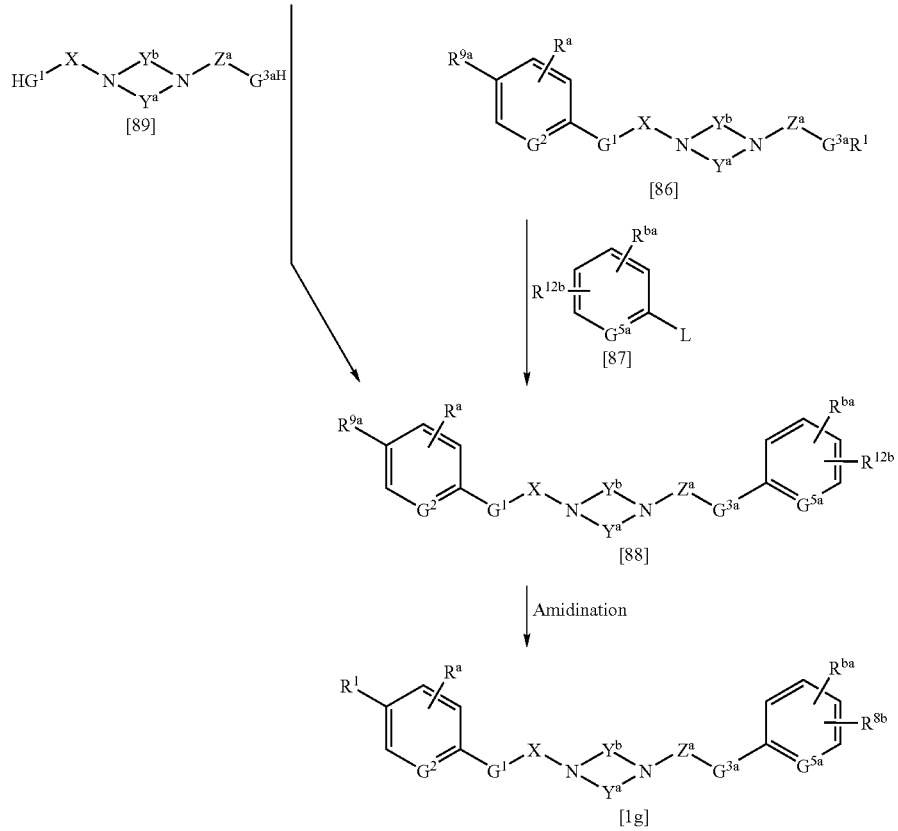

wherein each of $R^1$, $R^{8a}$, $R^a$, $R^{ba}$, X, $Y^a$, $Y^b$, $Z^a$, $G^1$, $G^2$ $G^3a$ $G^{5a}$, and L has the same meaning as described above; and each of $R^{9a}$ and $R^{12b}$ represents a cyano group; and R' represents a protecting group of an amino, hydroxyl or thiol group.

(13-a)

The compound represented by general formula [86] can be produced by reacting the compound represented by general formula [84] with the compound represented by general formula [85] in the presence or absence of a base, and then removing a protecting group.

A solvent used in this reaction is not particularly limited, as long as it does not affect the reaction. Examples of a solvent may include: alcohols such as methanol, ethanol, isopropanol, or tert-butanol; amides such as N,N-dimethylformamide, N,N-dimethylacetamide, or 1-methyl-2-pyrrolidone; halogenated hydrocarbons such as methylene chloride, chloroform, or dichloroethane; aromatic hydrocarbons such as benzene, toluene, or xylene; ethers such as dioxane, tetrahydrofuran, anisole, diethylene glycol diethyl ether, or ethylene glycol monomethyl ether; nitrites such as acetonitrile; ketones such as acetone or 2-butanone; and sulfoxides such as dimethyl sulfoxide. These solvents may be used in combination.

Examples of a base that is used in this reaction as desired may include: metal alkoxides such as sodium methoxide, sodium ethoxide, potassium tert-butoxide, or sodium tert-butoxide; inorganic bases such as sodium hydroxide, potassium hydroxide, sodium bicarbonate, sodium carbonate, potassium carbonate, sodium hydride, or potassium hydride; and organic bases such as triethylamine or pyridine. Such a base may be used with respect to the compound represented by general formula [85] at a molar ratio of 1:1 or greater, and preferably at a molar ratio of 1:1 to 3:1.

In this reaction, the compound represented by general formula [84] may be used with respect to the compound represented by general formula [85] at a molar ratio of 1:1 or greater, and preferably at a molar ratio of 1:1 to 5:1.

This reaction may be carried out at 0° C. to 200° C., and preferably at 0° C. to 150° C., for 1 minute to 24 hours.

Moreover, a protecting group of an amino, hydroxyl or thiol group represented by R' may be removed by known methods.

(13-b)

The compound represented by general formula [88] can be produced by reacting the compound represented by general formula [86] with the compound represented by general formula [87], or by reacting the compound represented by general formula [84] with the compound represented by general formula [89], according to the scheme 13-a.

In this reaction, the compound represented by general formula [84] may be used with respect to the compound represented by general formula [89] at a molar ratio of 2:1 or greater, and preferably at a molar ratio of 2:1 to 5:1.

(13-c)

The compound represented by general formula [1g] can be produced by amidinating the compound represented by general formula [88] according to the scheme 1-b or scheme 2.

[Scheme 14]

A compound represented by general formula [1h] can be produced, for example, by the following scheme:

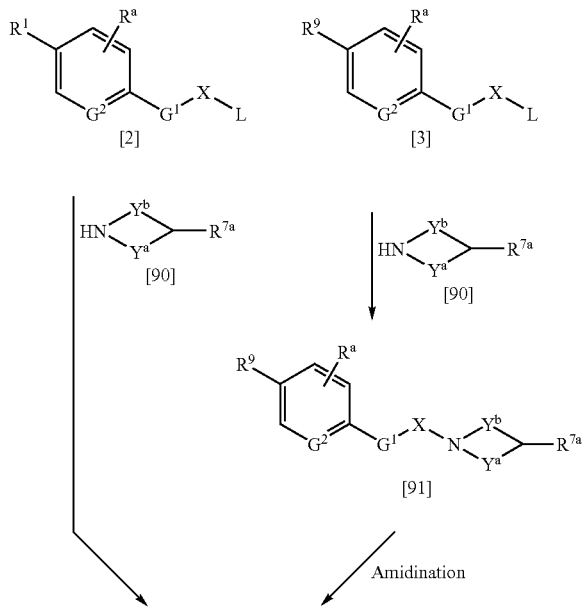

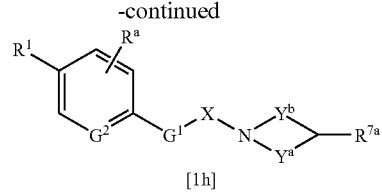

wherein each of $R^1$, $R^{7a}$, $R^9$, $R^a$, X, $Y^a$, $Y^b$, $G^1$, $G^2$, and L has the same meaning as described above.

The compound represented by general formula [1h] can be produced by reacting the compound represented by general formula [2] with the compound represented by general formula [90] according to the scheme 1-a.

In addition, the compound represented by general formula [1h] can also be produced by amidinating the compound represented by general formula [91] according to the scheme 1-b or scheme 2.

The compound represented by general formula [91] can be produced by reacting the compound represented by general formula [3] with the compound represented by general formula [90] according to the scheme 1-a.

[Scheme 15]

A compound represented by general formula [1i] can be produced, for example, by the following scheme:

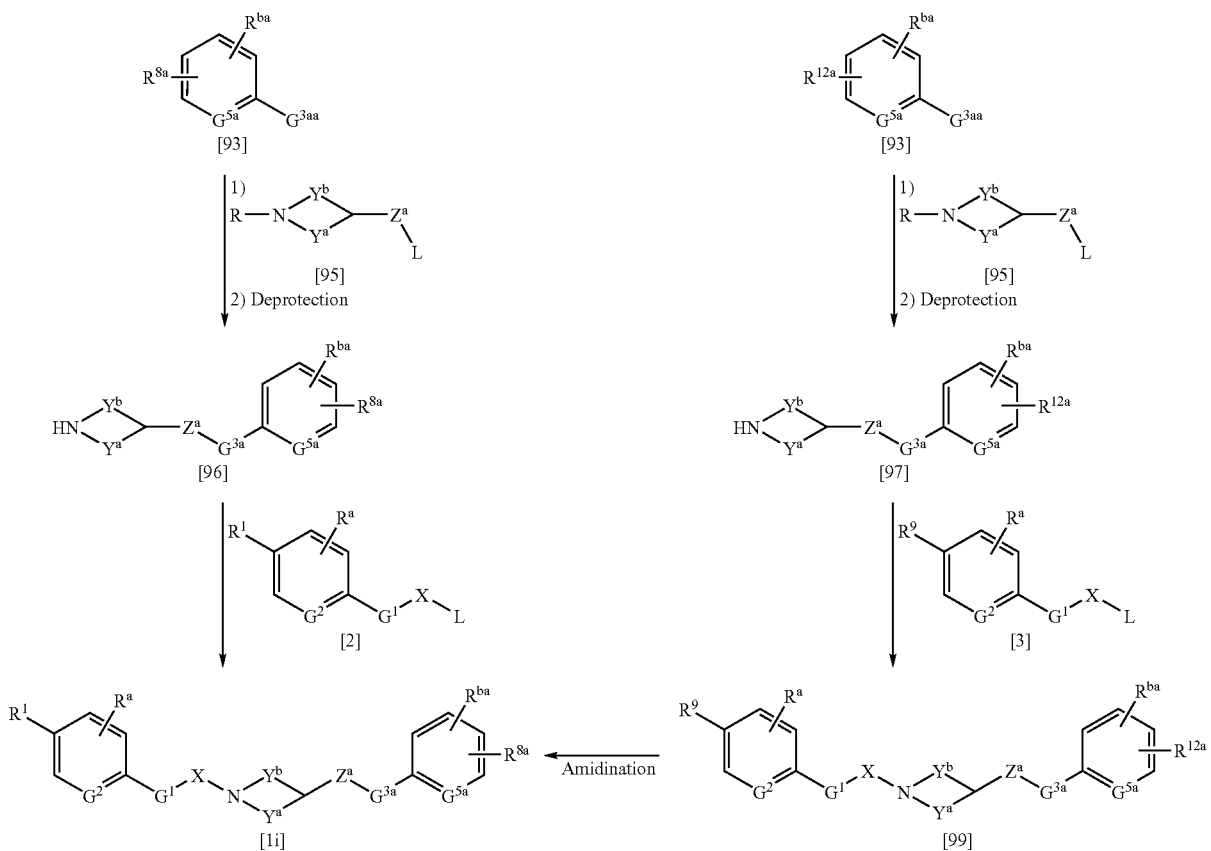

wherein $G^{3aa}$ represents a hydroxyl group, amino group, or thiol group; and each of R, $R^1$, $R^{8a}$, $R^9$, $R^{12a}$, $R^a$, $R^{ba}$, X, $Y^a$, $Y^b$, $Z^a$, $G^1$, $G^2$, $G^{3a}$, $G^{5a}$, and L has the same meaning as described above.

(15-a)

The compound represented by general formula [96] can be produced by reacting the compound represented by general formula [93] with the compound represented by general formula [95] according to the scheme 1-1, and then removing a secondary amine protecting group according to known methods.

Examples of the compound represented by general formula [95] may include: 1-tert-butoxycarbonyl-4-(iodomethyl)piperidine, 1-tert-butoxycarbonyl-4-(iodoethyl)piperidine, and 1-benzyl-4-(2-chloroethyl)piperidine, which are described in the Journal of Medicinal Chemistry (J. Med. Chem.), vol. 44, pp. 2,707 to 2,717, 2001; 4-[1-(tert-butoxycarbonyl)piperidin-4-yl]butylbromide and 3-[1-(tert-butoxycarbonyl)piperidin-4-yl]propylbromide, which are described in the same above publication, vol. 37, pp. 2,537 to 2,551, 1994; 1-(tert-butoxycarbonyl)-3-(methanesulfonyloxymethyl) pyrrolidine and 1-(tert-butoxycarbonyl)-3-(methanesulfonyloxy) pyrrolidine, which are described in the same above publication, vol. 42, pp. 677 to 690, 1999; and 1-tert-butoxycarbonyl-4-(hydroxymethyl)piperidine mesylate described in U.S. Pat. No. 9,311,623.

(15-b)

The compound represented by general formula [97] can be produced by reacting the compound represented by general formula [94] with the compound represented by general formula [95] according to the scheme 1-1, and then removing a secondary amine protecting group.

The compound represented by general formula [99] can be produced by reacting the compound represented by general formula [97] with the compound represented by general formula [3] according to the scheme 1-a.

(15-c)

The compound represented by general formula [1i] can be produced by reacting the compound represented by general formula [96] with the compound represented by general formula [2] according to the scheme 1-a.

In addition, the compound represented by general formula [1i] can also be produced by amidinating the compound represented by general formula [99] according to the scheme 1-b or scheme 2.

[Scheme 16]

A compound represented by general formula [1j] can be produced, for example, by the following scheme:

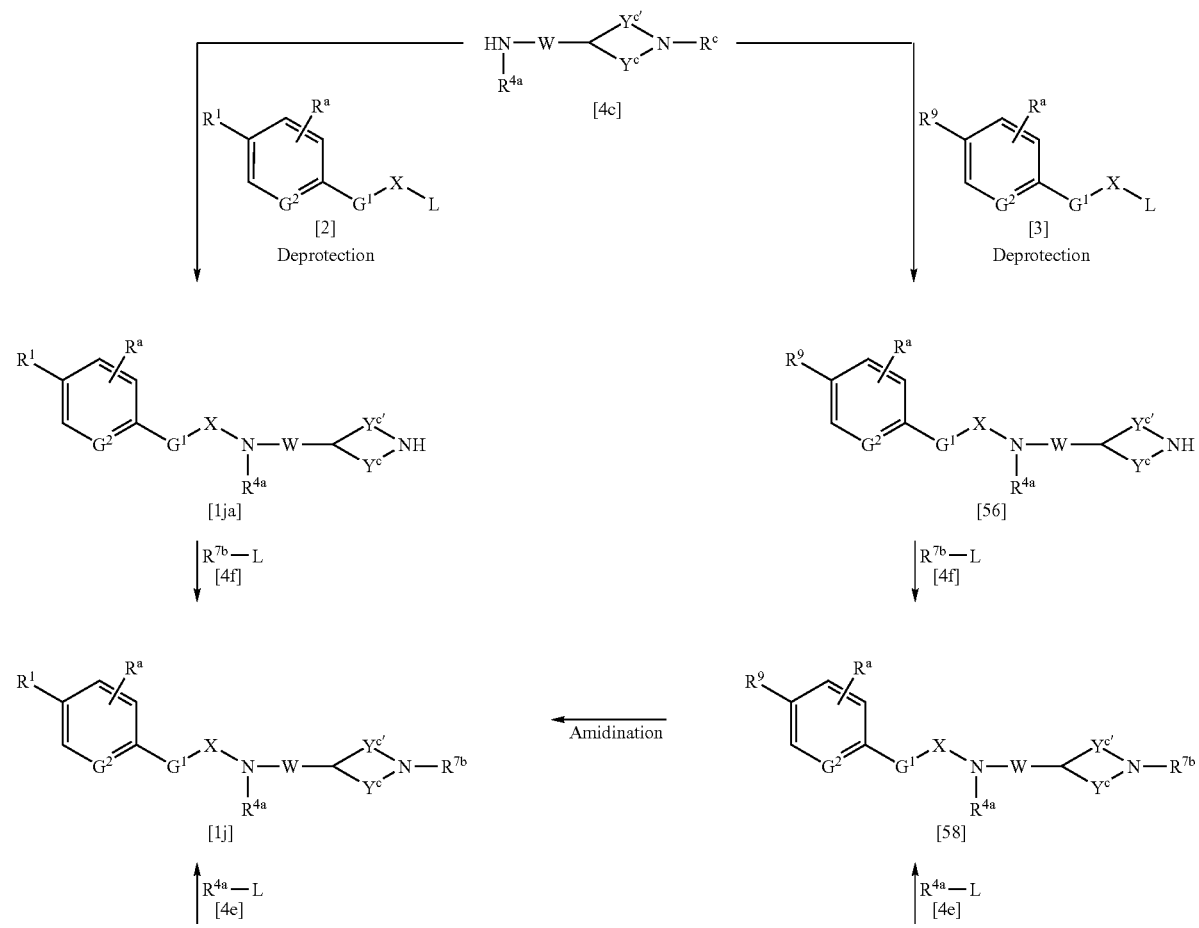

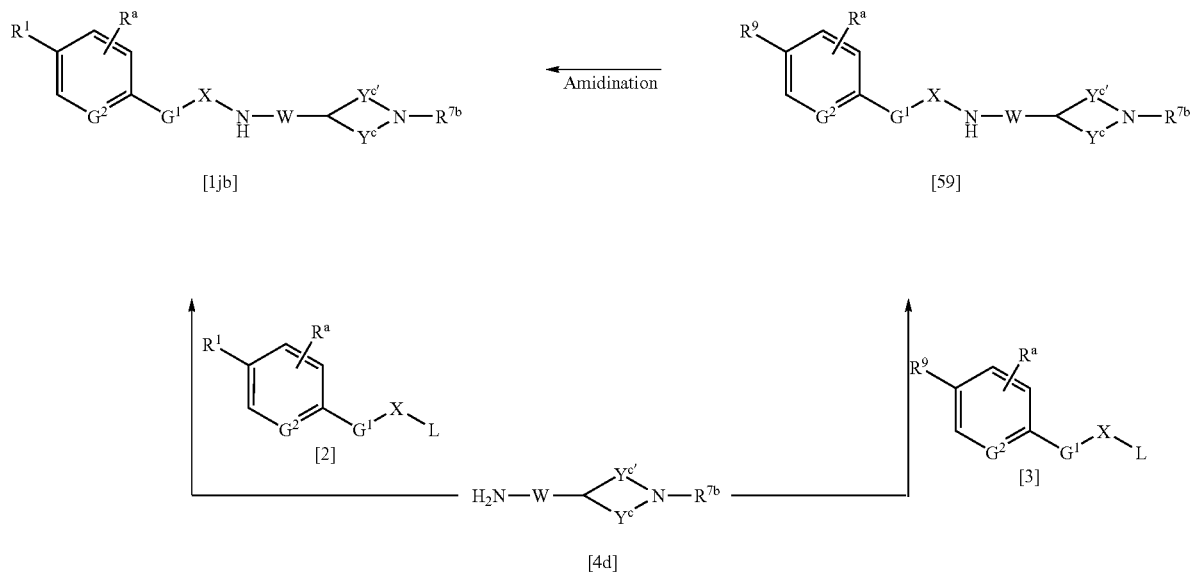

wherein each of $R^a$, $R^1$, $R^{7b}$, $R^9$, X, $G^1$, $G^2$, $Y^c$, $Y^{c'}$, L, and W has the same meaning as described above; $R^c$ represents an amino protecting group; and $R^{4a}$ represents an amino protecting group that is different from $R^c$, or an unsubstituted or substituted alkyl, cycloalkyl or alkenyl group.

(16-a)

The compound represented by general formula [1ja] can be produced by reacting the compound represented by general formula [2] with the compound represented by general formula [4c] in the presence or absence of a base, and then subjecting the reaction product to a deprotection reaction for an amino protecting group.

The compound represented by general formula [1jb] can be produced by reacting the compound represented by general formula [2] with the compound represented by general formula [4d] in the presence or absence of a base.

These reactions may be carried out according to the scheme 1-a.

Examples of the compound represented by general formula [4c] may include: 4-amino-1-benzyl piperidine, 3-amino-1-benzylpyrrolidine, 2-(aminomethyl)-1-(tert-butoxycarbonyl)pyrrolidine, and 3-amino-1-benzyl piperidine [the Journal of Medicinal Chemistry (J. Med. Chem.), vol. 23, pp. 848 to 851, 1980]; 4-(aminomethyl)-1-benzylpiperidine [the same above publication, vol. 37, pp. 2,721 to 2,734, 1994]; 4-(2-aminoethyl)-1-benzylpiperidine, and 2-(aminomethyl)-1-benzylpiperidine [the same above publication, vol. 33, pp. 1,880 to 1,887, 1990]; 3-(aminomethyl)-1-(tert-butoxycarbonyl)pyrrolidine [the same above publication, vol. 42, pp. 677 to 690, 1999]; 3-amino-1-benzylhomopiperidine [the same above publication, vol. 39, pp. 4,704 to 4,716, 1996]; and 4-amino-1-benzylhomopiperidine [the same above publication, vol. 44, pp. 1,380 to 1,395, 2001].

(16-b)

The compound represented by general formula [1j] can be produced by reacting the compounds represented by general formulas [1ja] and [1jb] with the compounds represented by general formulas [4f] and [4e], respectively, in the presence or absence of a base.

These reactions may be carried out according to the scheme 1-a.

(16-c)

The compound represented by general formula [58] can be produced by reacting the compounds represented by general formulas [56] and [59] with the compounds represented by general formulas [4f] and [4e], respectively, in the presence or absence of a base. The compounds represented by general formulas [56] and [59] can be produced by reacting the compound represented by general formula [3] with the compounds represented by general formulas [4c] and [4d], respectively.

These reactions may be carried out according to the scheme 1-a.

(16-d)

The compounds represented by general formulas [1j] and [1jb] can be produced by amidinating the compounds represented by general formulas [58] and [59], respectively.

Amidination may be carried out according to the scheme 1-b or scheme 2.

[Scheme 17]

A compound represented by general formula [1k] can be produced, for example, by the following scheme:

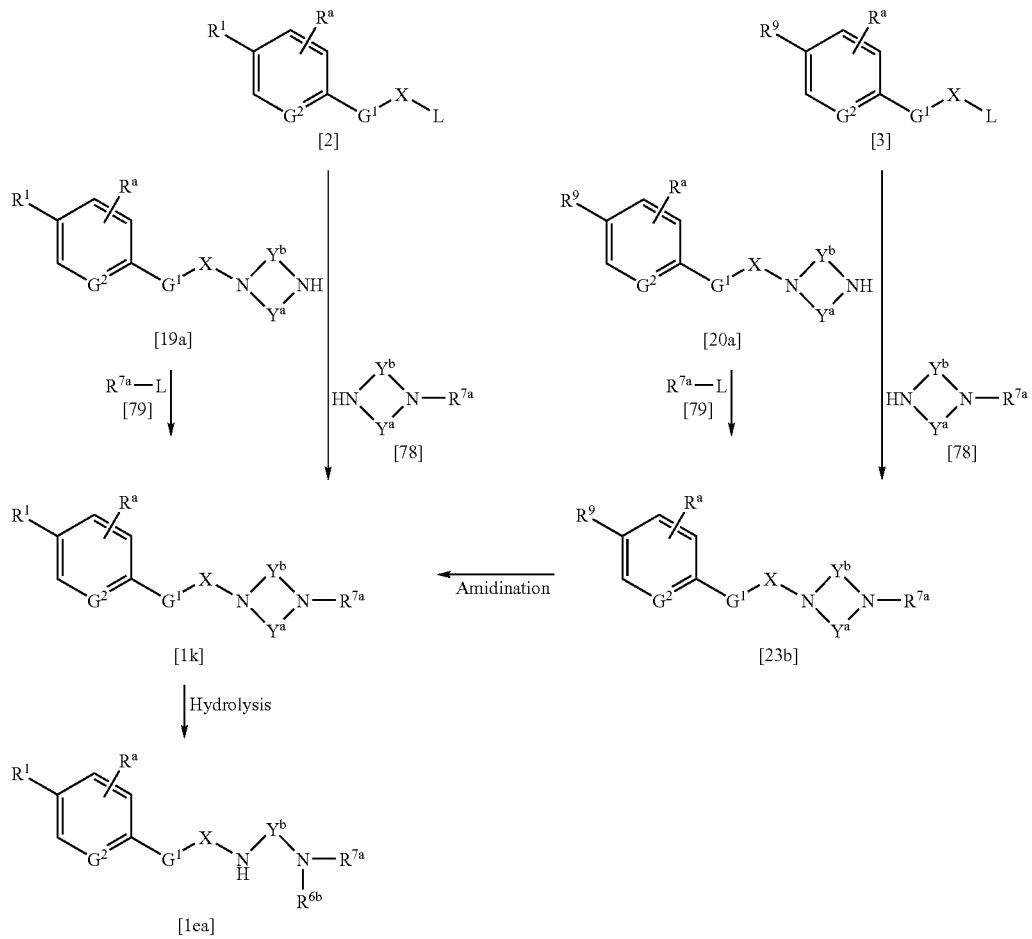

wherein $R^{6b}$ represents an unsubstituted or substituted alkyl group; and each of $R^1$, $R^{7a}$, $R^9$, $R^a$, X, $Y^a$, $Y^b$, $G^1$, $G^2$, and L has the same meaning as described above.

(17-a)

The compound represented by general formula [1k] can be produced by reacting the compound represented by general formula [19a] with the compound represented by general formula [79], or reacting the compound represented by general formula [2] with the compound represented by general formula [78], according to the scheme 6-a.

(17-b)

The compound represented by general formula [23b] can be produced by reacting the compound represented by general formula [20a] with the compound represented by general formula [79], or reacting the compound represented by general formula [3] with the compound represented by general formula [78], according to the scheme 6-a.

The compound represented by general formula [1k] can be produced by amidinating the compound represented by general formula [23b] according to the scheme 1-b or scheme 2.

(17-c)

The compound represented by general formula [1ea] can be produced by hydrolysis of the compound represented by general formula [1k] according to the scheme 4-a.

Salts of the compounds described in the above schemes 1 to 17 can also be used. Examples of such salts are the same as those described in the compound represented by general formula [1].

Intermediates of the products obtained by the above described schemes 1 to 17 can also be used in the subsequent reactions without being isolated.

Among the compounds obtained by the above described schemes 1 to 17, with regard to those having a functional group such as an amino group, cyclic amino group, hydroxyl group, aldehyde group, or carboxyl group, their functional groups may previously be protected with common protecting groups, as necessary, and these protecting groups may be removed by known methods after completion of the reaction.

The thus obtained compound represented by general formula [1] or a salt thereof, is subject to known reactions such as condensation, addition, oxidization, reduction, rearrangement, substitution, halogenation, dehydration, or hydrolysis, or these reactions are appropriately applied in combination, so that the above compound or a salt thereof can be induced to another compound represented by general formula [1] or a salt thereof.

Moreover, in a case where an isomer (e.g., optical isomer, geometric isomer, tautomer, etc.) exists in the compounds obtained by the above schemes, these isomers can also be used. Furthermore, a solvate, a hydrate, and various forms of crystals can also be used.

When the compound of the present invention is used as a pharmaceutical, generally, pharmaceutical aids that are used in pharmaceutical preparation, such as an excipient, carrier, or diluent may be appropriately mixed with the compound. According to conventional methods, the thus produced pharmaceutical can be administered orally or parenterally in the form of a tablet, capsule, powder, syrup, granule, pill, suspension, emulsion, liquid, powdered preparation, suppository, eye drop, nose drop, ear drop, plaster, ointment, or injection. Moreover, the administration method, the dosage, and the number of administration can be selected, as appropriate, depending on the age, body weight, and symptom of patients. Generally, for an adult, an amount of 0.01 to 1,000 mg/kg may be administered orally or parenterally (for example, an injection, an drop, administration into a rectum site, etc.) per day, once or dividedly into several times.

Next, pharmacological actions of representative compounds of the present invention will be explained below.

TEST EXAMPLE 1

Antifungal Action

50% growth inhibitory concentration ($IC_{50}$) was measured according to the microbroth dilution method, using, as a reference, the antifungal agent sensitivity test method proposed by the subcommittee for the antifungal agent sensitivity test, the Japanese Society for Medical Mycology (Japanese Journal of Medical Mycology, vol. 36, No. 1, pp. 62 to 64, 1995). Synthetic amino acid medium, fungal (SAAMF, manufactured by Nippon Bio-Supp. Center) was used as a medium for measurement of sensitivity. *Candida albicans* TIMM 1623 was cultured at 30° C. overnight on a Sabouraud agar plate medium (Eiken Chemical Co., Ltd.), and the obtained culture was suspended in a sterilized physiological saline solution. Thereafter, the suspension was diluted with a measurement medium such that the number of cells became $1 \times 10^4$ cells/ml, thereby producing an inoculum organism solution. 175 µl of a medium, 5 µl of a test agent (an agent diluted solvent in a growth control well), and 20 µl of the inoculum organism solution were added to a 96-well microplate (flat bottom, manufactured by Sumitomo Bakelite Co., Ltd.), and the mixture was stirred with a mixer. Thereafter, using a well Reader SME3400 (Scinics Co., Ltd.), an initial turbidity at a wavelength of 630 nm was measured. The above mixture was cultured at 35° C., and 36 hours later, a final turbidity was measure in the same manner. For an agent-diluted line, values were obtained by subtracting the initial turbidities from the final turbidities. For a growth control line also, values were obtained by subtracting the initial turbidities from the final turbidities. $IC_{50}$ was defined as the lowest agent concentration among the test agent concentrations having a turbidity equal to or lower than the 50% value ($IC_{50}$ calculated value) of a value obtained by subtracting the initial turbidity of a growth control from the final turbidity thereof. The results regarding the $IC_{50}$ value to each cell strain are shown in Table 14.

TABLE 14

| Example No. | $IC_{50}$ (µg/mL) |
| --- | --- |
| 2 | 2 |
| 3-2 | 0.5 |
| 5 | 0.25 |
| 7 | 0.5 |
| 9-2 | 0.5 |
| 10 | 1 |
| 19 | 0.125 |
| 20 | 0.125 |
| 21 | 0.25 |
| 22 | 2 |
| 23 | 2 |
| 24 | 0.0078 |
| 25 | 0.0156 |
| 26 | 0.0625 |
| 27 | 0.0313 |
| 32 | 0.0313 |
| 40-2 | 0.0039 |
| 42 | 0.0156 |
| 43 | 0.0313 |
| 55 | 0.0156 |
| 56 | 0.0039 |
| 57 | 0.0313 |
| 58 | 0.0313 |
| 74 | 0.125 |

TEST EXAMPLE 2

Therapeutic Effect of *Candida albicans* on Mouse Systemic Infection

*Candida albicans* TIMM 1623 was cultured at 30° C. overnight on a Sabouraud agar plate medium (Eiken Chemical Co., Ltd.), and the obtained culture was suspened in a sterilized physiological saline solution. Thus, a fungal solution for infection, having a concentration of $1 \times 10^7$ cells/ml, was prepared. This fungal solution was inoculated in a concentration of 0.2 ml ($2 \times 10^6$ CFU/mouse) into the tail vein of each of five ICR male mice (4-week-old, body weight of 20±1 g). 2 hours later, 0.2 ml of a solution, which had been prepared by dissolving a test compound into a sterilized physiological saline solution and setting the concentration at 0.01 mg/ml, was administered once into the dorsal subcutis of each mouse. To mice of a control group, an equal amount of a sterilized physiological saline solution was administered.

Viability of the mice was observed until the $14^{th}$ day after the infection, and the cumulative survival rate (T/C) of the treatment group to the control group was calculated, and the obtained value was used as an index of the life-prolonging effect.

As a result, it was found that, in the case of the compound in Example 24, T/C was 180 with administration of 0.1 mg/kg.

TEST EXAMPLE 3

Therapeutic Effect of *Candida albicans* on Mouse Systemic Infection

*Candida albicans* TIMM 1623 was cultured at 30° C. overnight on a Sabouraud agar plate medium (Eiken Chemi cal Co., Ltd.), and the cultured fumgus was suspended in a sterilized physiological saline solution. Thus, a fungal solution for infection, having a concentration of approximately $10^7$ cells/ml, was prepared. 0.2 ml of this fungal solution was inoculated into the tail vein of each of five ICR male mice (4-week-old, body weight of 20±1 g). 2 hours after the infection, 0.2 ml of a solution, which had been prepared by dissolving a test compound into a sterilized physiological saline solution and adjusting the concentration at 0.01 mg/ml, was administered once into the dorsal subcutis of each mouse. From the following day, the same solution was administered thereto once a day for 6 days. Thus, the above solution was administered into the dorsal subcutis of the mice 7 times in total. To mice of a control group, an equal amount of a sterilized physiological saline solution was administered. Viability of the mice was observed until the $28^{th}$ day after the infection.

As a result, it was found that the mice of the control group all died by the $28^{th}$ day after the infection, but that the mice of the compound administration groups in Example 24, Example 40-2, and Example 56 survived at a ratio of 3/5, 4/5, and 4/5, respectively.

EXAMPLES

The present invention will be described below in the following reference examples and examples. However, these examples are not intended to limit the scope of the present invention.

It is to be noted that mixing ratios of eluents all represented volume ratios, and that B.W. silica gel BW-127ZH (manufactured by Fuji Silysia Chemical Ltd.) was used as a carrier in column chromatography, unless otherwise specified.

The symbols in each example represent the following meanings:
$d_6$-DMSO: deuterated dimethyl sulfoxide
Me: methyl
Et: ethyl
Bn: benzyl
Ac: acetyl
Cbz: benzyloxycarbonyl
Boc: tert-butoxycarbonyl Reference Example 1

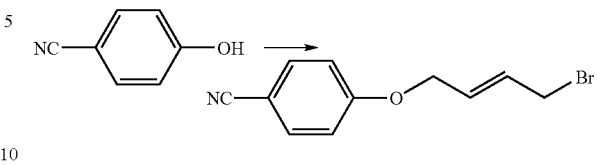

2.78 g of 4-cyanophenol was dissolved in 40 ml of 2-butanone, and then, 3.23 g of potassium carbonate and 5.00 g of 1,4-dibromo-2-butene were added thereto at room temperature, followed by stirring at 70° C. for 4 hours. Insoluble products were removed by filtration with Celite, and thereafter, the solvent was removed under reduced pressure. The obtained residue was then purified by silica gel column chromatography [eluent; n-hexane:ethyl acetate=5:1] to obtain 2.49 g of a colorless oil product, 4-{[(E)-4-bromo-2-butenyl]oxy}benzonitrile.

$^1$H-NMR (CDCl$_3$) δ: 3.99 (2H, dd, J=7.3, 0.7 Hz), 4.61 (2H, dd, J=5.1, 0.7 Hz), 5.92-6.02 (1H, m), 6.08 (1H, dtt, J=15.4, 7.3, 0.7 Hz), 6.92-6.98 (2H, m), 7.56-7.62 (2H, m)

Reference Example 2

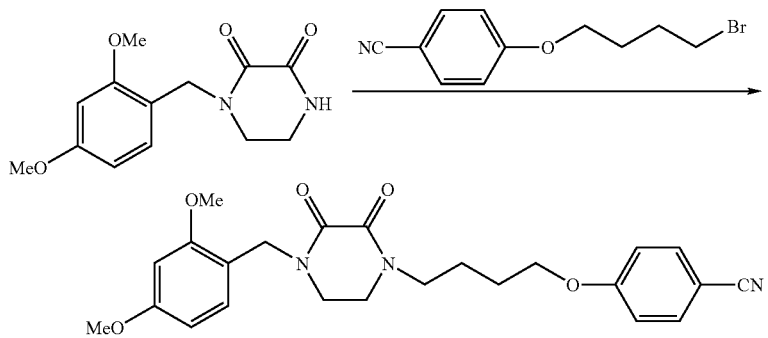

0.79 g of 1-(2,4-dimethoxybenzyl)-2,3-piperazinedione was dissolved in 9.0 ml of N,N-dimethylformamide, and 0.12 g of 60% sodium hydride was added thereto while cooled by ice, followed by stirring at room temperature for 2 hours. While cooled by ice, 6.0 ml of an N,N-dimethylformamide solution containing 0.84 g of 4-(4-bromobutoxy)benzonitrile was added dropwise thereto, followed by stirring at room temperature for 75 minutes. 30 ml of water and 30 ml of chloroform were added to the reaction mixture, so that the organic layer was separated. The separated organic layer was washed successively with water, and with a saturated aqueous solution of sodium chloride, and then dried over anhydrous magnesium sulfate. Thereafter, the solvent was removed under reduced pressure. The obtained residue was then purified by silica gel column chromatography [eluent; chloroform methanol=20:1] to obtain 1.16 g of a white solid, 4-{4-[4-(2,4-dimethoxybenzyl)-2,3-dioxo-1-piperazinyl]butoxy}benzonitrile.

$^1$H-NMR (CDCl$_3$) δ: 1.70-1.90 (4H, m), 3.42-3.48 (4H, m), 3.53 (2H, t, J=6.8 Hz), 3.80 (3H, s), 3.81 (3H, s), 4.03 (2H, t, J=5.7 Hz), 4.63 (2H, s), 6.42-6.48 (2H, m), 6.90-6.94 (2H, m), 7.24-7.28 (1H, m), 7.50-7.59 (2H, m)

Reference Example 3

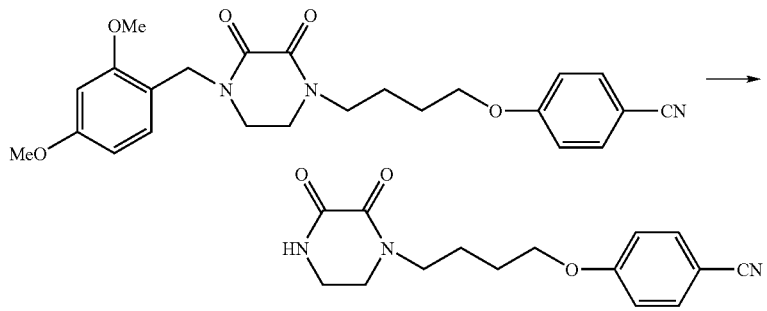

1.09 g of 4-{4-[4-(2,4-dimethoxybenzyl)-2,3-dioxo-1-piperazinyl]butoxy}benzonitrile was suspended in 2.5 ml of anisole, and 12.5 ml of trifluoroacetic acid was added thereto at room temperature, followed by heating to reflux for 2 hours. After completion of the reaction, the solvent was removed under a reduced pressure, and the obtained residue was then purified by silica gel column chromatography [eluent; chloroform ethanol=30:1] to obtain 0.30 g of a white solid, 4-[4-(2,3-dioxo-1-piperazinyl)butoxy]benzonitrile.

$^1$H-NMR (CDCl$_3$) δ: 1.76-1.88 (4H, m), 3.54-3.62 (6H, m), 4.05 (2H, t, J=5.6 Hz), 6.90-6.96 (2H, m), 7.50-7.60 (2H, m), 8.46 (1H, brs)

Reference Example 4

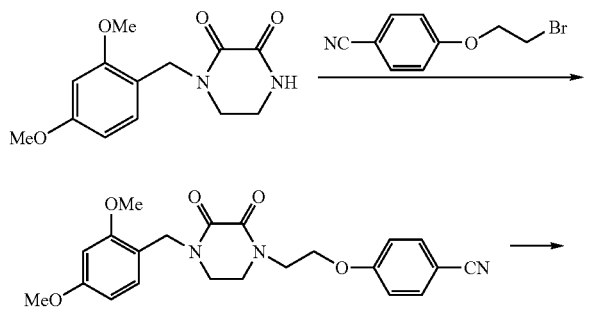

The following compound was obtained in the same manner as Reference examples 2 and 3.

4-[2-(2,3-dioxo-1-piperazinyl)ethoxy]benzonitrile $^1$H-NMR (CDCl$_3$) δ: 3.55-3.60 (2H, m), 3.75-3.82 (2H, m), 3.91 (2H, t, J=5.0 Hz), 4.27 (2H, t, J=5.0 Hz), 6.91-6.96 (2H, m), 7.47 (1H, brs), 7.57-7.63 (2H, m)

Reference Example 5

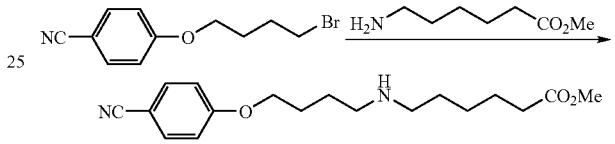

0.50 g of 4-(4-bromobutoxy)benzonitrile was dissolved in 5 ml of ethanol. Thereafter, 1.1 g of 6-aminohexanoic acid methyl ester hydrochloride and 1.4 ml of triethylamine were successively added to the solution, followed by heating to reflux for 4 hours. After completion of the reaction, the mixture was cooled to room temperature, and the solvent was removed under a reduced pressure. 20 ml of water was added to the obtained residue, and then, extraction was carried out with 20 ml of ethyl acetate 5 times. The obtained organic layer was dried over anhydrous magnesium sulfate, and the solvent was then removed under reduced pressure. The obtained residue was purified by silica gel column chromatography [eluent; chloroform methanol=30:1] to obtain 0.65 g of a colorless oil product, 6-{[4-(4-cyanophenoxy)butyl]amino}hexanoic acid methyl ester.

$^1$H-NMR (CDCl$_3$) δ: 1.35-1.45 (2H, m), 1.58-1.70 (2H, m), 1.84-2.00 (4H, m), 2.05-2.20 (2H, m), 2.30 (2H, t, J=7.2 Hz), 2.90-3.10 (4H, m), 3.66 (3H, s), 4.02 (2H, t, J=5.9 Hz), 6.90-6.96 (2H, m), 7.55-7.60 (2H, m), 9.41 (1H, brs)

Reference Example 6

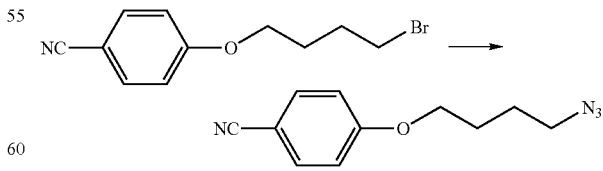

0.80 g of 4-(4-bromobutoxy)benzonitrile was dissolved in 8.0 ml of dimethyl sulfoxide, and 0.23 g of sodium azide was added thereto, followed by stirring at room temperature for 12 hours. 30 ml of water and 20 ml of ethyl acetate were added to the reaction mixture, so that the organic layer was separated. The separated organic layer was washed with a saturated aqueous solution of sodium chloride, and then dried over anhydrous magnesium sulfate. The solvent was removed under a reduced pressure to obtain 0.71 g of a colorless oil product, 4-(4-azidobutoxy)benzonitrile.

IR(neat)cm$^{-1}$: 2224, 2098, 1606

$^1$H-NMR (CDCl$_3$) δ: 1.74-1.96 (4H, m), 3.38 (2H, t, J=6.6 Hz), 4.04 (2H, t, J=6.1 Hz), 6.90-6.98 (2H, m), 7.56-7.62 (2H, m)

Reference Example 7

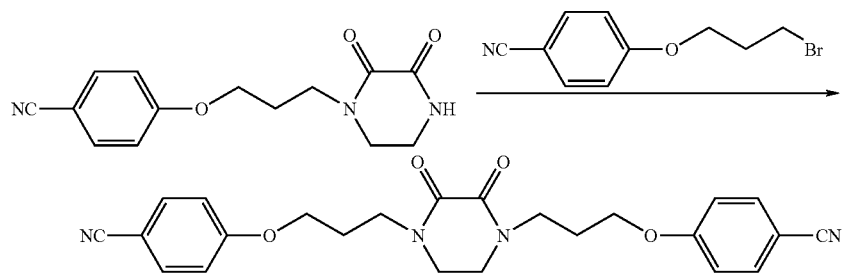

2.19 g of 4-[3-(2,3-dioxo-1-piperazinyl)propoxy]-benzonitrile was dissolved in 24.0 ml of N,N-dimethylformamide, and 0.32 g of 60% sodium hydride was added thereto, followed by stirring at room temperature for 1 hour. While cooled by ice, 8.0 ml of N,N-dimethylformamide solution containing 1.92 g of 4-(3-bromo-propoxy)-benzonitrile was added dropwise thereto, followed by stirring at room temperature for 3 hours. 30 ml of water and 30 ml of chloroform were added to the reaction mixture, and the mixture was adjusted to pH 1 with 1 mol/L hydrochloric acid. Thereafter, the organic layer was separated. The obtained organic layer was washed successively with water and with a saturated aqueous solution of sodium chloride, and then dried over anhydrous magnesium sulfate. The solvent was removed under a reduced pressure to obtain 3.30 g of a white solid, 4-(3-{4-[3-(4-cyanophenoxy)propyl]-2,3-dioxo-1-piperazinyl}propoxy)benzonitrile.

IR(KBr)cm$^{-1}$: 2222, 1660, 1603 $^1$H-NMR (d$_6$-DMSO) δ: 1.96-2.03 (4H, m), 3.50 (4H, t, J=6.8 Hz), 3.55 (4H, s), 4.09 (4H, t, J=6.1 Hz), 7.07-7.11 (4H, m), 7.74-7.78 (4H, m)

Reference Example 8

The following compound was obtained in the same manner as Reference example 1.

4-(3-chloropropoxy)-3-methylbenzonitrile $^1$H-NMR (CDCl$_3$) δ: 2.22. (3H, s), 2.28-2.32 (2H, m), 3.77 (2H, t, J=6.4 Hz), 4.18 (2H, t, J=5.9 Hz), 6.87 (1H, d, J=8.4 Hz), 7.40-7.50 (2H, m)

Reference Example 9

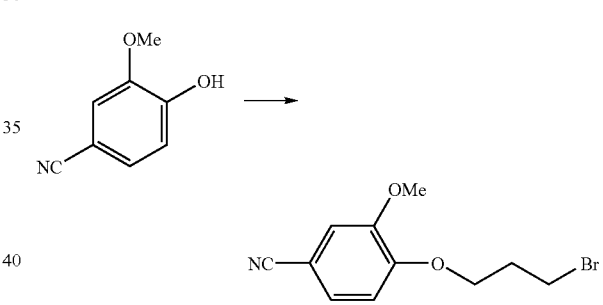

The following compound was obtained in the same manner as Reference example 1.

4-(3-bromopropoxy)-3-methoxybenzonitrile $^1$H-NMR (CDCl$_3$) δ: 2.37-2.43 (2H, m), 3.63 (2H, t, J=6.3 Hz), 3.88 (3H, s), 4.21 (2H, t, J=6.0 Hz), 6.93 (1H, d, J=8.3 Hz), 7.09 (1H, d, J=1.7 Hz), 7.26-7.29 (1H, m)

Reference Example 10

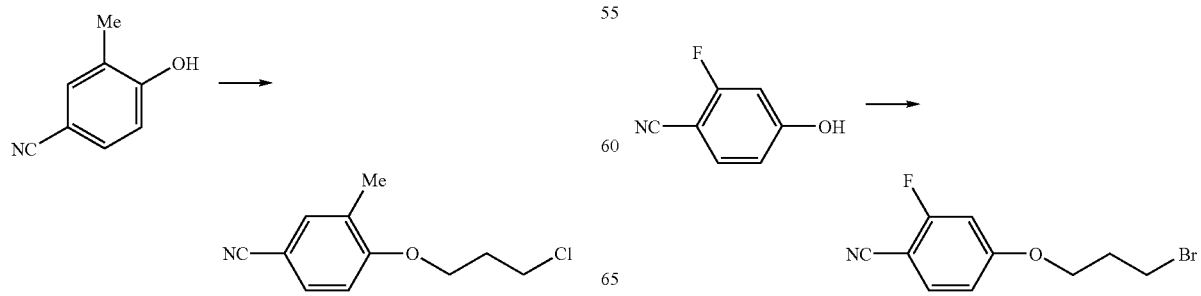

The following compound was obtained in the same manner as Reference example 1.

4-(3-bromopropoxy)-2-fluorobenzonitrile $^1$H-NMR (CDCl$_3$) δ: 2.32-2.38 (2H, m), 3.59 (2H, t, J=6.3 Hz), 4.17 (2H, t, J=5.9 Hz), 6.72-6.80 (2H, m), 7.53 (1H, d-d, J=7.6, 8.5 Hz)

Reference Example 11

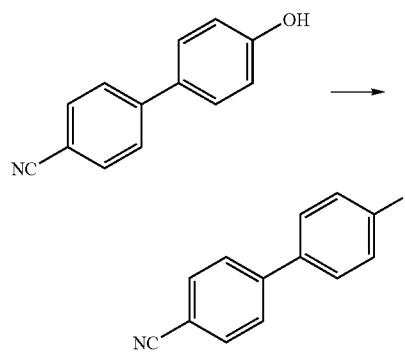

The following compound was obtained in the same manner as Reference example 1.

4'-(3-chloropropoxy)[1,1'-biphenyl]-4-carbonitrile $^1$H-NMR (CDCl$_3$) δ: 2.24-2.30 (2H, m), 3.77 (2H, t, J=6.4 Hz), 4.17 (2H, t, J=5.8 Hz), 6.99-7.02 (2H, m), 7.51-7.55 (2H, m), 7.62-7.69 (4H, m)

Reference Example 12

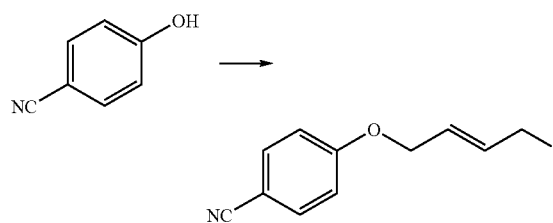

The following compound was obtained in the same manner as Reference example 1.

4-{[(E)-4-chloro-2-butenyl]oxy}benzonitrile $^1$H-NMR (CDCl$_3$) δ: 4.10-4.11 (2H, m), 4.60-4.61 (2H, m), 6.00-6.03 (2H, m), 6.94-6.97 (2H, m), 7.57-7.61 (2H, m)

Reference Example 13

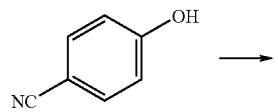

-continued

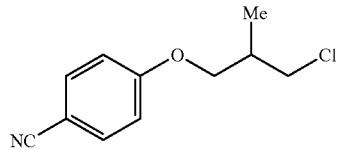

The following compound was obtained in the same manner as Reference example 1.

4-(3-chloro-2-methylpropoxy)benzonitrile $^1$H-NMR (CDCl$_3$) δ: 1.16 (3H, d, J=6.8 Hz), 2.35-2.42 (1H, m), 3.63-3.72 (2H, m), 3.95-4.03 (2H, m), 6.95-6.97 (2H, m), 7.58-7.60 (2H, m)

Reference Example 14

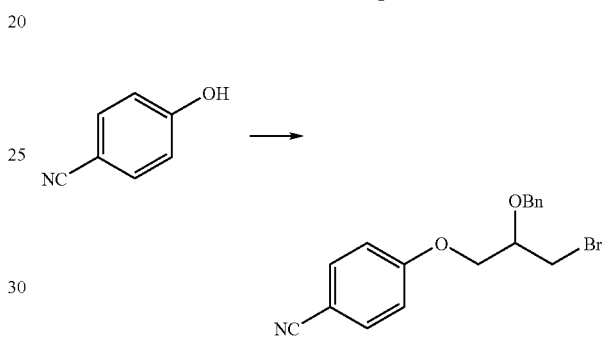

The following compound was obtained in the same manner as Reference example 1.

4-[2-(benzyloxy)-3-bromopropoxy]benzonitrile $^1$H-NMR (CDCl$_3$) δ: 3.56-3.65 (2H, m), 3.97-4.02 (1H, m), 4.14-4.21 (2H, m), 4.66, 4.76 (2H, ABq, J=12.0 Hz), 6.92-6.96 (2H, m), 7.31-7.37 (5H, m), 7.56-7.60 (2H, m)

Reference Example 15

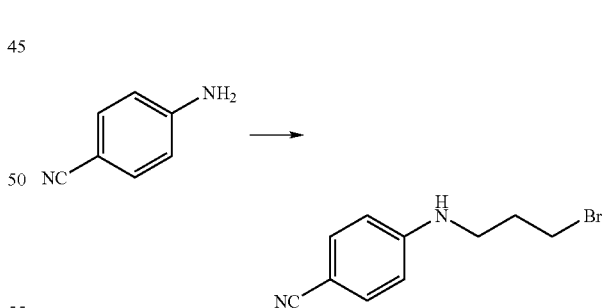

9.45 g of 4-aminobenzonitrile was suspended in 20.3 ml of 1,3-dibromopropane, and 21.0 ml of N,N-diisopropylethylamine was added thereto, followed by stirring at 110° C. for 2 hours. After completion of the reaction, chloroform, water, and a saturated sodium bicarbonate solution were added to the reaction solution. Thereafter, the organic layer was separated. The separated organic layer was washed with a saturated aqueous solution of sodium chloride, and then dried over anhydrous magnesium sulfate. Thereafter, it was concentrated under a reduced pressure. The obtained residue was purified by silica gel column chromatography [eluent;

n-hexane:ethyl acetate=5:1] to obtain 5.21 g of a pale yellow solid, 4-[(3-bromopropyl)amino]benzonitrile.

$^1$H-NMR (CDCl$_3$) δ: 2.13-2.20 (2H, m), 3.39 (2H, t, J=6.6 Hz), 3.50 (2H, t, J=6.2 Hz), 4.35 (1H, s), 6.57-6.61 (2H, m), 7.41-7.44 (2H, m)

Reference Example 16

Reference Example 16-1

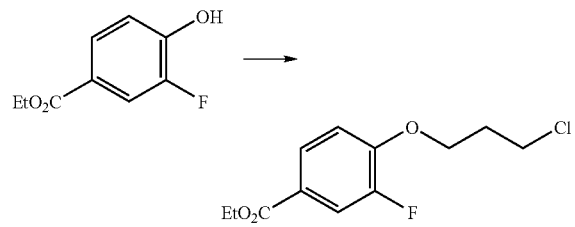

3.85 g of ethyl 3-fluoro-4-hydroxybenzoate was dissolved in 46 ml of acetone, and then, 2.89 g of potassium carbonate and 3.29 g of 1-bromo-3-chloropropane were added thereto at room temperature, followed by stirring under heating reflux for 5 hours. Thereafter, 1.45 g of potassium carbonate and 1.65 g of 1-bromo-3-chloropropane were further added thereto, and the obtained mixture was stirred at the same temperature for 4 hours. Thereafter, the temperature was cooled to room temperature. The reaction mixture was filtrated with Celite, and the obtained filtrate was concentrated under a reduced pressure. The obtained residue was purified by silica gel column chromatography [eluent; n-hexane:ethyl acetate=10:1] to obtain 4.04 g of a colorless oil product, ethyl 4-(3-chloropropoxy)-3-fluorobenzoate.

$^1$H-NMR (CDCl$_3$) δ: 1.38 (3H, t, J=7.1 Hz), 2.27-2.33 (2H, m), 3.78 (2H, t, J=6.2 Hz), 4.25 (2H, t, J=5.8 Hz), 4.35 (2H, q, J=7.1 Hz), 6.70 (1H, t, J=8.4 Hz), 7.74-7.82 (2H, m)

Reference Example 16-2

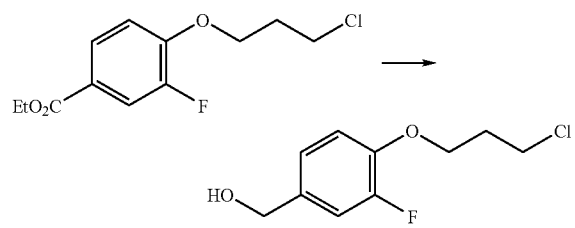

4.00 g of ethyl 4-(3-chloropropoxy)-3-fluorobenzoate was dissolved in 40 ml of tetrahydrofuran, and then, while cooled by ice, 0.70 g of lithium aluminum hydride was added thereto dividedly 3 times. The mixture was stirred at the same temperature for 1.5 hours. Thereafter, ethyl acetate, and then water were added thereto. The reaction mixture was filtrated with Celite, so that the organic layer was separated. The separated organic layer was dried over anhydrous magnesium sulfate, and then, the solvent was removed under a reduced pressure to obtain 3.40 g of a colorless oil product, [4-(3-chloropropoxy)-3-fluorophenyl]methanol.

$^1$H-NMR (CDCl$_3$) δ: 1.60-2.00 (1H, br), 2.23-2.30 (2H, m), 3.78 (2H, t, J=6.2 Hz), 4.19 (2H, t, J=5.8 Hz), 4.60-4.63 (2H, m), 6.95-7.14 (3H, m)

Reference Example 16-3

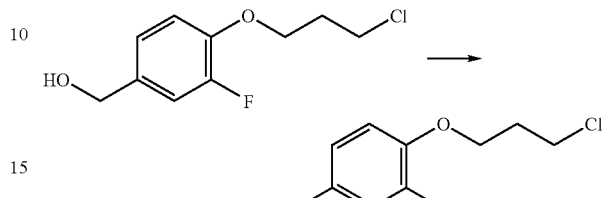

3.30 g of [4-(3-chloropropoxy)-3-fluorophenyl]methanol was dissolved in 33 ml of chloroform, and 13.1 g of manganese dioxide was added thereto at room temperature, followed by stirring at 50° C. to 60° C. for 2 hours. After cooling to room temperature, the reaction mixture was filtrated with Celite, and the obtained filtrate was concentrated under a reduced pressure to obtain 3.30 g of a pale yellow oil product, 4-(3-chloropropoxy)-3-fluorobenzaldehyde.

IR(neat)cm$^{-1}$: 1690, 1610, 1515, 1442, 1282

Reference example 16-4

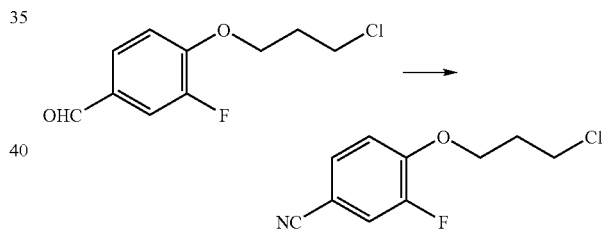

3.30 g of 4-(3-chloropropoxy)-3-fluorobenzaldehyde was dissolved in 40 ml of formic acid, and 1.11 g of hydroxylamine hydrochloride and 2.07 g of sodium formate were added thereto at room temperature, followed by stirring at 90° C. to 100° C. for 3 hours. The reaction mixture was concentrated under a reduced pressure, so that it became approximately one third of its amount, and then, water and ethyl acetate were added thereto. Thereafter, sodium carbonate was added to the mixture for neutralization. The organic layer was separated, and the separated organic layer was dried over anhydrous magnesium sulfate. The solvent was removed under a reduced pressure, and the obtained residue was purified by silica gel column chromatography [eluent; n-hexane:ethyl acetate=8:1] to obtain 2.87 g of a colorless oil product, 4-(3-chloropropoxy)-3-fluorobenzonitrile.

$^1$H-NMR (CDCl$_3$) δ: 2.28-2.34 (2H, m), 3.77 (2H, t, J=6.2 Hz), 4.26 (2H, t, J=5.8 Hz), 7.02-7.07 (1H, m), 7.35-7.44 (2H, m)

Reference Example 17

Reference example 17-1

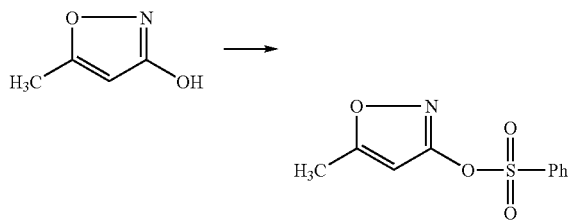

0.70 g of 5-methyl-3-hydroxyisoxazole was dissolved in 10 ml of pyridine, and 1.1 ml of triethylamine and 0.90 ml of benzenesulfonyl chloride were added thereto while cooled by ice, followed by heating to reflux for 1 hour. After cooling to room temperature, the solvent was removed under a reduced pressure. 20 ml of water and 30 ml of ethyl acetate were added to the obtained residue, so that the organic layer was separated. The aqueous layer was extracted twice with 20 ml of ethyl acetate. The obtained organic layer was combined, and then washed with water, 1 mol/L hydrochloric acid, and a saturated sodium bicarbonate solution, dried over anhydrous magnesium sulfate, followed by concnetration under a reduced pressure. The obtained residue was purified by silica gel column chromatography [eluent; toluene:ethyl acetate=20:1] to obtain 1.50 g of a colorless oil product, 5-methyl-3-isoxazolyl benzenesulfonate.

$^1$H-NMR (CDCl$_3$) δ: 2.40 (3H, d, J=0.6 Hz), 6.05 (1H, q, J=0.6 Hz), 7.56-7.61 (2H, m), 7.70-7.74 (1H, m), 7.97-7.99 (2H, m)

Reference Example 17-2

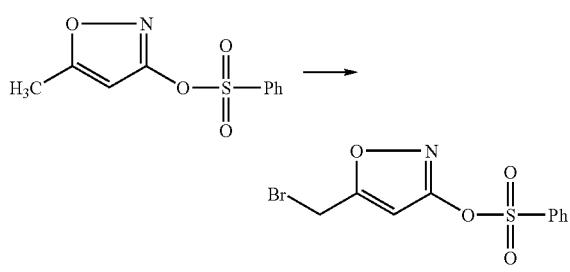

10 ml of benzene was added to 1.00 g of 5-methyl-3-isoxazolyl benzenesulfonate, and then, 1.10 g of N-bromosuccinimide and 0.05 g of benzoyl peroxide were added thereto at room temperature, followed by heating to reflux for 1 hour. 1 hour later, 0.05 g of benzoyl peroxide was further added thereto, followed by heating to reflux for 2 hours. Thereafter, 0.05 g of 2,2'-azobis(isobutyronitrile) was added thereto, followed by heating to reflux for 3 hours. Thereafter, 0.05 g of 2,2'-azobis(isobutyronitrile) was further added thereto, followed by heating to reflux for 6 hours. After cooling to room temperature, 30 ml of toluene and 20 ml of water were added to the reaction mixture, so that the organic layer was separated. The aqueous layer was extracted twice with 20 ml of toluene. The combined organic layer was washed with a saturated aqueous solution of sodium chloride, and then dried over anhydrous magnesium sulfate, followed by concentration under reduced pressure. The obtained residue was purified by silica gel column chromatography [eluent; n-hexane:benzene=1:1] to obtain 0.65 g of a colorless oil product, 5-(bromomethyl)-3-isoxazolyl benzenesulfonate.

$^1$H-NMR (CDCl$_3$) δ: 4.37 (2H, s), 6.39 (1H, s), 7.60-7.63 (2H, m), 7.73-7.74 (1H, m), 7.97-8.00 (2H, m)

Reference Example 18

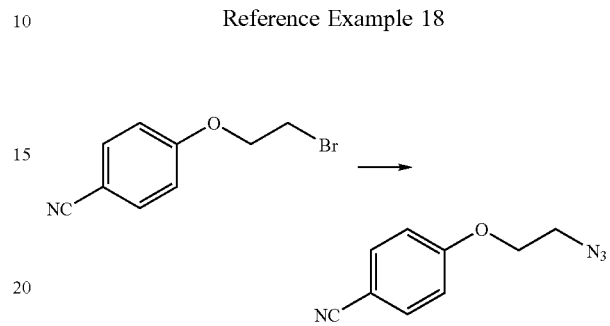

The following compound was obtained in the same manner as Reference example 6.

4-(2-azidoethoxy)benzonitrile $^1$H-NMR (CDCl$_3$) δ: 3.63-3.66 (2H, m), 4.18-4.21 (2H, m), 6.97-6.99 (2H, m), 7.58-7.62 (2H, m)

Reference Example 19

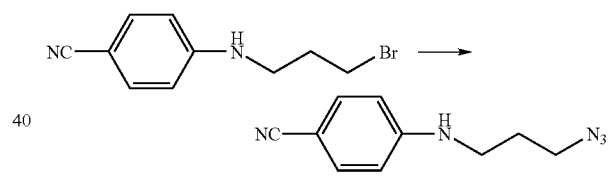

The following compound was obtained in the same manner as Reference example 6.

4-[(3-azidopropyl)amino]benzonitrile $^1$H-NMR (CDCl$_3$) δ: 1.87-1.93 (2H, m), 3.27-3.32 (2H, m), 3.46 (2H, t, J=6.4 Hz), 4.38 (1H, brs), 6.57 (2H, d, J=8.8 Hz), 7.43 (2H, d, J=8.8 Hz)

Reference Example 20

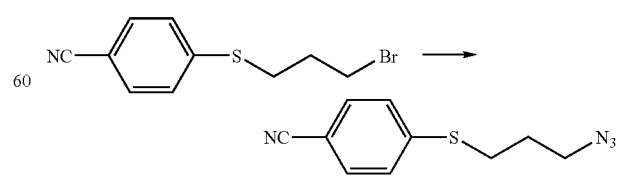

The following compound was obtained in the same manner as Reference example 6.

4-[(3-azidoprbpyl)sulfanyl]benzonitrile $^1$H-NMR (CDCl$_3$) δ: 1.92-1.98 (2H, m), 3.08 (2H, t, J=7.2 Hz), 3.48 (2H, t, J=6.2 Hz), 7.31-7.34 (2H, m), 7.53-7.56 (2H, m)

Reference Example 21

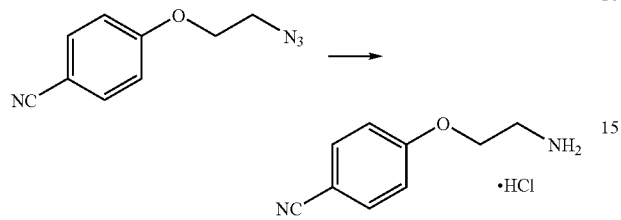

1.75 g of 4-(2-azidoethoxy)benzonitrile was dissolved in 15 ml of acetic acid, and 0.36 g of 5% palladium-carbon was added thereto at room temperature, followed by stirring under a hydrogen atmosphere at room temperature under atmospheric pressure for 7 hours. After completion of the reaction, the catalyst was removed by filtration, and the filtrate was concentrated under a reduced pressure. Isopropanol was added to the obtained residue, and the mixture was filtrated, so as to obtain 1.64 g of a white solid, 4-(2-aminoethoxy)benzonitrile hydro chloride "nitrile hydrochloride".

$^1$H-NMR (d$_6$-DMSO) δ: 3.22 (2H, t, J=5.2 Hz), 4.30 (2H, t, J=5.2 Hz), 7.14-7.18 (2H, m), 7.79-7.83 (2H, m), 8.40 (2H, brs)

Reference Example 22

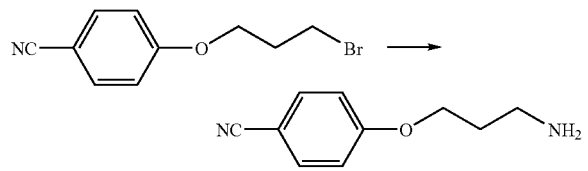

2.00 g of 4-(3-bromopropoxy)benzonitrile was dissolved in 20 ml of dimethyl sulfoxide, and 0.50 g of sodium azide was added thereto, followed by stirring at room temperature for 5 hours. Water and ethyl acetate were added to the reactoin mixture, so that orgnaic layers were separated. The separated organic layer was washed with a saturated aqueous solution of sodium chloride, and then dried over anhydrous magnesium sulfate. The solvent was then removed under a reduced pressure. The obtained residue was dissolved in 20 ml of ethanol, and 0.20 g of 5% palladium-carbon was added thereto, followed by stirring under a hydrogen atmosphere at room temperature under atmospheric pressure for 5 hours. After completion of the reaction, the catalyst was removed by filtration, and the filtrate was concentrated under a reduced pressure. Ethyl acetate and hydrochloric acid were added to the obtained residue, and aqueous layer was separated. Organic layers were extracted with water, and they were combined with the separated aqueous layer, followed by concentation under a reduced pressure. Water and chloroform were added to the obtained residue, and then, a 5 mol/L sodium hydroxide aqueous solution was added thereto to adjust pH to 12.5. The organic layer was separated, and the separated organic layer was dried over anhydrous magnesium sulfate. The solvent was removed under a reduced pressure to obtain 0.96 g of a pale yellow oil product, 4-(3-aminopropoxy)benzonitrile.

$^1$H-NMR (CDCl$_3$) δ: 1.20-1.60 (2H, br), 1.92-1.98 (2H, m), 2.92 (2H, t, J=6.7 Hz), 4.11 (2H, t, J=6.1 Hz), 6.95 (2H, d, J=8.9 Hz), 7.58 (2H, d, J=8.9 Hz)

Reference Example 23

Reference Example 23-1

The following compound was obtained in the same manner as Reference example 2.

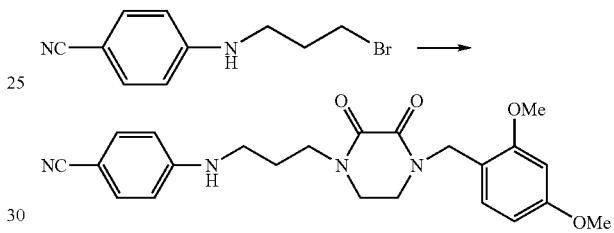

4-({3-[4-(2,4-dimethoxybenzyl)-2,3-dioxo-1-piperazinyl]propyl}amino)benzonitrile $^1$H-NMR (CDCl$_3$) δ: 1.78-1.84 (2H, m), 3.20-3.25 (2H, m), 3.39 (4H, s), 3.55 (2H, t, J=6.1 Hz), 3.81 (3H, s), 4.62 (2H, s), 5.22 (1H, t, J=6.2 Hz), 6.46-6.48 (2H, m), 6.52-6.55 (2H, m), 7.25-7.27 (1H, m), 7.34-7.36 (2H, m)

Reference Example 23-2

The following compound was obtained in the same manner as Reference example 3.

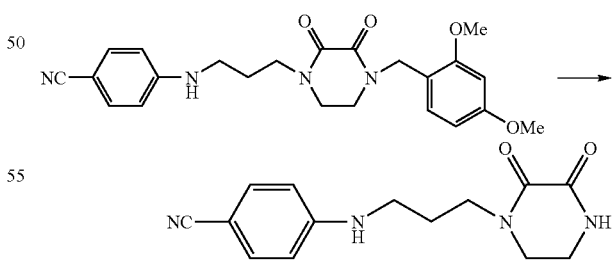

4-{[3-(2,3-dioxo-1-piperazinyl)propyl]amino}benzonitrile $^1$H-NMR (CDCl$_3$) δ: 1.84-1.90 (2H, m), 3.24 (2H, t, J=6.0 Hz), 3.53-3.57 (4H, m), 3.62 (2H, t, J=6.2 Hz), 5.12 (1H, brs), 6.56-6.59 (2H, m), 7.17 (1H, brs), 7.40-7.42 (2H, m)

Reference Example 24

The following compound was obtained in the same manner as Reference examples 2 and 3.

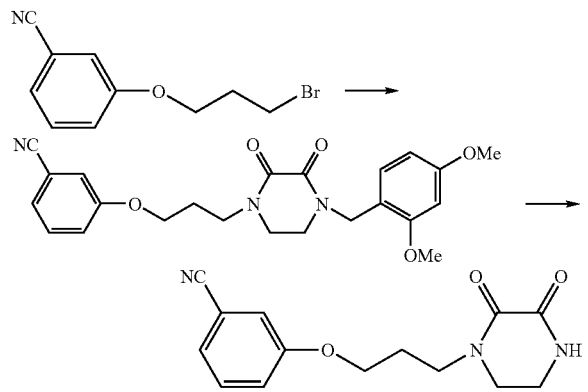

3-[3-(2,3-dioxo-1-piperazinyl)propoxy]benzonitrile $^1$H-NMR (CDCl$_3$) δ: 2.13-2.17 (2H, m), 3.56-3.59 (2H, m), 3.62-3.64 (2H, m), 3.71 (2H, t, J=7.1 Hz), 4.05 (2H, t, J=5.8 Hz), 7.05 (1H, s), 7.11-7.13 (2H, m), 7.25-7.26 (1H, m), 7.37-7.39 (1H, m)

Reference Example 25

Reference Example 25-1

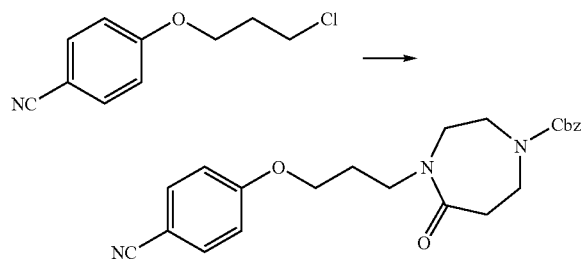

1.00 g of 4-(3-chloropropoxy)benzonitrile was dissolved in 20 ml of dimethylformamide, and then, 0.25 g of 60% sodium hydride was added thereto under cooling on ice. Thereafter, the reaction mixture was warmed to room temperature. 1.50 g of benzyl 5-oxo-1,4-diazepane-1-carboxylate was added to the mixture, followed by stirring at 65° C. to 75° C. for 2.5 hours. The reaction mixture was cooled to room temperature, and poured into a mixed solution consisting of ice water and ethyl acetate. The mixture was acidified with hydrochloric acid, and then, the organic layer was separated. The separated organic layer was washed with a saturated aqueous solution of sodium chloride, and then dried over anhydrous magnesium sulfate. The solvent was removed under a reduced pressure. The obtained residue was purified by silica gel column chromatography [eluent; ethyl acetate] to obtain 0.91 g of a colorless oil product, benzyl 4-[3-(4-cyanophenoxy)propyl]-5-oxo-1,4-diazepane-1-carboxylate.

$^1$H-NMR (CDCl$_3$) δ: 2.03-2.05 (2H, m), 2.66 (2H, brs), 3.46-3.50 (2H, m), 3.59 (2H, t, J=6.8 Hz), 3.67 (4H, s), 4.02 (2H, t, J=6.2 Hz), 5.14 (2H, s), 6.92 (2H, d, J=8.8 Hz), 7.32-7.38 (5H, m), 7.57 (2H, d, J=8.8 Hz)

Reference Example 25-2

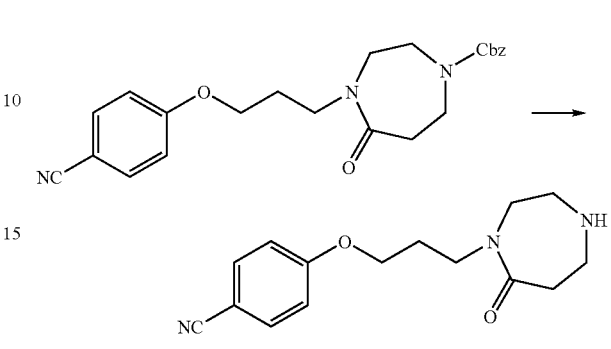

0.62 g of benzyl 4-[3-(4-cyanophenoxy)propyl]-5-oxo-1,4-diazepane-1-carboxylate was dissolved in a mixed solution consisting of 13.0 ml of ethanol and 4.5 ml of N,N-dimethylformamide, and then, 0.32 g of 5% palladium-carbon was added thereto, followed by stirring under a hydrogen atmosphere at room temperature under atmosphere pressure for 4 hours. After completion of the reaction, the catalyst was removed by filtration, and the filtrate was concentrated under a reduced pressure to obtain 0.44 g of a yellow oil product, 4-[3-(7-oxo-1,4-diazepan-1-yl)propoxy]benzonitrile.

$^1$H-NMR (CDCl$_3$) δ: 2.00-2.08 (2H, m), 2.65-2.67 (2H, m), 2.93-2.98 (4H, m), 3.44-3.46 (2H, m), 3.57 (2H, t, J=7.2 Hz), 4.04 (2H, t, J=6.2 Hz), 6.93-6.96 (2H, m), 7.57-7.60 (2H, m)

Reference Example 26

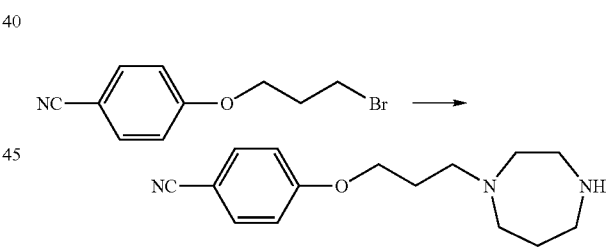

1.70 g of homopiperazine was dissolved in 20 ml of N,N-dimethylformamide, and then, 1.60 g of potassium carbonate and 1.00 g of 4-(3-bromopropoxy)benzonitrile were added thereto, followed by stirring at room temperature for 12 hours. A 1 mol/L sodium hydroxide aqueous solution and chloroform were added to the reaction mixture, so that organic layer was separated. The separated organic layer was dried over anhydrous magnesium sulfate, and then, the solvent was removed under a reduced pressure. The obtained oil product was purified by silica gel column chromatography [eluent; chloroform:methanol=5:1] to obtain 1.00 g of a colorless oil product, 4-[3-(1,4-diazepan-1-yl)propoxy]benzonitrile.

$^1$H-NMR (CDCl$_3$) δ: 1.50-1.70 (1H, m), 1.73-1.79 (1H, m), 1.93-2.00 (1H, m), 2.66-2.73 (6H, m), 2.90-2.95 (4H, m), 4.08 (2H, t, J=6.4 Hz), 6.94-6.97 (2H, m), 7.56-7.59 (2H, m)

Reference Example 27

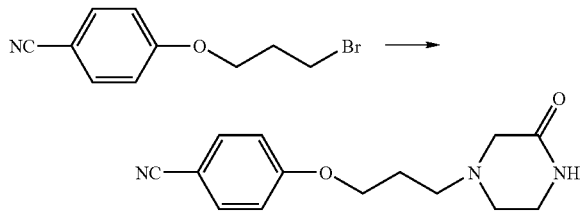

The following compound was obtained in the same manner as Reference example 26.

4-[3-(3-oxo-1-piperazinyl)propoxy]benzonitrile

¹H-NMR (CDCl₃) δ: 1.97-2.03 (2H, m), 2.62 (2H, t, J=7.0 Hz), 2.67-2.69 (2H, m), 3.16 (2H, s), 3.35-3.39 (2H, m), 4.08 (2H, t, J=6.4 Hz), 6.65 (1H, brs), 6.93-6.96 (2H, m), 7.56-7.60 (2H, m)

Reference Example 28

Reference Example 28-1

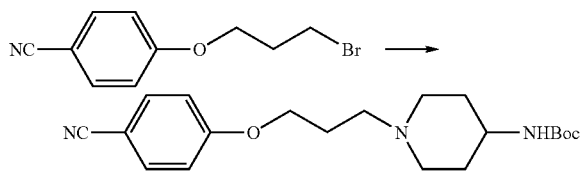

1.44 g of 4-tert-butoxycarbonylaminopiperidine was dissolved in 14 ml of N,N-dimethylformamide. Thereafter, 1.99 g of potassium carbonate and 1.87 g of 4-(3-bromopropoxy) benzonitrile were successively added to the above solution, followed by stirring at room temperature for 24 hours. Water and ethyl acetate were added to the reaction mixture, so that the organic layer was separated. The separated organic layer was washed with a saturated aqueous solution of sodium chloride, and then dried over anhydrous magnesium sulfate. Thereafter, the solvent was removed under a reduced pressure. The obtained solid was filtrated with a mixed solution consising of n-hexane and diisopropyl ether to obtain 2.12 g of tert-butyl 1-[3-(4-cyanophenoxy)propyl]-4-piperidinylcarbamate.

¹H-NMR (CDCl₃) δ: 1.38-1.45 (2H, m), 1.45 (9H, s), 1.92-2.11 (6H, m), 2.49 (2H, t, J=7.2 Hz), 2.82-2.85 (2H, m), 3.40-3.60 (1H, m), 4.05 (2H, t, J=6.2 Hz), 4.30-4.50 (1H, m), 6.92-6.95 (2H, m), 7.56-7.59 (2H, m)

Reference Example 28-2

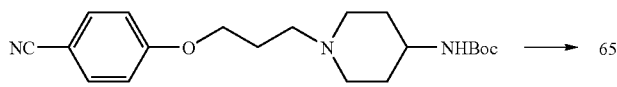

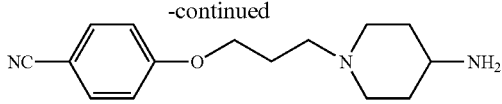

2.12 g of tert-butyl 1-[3-(4-cyanophenoxy)propyl]-4-piperidinylcarbamate was dissolved in 20 ml of 6 mol/L hydrochloric acid, followed by stirring at room temperature for 3 days. The reaction mixture was concentrated under a reduced pressure, and then, water and chloroform were added to the obtained solid. Thereafter, the mixture was adjusted to pH 13.0 with a 5 mol/L sodium hydroxide aqueous solution. The organic layer was separated, and then the water layer was extracted with chloroform 4 times. The combined organic layer was dried over anhydrous magnesium sulfate, and then concentrated under a reduced pressure to obtain 1.64 g of a white solid, 4-[3-(4-amino-1-piperidinyl)propoxy]benzonitrile.

¹H-NMR (CDCl₃) δ: 1.00-1.70 (4H, m), 1.78-1.85 (2H, m), 1.95-2.05 (4H, m), 2.49 (2H, t, J=7.2 Hz), 2.63-2.70 (1H, m), 2.82-2.90 (2H, m), 4.06 (2H, t, J=6.3 Hz), 6.93-6.96 (2H, m), 7.56-7.59 (2H, m)

Reference Example 29

Reference Example 29-1

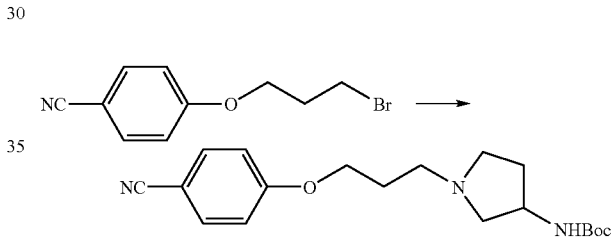

The following compound was obtained in the same manner as Reference example 28-1.

tert-butyl 1-[3-(4-cyanophenoxy)propyl]-3-pyrrolidinylcarbamate

¹H-NMR (CDCl₃) δ: 1.44 (9H, s), 1.52-1.65 (2H, m), 1.95-2.01 (2H, m), 2.10-2.38 (2H, m), 2.52-2.64 (1H, m), 2.59 (2H, t, J=6.7 Hz), 2.70-2.90 (1H, m), 4.07 (2H, t, J=6.7 Hz), 4.10-4.20 (1H, m), 4.74-4.84 (1H, m), 6.94 (2H, d, J=8.8 Hz), 7.58 (2H, d, J=8.8 Hz)

Reference Example 29-2

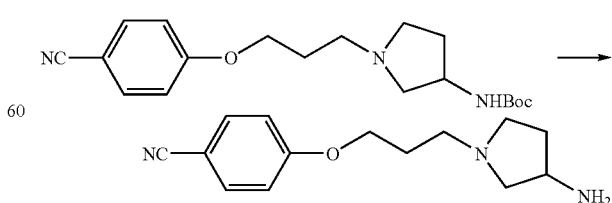

The following compound was obtained in the same manner as Reference example 28-2.

4-[3-(3-amino-1-pyrrolidinyl)propoxy]benzonitrile $^1$H-NMR (CDCl$_3$) δ: 1.36-1.75 (3H, m), 1.96-2.05 (2H, m), 2.12-2.24 (1H, m), 2.32-2.35 (1H, m), 2.44-2.50 (1H, m), 2.52-2.67 (2H, m), 2.67-2.80 (2H, m), 3.48-3.56 (1H, m), 4.08 (2H, t, J=6.3 Hz), 6.94 (2H, d, J=8.8 Hz), 7.57 (2H, d, J=8.8 Hz)

Reference Example 30

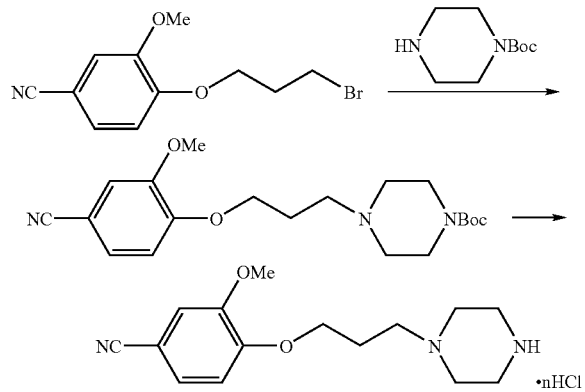

The following compound was obtained in the same manner as Reference example 28. 3-methoxy-4-[3-(1-piperazinyl)propoxy]benzonitrile hydrochloride $^1$H-NMR (d$_6$-DMSO) δ: 2.10-2.30 (2H, m), 3.10-3.90 (10H, m), 3.82 (3H, s), 4.16 (2H, t, J=6.0 Hz), 7.14 (1H, d, J=9.0 Hz), 7.42-7.44 (2H, m), 9.40-9.70 (3H, br)

Reference Example 31

Reference Example 31-1

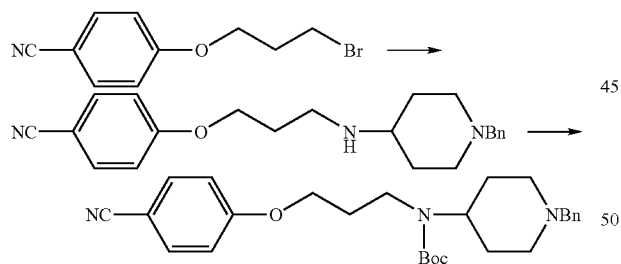

0.75 g of 4-amino-1-benzylpiperidine was dissolved in 6.0 ml of N,N-dimethylformamide, and then, 0.90 g of potassium carbonate and 0.85 g of 4-(3-bromopropoxy) benzonitrile were added thereto, followed by stirring at room temperature for 3 days. Water, chloroform, and potassium carbonate were added to the reaction mixture, so that the organic layer was separated. Thereafter, the aqueous layer was extracted with chloroform. The combined organic layer was dried over anhydrous magnesium sulfate, and the solvent was then removed under a reduced pressure. The obtained oil product was dissolved in 10 ml of chloroform, and then, 1.0 ml of triethylamine and 0.85 g of di-tert-butyl dicarbonate were added thereto, followed by stirring at room temperature for 12 hours. This reaction mixture was concentrated under a reduced pressure. The obtained oil product was purified by silica gel column chromatography [eluent; n-hexane ethyl acetate=1:1] to obtain 1.56 g of a colorless oil product, tert-butyl 1-benzyl-4-piperidinyl[3-(4-cyanophenoxy)propyl]carbamate.

$^1$H-NMR (CDCl$_3$) δ: 1.45 (9H, s), 1.50-1.80 (4H, m), 1.80-2.12 (5H, m), 2.90-2.96 (2H, m), 3.29 (2H, brs), 3.49 (2H, s), 4.00 (2H, t, J=6.1 Hz), 6.90-6.94 (2H, m), 7.20-7.40 (5H, m), 7.54-7.60 (2H, m)

Reference Example 31-2

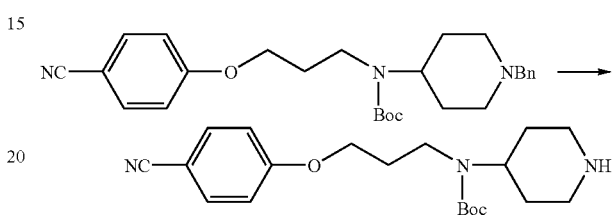

1.56 g of tert-butyl 1-benzyl-4-piperidinyl[3-(4-cyanophenoxy)propyl]carbamate was dissolved in 20 ml of methanol, and then, 0.30 g of 5% palladium-carbon was added to the solution, followed by stirring under a hydrogen atmosphere at room temperature under an atmospheric pressure for 18 hours. After completion of the reaction, the catalyst was removed, and the solvent was then removed under a reduced pressure to obtain 1.05 g of tert-butyl 3-(4-cyanophenoxy)propyl(4-piperidinyl)carbamate.

$^1$H-NMR (CDCl$_3$) δ: 1.44 (9H, s), 1.50-2.30 (8H, m), 2.82-2.94 (2H, m), 3.26-3.34 (2H, m), 3.46-3.54 (1H, m), 4.01 (2H, t, J=6.2 Hz), 6.93-7.00 (2H, m), 7.54-7.60 (2H, m)

Reference Example 32

Reference Example 32-1

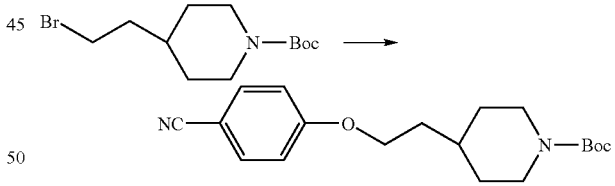

4.91 g of tert-butyl 4-(2-bromoethyl)-1-piperidinecarboxylate was dissolved in 50 ml of 2-butanone, and then, 2.00 g of 4-cyanophenol and 4.64 g of potassium carbonate were added thereto, followed by heating to reflux for 4 hours. After cooling to room temperature, 50 ml of water and 50 ml of ethyl acetate were added to the reaction mixture, so that the organic layer was separated. The separated organic layer was washed with saturated aqueous solution of sodium chloride dried over anhydrous magnesium sulfate, and the solvent was then removed under a reduced pressure. The obtained residue was purified by silica gel column chromatography [eluent; n-hexane:ethyl acetate=2:1] to obtain 3.61 g of a colorless oil product, tert-butyl 4-[2-(4-cyanophenoxy)ethyl]-1-piperidinecarboxylate.

¹H-NMR (CDCl₃) δ: 1.00-1.30 (2H, m), 1.46 (9H, s), 1.50-2.04 (5H, m), 2.62-2.76 (2H, m), 4.05 (2H, t, J=6.2 Hz), 4.00-4.18 (2H, m), 6.93 (2H, d, J=8.5 Hz), 7.58 (2H, d, J=8.5 Hz)

Reference Example 32-2

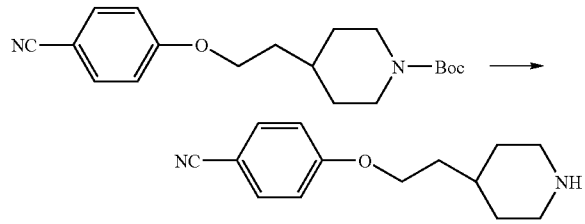

The following compound was obtained in the same manner as Reference example 28-2.

4-[2-(4-piperidinyl)ethoxy]benzonitrile

¹H-NMR (CDCl₃) δ: 1.16-1.27 (2H, m), 1.60-1.78 (5H, m), 1.80-2.05 (1H, m), 2.59-2.66 (2H, m), 3.08-3.11 (2H, m), 4.05 (2H, t, J=6.3 Hz), 6.91-6.95 (2H, m), 7.56-7.59 (2H, m)

Reference Example 33

-continued

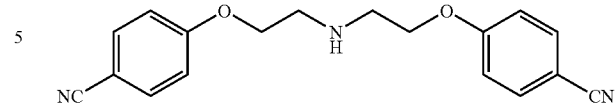

1.60 g of 4-(2-aminoethoxy)benzonitrile hydrochloride was suspended in 16 ml of N,N-dimethylformamide, and then, 3.75 g of triethylamine and 1.21 g of 4-(2-bromoethoxy)benzonitrile were added thereto at room temperature, followed by stirring at 50° C. to 60° C. for 9 hours. After cooling to room temperature, water and chloroform were added to the reaction mixture, and potassium carbonate was then added thereto, so that the solution was converted into alkaline. Thereafter, the organic layer was separated. The separated organic layer was washed with saturated aqueous solution of sodium chloride, and then dried over anhydrous magnesium sulfate. The solvent was removed under a reduced pressure, and the obtained residue was purified by silica gel column chromatography [eluent; chloroform:ethanol=10:1]. The obtained solid was filtrated with toluene-ethyl acetate to obtain 0.36 g of a white solid, 4-(2-{[2-(4-cyanophenoxy)ethyl]amino}ethoxy)benzonitrile.

¹H-NMR (CDCl₃) δ: 3.13 (4H, t, J=5.1 Hz), 4.15 (4H, t, J=5.1 Hz), 6.96 (4H, d, J=8.6 Hz), 7.58 (4H, d, J=8.6 Hz)

Reference Example 34

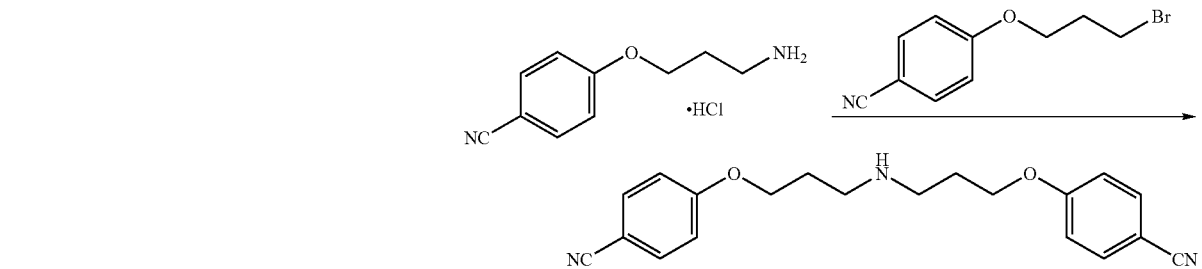

The following compound was obtained in the same manner as Reference example 33. 4-(3-{[3-(4-cyanophenoxy)propyl]amino}propoxy)benzonitrile ¹H-NMR (CDCl₃) δ: 2.10-2.20 (4H, m), 2.96 (4H, t, J=7.0 Hz), 4.12 (4H, t, J=6.2 Hz), 6.92-6.95 (4H, m), 7.55-7.58 (4H, m)

Reference Example 35

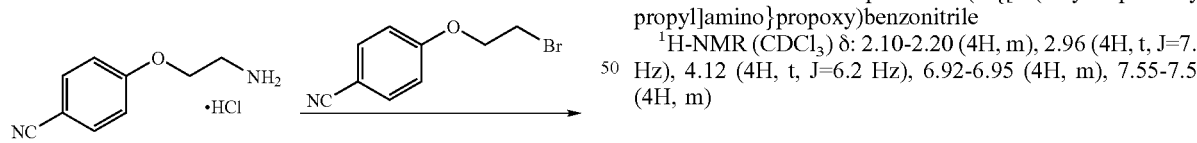

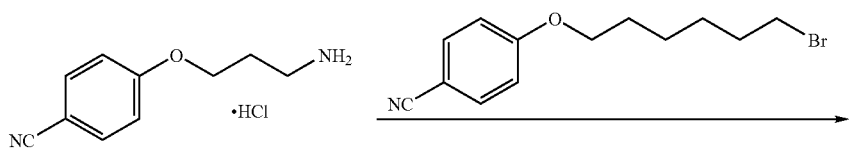

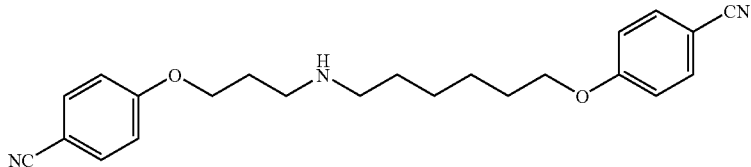

The following compound was obtained in the same manner as Reference example 33.

4-(3-{[6-(4-cyanophenoxy)hexyl]amino}propoxy)benzonitrile $^1$H-NMR (CDCl$_3$) δ: 1.38-1.58 (7H, m), 1.77-1.84 (2H, m), 1.97-2.03 (2H, m), 2.64 (2H, t, J=7.4 Hz), 2.81 (2H, t, J=6.8 Hz), 3.99 (2H, t, J=6.4 Hz), 4.09 (2H, t, J=6.2 Hz), 6.91-6.95 (4H, m), 7.56-7.60 (4H, m)

Reference Example 36

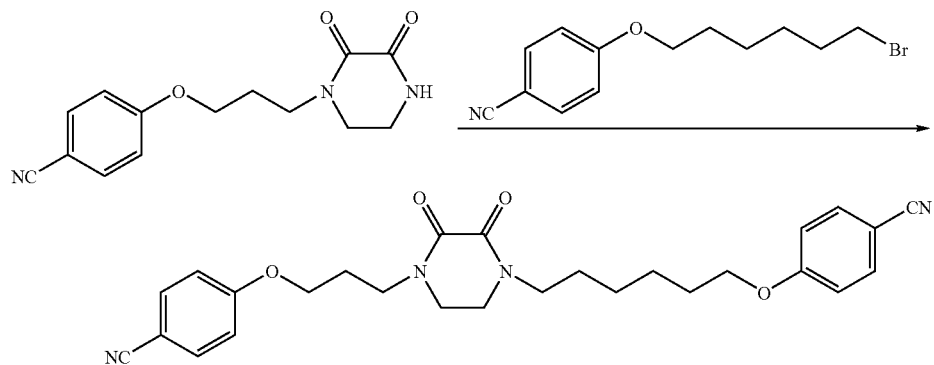

The following compound was obtained in the same manner as Reference example 7.

4-[(6-{4-[3-(4-cyanophenoxy)propyl]-2,3-dioxo-1-piperazinyl}hexyl)oxy]benzonitrile $^1$H-NMR (CDCl$_3$) δ: 1.30-1.68 (6H, m), 1.74-1.90 (2H, m), 2.10-2.20 (2H, m), 3.44-3.62 (6H, m), 3.67 (2H, t, J=7.0 Hz), 3.99 (2H, t, J=6.2 Hz), 4.07 (2H, t, J=6.2 Hz), 6.91-6.94 (4H, m), 7.56-7.59 (4H, m)

Reference Example 37

The following compound was obtained in the same manner as Reference example 7.

3-(3-{4-[3-(4-cyanophenoxy)propyl]-2,3-dioxo-1-piperazinyl}propoxy)benzonitrile $^1$H-NMR (d$_6$-DMSO) δ: 1.94-2.04 (4H, m), 3.46-3.58 (8H, m), 4.02-4.12 (4H, m), 7.09 (2H, d, J=8.4 Hz), 7.24-7.54 (4H, m), 7.76 (2H, d, J=8.4 Hz)

Reference Example 38

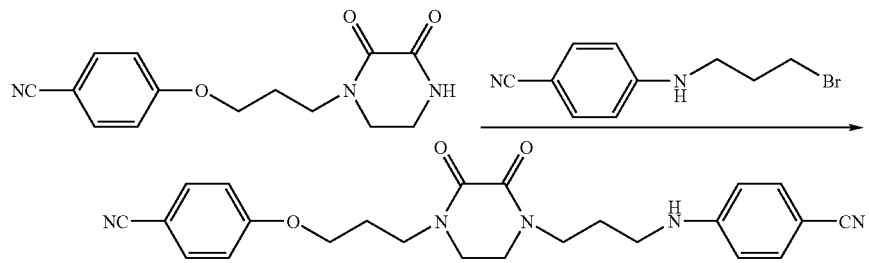

The following compound was obtained in the same manner as Reference example 7.

4-[(3-{4-[3-(4-cyanophenoxy)propyl]-2,3-dioxo-1-piperazinyl}propyl)amino]benzonitrile ¹H-NMR (d₆-DMSO) δ: 1.75-1.82 (2H, m), 1.96-2.02 (2H, m), 3.06-3.11 (2H, m), 3.42 (2H, t, J=7.2 Hz), 3.49-3.53 (6H, m), 4.09 (2H, t, J=6.4 Hz), 6.63 (2H, d, J=8.8 Hz), 6.67 (1H, t, J=5.2 Hz), 7.09 (2H, d, J=8.8 Hz), 7.44 (2H, d, J=8.8 Hz), 7.76 (2H, d, J=8.8 Hz)

Reference Example 39

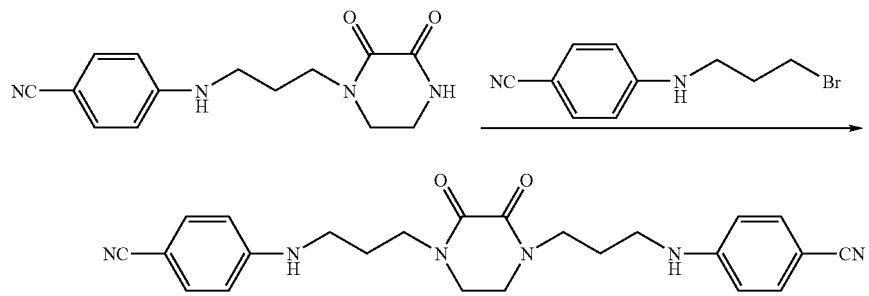

The following compound was obtained in the same manner as Reference example 7.

4-[(3-{4-[3-(4-cyanoanilino)propyl]-2,3-dioxo-1-piperazinyl}propyl)amino]benzonitrile ¹H-NMR (d₆-DMSO) δ: 1.75-1.82 (4H, m), 3.07-3.11 (4H, m), 3.42 (4H, t, J=7.1 Hz), 3.52 (4H, s), 6.63 (4H, d, J=8.8 Hz), 6.67 (2H, t, J=5.4 Hz), 7.44 (4H, d, J=8.8 Hz)

Reference Example 40

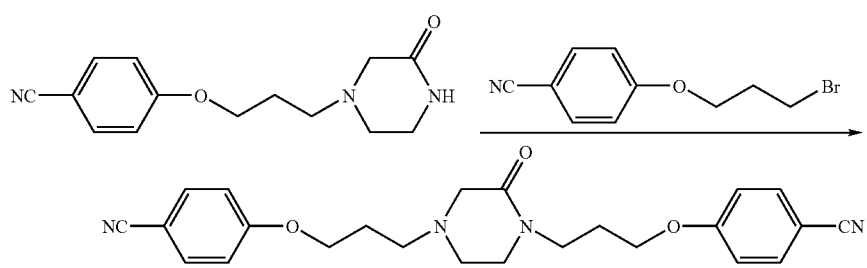

The following compound was obtained in the same manner as Reference example 7.

4-(3-{4-[3-(4-cyanophenoxy)propyl]-2-oxo-1-piperazinyl}propoxy)benzonitrile $^1$H-NMR (CDCl$_3$) δ: 1.96-2.13 (4H, m), 2.59 (2H, t, J=7.0 Hz), 2.71 (2H, t, J=5.4 Hz), 3.15 (2H, s), 3.37 (2H, t, J=5.4 Hz), 3.57 (2H, t, J=7.0 Hz), 4.04-4.09 (4H, m), 6.93-6.95 (4H, m), 7.56-7.59 (4H, m)

Reference Example 41

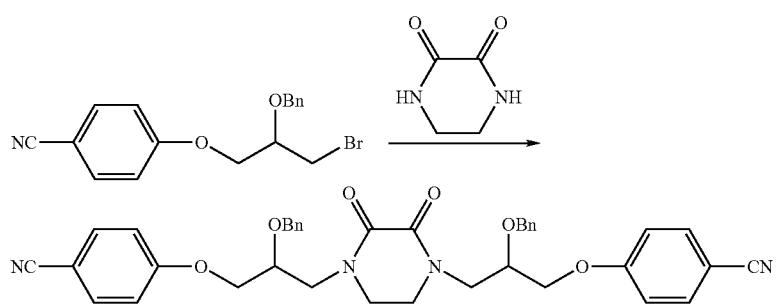

0.15 g of 2,3-piperazinedione was suspended in 6.5 ml of N,N-dimethylformamide, and then, 0.11 g of 60% sodium hydride was added thereto under cooling on ice, followed by stirring for 20 minutes. The reaction mixture was warmed to room temperature, and 0.91 g of 4-[2-(benzyloxy)-3-bromopropoxy]benzonitrile was added thereto, followed by stirring for 7.5 hours. Thereafter, 6.5 ml of dimethyl sulfoxide was added to the reaction mixture, and the mixture was left overnight. 20 ml of water and 20 ml of ethyl acetate were added to the reaction mixture, so that the organic layer was separated. The aqueous layer was extracted with 20 ml of ethyl acetate 3 times. The organic layers were combined, and the thus obtained layer was washed with a saturated aqueous solution of sodium chloride and then dried over anhydrous magnesium sulfate. Thereafter, the resultant solution was concentrated under a reduced pressure. The obtained residue was purified by silica gel column chromatography [eluent; n-hexane:ethyl acetate=1:2] to obtain 0.58 g of a white solid, 4-(2-(benzyloxy)-3-{4-[2-(benzyloxy)-3-(4-cyanophenoxy)propyl]-2,3-dioxo-1-piperazinyl}propoxy)benzonitrile.

$^1$H-NMR (CDCl$_3$) δ: 3.41-3.58 (6H, m), 3.78-3.86 (2H, m), 4.00-4.06 (2H, m), 4.14-4.19 (4H, m), 4.57-4.75 (4H, m), 6.93-6.95 (4H, m), 7.27-7.33 (10H, m), 7.57-7.59 (4H, m)

Reference Example 42

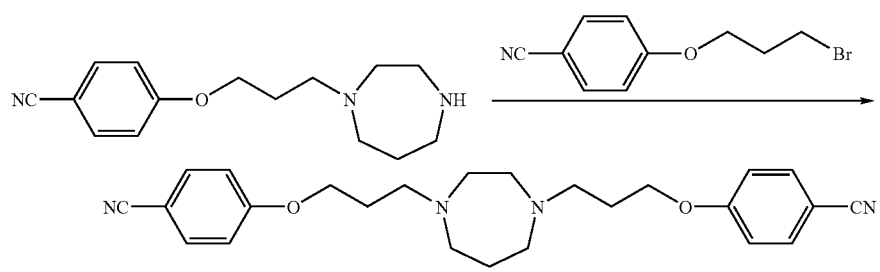

0.97 g of 4-[3-(1,4-diazepan-1-yl)propoxy]benzonitrile was dissolved in 10 ml of N,N-dimethylformamide, and then, 1.03 g of potassium carbonate and 0.97 g of 4-(3-bromopropoxy)benzonitrile were added thereto, followed by stirring at room temperature for 12 hours. Water and ethyl acetate were added to the reaciton mixture, so that the organic layer was separated. The organic layer was dried over anhydrous magnesium sulfate, and the solvent was then removed under a reduced pressure. The obtained oil product was purified by silica gel column chromatography [eluent; chloroform:methanol=30:1] to obtain 1.13 g of a white solid, 4-(3-{4-[3-(4-cyanophenoxy)propyl]-1,4-diazepan-1-yl}propoxy)benzonitrile.

$^1$H-NMR (CDCl$_3$) δ: 1.70-1.90 (2H, m), 1.93-2.00 (4H, m), 2.66 (4H, t, J=7.1 Hz), 2.71-2.74 (8H, m), 4.07 (4H, t, J=6.3 Hz), 6.92-6.96 (4H, m), 7.56-7.59 (4H, m)

Reference Example 43

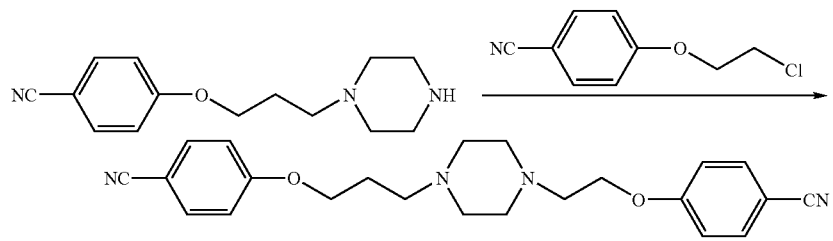

The following compound was obtained in the same manner as Reference example 42.

4-(3-{4-[2-(4-cyanophenoxy)ethyl]-1-piperazinyl}propoxy)benzonitrile

¹H-NMR (CDCl₃) δ: 1.97-2.03 (2H, m), 2.52-2.62 (10H, m), 2.84 (2H, t, J=5.6 Hz), 4.07 (4H, t, J=6.2 Hz), 4.15 (2H, t, J=5.6 Hz), 6.93-6.96 (4H, m), 7.56-7.59 (4H, m)

Reference Example 44

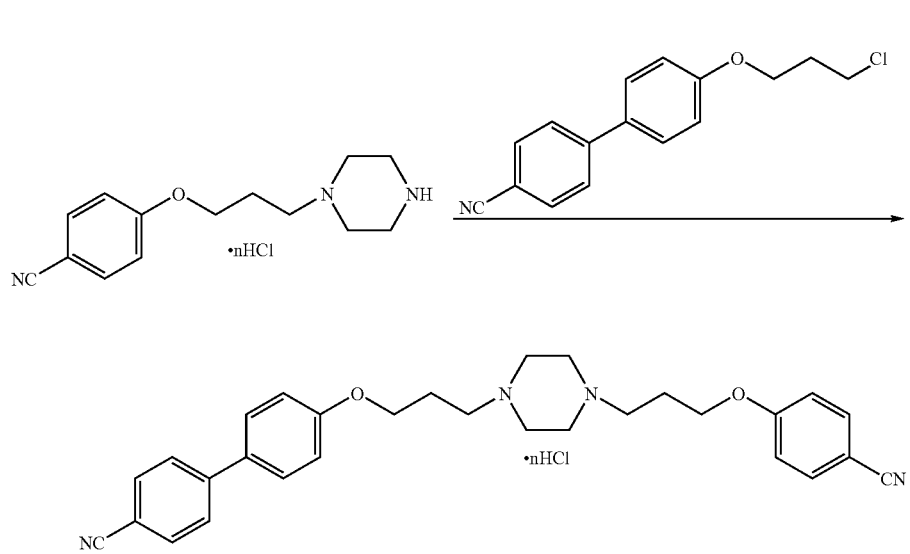

The following compound was obtained in the same manner as Reference example 42.

4'-(3-{4-[3-(4-cyanophenoxy)propyl]-1-piperazinyl}propoxy)[1,1'-biphenyl]-4-carbonitrile Hydrochloride ¹H-NMR (d₆-DMSO) δ: 2.10-2.30 (4H, m), 3.20-4.00 (12H, m), 4.16 (2H, t, J=6.4 Hz), 4.20 (2H, t, J=6.2 Hz), 7.08-7.14 (4H, m), 7.72-7.91 (8H, m)

Reference Example 45

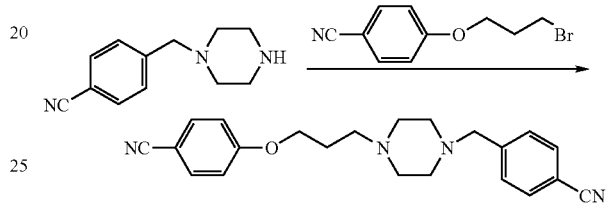

The following compound was obtained in the same manner as Reference example 42.

4-{3-[4-(4-cyanobenzyl)-1-piperazinyl]propoxy}benzonitrile

¹H-NMR (CDCl₃) δ: 1.94-2.02 (2H, m), 2.30-2.70 (10H, m), 3.55 (2H, s), 4.06 (2H, t, J=6.4 Hz), 6.92-6.96 (2H, m), 7.45 (2H, d, J=8.3 Hz), 7.55-7.62 (4H, m)

Reference Example 46

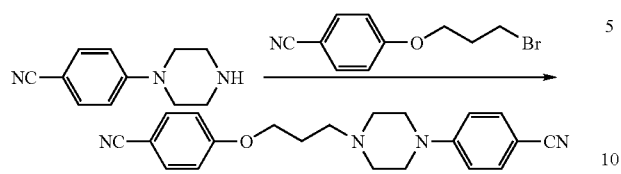

The following compound was obtained in the same manner as Reference example 42.

4-{4-[3-(4-cyanophenoxy)propyl]-1-piperazinyl}benzonitrile $^1$H-NMR (CDCl$_3$) δ: 1.99-2.06 (2H, m), 2.56-2.62 (6H, m), 3.32-3.35 (4H, m), 4.10 (2H, t, J=6.2 Hz), 6.84-6.88 (2H, m), 6.93-6.98 (2H, m), 7.48-7.53 (2H, m), 7.56-7.60 (2H, m)

Reference Example 47

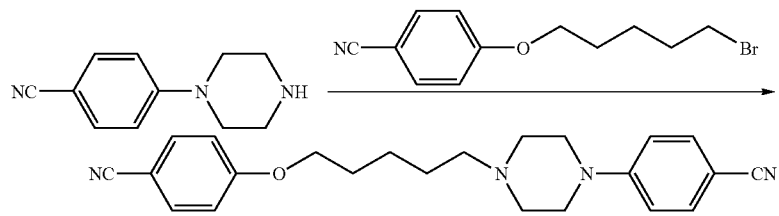

The following compound was obtained in the same manner as Reference example 42.

4-{4-[5-(4-cyanophenoxy)pentyl]-1-piperazinyl}benzonitrile $^1$H-NMR (CDCl$_3$) δ: 1.48-1.65 (4H, m), 1.81-1.88 (2H, m), 2.41-2.45 (2H, m), 2.57-2.60 (4H, m), 3.33-3.35 (4H, m), 4.01 (2H, t, J=6.4 Hz), 6.83-6.88 (2H, m), 6.90-6.95 (2H, m), 7.47-7.52 (2H, m), 7.56-7.60 (2H, m)

Reference Example 48

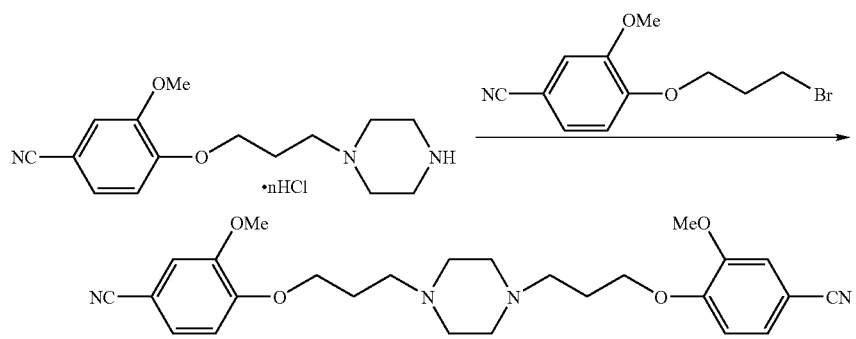

The following compound was obtained in the same manner as Reference example 42.

4-(3-{4-[3-(4-cyano-2-methoxyphenoxy)propyl]-1-piperazinyl}propoxy)-3-methoxybenzonitrile $^1$H-NMR (CDCl$_3$) δ: 2.00-2.07 (4H, m), 2.30-2.70 (8H, m), 2.52 (4H, t, J=7.1 Hz), 3.88 (6H, s), 4.13 (4H, t, J=6.6 Hz), 6.92 (2H, d, J=8.3 Hz), 7.07 (2H, d, J=2.0 Hz), 7.25 (2H, dd, J=2.0, 8.3 Hz)

Reference Example 49

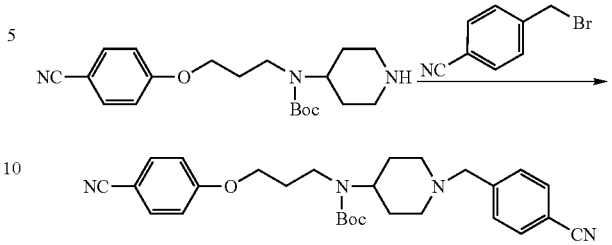

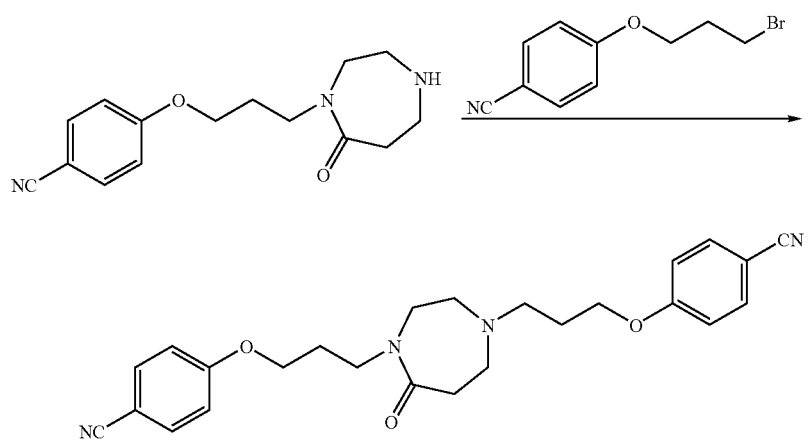

The following compound was obtained in the same manner as Reference example 42.

4-(3-{4-[3-(4-cyanophenoxy)propyl]-7-oxo-1,4-diazepan-1-yl}propoxy)benzonitrile $^1$H-NMR (CDCl$_3$) δ: 1.76-2.08 (4H, m), 2.58-2.68 (8H, m), 3.46-3.48 (2H, m), 3.54-3.58 (2H, m), 4.03 (2H, t, J=6.2 Hz), 4.06 (2H, t, J=6.0 Hz), 6.92-6.95 (4H, m), 7.56-7.60 (4H, m)

Reference Example 50

The following compound was obtained in the same manner as Reference example 42.

tert-butyl 1-(4-cyanobenzyl)-4-piperidinyl [3-(4-cyanophenoxy)propyl]carbamate $^1$H-NMR (CDCl$_3$) δ: 1.46 (9H, s), 1.60-1.80 (4H, m), 1.90-2.20 (4H, m), 2.80-2.90 (2H, m), 3.08-3.40 (2H, m), 3.40-3.60 (1H, m), 3.53 (2H, s), 4.02 (2H, t, J=6.1 Hz), 6.91-6.95 (2H, m), 7.44 (2H, d, J=8.7 Hz), 7.57-7.62 (4H, m)

Reference Example 51

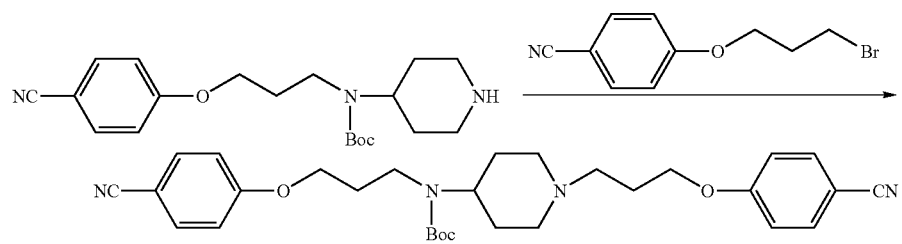

The following compound was obtained in the same manner as Reference example 42.

tert-butyl 3-(4-cyanophenoxy)propyl{1-[3-(4-cyanophenoxy)propyl]-4-piperidinyl}carbamate ¹H-NMR (CDCl₃) δ: 1.46 (9H, s), 1.65-1.80 (4H, m), 1.96-2.10 (6H, m), 2.50 (2H, t, J=7.3 Hz), 2.80-3.00 (3H, m), 3.20-3.40 (2H, m), 4.01 (2H, t, J=5.9 Hz), 4.05 (2H, t, J=6.1 Hz), 6.91-6.95 (4H, m), 7.58 (4H, d, J=8.8 Hz)

Reference Example 52

4-[3-(4-{[3-(4-cyanophenoxy)propyl]amino}-1-piperidinyl)propoxy]benzonitrile

¹H-NMR (CDCl₃) δ: 1.34-1.44 (2H, m), 1.45-1.70 (1H, br), 1.85-2.06 (8H, m), 2.40-2.60 (1H, m), 2.50 (2H, t, J=7.2 Hz), 2.82 (2H, t, J=6.8 Hz), 2.85-2.95 (2H, m), 4.06 (2H, t, J=6.3 Hz), 4.10 (2H, t, J=6.1 Hz), 6.93-6.95 (4H, m), 7.55-7.59 (4H, m)

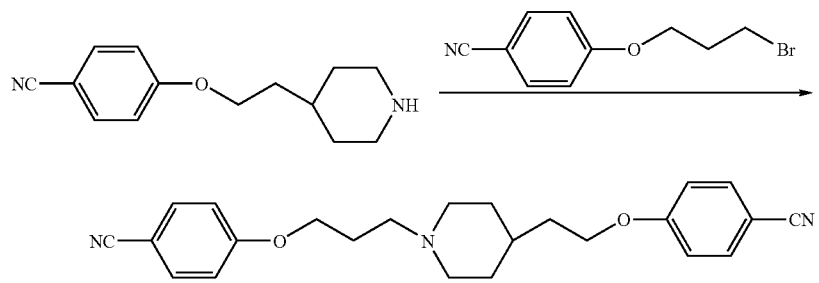

The following compound was obtained in the same manner as Reference example 42.

4-(2-{1-[3-(4-cyanophenoxy)propyl]-4-piperidinyl}ethoxy)benzonitrile

¹H-NMR (CDCl₃) δ: 1.20-1.40 (2H, m), 1.50-1.60 (1H, m), 1.70-1.78 (4H, m), 1.93-2.03 (4H, m), 2.47-2.51 (2H, m), 2.91-2.94 (2H, m), 4.05 (2H, t, J=6.1 Hz), 4.06 (2H, t, J=6.1 Hz), 6.93 (2H, d, J=8.5 Hz), 6.94 (2H, d, J=8.5 Hz), 7.57 (2H, d, J=8.5 Hz), 7.58 (2H, d, J=8.5 Hz)

Reference Example 53

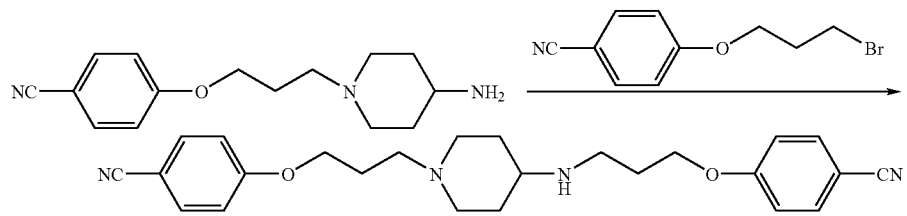

Reference Example 54

The following compound was obtained in the same manner as Reference example 42.

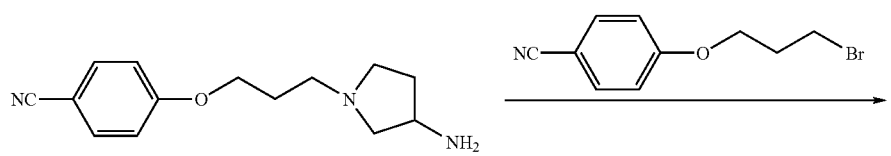

-continued

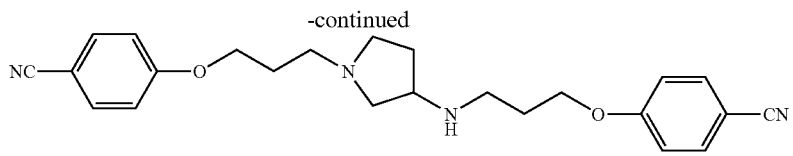

The following compound was obtained in the same manner as Reference example 42.

4-[3-(3-{[3-(4-cyanophenoxy)propyl]amino}-1-pyrrolidinyl)propoxy]benzonitrile $^1$H-NMR (CDCl$_3$) δ: 1.60-2.22 (7H, m), 2.50-2.90 (8H, m), 3.30-3.50 (1H, m), 4.08 (2H, t, J=6.3 Hz), 4.10 (2H, t, J=6.3 Hz), 6.94 (4H, d, J=8.8 Hz), 7.57 (4H, d, J=8.8 Hz)

Reference Example 55

The following compound was obtained in the same manner as Reference example 55.

4-(3-{4-[3-(4-cyano-2-methylphenoxy)propyl]-1-piperazinyl}propoxy)-3-methylbenzonitrile $^1$H-NMR (CDCl$_3$) δ: 1.99-2.05 (4H, m), 2.21 (6H, s), 2.40-2.56 (12H, m), 4.07 (4H, t, J=6.3 Hz), 6.85 (2H, d, J=8.4 Hz), 7.40 (2H, brs), 7.47 (2H, dd, J=1.4, 8.4 Hz)

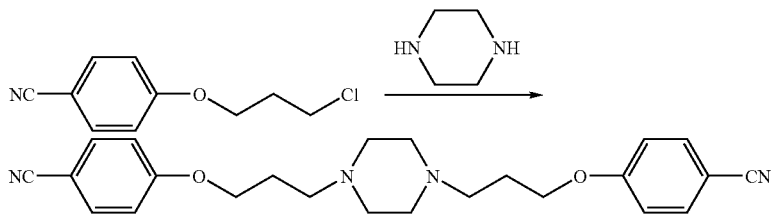

2.98 g of piperazine was dissolved in 14 ml of dimethyl sulfoxide, and then, 24 ml of N,N-diisopropylethylamine and 13.5 g of 4-(3-chloropropoxy)benzonitrile were added thereto at room temperature, followed by stirring at 110° C. for 3 hours. After cooling to room temperature, a precipitate was filtrated with a mixed solvent consisting of methylene chloride and diisopropyl ether to obtain 6.65 g of a solid, 4-(3-{4-[3-(4-cyanophenoxy)propyl]-1-piperazinyl}propoxy)benzonitrile.

$^1$H-NMR (CDCl$_3$) δ: 1.96-2.03 (4H, m), 2.50-2.54 (12H, m), 4.07 (4H, t, J=6.2 Hz), 6.93-6.96 (4H, m), 7.55-7.58 (4H, m)

Reference Example 56

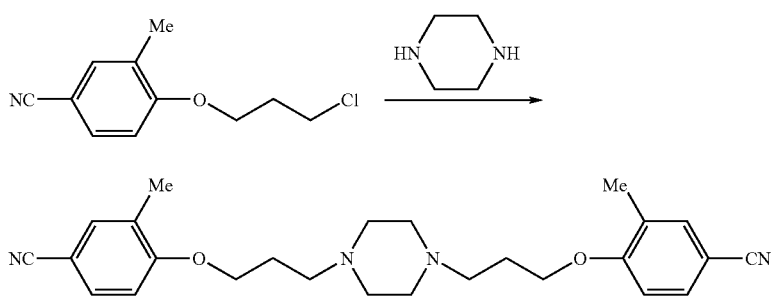

Reference Example 57

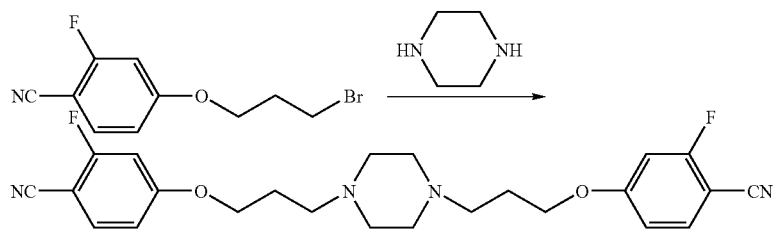

The following compound was obtained in the same manner as Reference example 55.

4-(3-{4-[3-(4-cyano-3-fluorophenoxy)propyl]-1-piperazinyl}propoxy)-2-fluorobenzonitrile $^1$H-NMR (CDCl$_3$) δ: 1.95-2.02 (4H, m), 2.30-2.70 (12H, m), 4.07 (4H, t, J=6.3 Hz), 6.71-6.77 (4H, m), 7.50 (2H, dd, J=7.7, 8.7 Hz)

Reference Example 58

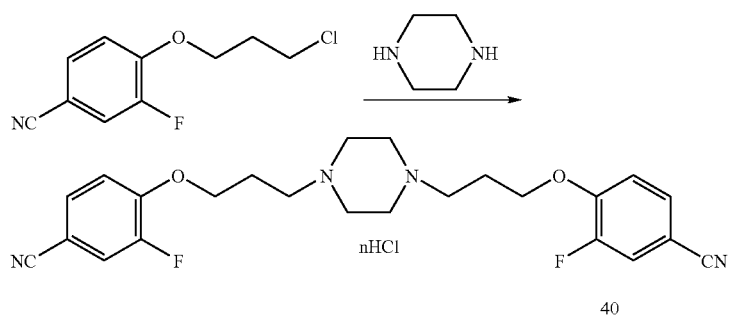

The following compound was obtained in the same manner as Reference example 55.

4-(3-{4-[3-(4-cyano-2-fluorophenoxy)propyl]-1-piperazinyl}propoxy)-3-fluorobenzonitrile Hydrochloride $^1$H-NMR (d$_6$-DMSO) δ: 2.20-2.40 (4H, m), 3.10-4.00 (12H, m), 4.29 (4H, t, J=6.0 Hz), 7.35-7.39 (2H, m), 7.70-7.72 (2H, m), 7.86-7.89 (2H, m)

Reference Example 59

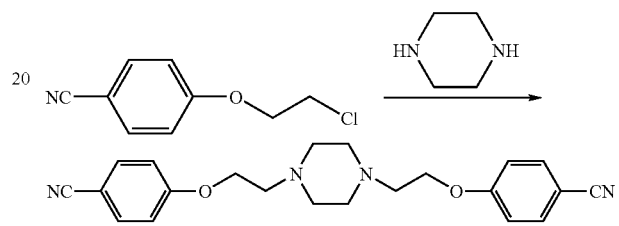

The following compound was obtained in the same manner as Reference example 55.

4-(2-{4-[2-(4-cyanophenoxy)ethyl]-1-piperazinyl}ethoxy)benzonitrile $^1$H-NMR (CDCl$_3$) δ: 2.50-2.70 (8H, m), 2.84 (4H, t, J=5.7 Hz), 4.14 (4H, t, J=5.7 Hz), 6.93-6.97 (4H, m), 7.57-7.60 (4H, m)

Reference Example 60

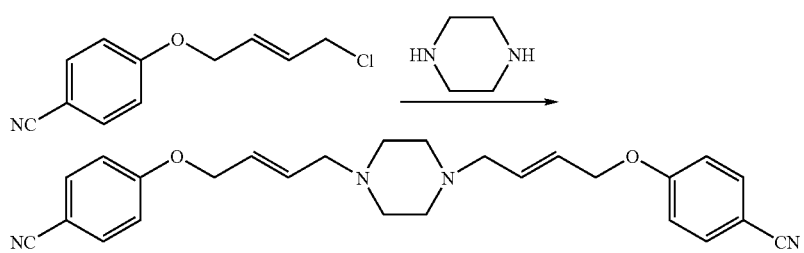

The following compound was obtained in the same manner as Reference example 55.

4-[((E)-4-{4-[(E)-4-(4-cyanophenoxy)-2-butenyl]-1-piperazinyl}-2-butenyl)oxy]benzonitrile ¹H-NMR (CDCl₃) δ: 2.30-2.70 (8H, m), 3.05 (4H, d, J=5.6 Hz), 4.57 (4H, d, J=4.8 Hz), 5.81-5.94 (4H, m), 6.93-6.95 (4H, m), 7.56-7.59 (4H, m)

Reference Example 61

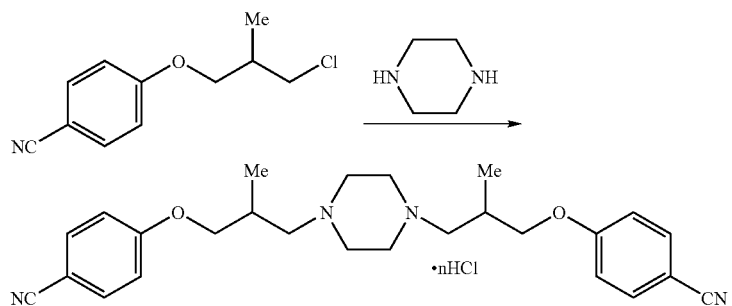

The following compound was obtained in the same manner as Reference example 55.

4-(3-{4-[3-(4-cyanophenoxy)-2-methylpropyl]-1-piperazinyl}-2-methylpropoxy)benzonitrile Hydrochloride ¹H-NMR(CD₃OD) δ: 1.22 (6H, d, J=6.8 Hz), 2.50-2.70 (2H, m), 3.00-3.80 (12H, m), 4.05-4.15 (4H, m), 7.10-7.15 (4H, m), 7.66-7.70 (4H, m)

Reference Example 62

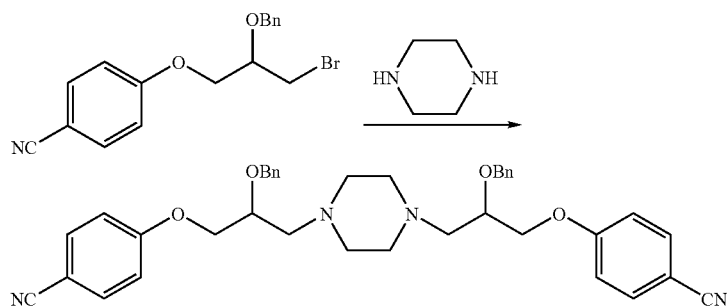

The following compound was obtained in the same manner as Reference example 55.

4-(2-(benzyloxy)-3-{4-[2-(benzyloxy)-3-(4-cyanophenoxy)propyl]-1-piperazinyl}propoxy)benzonitrile ¹H-NMR (CDCl₃) δ: 2.40-2.63 (12H, m), 3.85-3.95 (2H, m), 4.07-4.21 (4H, m), 4.71 (4H, s), 6.94-6.98 (4H, m), 7.27-7.35 (10H, m), 7.55-7.59 (4H, m)

Reference Example 63

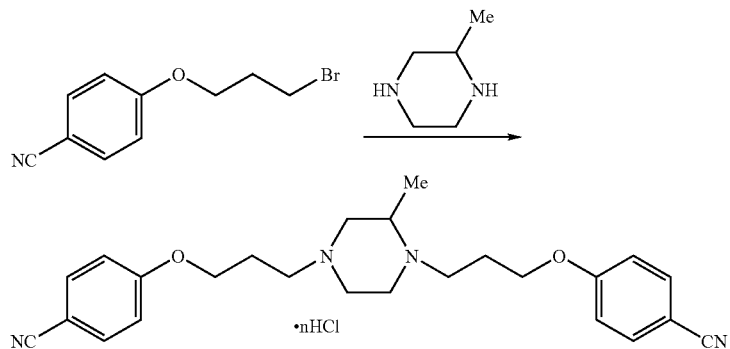

The following compound was obtained in the same manner as Reference example 55.

4-(3-{4-[3-(4-cyanophenoxy)propyl]-2-methyl-1-piperazinyl}propoxy)benzonitrile Hydrochloride $^1$H-NMR (d$_6$-DMSO) δ: 1.30-1.50 (3H, m), 2.00-2.40 (4H, m), 3.10-4.00 (11H, m), 4.10-4.30 (4H, m), 7.11-7.15 (4H, m), 7.79 (4H, d, J=8.4 Hz)

Reference Example 64

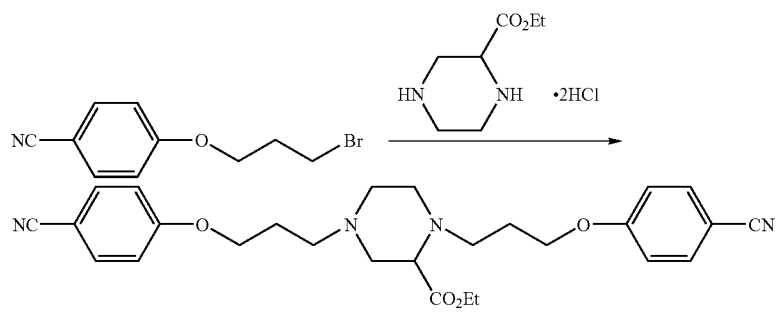

The following compound was obtained in the same manner as Reference example 55.

ethyl 1,4-bis[3-(4-cyanophenoxy)propyl]-2-piperazinecarboxylate $^1$H-NMR (CDCl$_3$) δ: 1.22 (3H, t, J=7.1 Hz), 1.92-2.00 (4H, m), 2.36-2.80 (BH, m), 2.83-2.90 (1H, m), 3.10-3.15 (1H, m), 3.24-3.30 (1H, m), 4.03-4.20 (6H, m), 6.92-6.96 (4H, m), 7.56-7.59 (4H, m)

Reference Example 65

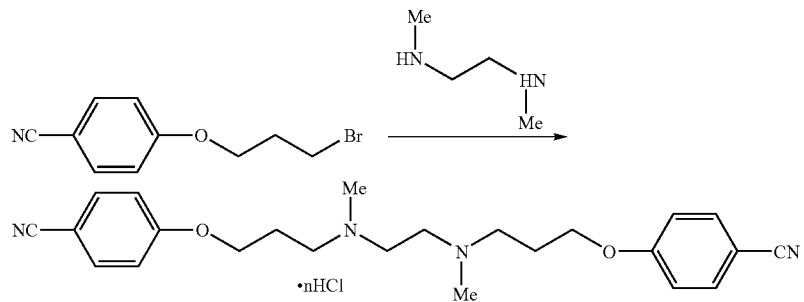

The following compound was obtained in the same manner as Reference example 55.

4-{3-[{2-[[3-(4-cyanophenoxy)propyl](methyl)amino]ethyl}(methyl)amino]propoxy}benzonitrile Hydrochloride $^1$H-NMR (d$_6$-DMSO) δ: 2.23-2.29 (4H, m), 2.85 (6H, s), 3.28-3.70 (8H, m), 4.19 (4H, t, J=6.0 Hz), 7.13 (4H, d, J=8.6 Hz), 7.79 (4H, d, J=8.6 Hz), 11.57 (2H, brs)

Reference Example 66

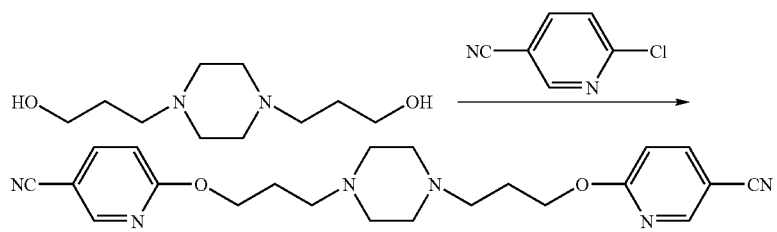

0.40 g of 3-[4-(3-hydroxypropyl)-1-piperazinyl]-1-propanol was suspended in 4.0 ml of N,N-dimethylformamide, and then, 0.16 g of 60% sodium hydride was added thereto, followed by stirring for 1 hour. Thereafter, 0.57 g of 2-chloro-5-cyanopyridine was added thereto, and the mixture was stirred at room temperature for 4 hours. Thereafter, 5 ml of diisopropyl ether and 5 ml of water were added to the reaction solution, and a precipitate was then filtrated to obtain 0.50 g of a solid, 6-[3-(4-{3-[(5-cyano-2-pyridinyl)oxy]propyl}-1-piperazinyl)propoxy]nicotinonitrile.

$^1$H-NMR (CDCl$_3$+CD$_3$OD) δ: 1.90-2.10 (4H, m), 2.50-2.62 (12H, m), 4.42 (4H, t, J=6.4 Hz), 6.85 (2H, dd, J=0.6, 8.8 Hz), 7.83 (2H, dd, J=2.4, 8.8 Hz), 8.48 (2H, dd, J=0.6, 2.4 Hz)

Reference Example 67

Reference Example 67-1

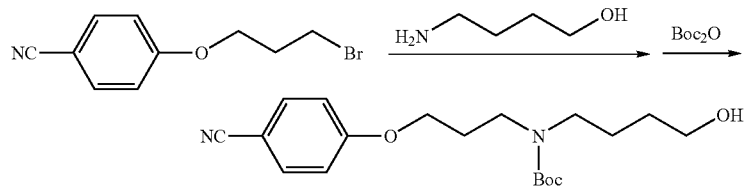

1.00 g of 4-(3-bromopropoxy)benzonitrile was dissolved in 10 ml of N,N-dimethylformamide. 0.73 ml of 4-aminobutyl alcohol and 1.06 g of potassium carbonate were successively added to the obtained solution, and the mixture was stirred at room temperature for 12 hours. Thereafter, a 1 mol/L sodium hydroxide aqueous solution and chloroform were added to the reaction mixture, so that the organic layer was separated. Thereafter, the aqueous layer was extracted twice with chloroform. The separated organic layer was combined, dried over anhydrous magnesium sulfate. The solvent was removed under a reduced pressure. The obtained oil product was dissolved in 10 ml of chloroform, and then, 1.08 ml of triethylamine and 1.68 g of di-tert-butyl dicarbonate were added to the solution, followed by stirring at room temperature for 4 days. The solvent was removed under a reduced pressure. Thereafter, ethyl acetate and water were added to the residue, so that the organic layer was separated. The separated organic layer was washed successively with water and with a saturated aqueous solution of sodium chloride, and then dried over anhydrous magnesium sulfate. Thereafter, the solvent was removed under a reduced pressure. The obtained oil product was purified by silica gel column chromatography [eluent; n-hexane:ethyl acetate=1:1] to obtain 0.63 g of a colorless oil product, tert-butyl 3-(4-cyanophenoxy)propyl(4-hydroxybutyl)carbamate.

$^1$H-NMR (CDCl$_3$)δ: 1.43 (9H, s), 1.53-1.80 (5H, m), 2.00-2.10 (2H, m), 3.10-3.30 (2H, m), 3.38 (2H, t, J=6.8 Hz), 3.60-3.80 (2H, m), 4.02 (2H, t, J=6.1 Hz), 6.90-6.95 (2H, m), 7.55-7.60 (2H, m)

Reference Example 67-2

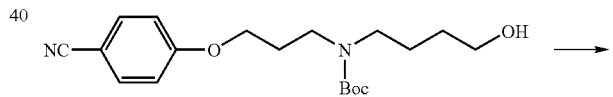

-continued

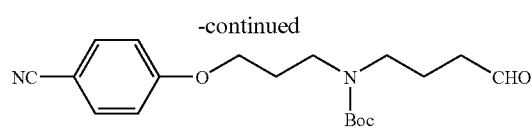

A mixed solution consisting of 0.32 ml of oxalyl chloride and 14 ml of tetrahydrofuran was cooled to −60° C., and 0.35 ml of dimethyl sulfoxide was then added dropwise to the solution. The mixed solution was stirred at −60° C. for 5 minutes, and thereafter, 6 ml of a tetrahydrofuran solution containing 0.63 g of tert-butyl 3-(4-cyanophenoxy)propyl (4-hydroxybutyl)carbamate was added dropwise thereto over 5 minutes. The obtained mixed solution was stirred at −60° C. for 2 hours, and thereafter, 1.77 ml of triethylamine was added dropwise thereto. After the reaction mixture was warmed to room temperature, water and chloroform were added thereto, so that the organic layer was separated. The separated organic layer was washed with a saturated aqueous solution of sodium chloride, and then dried over anhydrous magnesium sulfate. Thereafter, the solvent was removed under a reduced pressure. The obtained oil product was purified by silica gel column chromatography [eluent; n-hexane:ethyl acetate=1:1] to obtain 0.65 g of a colorless oil product, tert-butyl 3-(4-cyanophenoxy)propyl(4-oxobutyl)carbamate.

$^1$H-NMR (CDCl$_3$) δ: 1.56 (9H, s), 1.83-1.90 (2H, m), 1.90-2.10 (2H, m), 2.47 (2H, t, J=6.9 Hz), 3.23 (2H, t, J=6.9 Hz), 3.37 (2H, t, J=6.9 Hz), 4.02 (2H, t, J=6.1 Hz), 6.91-6.95 (2H, m), 7.55-7.60 (2H, m), 9.78 (1H, s)

Reference Example 67-3

0.65 g of tert-butyl 3-(4-cyanophenoxy)propyl(4-oxobutyl)carbamate was dissolved in 10 ml of methylene chloride. While cooled by ice, 15 ml of a methylene chloride solution containing 0.50 g of 4-(3-aminopropoxy)benzonitrile was added to the solution, and thereafter, 0.60 g of triacetoxy sodium borohydride was added thereto. After this reaction mixture was warmed to room temperature, the mixture was stirred for 19.5 hours. The reaction mixture was slowly added to a mixture consisting of a 10% potassium carbonate aqueous solution and chloroform, and the organic layer was separated. The separated organic layer was washed with a saturated aqueous solution of sodium chloride, and then dried over anhydrous magnesium sulfate. The solvent was then removed under a reduced pressure. The obtained oil product was dissolved in 10 ml of chloroform, and then, 0.39 ml of triethylamine and 0.62 g of di-tert-butyl dicarbonate were added to the solution, followed by stirring at room temperature for 3 days. The solvent was removed under a reduced pressure, and the residue was purified by silica gel column chromatography [eluent; n-hexane ethyl acetate=2:1] to obtain 0.90 g of a colorless oil product, tert-butyl 4-{(tert-butoxycarbonyl)[3-(4-cyanophenoxy)propyl]amino}butyl[3-(4-cyanophenoxy)propyl]carbamate.

$^1$H-NMR (CDCl$_3$) δ: 1.42 (18H, s), 1.45-1.55 (4H, m), 1.90-2.10 (4H, m), 3.10-3.30 (4H, m), 3.30-3.50 (4H, m), 4.01 (4H, t, J=6.0 Hz), 6.90-6.95 (4H, m), 7.58 (4H, d, J=8.8 Hz)

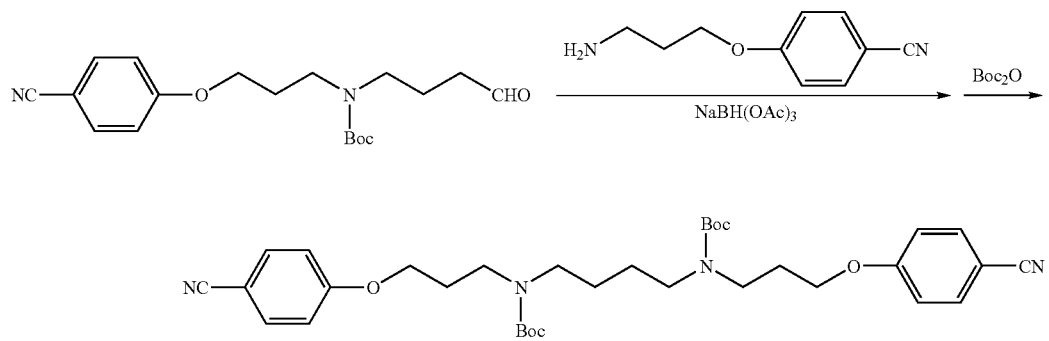

Reference Example 68

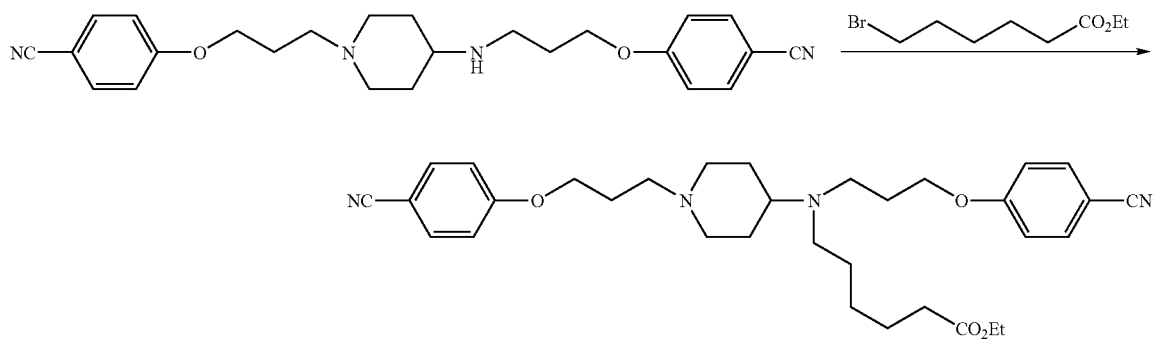

0.50 g of 4-[3-(4-{[3-(4-cyanophenoxy)propyl]amino}-1-piperidinyl)propoxy]benzonitrile was dissolved in 5.0 ml of N,N-dimethylformamide, and then, 0.21 ml of ethyl 6-bromohexanoate and 0.49 g of potassium carbonate were successively added to the solution, followed by stirring at room temperature for 7 days. Ethyl acetate and water were added to the reaction mixture, so that the organic layer was separated. The obtained organic layer was washed with a saturated saline solution, and then dried over anhydrous magnesium sulfate. The resultant solution was then concentrated under a reduced pressure. The obtained oil product was purified by silica gel column chromatography [eluent; chloroform:methanol=40:1] to obtain 0.40 g of a colorless oil product, ethyl 6-([3-(4-cyanophenoxy)propyl]{1-[3-(4-cyanophenoxy)propyl]-4-piperidinyl}amino)hexanoate.

$^1$H-NMR (CDCl$_3$) δ: 1.25 (3H, t, J=7.1 Hz), 1.20-1.66 (10H, m), 1.85-1.99 (6H, m), 2.25 (2H, t, J=7.6 Hz), 2.42-2.49 (5H, m), 2.61 (2H, t, J=6.6 Hz), 2.90-3.10 (2H, m), 4.05 (2H, t, J=6.2 Hz), 4.05 (2H, t, J=6.0 Hz), 4.12 (2H, q, J=7.1 Hz), 6.91-6.96 (4H, m), 7.55-7.60 (4H, m)

Reference Example 69

Reference Example 69-1

1.85 g of 4-[3-(1-piperazinyl)propoxy]benzonitrile was dissolved in 10 ml of N,N-dimethylformamide, and then, 1.77 g of potassium carbonate and 1.79 g of tert-butyl 6-bromohexylcarbamate were successively added thereto, followed by stirring at room temperature for 22 hours. Thereafter, a 1 mol/L sodium hydroxide aqueous solution and chloroform were added to the reaction mixture, so that the organic layer was separated. Thereafter, the aqueous layer was extracted with chloroform. The organic layers were combined, and dried over anhydrous magnesium sulfate. The solvent was then removed under a reduced pressure. The obtained oil product was purified by silica gel column chromatography [eluent; chloroform:methanol=10:1] to obtain 3.46 g of a colorless oil product, tert-butyl 6-{4-[3-(4-cyanophenoxy)propyl]-1-piperazinyl}hexylcarbamate.

$^1$H-NMR (CDCl$_3$) δ: 1.20-1.80 (8H, m), 1.44 (9H, s), 1.96-2.02 (2H, m), 2.32-2.54 (12H, m), 3.00-3.20 (2H, m),

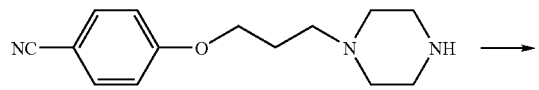

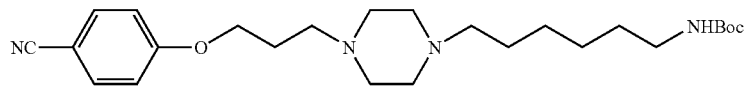

4.06 (2H, t, J=6.3 Hz), 4.50 (1H, brs), 6.92-6.96 (2H, m), 7.55-7.59 (2H, m)

Reference Example 69-2

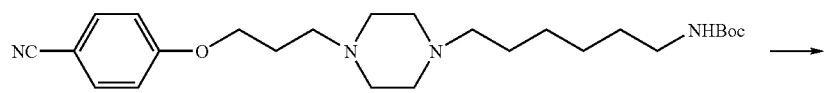

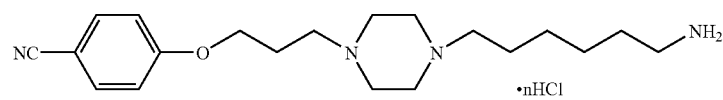

3.46 g of tert-butyl 6-{4-[3-(4-cyanophenoxy)propyl]-1-piperazinyl}hexylcarbamate was dissolved in 30 ml of 6 mol/L hydrochloric acid, and the obtained solution was stirred at room temperature for 12 hours. Thereafter, the solvent was removed under a reduced pressure. The obtained residue was filtrated with ethyl acetate-ethanol to obtain 2.51 g of a solid, 4-{3-[4-(6-aminohexyl)-1-piperazinyl]propoxy}benzonitrile Hydrochloride.

$^1$H-NMR (d$_6$-DMSO) δ: 1.20-1.80 (8H, m), 2.10-2.30 (2H, m), 2.74-2.79 (2H, m), 3.00-3.90 (14H, m), 4.19 (2H, t, J=6.0 Hz), 7.12 (2H, d, J=8.8 Hz), 7.79 (2H, d, J=8.8 Hz), 7.91 (3H, brs)

Reference Example 69-3

Water and chloroform were added to 0.70 g of 4-{3-[4-(6-aminohexyl)-1-piperazinyl]propoxy}benzonitrile Hydrochloride, and the mixture was then adjusted to pH 12.5 with a 5 mol/L sodium hydroxide aqueous solution. The organic layer was separated, and the aqueous layer was then extracted with chloroform 4 times. The organic layers were combined, and dried over anhydrous magnesium sulfate. The solvent was then removed under a reduced pressure. The obtained oil product was dissolved in 10 ml of tetrahydrofuran. Thereafter, 0.21 ml of triethylamine, 0.15 ml of acetic anhydride, and 0.01 g of 4-(dimethylamino) pyridine were successively added to the solution, followed by stirring at room temperature for 16 hours. Water, chloroform, and potassium carbonate were added to the reaction mixture, so that the organic layer was separated. The organic layer was dried over anhydrous magnesium sulfate, and then concentrated under a reduced pressure. The obtained residue was purified by silica gel column chromatography [eluent; chloroform:methanol=10:1] to obtain 0.75 g of a white solid, N-(6-{4-[3-(4-cyanophenoxy)propyl]-1-piperazinyl}hexyl)acetamide.

$^1$H-NMR (CDCl$_3$) δ: 1.20-1.80 (8H, m), 1.97 (3H, s), 1.90-2.10 (2H, m), 2.31-2.60 (12H, m), 3.21-3.26 (2H, m), 4.06 (2H, t, J=6.2 Hz), 5.42 (1H, brs), 6.94 (2H, d, J=9.0 Hz), 7.57 (2H, d, J=9.0 Hz)

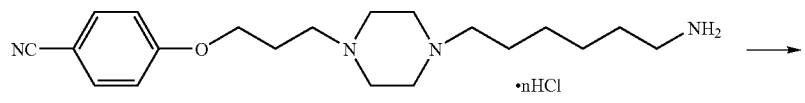

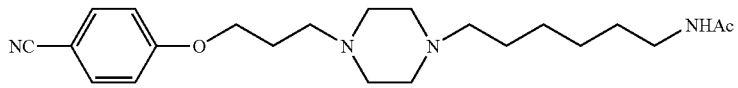

Reference Example 70

Reference Example 70-1

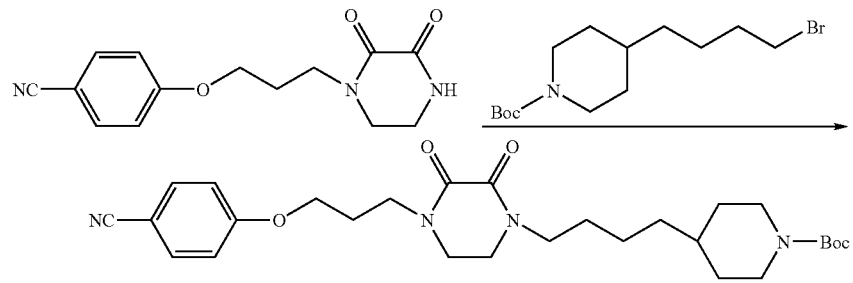

The following compound was obtained in the same manner as Reference example 7.

tert-butyl 4-(4-{4-[3-(4-cyanophenoxy)propyl]-2,3-dioxo-1-piperazinyl}butyl)-1-piperidinecarboxylate $^1$H-NMR (CDCl$_3$) δ: 1.00-1.11 (2H, m), 1.22-1.64 (9H, m), 1.45 (9H, s), 2.14 (2H, quint, J=6.4 Hz), 2.50-2.60 (2H, m), 3.47 (2H, t, J=11.6 Hz), 3.50-3.59 (4H, m), 3.67 (2H, t, J=6.8 Hz), 4.00-4.15 (2H, m), 4.07 (2H, t, J=6.4 Hz), 6.93 (2H, d, J=9.2 Hz), 7.59 (2H, d, J=9.2 Hz)

Reference Example 70-2

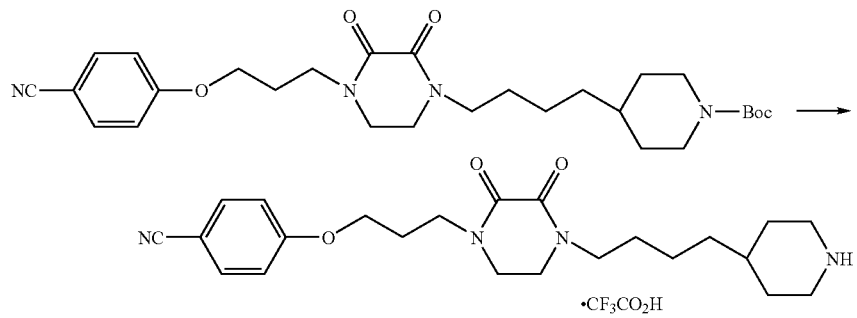

0.42 g of tert-butyl 4-(4-{4-[3-(4-cyanophenoxy)propyl]-2,3-dioxo-1-piperazinyl}butyl)-1-piperidinecarboxylate was dissolved in 8.2 ml of methylene chloride, and then 3.1 ml of trifluoroacetic acid was added thereto under cooling on ice, followed by stirring at room temperature for 2 hours. The reaction mixture was concentrated under a reduced pressure. The obtained residue was purified by silica gel column chromatography [eluent; chloroform:ethanol=5:1] to obtain 0.42 g of a pale yellow amorphous solid, 4-(3-{2,3-dioxo-4-[4-(4-piperidinyl)butyl]-1-piperazinyl}propoxy)benzonitrile trifluoroacetate.

$^1$H-NMR (CDCl$_3$) δ: 1.20-1.90 (11H, m), 2.13 (2H, quint, J=6.4 Hz), 2.77-2.88 (2H, m), 3.35-3.68 (10H, m), 4.07 (2H, t, J=6.0 Hz), 6.94 (2H, d, J=9.0 Hz), 7.58 (2H, d, J=9.0 Hz), 8.90-9.20 (1H, br), 9.30-9.50 (1H, br)

Reference Example 71

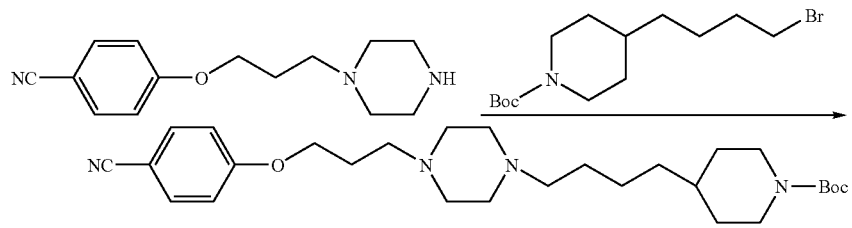

The following compound was obtained in the same manner as Reference example 42.

tert-butyl 4-(4-{4-[3-(4-cyanophenoxy)propyl]-1-piperazinyl}butyl)-1-piperidinecarboxylate $^1$H-NMR (CDCl$_3$) δ: 1.00-1.11 (2H, m), 1.20-1.80 (9H, m), 1.45 (9H, s), 1.94-2.02 (2H, m), 2.28-2.78 (14H, m), 3.96-4.14 (2H, m), 4.06 (2H, t, J=6.3 Hz), 6.90-6.98 (2H, m), 7.56-7.60 (2H, m)

Reference Example 72

Reference Example 72-1

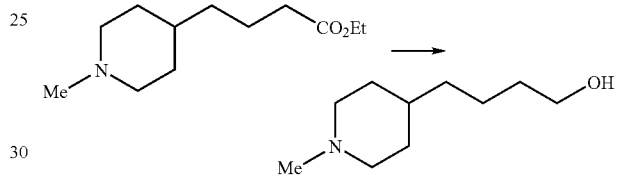

0.80 g of lithium aluminum hydride was suspended in 14 ml of tetrahydrofuran. Thereafter, 28 ml of a tetrahydrofuran solution containing 3.00 g of ethyl 4-(1-methyl-4-piperidinyl)butyrate was added dropwise to the suspension at 10° C. over 45 minutes. The mixture was stirred at the same temperature for 30 minutes, and the reaction mixture was warmed to room temperature, followed by further stirring for 1 hour. Thereafter, 20 ml of a 1 mol/L sodium hydroxide aqueous solution was added to the reaction solution under cooling on ice, and the reaction mixture was filtrated with Celite. The filtrate was concentrated under reduced pressure, and 1 mol/L hydrochloric acid was then added to the obtained residue, so that the residue was adjusted to pH 2. Thereafter, it was washed twice with 20 ml of chloroform. The aqueous layer was adjusted to pH 10.5 with a 1 mol/L sodium hydroxide aqueous solution, and then extracted twice with 40 ml of chloroform. The combined organic layer was dried over anhydrous magnesium sulfate. The solvent was then removed under a reduced pressure to obtain 1.31 g of a colorless oil product, 4-(1-methyl-4-piperidinyl)-1-butanol.

$^1$H-NMR (CDCl$_3$) δ: 1.20-1.28 (5H, m), 1.33-1.41 (2H, m), 1.52-1.59 (2H, m), 1.66-1.69 (2H, m), 1.88 (2H, t, J=11.6 Hz), 1.99 (1H, brs), 2.24 (3H, s), 2.78-2.86 (2H, m), 3.63 (2H, t, J=6.6 Hz)

Reference Example 72-2

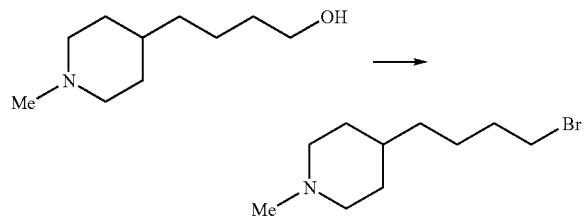

0.38 g of 4-(1-methyl-4-piperidinyl)-1-butanol was dissolved in 16 ml of tetrahydrofuran, and then, 0.57 g of triphenylphosphine and 0.73 g of carbon tetrabromide were successively added thereto under cooling on ice. The mixture was left at room temperature overnight. Thereafter, a precipitate was filtrated, and the filtrate was concentrated under a reduced pressure. 20 ml of diethyl ether and 20 ml of water were added to the obtained residue, and the mixture was adjusted to pH 1 with 1 mol/L hydrochloric acid. Then, aqueous layer was separated. The obtained aqueous layer was adjusted to pH 10.5 with 1 mol/L sodium hydroxide, and then extracted with 20 ml of ethyl acetate. The ethyl acetate layer was dried over anhydrous magnesium sulfate, and then concentrated under a reduced pressure to obtain 0.30 g of a yellow oil product, 4-(4-bromobutyl)-1-methylpiperidine.

$^1$H-NMR (CDCl$_3$) δ: 1.21-1.29 (5H, m), 1.41-1.48 (2H, m), 1.66-1.68 (2H, m), 1.78-1.91 (4H, m), 2.25 (3H, s), 2.83 (2H, d, J=12.0 Hz), 3.41 (2H, t, J=6.4 Hz)

Reference Example 72-3

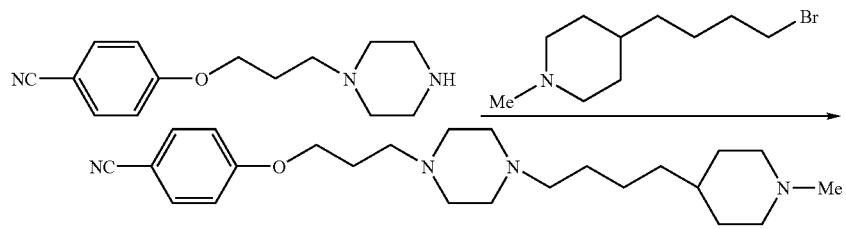

The following compound was obtained in the same manner as Reference example 42.

4-(3-{4-[4-(1-methyl-4-piperidinyl)butyl]-1-piperazinyl}propoxy)benzonitrile $^1$H-NMR (CDCl$_3$) δ: 1.20-1.34 (6H, m), 1.43-1.51 (2H, m), 1.51-1.70 (5H, m), 1.85-1.90 (2H, m), 1.95-2.02 (2H, m), 2.25 (3H, s), 2.30-2.35 (2H, m), 2.40-2.50 (8H, m), 2.83 (2H, d, J=11.6 Hz), 4.06 (2H, t, J=6.4 Hz), 6.94 (2H, d, J=9.2 Hz), 7.57 (2H, d, J=9.2 Hz)

Reference Example 73

Reference Example 73-1

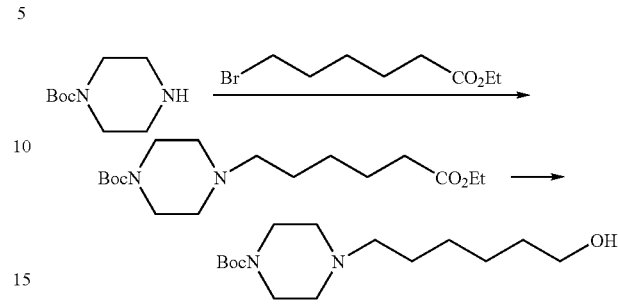

3.00 g of 1-tert-butoxycarbonylpiperazine was dissolved in 30 ml of N,N-dimethylformamide. Thereafter, 6.68 g of potassium carbonate and 2.86 g of ethyl 6-bromohexanoate were successively added to the solution, and the mixture was stirred at room temperature for 16 hours. The reaction mixture was added to a mixed solvent of 30 ml of ethyl acetate and 120 ml of water, so that the organic layer was separated. The separated organic layer was washed with a saturated aqueous solution of sodium chloride, and then dried over anhydrous magnesium sulfate. The resultant product was concentrated under reduced pressure to obtain 5.68 g of tert-butyl 4-(6-ethoxy-6-oxyhexyl)-1-piperazinecarboxylate. 5.68 g of tert-butyl 4-(6-ethoxy-6-oxyhexyl)-1-piperazinecarboxylate was dissolved in tetrahydrofuran. Thereafter, while cooled by ice, 52 ml of a tetrahydrofuran solution containing a 1 mol/L borane-tetrahydrofuran complex was added to the above solution, followed by stirring at room temperature for 24 hours. Thereafter, 11.5 ml of acetone was added dropwise to the reaction mixture under cooling on ice, and 52 ml of 2 mol/L hydrochloric acid was then added thereto. The solvent was removed, until the temperature of the reaction mixture became 80° C. or higher. Thereafter, the mixture was heated to reflux for 4 hours. After cooling to room temperature, chloroform and water were added to the reaction mixture. The obtained mixture was then adjusted to pH 11.0 with a 5 mol/L sodium hydroxide aqueous solution. The organic layer was separated, and then, the aqueous layer was extracted with chloroform 20 times. The obtained organic layer was dried over anhydrous magnesium sulfate, and then concentrated under a reduced pressure. The obtained residue was dissolved in 35 ml of chloroform, and 4.42 g of di-tert-butyl dicarbonate was then added thereto under cooling on ice. The mixture was stirred at room temperature for 15 hours. Thereafter, chloroform, water, and potassium carbonate were added to the reaction mixture, so that the organic layer was separated. The aqueous layer was then extracted with chloroform. The obtained organic layer was combined, and then dried over anhydrous magnesium sulfate. The solvent was removed under reduced pressure. 7.88 g of the obtained oil product was purified by silica gel column chromatography [eluent; chloroform:methanol=10:1] to obtain 3.55 g of a colorless oil product, tert-butyl 4-(6-hydroxyhexyl)-1-piperazinecarbonxylate.

$^1$H-NMR (CDCl$_3$) δ: 1.25-1.70 (6H, m), 1.46 (9H, s), 2.25-2.50 (6H, m), 2.45 (2H, dt, J=1.7, 7.3 Hz), 3.35-3.50 (4H, m), 9.77 (1H, t, J=1.7 Hz)

Reference Example 73-3

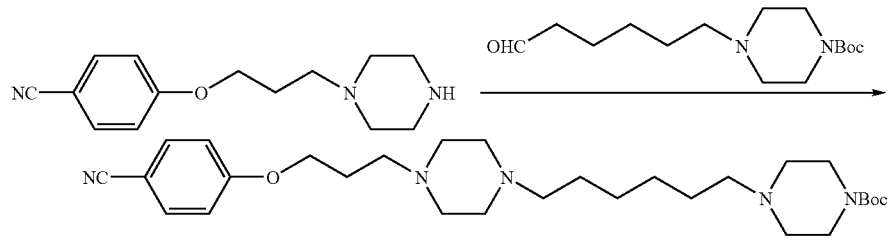

$^1$H-NMR (CDCl$_3$) δ: 1.28-1.70 (9H, m), 1.46 (9H, s), 2.26-2.42 (6H, m), 3.38-3.48 (4H, m), 3.65 (2H, t, J=6.6 Hz)

Reference Example 73-2

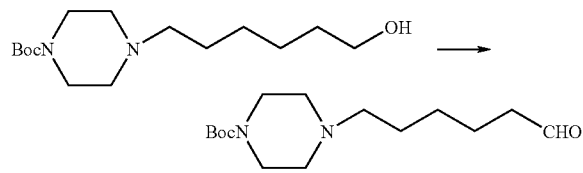

A mixed solution of 1.85 ml of oxalyl chloride and 70 ml of chloroform was cooled to −60° C., and 2.03 ml of dimethyl sulfoxide was added dropwise thereto. The mixture was stirred at −60° C. for 5 minutes, and then, 20 ml of chloroform solution containing 3.05 g of tert-butyl 4-(6-hydroxyhexyl)-1-piperazinecarboxylate was added dropwise thereto over 5 minutes. The obtained mixture was stirred at a temerature ranging from −60° C. to −40° C. for 2 hours, and then, 10.3 ml of triethylamine was added dropwise thereto. The reaction mixture was warmed to room temperature. Thereafter, water and potassium carbonate were added thereto, so that the organic layer was separated. The separated organic layer was washed with saturated aqueous solution of sodium chloride, and then dried over anhydrous magnesium sulfate. The solvent was then removed under a reduced pressure. The obtained oil product was purified by silica gel column chromatography [eluent; chloroform:methanol=20:1] to obtain 3.07 g of a colorless oil product, tert-butyl 4-(6-oxohexyl)-1-piperazinecarboxylate.

0.80 g of tert-butyl 4-(6-oxohexyl)-1-piperazinecarboxylate was dissolved in 10 ml of methylene chloride. While cooled by ice, 20 ml of a methylene chloride solution containing 2.12 g of 4-[3-(1-piperazinyl)propoxy]benzonitrile was added to the solution. Thereafter, 0.89 g of triacetoxy sodium borohydride was added thereto. The reaction mixture was warmed to room temperature, and the mixture was then stirred for 18 hours. The reaction mixure was slowly added to a mixture of 10% potassium carbonate aqueous soltuion and chloroform, so that the organic layer was separated. The separated organic layer was dried over anhydrous magnesium sulfate, and the solvent was then removed under a reduced pressure. Thereafter, the residue was purified by silica gel column chromatography [eluent; n-hexane:ethyl acetate=2:1] to obtain 1.41 g of a colorless oil product, tert-butyl 4-(6-{4-[3-(4-cyanophenoxy)propyl]-1-piperazinyl}hexyl)-1-piperazinecarboxylate.

$^1$H-NMR (CDCl$_3$) δ: 1.25-1.70 (8H, m), 1.46 (9H, s), 1.92-2.04 (2H, m), 2.20-2.70 (18H, m), 3.35-3.50 (4H, m), 4.06 (2H, t, J=6.3 Hz), 6.90-6.98 (4H, m), 7.54-7.62 (4H, m)

Example 1

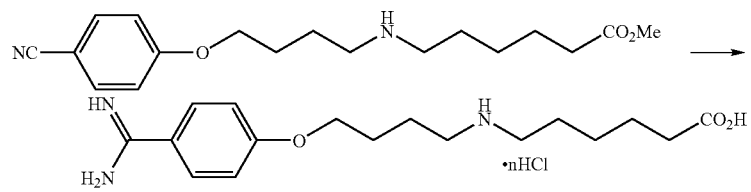

0.65 g of 6-{[4-(4-cyanophenoxy)butyl]amino}hexanoic acid methyl ester was dissolved in 7.0 ml of ethanol. While cooled by ice, hydrogen chloride gas was blown into the solution, followed by stirring at room temperature for 2 days.

After completion of the reaction, the solvent was removed under a reduced pressure. The obtained residue was dissolved in 7.0 ml of ethanol, and 0.38 g of ammonium acetate was added thereto, followed by heating to reflux for 2 hours. After completion of the reaction, the reaction mixture was cooled to room temperature. The solvent was removed under a reduced pressure, and then, 10 ml of ethyl acetate was added to the obtained residue to obtain a solid by filtration.

The obtained solid was dissolved in 6 ml of water, and 2 ml of 6 mol/L hydrochloric acid was added thereto, followed by heating to reflux for 1 hour. After completion of the reaction, the reaction product was cooled to room temperature, and the solvent was removed under a reduced pressure. Isopropanol was added to the obtained residue, and filtration was carried out to obtain 0.34 g of a colorless solid, 6-[(4-{4-[amino(imino)methyl]phenoxy}butyl)amino]hexanoic acid hydrochloride.

IR(KBr)cm$^{-1}$: 3320, 1677, 1611 $^1$H-NMR (d$_6$-DMSO) δ: 1.25-1.40 (2H, m), 1.45-1.58 (2H, m), 1.58-1.69 (2H, m), 1.72-1.90 (4H, m), 2.22 (2H, t, J=7.2 Hz), 2.80-2.99 (4H, m), 4.08-4.25 (2H, m), 7.16 (2H, d, J=8.3 Hz), 7.86 (2H, d, J=8.3 Hz), 8.91 (2H, brs), 9.00 (2H, brs), 9.24 (2H, brs).

Example 2

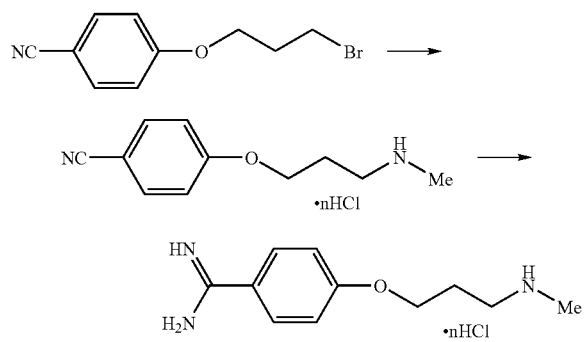

The following compound was obtained in the same manner as Reference example 5 and Example 1.

4-[3-(methylamino)propoxy]benzamidine Hydrochloride

IR(KBr)cm$^{-1}$: 3308, 3164, 2797, 1676, 1610 $^1$H-NMR (d$_6$-DMSO) δ: 2.13-2.21 (2H, m), 2.55 (3H, s), 3.01-3.08 (2H, m), 4.23 (2H, t, J=6.2 Hz), 7.17 (2H, d, J=8.8 Hz), 7.96 (2H, d, J=8.8 Hz), 9.21 (2H, brs), 9.46 (4H, brs)

Example 3

Example 3-1

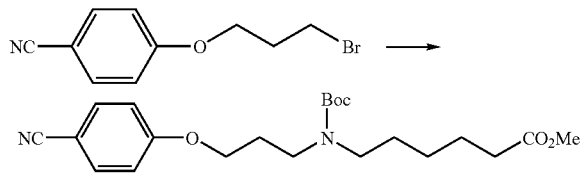

2.3 g of 6-aminohexanoic acid methyl ester hydrochloride was dissolved in 8.4 ml of N,N-dimethylformamide. Thereafter, 1.7 ml of triethylamine and 0.20 g of 4-(3-bromopropoxy)benzonitrile were added to the solution, followed by stirring at 70° C. to 80° C. for 1.2 hours. Thereafter, 0.80 g of 4-(3-bromopropoxy)benzonitrile was added to the reaction solution, followed by stirring at 70° C. to 80° C. for 6 hours. After cooling to room temperature, 20 ml of water and 20 ml of ethyl acetate were added to the reaction solution, so that the organic layer was separated. The aqueous layer was adjusted to pH 9 with a sodium hydroxide aqueous solution. Thereafter, sodium chloride was added thereto until the solution became saturated. Thereafter, it was extracted with 20 ml of ethyl acetate 5 times. The obtained organic layer was combined, and the thus obtained layers were dried over anhydrous magnesium sulfate. The solvent was then removed under a reduced pressure. The obtained residue was purified by silica gel column chromatography [eluent; chloroform:ethanol=20:1], and then, 20 ml of methylene chloride and 20 ml of water were added thereto. Thereafter, 1.00 g of sodium carbonate and 1.1 ml of di-tert-butyl dicarbonate were added to the mixed solution, followed by stirring for 1 hour. After completion of the reaction, the organic layer was separated, and the aqueous layer was extracted twice with 30 ml of chloroform. The obtained organic layer was combined, and 10 ml of water was added thereto. The mixture was then adjusted to pH 2 with 1 mol/L hydrochloric acid. The organic layer was separated, washed with 0.5 mol/L hydrochloric acid and with water, and then dried over anhydrous magnesium sulfate. The solvent was removed under a reduced pressure to obtain 0.96 g of a yellow oil product, methyl 6-{(tert-butoxycarbonyl)[3-(4-cyanophenoxy)propyl]amino}hexanoate.

$^1$H-NMR (CDCl$_3$) δ: 1.24-1.47 (4H, m), 1.53 (9H, s), 1.60-1.72 (2H, m), 1.96-2.09 (2H, m), 2.27-2.37 (2H, m), 3.12-3.40 (4H, m), 3.67 (3H, s), 3.98-4.05 (2H, m), 6.90-6.96 (2H, m), 7.54-7.62 (2H, m)

Example 3-2

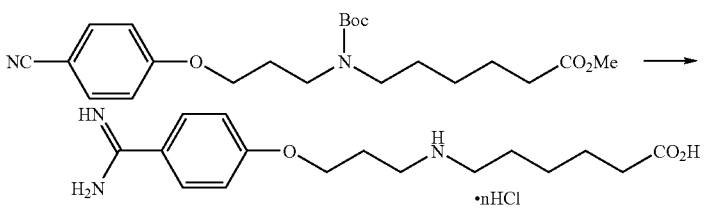

The following compound was obtained in the same manner as Example 1.

6-[(3-{4-[amino(imino)methyl]phenoxy}propyl)amino]hexanoic Acid Hydrochloride

IR(KBr)cm$^{-1}$: 3122, 1700, 1676, 1608 $^1$H-NMR (d$_6$-DMSO) δ: 1.25-1.40 (2H, m), 1.45-1.60 (2H, m), 1.60-1.72 (2H, m), 2.12-2.26 (4H, m), 2.86 (2H, brs), 3.02 (2H, brs), 4.22 (2H, t, J=6.1 Hz), 7.16 (2H, d, J=8.9 Hz), 7.91 (2H, d, J=8.9 Hz), 9.1-9.4 (6H, m), 12.1 (1H, brs)

Example 4

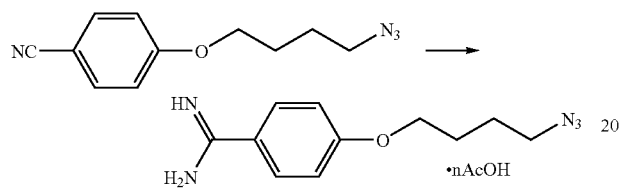

0.70 g of 4-(4-azidobutoxy)benzonitrile was dissolved in 7.0 ml of ethanol, and while cooling on ice, hydrogen chloride gas was blown into the solution. The solution was stirred at room temperature for 12 hours, and the solvent was then removed under a reduced pressure. The obtained residue was suspended in 7.0 ml of ethanol, and 0.57 g of ammonium acetate was added thereto, followed by heating to reflux for 3 hours. Thereafter, the reaction solution was cooled to room temperature, and the solvent was then removed under a reduced pressure. 10 ml of ethyl acetate was added to the obtained residue, and filtration was carried out to obtain 0.95 g of a white solid, 4-(4-azidobutoxy)benzamidine acetate.

IR(KBr)cm$^{-1}$: 3252, 2957, 2096, 1700, 1612 $^1$H-NMR (d$_6$-DMSO) δ: 1.60-1.90 (7H, m), 3.42 (2H, t, J=6.7 Hz), 4.12 (2H, t, J=6.2 Hz), 7.15 (2H, d, J=8.8 Hz), 7.3 (3H, brs), 7.84 (2H, d, J=8.8 Hz)

Example 5

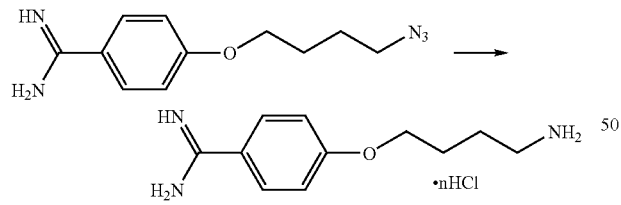

0.48 g of 4-(4-azidobutoxy)benzamidine was dissolved in 5.0 ml of methanol, and 0.08 g of 5% palladium-carbon was then added thereto, followed by stirring under a hydrogen atmosphere at ambient temperature under atmospheric pressure for 7.5 hours. After completion of the reaction, the catalyst was removed by filtration, and the solvent was removed under a reduced pressure. The obtained residue was dissolved in 10 ml of ethanol, and a 10 mol/L hydrogen chloride ethanol solution was then added to the solution. The solvent was then removed under a reduced pressure. The obtained residue was recrystallized with isopropanol to obtain 0.20 g of 4-(4-aminobutoxy)benzamidine hydrochloride:

IR(KBr)cm$^{-1}$: 3043, 1668, 1608 $^1$H-NMR (d$_6$-DMSO) δ: 1.65-1.86 (4H, m), 2.84 (2H, t, J=7.3 Hz), 4.11 (2H, t, J=6.1 Hz), 7.16 (2H, d, J=9.0 Hz), 7.8 (3H, brs), 7.87 (2H, d, J=9.0 Hz), 9.0 (1H, brs), 9.3 (2H, brs)

Example 6

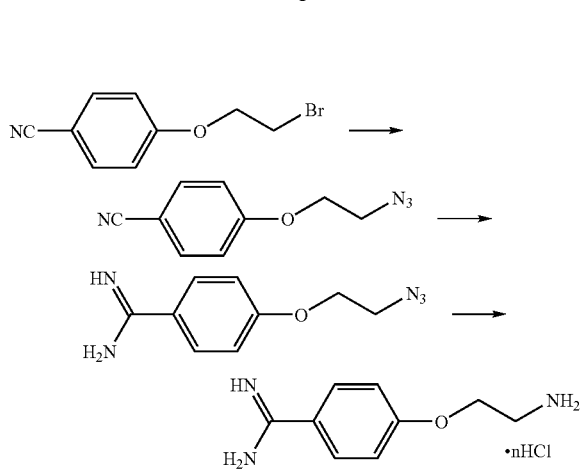

The following compound was obtained in the same manner as Reference example 6 and Examples 4 and 5.

4-(2-aminoethoxy)benzamidine Hydrochloride

IR(KBr)cm$^{-1}$: 3121, 1669, 1611 $^1$H-NMR (d$_6$-DMSO) δ: 3.23 (2H, t, J=5.1 Hz), 4.32 (2H, t, J=5.1 Hz), 7.17-7.23 (2H, m), 7.46 (7H, brs), 7.85-7.92 (2H, m)

Example 7

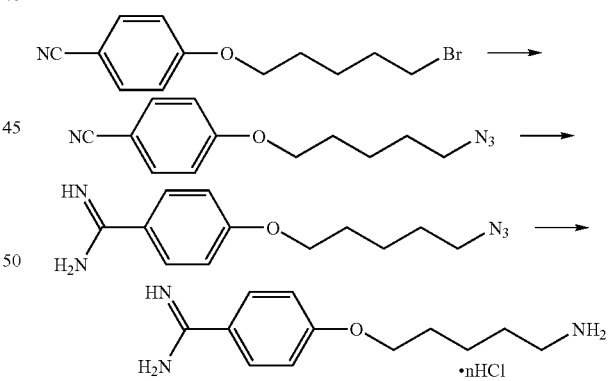

The following compound was obtained in the same manner as Reference example 6 and Examples 4 and 5.

4-[(5-aminopentyl)oxy]benzamidine Hydrochloride

IR(KBr)cm$^{-1}$: 3353, 1676, 1610 $^1$H-NMR (d$_6$-DMSO) δ: 1.41-1.52 (2H, m), 1.59-1.69 (2H, m), 1.69-1.80 (2H, m), 2.78 (2H, brs), 4.09 (2H, t, J=6.3 Hz), 7.15 (2H, d, J=9.1 Hz), 7.86 (2H, d, J=9.1 Hz), 7.98 (2H, brs), 8.99 (2H, brs), 9.23 (2H, brs)

Example 8

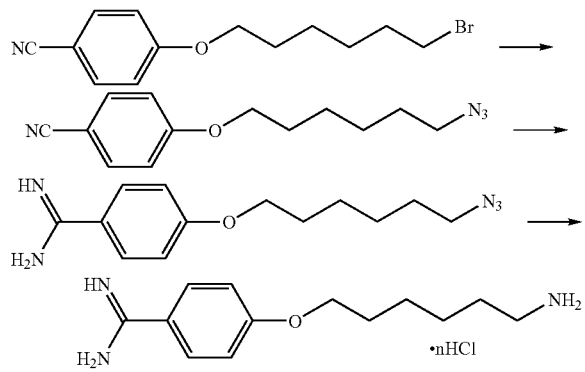

The following compound was obtained in the same manner as Reference example 6 and Examples 4 and 5.

4-[(6-aminohexyl)oxy]benzamidine Hydrochloride

IR(KBr)cm$^{-1}$: 3039, 1677, 1609 $^1$H-NMR (d$_6$-DMSO) δ: 1.41 (4H, brs), 1.58-1.66 (2H, m), 1.69-1.78 (2H, m), 2.73-2.81 (2H, m), 4.10 (2H, t, J=5.6 Hz), 7.15 (2H, d, J=8.4 Hz), 7.94 (2H, d, J=8.4 Hz), 8.24 (2H, brs), 9.00-9.30 (3H, brm), 9.43 (2H, brs)

Example 9

Example 9-1

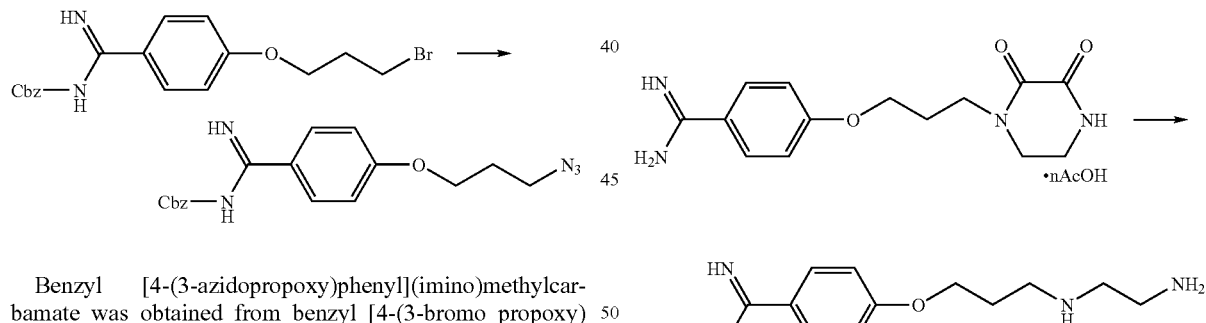

Benzyl [4-(3-azidopropoxy)phenyl](imino)methylcarbamate was obtained from benzyl [4-(3-bromo propoxy)phenyl](imino)methylcarbamate in the same manner as Reference example 6.

$^1$H-NMR (CDCl$_3$) δ: 2.00-2.10 (2H, m), 3.52 (2H, t, J=6.4 Hz), 4.09 (2H, t, J=6.0 Hz), 4.50-4.90 (1H, br), 5.21 (2H, s), 6.44 (1H, brs), 6.90-6.95 (2H, m), 7.25-7.50 (5H, m), 7.80-7.90 (2H, m)

Example 9-2

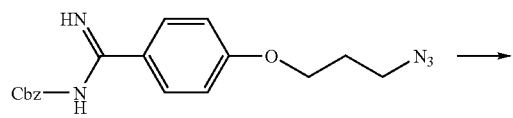

0.51 g of benzyl [4-(3-azidopropoxy)phenyl](imino)methylcarbamate was dissolved in 16 ml of N,N-dimethylformamide. Thereafter, 0.26 g of 5% palladium-carbon suspended in 12 ml of N,N-dimethylformamide was added to the above solution, and the obtained mixture was stirred under a hydrogen atmosphere at room temperature under atmospheric pressure for 3.5 hours. 3.5 hours later, 0.4 ml of 6 mol/L hydrochloric acid was added to the reaction mixture, and the mixture was stirred under a hydrogen atmosphere at room temperature for 1.8 hours, and then at 40° C. to 45° C. for 1.8 hours. After completion of the reaction, the catalyst was removed by filtration, and the solvent was removed under a reduced pressure. 6 mol/L hydrochloric acid was added to the obtained residue, and the solvent was then removed under a reduced pressure. Isopropanol was added to the obtained residue, and thereafter, a precipitate was filtrated to obtain 0.12 g of 4-(3-aminopropoxy)benzamidine Hydrochloride.

IR(KBr)cm$^{-1}$: 3346, 3100, 1668, 1609 $^1$H-NMR (d$_6$-DMSO) δ: 2.04-2.12 (2H, m), 2.90-3.00 (2H, brm), 4.21 (2H, t, J=6.2 Hz), 7.17 (2H, d, J=8.9 Hz), 7.89 (2H, d, J=8.9 Hz), 8.24 (3H, brs), 9.11 (2H, brs), 9.31 (2H, brs)

Example 10

0.20 g of 4-[3-(2,3-dioxo-1-piperazinyl)propoxy]benzamidine acetate was dissolved in 5.0 ml of 6 mol/L hydrochloric acid, followed by heating to reflux for 1 hour. The solvent was then removed under a reduced pressure. The obtained residue was filtrated with ethanol to obtain 0.14 g of a colorless solid, 4-{3-[(2-aminoethyl)amino]propoxy}benzamidine hydrochloride.

IR(KBr)cm$^{-1}$: 3368, 2716, 1674, 1608 $^1$H-NMR (d$_6$-DMSO) δ: 2.10-2.21 (2H, m), 3.12 (2H, t, J=6.8 Hz), 3.25 (4H, s), 4.25 (2H, t, J=6.0 Hz), 7.18 (2H, d, J=8.8 Hz), 7.91 (2H, d, J=8.8 Hz), 8.63 (2H, brs), 9.18 (2H, brs), 9.36 (2H, brs), 9.98 (2H, brs)

Example 11

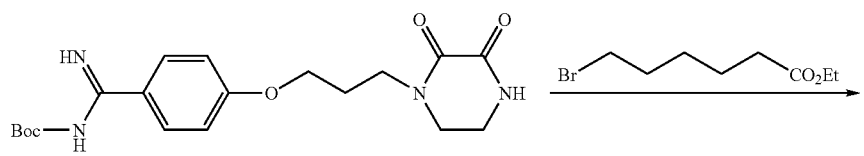

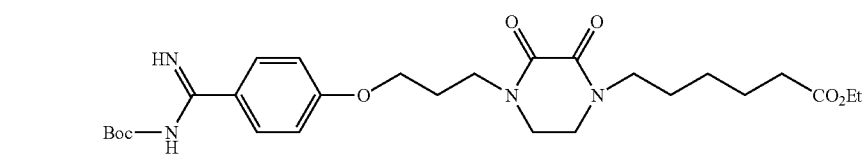

0.30 g of tert-butyl {4-[3-(2,3-dioxo-1-piperazinyl)propoxy]phenyl}(imino)methylcarbamate was dissolved in 3.9 ml of N,N-dimethylformamide, and while cooled by ice, 31 mg of 60% sodium hydride was added to the solution, followed by stirring at room temperature for 30 minutes. Subsequently, 0.12 ml of 6-bromohexanoic acid ethyl ester was added dropwise to the reaction mixture, followed by stirring at room temperature for 2 hours. 20 ml of ice and 20 ml of ethyl acetate were added to the reaction mixture. The mixture was adjusted to pH 5 with 1 mol/L hydrochloric acid, and the aqueous layer was separated. The obtained aqueous layer was adjusted to pH 10.5 with a 1 mol/L sodium hydroxide aqueous solution, and then extracted with 50 ml of ethyl acetate. The obtained organic layer was washed with a saturated aqueous solution of sodium chloride, and then dried over anhydrous magnesium sulfate. The solvent was removed under a reduced pressure. Toluene and diisopropyl ether were added to the obtained residue, and filtration was carried out to obtain 0.10 g of a white solid, 6-[4-(3-{4-[[(tert-butoxycarbonyl)amino](imino)methyl]phenoxy}propyl)-2,3-dioxo-1-piperazinyl]hexanoic acid ethyl ester.

IR(KBr)cm$^{-1}$: 3374, 1734, 1692, 1616 $^1$H-NMR (CDCl$_3$) δ: 1.25 (3H, t, J=7.1 Hz), 1.30-1.40 (2H, m), 1.55 (9H, s), 1.55-1.70 (4H, m), 2.10-2.20 (2H, m), 2.29 (2H, t, J=7.4 Hz), 3.40-3.60 (6H, m), 3.67 (2H, t, J=6.9 Hz), 4.06 (2H, t, J=6.0 Hz), 4.11 (2H, q, J=7.1 Hz), 6.90 (2H, d, J=8.8 Hz), 7.84 (2H, d, J=8.8 Hz)

Example 12

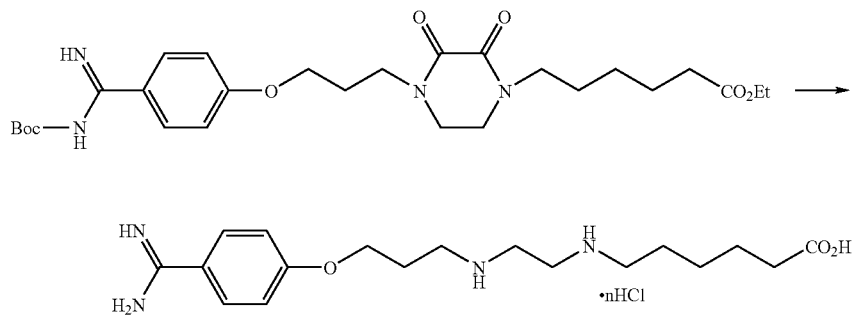

95 mg of 6-[4-(3-{4-[[(tert-butoxycarbonyl)amino](imino)methyl]phenoxy}propyl)-2,3-dioxo-1-piperazinyl] hexanoic acid ethyl ester was dissolved in 1.8 ml of 6 mol/L hydrochloric acid, followed by heating to reflux for 5 hours. After completion of the reaction, 6 mol/L hydrochloric acid was removed under a reduced pressure. Ethanol was added to the obtained residue, and filtration was carried out to obtain 73 mg of a white solid, 6-({2-[(3-{4-[amino(imino)methyl]phenoxy}propyl)amino]ethyl}amino)hexanoic acid hydrochloride.

IR(KBr)cm$^{-1}$: 3369, 2749, 1718, 1670, 1610 $^1$H-NMR (D$_2$O) δ: 1.2-1.3 (2H, m), 1.4-1.7 (4H, m), 2.0-2.3 (4H, m), 2.9-3.1 (2H, m), 3.1-3.4 (6H, m), 4.0-4.2 (2H, m), 6.9-7.1 (2H, m), 7.6-7.7 (2H, m)

Example 13

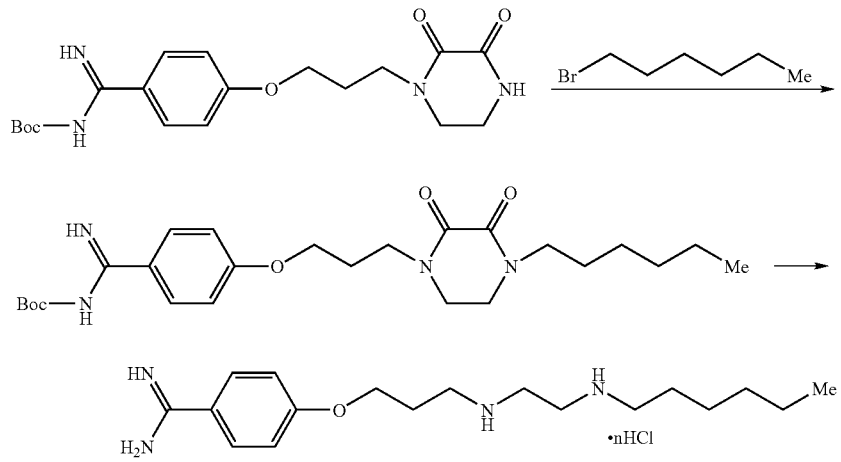

The following compound was obtained in the same manner as Examples 11 and 12.

4-(3-{[2-(hexylamino)ethyl]amino}propoxy)benzamidine Hydrochloride

IR(KBr)cm$^{-1}$: 2772, 1676, 1610 $^1$H-NMR (d$_6$-DMSO) δ: 0.88 (3H, t, J=6.6 Hz), 1.2-1.4 (6H, m), 1.6-1.7 (2H, m), 2.1-2.2 (2H, m), 2.8-3.0 (2H, m), 3.0-3.2 (2H, m), 3.2-3.4 (4H, m), 3.5 (2H, brs), 4.2-4.3 (2H, m), 7.17 (2H, d, J=7.8 Hz), 7.87 (2H, d, J=7.8 Hz), 9.16 (2H, brs), 9.25 (2H, brs)

Example 14

Example 14-1

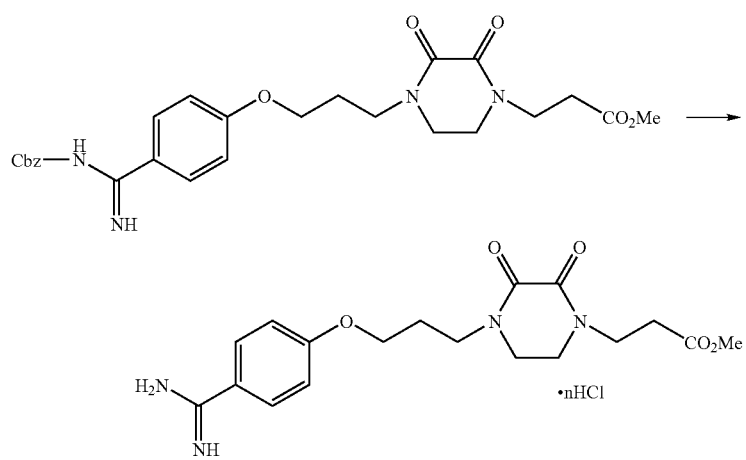

1.74 g of methyl 3-[4-(3-{4-[{[(benzyloxy)carbonyl]amino}(imino)methyl]phenoxy}propyl)-2,3-dioxo-1-piperazinyl]propanoate was dissolved in 10 ml of N,N-dimethylformamide. Thereafter, 0.52 g of 5% palladium-carbon suspended in 7.4 ml of N,N-dimethylformamide and 0.85 ml of 6 mol/L hydrochloric acid were added to the solution, followed by stirring under a hydrogen atmosphere at room temperature under atmospheric pressure for 2 hours. After completion of the reaction, the catalyst was removed by filtration, and the residue was washed with 20 ml of N,N-dimethylformamide. The filtrate was then concentrated under a reduced pressure. 20 ml of xylene was added to the obtained residue, and the mixture was further concentrated under a reduced pressure to obtain 1.37 g of methyl 3-[4-(3-{4-[amino(imino)methyl]phenoxy}propyl)-2,3-dioxo-1-piperazinyl]propanoate hydrochloride.

$^1$H-NMR (d$_6$-DMSO) δ: 1.95-2.05 (2H, m), 2.61 (2H, t, J=6.8 Hz), 3.50-3.58 (8H, m), 3.60 (3H, s), 4.12 (2H, t, J=6.0 Hz), 7.14 (2H, d, J=8.8 Hz), 7.88 (2H, d, J=8.8 Hz), 9.14 (2H, brs), 9.31 (2H, brs)

Example 14-2

The following compound was obtained in the same manner as Example 12.

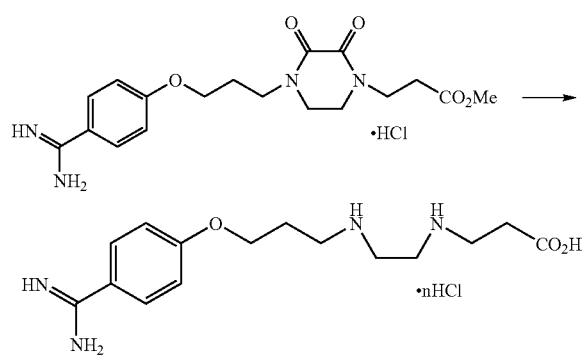

N-{2-[(3-{4-[amino(imino)methyl]phenoxy}propyl)amino]ethyl}-β-alanine hydrochloride IR(KBr)cm$^{-1}$: 3377, 3237, 2763, 1724, 1684, 1609
$^1$H-NMR (d$_6$-DMSO) δ: 2.10-2.20 (2H, m), 2.71 (2H, t, J 7.2 Hz), 3.09-3.18 (4H, m), 3.29 (4H, brs), 3.30-3.60 (4H, m), 4.22 (2H, t, J=6.0 Hz), 7.17 (2H, d, J=8.8 Hz), 7.85 (2H, d, J=8.8 Hz), 8.90 (2H, brs), 9.21 (2H, brs)

Example 15

Example 15-1

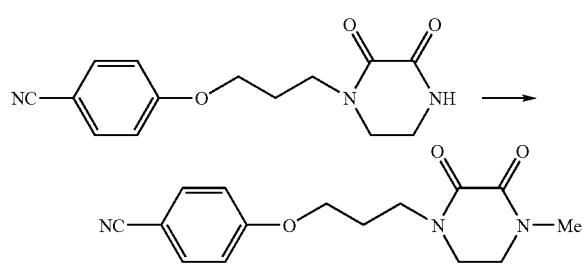

1.80 g of 4-[3-(2,3-dioxo-1-piperazinyl)propoxy]benzonitrile was dissolved in 33 ml of N,N-dimethylformamide, and while cooled by ice, 0.26 g of 60% sodium hydride was added to the solution, followed by stirring for 1 hour. Subsequently, 0.41 ml of methyl iodide was added to the reaction mixture, and then, 1.5 hours later, 0.41 ml of methyl iodide was further added thereto, followed by stirring at room temperature. After completion of the reaction, the reaction mixture was added to a mixed solution of ice water and chloroform, and the obtained mixture was then adjusted to pH 7.2 with hydrochloric acid. Thereafter, the organic layer was separated. The aqueous layer was extracted twice with 20 ml of chloroform, and the obtained organic layer was combined. The thus obtained layer was washed with a saturated aqueous solution of sodium chloride, and then dried over anhydrous magnesium sulfate. The obtained solution was then concentrated under a reduced pressure. The obtained residue was purified by silica gel column chromatography [eluent; chloroform:methanol=20:1] to obtain 1.48 g of a white solid, 4-[3-(4-methyl-2,3-dioxo-1-piperazinyl)propoxy]benzonitrile.

$^1$H-NMR (CDCl$_3$) δ: 2.10-2.18 (2H, m), 3.09 (3H, s), 3.56-3.63 (4H, m), 3.67 (2H, t, J=6.8 Hz), 4.07 (2H, t, J=6.4 Hz), 6.92-6.96 (2H, m), 7.56-7.60 (2H, m)

Example 15-2

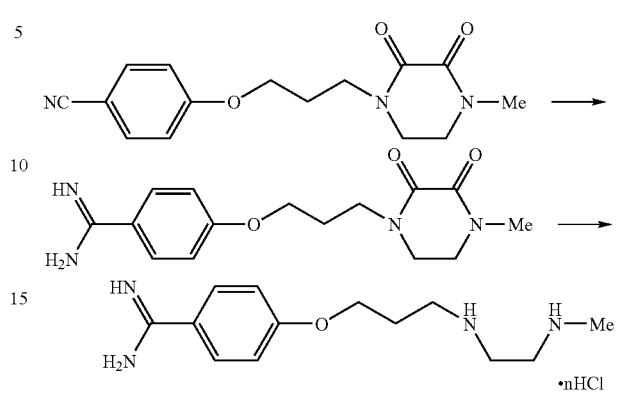

10 ml of ethanol and 2.5 ml of methylene chloride were added to 1.44 g of 4-[3-(4-methyl-2,3-dioxo-1-piperazinyl)propoxy]benzonitrile. While cooled by ice, hydrogen chloride gas was introduced into the mixture until it became saturated. It was left at rest at room temperature for 22.5 hours. After completion of the reaction, the solvent was removed under a reduced pressure. 10 ml of ethanol and 2.5 ml of methylene chloride were added to the obtained residue, and 0.97 g of ammonium acetate was then added thereto, followed by heating to reflux. After completion of the reaction, the temperature was cooled to room temperature, and the reaction solution was then concentrated under a reduced pressure. The obtained residue was filtrated with ethanol to obtain a white solid. 10 ml of 6 mol/L hydrochloric acid was added to the obtained white solid, and the mixture was subject to heating to reflux for 6 hours. The reaction mixture was concentrated under a reduced pressure, and the obtained white solid was filtrated with ethanol to obtain 1.26 g of 4-(3-{[2-(methylamino)ethyl]amino}propoxy)benzamidine hydrochloride.

IR(KBr)cm$^{-1}$: 2722, 1669, 1610 $^1$H-NMR (d$_6$-DMSO+D$_2$O) δ: 2.14-2.21 (2H, m), 2.68 (3H, s), 3.22 (2H, t, J=7.6 Hz), 3.30-3.37 (4H, m), 4.19-4.23 (2H, m), 7.19 (2H, d, J=8.8 Hz), 7.82 (2H, d, J=8.8 Hz)

Example 16

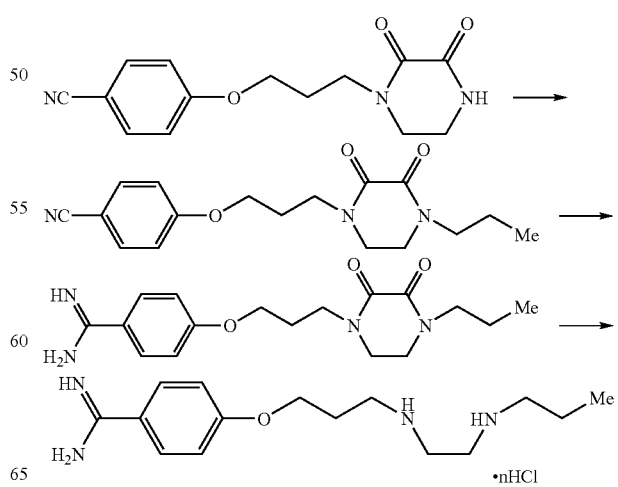

The following compound was obtained in the same manner as Example 15.

4-(3-{[2-(propylamino)ethyl]amino}propoxy)benzamidine Hydrochloride

IR(KBr)cm$^{-1}$: 3318, 2771, 1673, 1609 $^1$H-NMR (d$_6$-DMSO) δ: 0.94 (3H, t, J=7.0 Hz), 1.6-1.8 (2H, m), 2.18 (2H, brs), 2.90 (2H, brs), 3.13 (2H, brs), 3.34 (4H, brs), 4.25 (2H, brs), 7.1-7.7 (2H, m), 7.18 (2H, d, J=6.8 Hz), 7.89 (2H, d, J=6.8 Hz), 9.19 (2H, brs), 9.30 (2H, brs)

Example 17

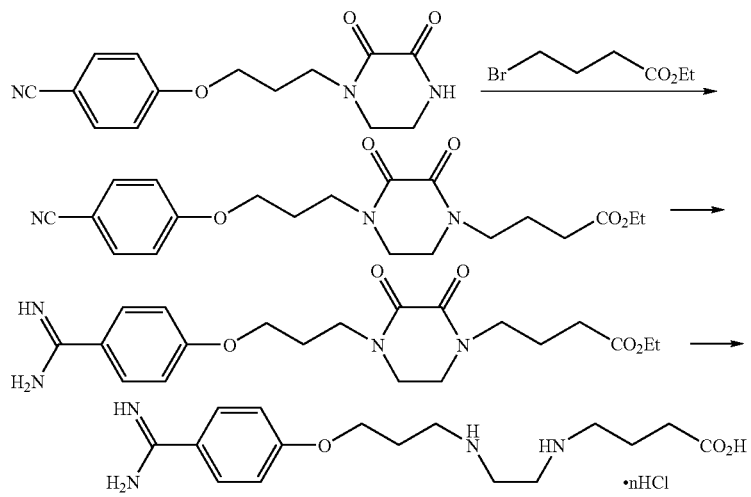

The following compound was obtained in the same manner as Example 15.

4-({2-[(3-{4-[amino(imino)methyl]phenoxy}propyl)amino]ethyl}amino)butyric Acid Hydrochloride IR(KBr)cm$^{-1}$: 3418, 2770, 1718, 1670, 1609 $^1$H-NMR (d$_6$-DMSO-D$_2$O) δ: 1.8-1.9 (2H, m), 2.1-2.2 (2H, m), 2.39 (2H, t, J=7.4 Hz), 3.00 (2H, t, J=7.6 Hz), 3.17 (2H, t, J=7.6 Hz), 3.30 (4H, s), 4.21 (2H, t, J=5.8 Hz), 7.17 (2H, d, J=9.0 Hz), 7.83 (2H, d, J=9.0 Hz)

Example 18

2.16 g of 4-(3-{4-[3-(4-cyanophenoxy)propyl]-2,3-dioxo-1-piperazinyl}propoxy)benzonitrile was suspended in 50.0 ml of ethanol. While cooled by ice, hydrogen chloride gas was blown into the suspension, followed by stirring at room temperature for 12 hours. After completion of the reaction, the solvent was removed under a reduced pressure to obtain 2.95 g of a pale yellow solid, ethyl 4-{3-[4-(3-{4-[ethoxy(imino)methyl]phenoxy}propyl)-2,3-dioxo-1-piperazinyl]propoxy}benzenecarboximidoate hydrochloride.

IR(KBr)cm$^{-1}$: 3393, 2875, 1684, 1608. $^1$H-NMR (d$_6$-DMSO) δ: 1.47 (6H, t, J=7.0 Hz), 1.95-2.05 (4H, m), 3.46-3.62 (8H, m), 4.15 (4H, t, J=6.0 Hz), 4.61 (4H, q, J=7.0 Hz), 7.16 (4H, d, J=9.0 Hz), 8.16 (4H, d, J=9.0 Hz), 11.22 (1H, brs), 11.96 (1H, brs)

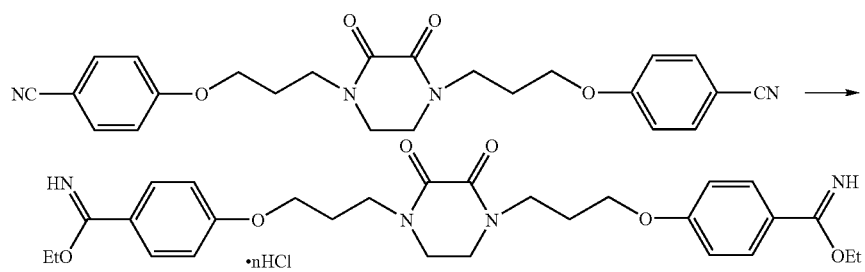

Example 19

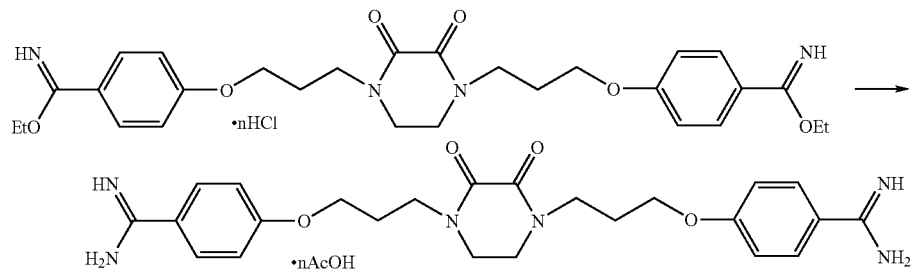

2.69 g of ethyl 4-{3-[4-(3-{4-[ethoxy(imino)methyl]phenoxy}propyl)-2,3-dioxo-1-piperazinyl]propoxy}benzenecarboximidoate hydrochloride was suspended in 45.0 ml of ethanol, and then, 1.60 g of ammonium acetate was added to the suspension. The mixture was subject to heating to reflux for 3 hours. The reaction mixture was cooled to room temperature, and a precipitate was filtrated to obtain 2.51 g of a colorless solid, 4-{3-[4-(3-{4-[amino(imino)methyl]phenoxy}propyl)-2,3-dioxo-1-piperazinyl]propoxy}benzamidine acetate.

IR(KBr)cm$^{-1}$: 3117, 1670, 1609 $^1$H-NMR(CD$_3$OD) δ: 1.90 (3H, s), 2.10-2.20 (4H, m), 3.64-3.76 (8H, m), 4.16 (4H, t, J=5.9 Hz), 7.10-7.20 (4H, m), 7.75-7.80 (4H, m)

The following compound was obtained in the same manner as Reference example 7 and Examples 18 and 19.

4-{2-[4-(2-{4-[amino(imino)methyl]phenoxy}ethyl)-2,3-dioxo-1-piperazinyl]ethoxy}benzamidine Acetate IR(KBr)cm$^{-1}$: 3203, 1674, 1612 $^1$H-NMR (d$_6$-DMSO) δ: 1.89 (6H, s), 3.67 (4H, s), 3.76 (4H, t, J=4.8 Hz), 4.26 (4H, t, J=4.8 Hz), 7.16 (4H, d, J=8.8 Hz), 7.81 (4H, d, J=8.8 Hz)

Example 20

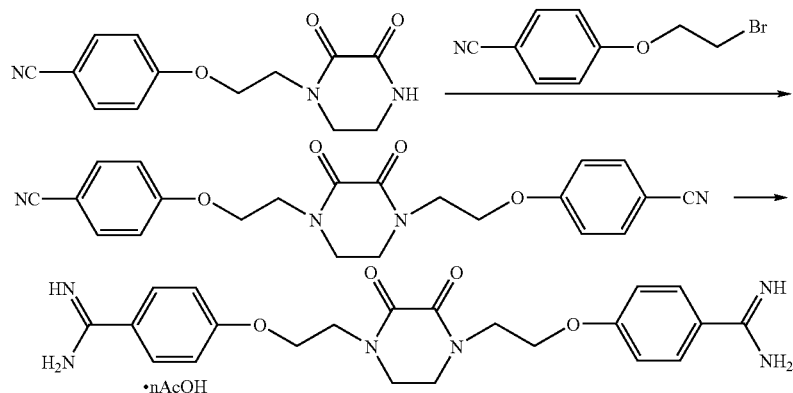

Example 21

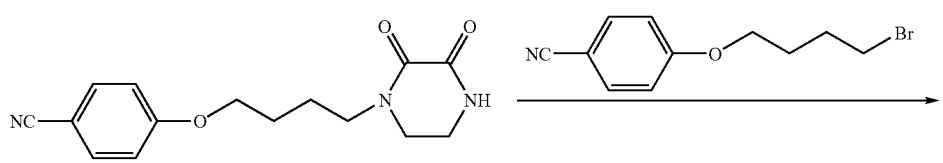

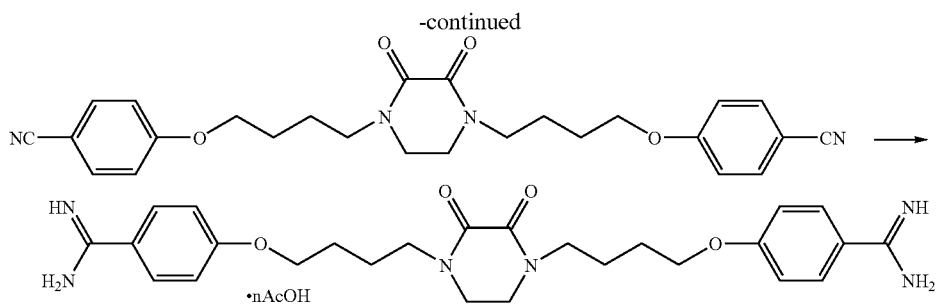

The following compound was obtained in the same manner as Reference example 7 and Examples 18 and 19.

4-{4-[4-(4-{4-[amino(imino)methyl]phenoxy}butyl)-2,3-dioxo-1-piperazinyl]butoxy}benzamidine Acetate IR(KBr)cm$^{-1}$: 3134, 3049, 1654, 1610 $^1$H-NMR (CD$_3$OD) δ: 1.80-1.86 (8H, m), 1.90 (6H, s), 3.56 (4H, t, J=6.6 Hz), 3.65 (4H, s), 4.14 (4H, t, J=5.5 Hz), 7.10-7.14 (4H, m), 7.75-7.80 (4H, m).

Example 22

The following compound was obtained in the same manner as Reference example 7 and Examples 18 and 19.

4-{3-[4-(2-{4-[amino(imino)methyl]phenoxy}ethyl)-2,3-dioxo-1-piperazinyl]propoxy}benzamidine Acetate IR(KBr)cm$^{-1}$: 3346, 3128, 1670, 1608 $^1$H-NMR (d$_6$-DMSO) δ: 1.97-2.04 (2H, m), 2.08 (6H, s), 3.53 (2H, t, J=6.8 Hz), 3.55-3.60 (2H, m), 3.67-3.71 (2H, m), 3.77 (2H, t, J=5.4 Hz), 4.11 (2H, t, J=6.0 Hz), 4.27 (2H, t, J=5.4 Hz), 7.12 (2H, d, J=8.8 Hz), 7.18 (2H, d, J=9.0 Hz), 7.86 (2H, d, J=8.8 Hz), 7.90 (2H, d, J=9.0 Hz), 9.22 (8H, brs)

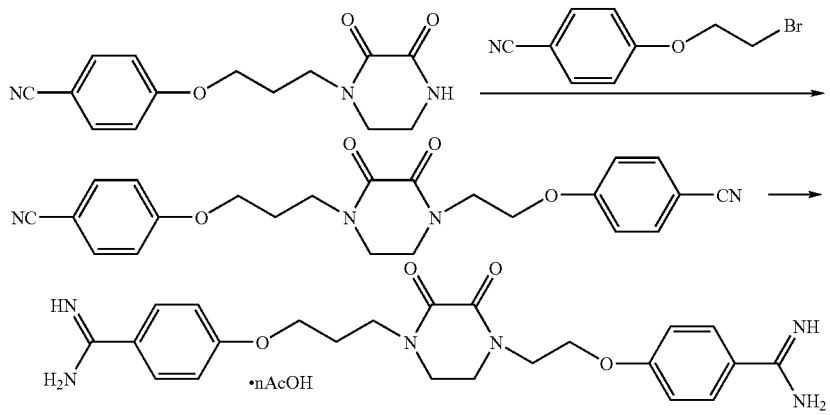

Example 23

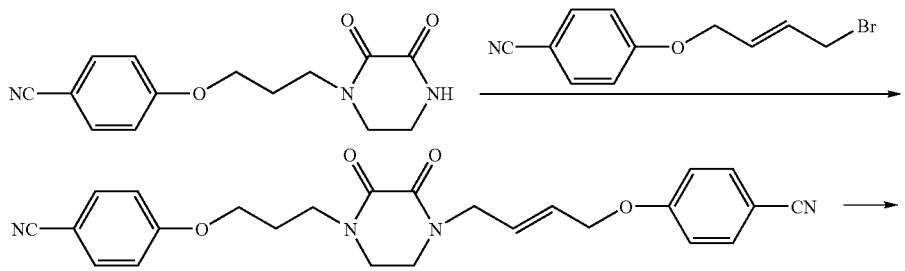

-continued

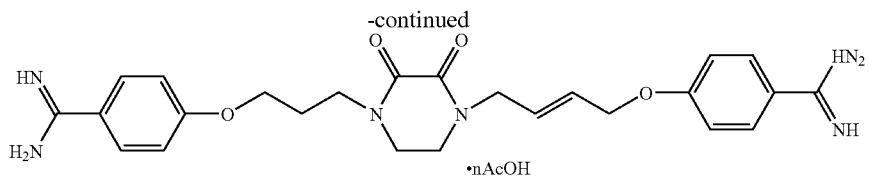

The following compound was obtained in the same manner as Reference example 7 and Examples 18 and 19.

4-({(E)-4-[4-(3-{4-[amino(imino)methyl]phenoxy}propyl)-2,3-dioxo-1-piperazinyl]-2-butenyl}oxy)benzamidine Acetate IR(KBr)cm$^{-1}$: 3164, 1669, 1610 $^1$H-NMR(D$_2$O) δ: 1.96 (6H, s), 2.10-2.20 (2H, m), 3.58-3.74 (6H, m), 4.10 (2H, d, J=5.4 Hz), 4.21 (2H, t, J=5.4 Hz), 4.75 (2H, d, J=4.9 Hz), 5.86 (1H, dt, J=15.6, 5.4 Hz), 5.93 (1H, dt, J=15.6, 4.9 Hz), 7.04 (2H, d, J=8.8 Hz), 7.10-7.20 (2H, m), 7.70-7.82 (4H, m)

Example 24

1.76 g of 4-{3-[4-(3-{4-[amino(imino)methyl]phenoxy}propyl)-2,3-dioxo-1-piperazinyl]propoxy} benzamidine acetate was dissolved in 30.0 ml of 6 mol/L hydrochloric acid, and the obtained solution was subject to heating to reflux for 5 hours. After completion of the reaction, 6 mol/L hydrochloric acid was removed under a reduced pressure. Ethanol was added to the obtained residue, and filtration was carried out to obtain 1.29 g of a colorless solid, 4-[3-({2-[(3-{4-[amino(imino)methyl]phenoxy}propyl)amino]ethyl}amino)propoxy]benzamidine hydrochloride.

IR(KBr)cm$^{-1}$: 3306, 3162, 2714, 1674, 1609 $^1$H-NMR (d$_6$-DMSO) δ: 2.14-2.22 (4H, m), 3.14 (4H, brs), 3.38 (4H,

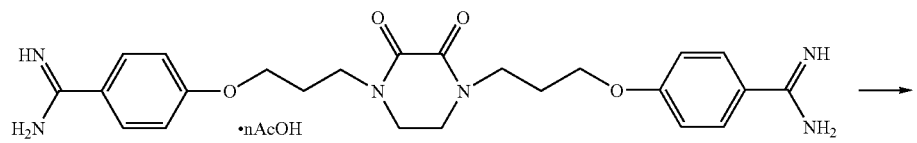

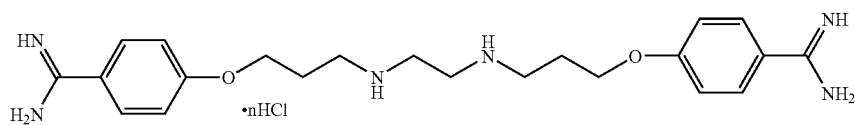

s), 4.24 (4H, t, J=6.1 Hz), 7.18 (4H, d, J=8.8 Hz), 7.87 (4H, d, J=8.8 Hz), 9.03 (4H, brs), 9.27 (4H, brs), 9.82 (4H, brs)

Example 25

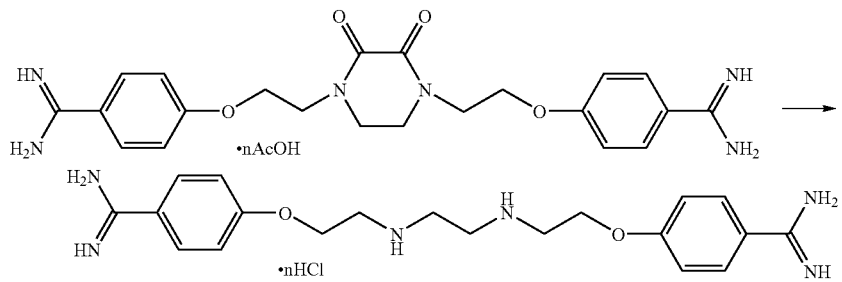

The following compound was obtained in the same manner as Example 24.

4-[2-({2-[(2-{4-[amino(imino)methyl]phenoxy}ethyl)amino]ethyl}amino)ethoxy]benzamidine Hydrochloride IR(KBr)cm$^{-1}$: 3312, 3097, 1662, 1609 $^1$H-NMR (d$_6$-DMSO) δ: 3.20-3.80 (10H, m), 4.44 (4H, brs), 7.24 (4H, d, J=8.4 Hz), 7.90 (2H, d, J=8.4 Hz), 9.11 (4H, brs), 9.32 (4H, brs), 9.98 (2H, brs)

Example 26

The following compound was obtained in the same manner as Example 24.

4-[4-({2-[(4-{4-[amino(imino)methyl]phenoxy}butyl)amino]ethyl}amino)butoxy]benzamidine Hydrochloride IR(KBr)cm$^{-1}$: 3320, 3164, 2717, 1676, 1609 $^1$H-NMR (d$_6$-DMSO) δ: 1.84 (8H, brs), 3.02 (4H, brs), 3.30-3.40 (4H, m), 4.13 (4H, brs), 7.17 (4H, d, J=8.5 Hz), 7.87 (4H, d, J=8.5 Hz), 9.04 (4H, brs), 9.27 (4H, brs), 9.68 (3H, brs)

Example 27

The following compound was obtained in the same manner as Example 24.

4-[3-({2-[(2-{4-[amino(imino)methyl]phenoxy}ethyl)amino]ethyl}amino)propoxy]benzamidine Hydrochloride IR(KBr)cm$^{-1}$: 3335, 3124, 2772, 1671, 1609 $^1$H-NMR (d$_6$-DMSO) δ: 2.20 (2H, brs), 3.14 (2H, brs), 3.30-3.60 (6H, brm), 4.26 (2H, brs), 4.46 (2H, brs), 7.17 (2H, d, J=7.8 Hz), 7.25 (4H, d, J=7.1 Hz), 7.80-8.00 (4H, brm), 9.19 (4H, brs), 9.30-9.50 (4H, brm), 10.05 (4H, brs)

Example 28

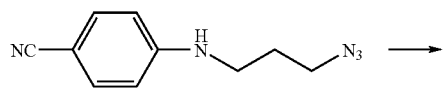

-continued

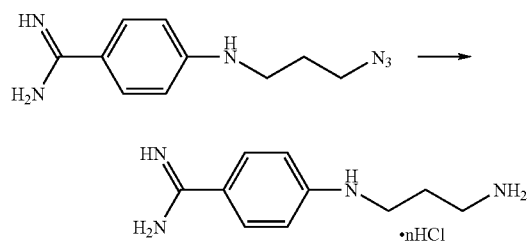

The following compound was obtained in the same manner as Examples 4 and 5.

4-[(3-aminopropyl)amino]benzamidine Hydrochloride $^1$H-NMR (d$_6$-DMSO) δ: 1.84-1.91 (2H, m), 2.84-2.91 (2H, m), 3.50-4.00 (2H, br), 6.72 (2H, d, J=8.8 Hz), 7.74 (2H, d, J=8.8 Hz), 8.28 (3H, s), 8.78 (2H, s), 8.98 (2H, s)

Example 29

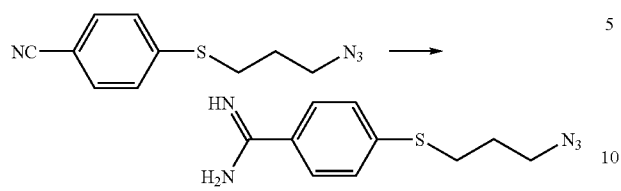

The following compound was obtained in the same manner as Example 4.

4-[(3-azidopropyl)sulfanyl]benzamidine $^1$H-NMR (d$_6$-DMSO) δ: 1.79-1.86 (2H, m), 3.07 (2H, t, J=7.4 Hz), 3.33 (1H, s), 3.47 (2H, t, J=6.6 Hz), 6.73 (2H, s), 7.35 (2H, d, J=8.4 Hz), 7.72 (2H, d, J=8.4 Hz)

Example 30

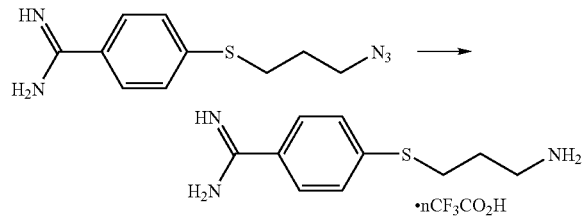

0.24 g of 4-[(3-azidopropyl)sulfanyl]benzamidine was dissolved in 4.0 ml of methanol. Thereafter, 0.18 g of 1,3-propanedithiol and 0.56 ml of triethylamine were added to the solution at room temperature, followed by stirring for 1 day. Thereafter, 2.16 g of 1,3-propanedithiol was further added thereto at room temperature, followed by stirring for 5 hours. Thereafter, 20 ml of water and 20 ml of ethyl acetate were added to the reaction mixture, and the aqueous layer was separated. Organic layer was extracted with 10 ml of water, and the obtained water layer was combined. 20 ml of 6 mol/L hydrochloric acid was added to the aqueous layer. The mixture was washed with chloroform 3 times, and then concentrated under a reduced pressure. The obtained residue was purified by silica gel column chromatography [eluent; chloroform methanol:trifluoroacetic acid=2000:1000:1] to obtain 0.10 g of a pale yellow solid, 4-[(3-aminopropyl)sulfanyl]benzamidine trifluoroacetate.

$^1$H-NMR (d$_6$-DMSO) δ: 1.88-1.96 (2H, m), 2.80-3.00 (2H, m), 3.17 (1H, s), 3.21 (2H, t, J=7.0 Hz), 7.54 (2H, d, J=8.8 Hz), 7.80 (2H, d, J=8.8 Hz), 8.10 (3H, s), 9.11 (2H, s), 9.37 (2H, s)

Example 31

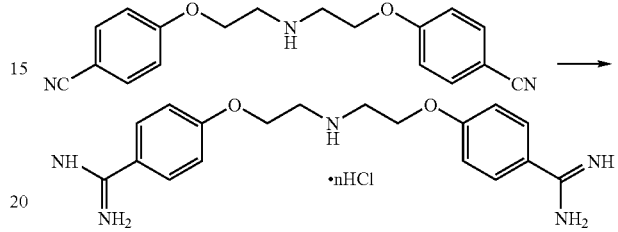

0.60 g of 4-(2-{[2-(4-cyanophenoxy)ethyl]amino}ethoxy)benzonitrile was dissolved in 20 ml of ethanol. Thereafter, while cooled by ice, hydrogen chloride gas was introduced into the solution, until it became saturated. The solution was left at rest at room temperature for 12 hours. After completion of the reaction, the reaction solution was concentrated under a reduced pressure. The obtained residue was dissolved in 30 ml of ethanol, and 1.20 g of ammonium acetate was then added thereto at room temperature. The mixture was stirred for 5.5 hours while being heated to reflux. After cooling to room temperature, the solvent was removed under a reduced pressure. Hydrochloric acid was added to the residue, and the solvent was removed again. Thereafter, the obtained solid was filtrated with a mixed solution of isopropanol and ethanol to obtain 0.31 g of a pale brown solid, 4-{2-[(2-{4-[amino(imino)methyl]phenoxy}ethyl)amino]ethoxy}benzamidine hydrochloride.

$^1$H-NMR (d$_6$-DMSO) δ: 3.35-3.55 (4H, m), 4.50 (4H, t, J=5.0 Hz), 7.22 (4H, d, J=9.0 Hz), 7.93 (4H, d, J=9.0 Hz), 9.21 (3H, s), 9.40 (4H, s), 9.88 (2H, brs)

Example 32

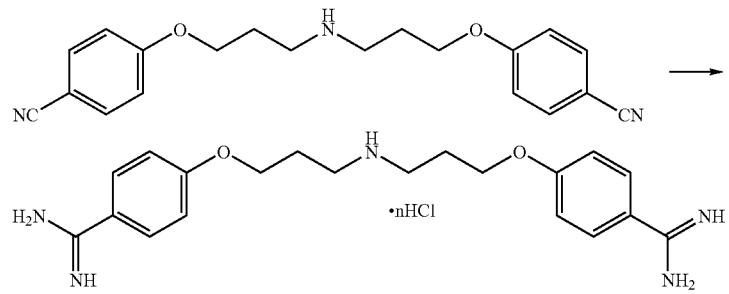

The following compound was obtained in the same manner as Example 31.

4-{3-[(3-{4-[amino(imino)methyl]phenoxy}propyl)amino]propoxy}benzamidine Hydrochloride $^1$H-NMR (d$_6$-DMSO) δ: 2.15-2.22 (4H, m), 3.00-3.20 (4H, m), 4.22 (4H, t, J=6.1 Hz), 7.16 (4H, d, J=9.0 Hz), 7.87 (4H, d, J=9.3 Hz), 9.00 (4H, s), 9.29 (6H, s)

Example 33

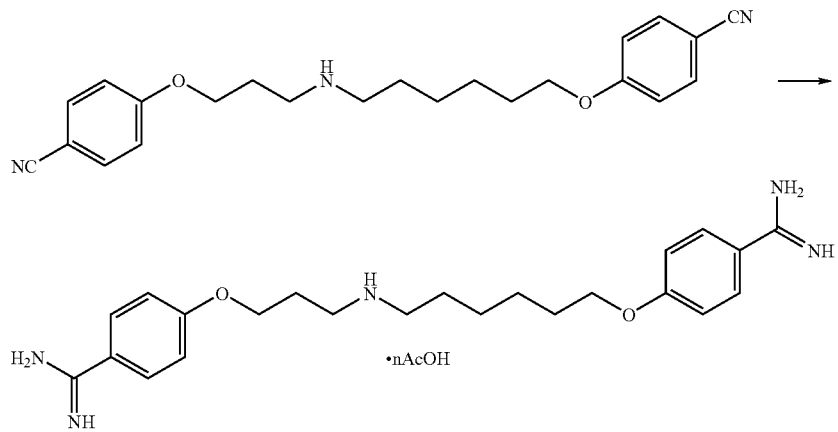

The following compound was obtained in the same manner as Example 31.

4-{3-[(6-{4-[amino(imino)methyl]phenoxy}hexyl)amino]propoxy}benzamidine Acetate $^1$H-NMR(D$_2$O) δ: 1.40-1.60 (4H, m), 1.74-1.87 (4H, m), 1.94 (6H, s), 2.23-2.30 (2H, m), 3.11-3.15 (2H, m), 3.31 (2H, t, J=7.4 Hz), 4.18 (2H, t, J=6.2 Hz), 4.30 (2H, t, J=5.6 Hz), 7.16-7.21 (4H, m), 7.78-7.82 (4H, m)

Example 34

The following compound was obtained in the same manner as Examples 18 and 19.

4-{3-[4-(6-{4-[amino(imino)methyl]phenoxy}hexyl)-2,3-dioxo-1-piperazinyl]propoxy}benzamidine Acetate $^1$H-NMR (d$_6$-DMSO+D$_2$O) δ: 1.26-1.36 (2H, m), 1.40-1.60 (4H, m), 1.70-1.80 (8H, m), 1.90-2.20 (2H, m), 3.30-3.45 (2H, m), 3.50-3.62 (6H, m), 4.07-4.14 (4H, m), 7.11-7.14 (4H, m), 7.76-7.79 (4H, m)

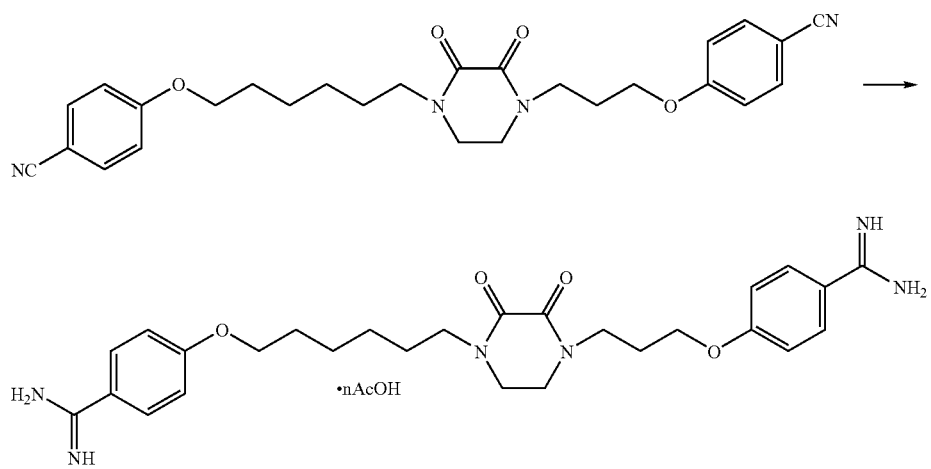

Example 35

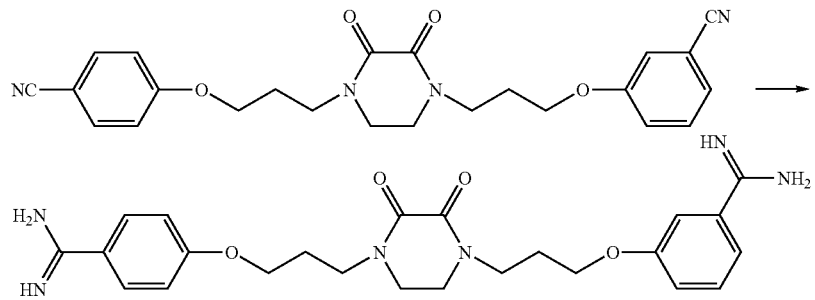

The following compound was obtained in the same manner as Examples 18 and 19.

3-{3-[4-(3-{4-[amino(imino)methyl]phenoxy}propyl)-2,3-dioxo-1-piperazinyl]propoxy}benzamidine $^1$H-NMR (d$_6$-DMSO) δ: 1.90-2.00 (4H, m), 3.51-3.57 (8H, m), 4.07-4.13 (4H, m), 7.12 (2H, d, J=8.8 Hz), 7.23-7.26 (1H, m), 7.36-7.38 (2H, m), 7.49 (1H, t, J=8.2 Hz), 7.81 (2H, d, J=8.8 Hz), 9.10-9.60 (6H, m)

Example 36

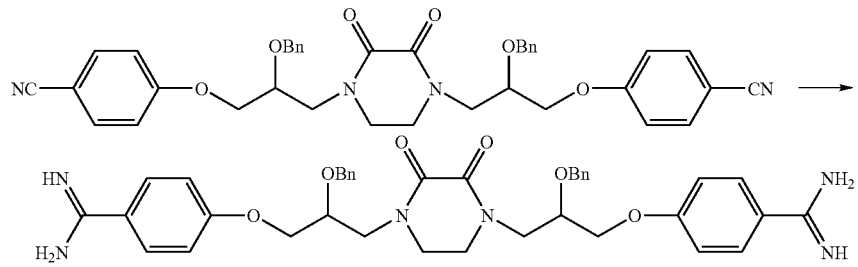

The following compound was obtained in the same manner as Examples 18 and 19.

4-[3-{4-[3-{4-[amino(imino)methyl]phenoxy}-2-(benzyloxy)propyl]-2,3-dioxo-1-piperazinyl}-2-(benzyloxy)propoxy]benzamidine $^1$H-NMR (d$_6$-DMSO) δ: 3.48-3.72 (6H, m), 4.00-4.08 (2H, m), 4.16-4.19 (2H, m), 4.24-4.28 (2H, m), 4.37 (2H, t, J=5.1 Hz), 4.59-4.70 (4H, m), 7.17 (4H, d, J=9.0 Hz), 7.23-7.30 (10H, m), 7.86 (4H, d, J=9.0 Hz), 8.80-9.40 (6H, m)

Example 37

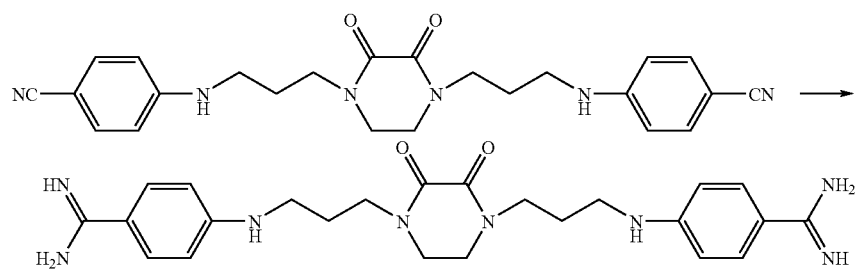

The following compound was obtained in the same manner as Examples 18 and 19.

4-({3-[4-(3-{4-[amino(imino)methyl]anilino}propyl)-2,3-dioxo-1-piperazinyl]propyl}amino)benzamidine $^1$H-NMR (d$_6$-DMSO) δ: 1.70-1.90 (4H, m), 3.11-3.16 (4H, m), 3.20-3.50 (4H, m), 3.55 (4H, s), 6.69 (4H, d, J=8.9 Hz), 6.93 (2H, t, J=5.4 Hz), 7.70 (4H, d, J=8.9 Hz), 8.10-8.90 (6H, br)

Example 38

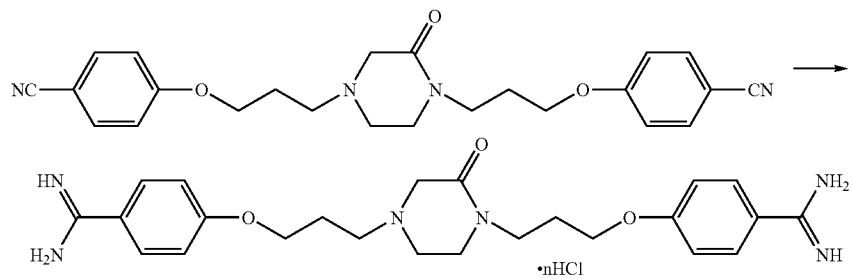

The following compound was obtained in the same manner as Examples 18 and 19.

4-{3-[4-(3-{4-[amino(imino)methyl]phenoxy}propyl)-2-oxo-1-piperazinyl]propoxy}benzamidine Hydrochloride $^1$H-NMR (d$_6$-DMSO) δ: 1.97-2.03 (2H, m), 2.20-2.40 (2H, m), 3.30-4.00 (10H, m), 4.15-4.23 (4H, m), 7.15-7.20 (4H, m), 7.90-7.94 (4H, m), 9.18-9.20 (4H, s), 9.38-9.40 (4H, m), 12.38 (1H, brs)

Example 39

The following compound was obtained in the same manner as Examples 18 and 19.

4-{3-[4-(3-{4-[amino(imino)methyl]phenoxy}propyl)-7-oxo-1,4-diazepan-1-yl]propoxy}benzamidine Acetate $^1$H-NMR(D$_2$O) δ: 1.94 (6H, s), 2.01-2.11 (4H, m), 2.67-2.82 (8H, m), 3.58-3.68 (4H, m), 4.18 (4H, t, J=5.6 Hz), 7.14-7.20 (4H, m), 7.80 (4H, d, J=8.4 Hz)

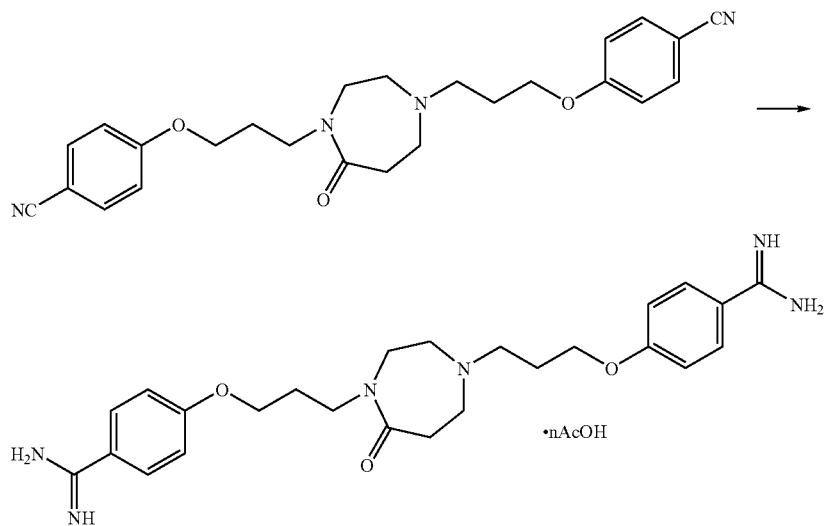

Example 40

Example 40-1

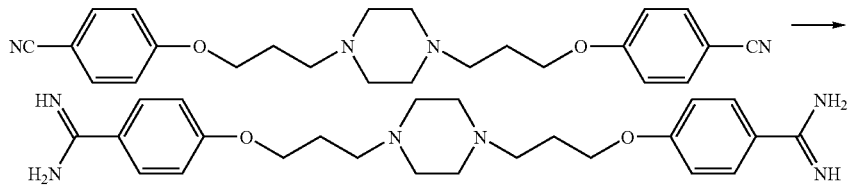

4.00 g of 4-(3-{4-[3-(4-cyanophenoxy)propyl]-1-piperazinyl}propoxy)benzonitrile was dissolved in 280 ml of ethanol. While cooled by ice, hydrogen chloride gas was blown into the solution, followed by stirring at room temperature for 2 days. After completion of the reaction, the solvent was removed under a reduced pressure. The obtained residue was suspended in 200 ml of ethanol, and 7.62 g of ammonium acetate was then added to the suspension at room temperature, followed by heating to reflux for 6 hours. After cooling to room temperature, the solvent was removed under a reduced pressure. 200 ml of water and 100 ml of chloroform were added to the obtained residue, and the mixture was then adjusted to pH 13 by addition of a 5.0 mol/L sodium hydroxide aqueous solution. A precipitate was filtrated, and the precipitate was washed with water, until the filtrate became neutral to obtain 4.04 g of a white solid, 4-{3-[4-(3-{4-[amino(imino)methyl]phenoxy}propyl)-1-piperazinyl]propoxy}benzamidine.

$^1$H-NMR (d$_6$-DMSO) δ: 1.70-2.00 (4H, m), 2.10-2.70 (12H, m), 4.03 (4H, t, J=6.2 Hz), 6.00-6.80 (6H, brs), 6.92 (4H, t, J=8.7 Hz), 7.71 (4H, t, J=8.7 Hz)

0.25 g of 4-{3-[4-(3-{4-[amino(imino)methyl]phenoxy}propyl)-1-piperazinyl]propoxy}benzamidine was suspended in 5.0 ml of ethanol. 1.5 ml of a 2.0 mol/L hydrogen chloride ethanol solution was added to the suspension. Thereafter, 3.0 ml of water was added for dissolution. The solvent was then removed under a reduced pressure. Thereafter, the residue was filtrated with ethanol to obtain 0.25 g of 4-{3-[4-(3-{4-[amino(imino)methyl]phenoxy}propyl)-1-piperazinyl]propoxy}benzamidine hydrochloride.

$^1$H-NMR (d$_6$-DMSO) δ: 2.10-2.30 (4H, m), 3.10-3.90 (14H, m), 4.10-4.30 (4H, m), 7.17 (4H, d, J=8.8 Hz), 7.86 (4H, d, J=8.8 Hz), 8.99 (4H, s), 9.24 (4H, s)

Example 40-2

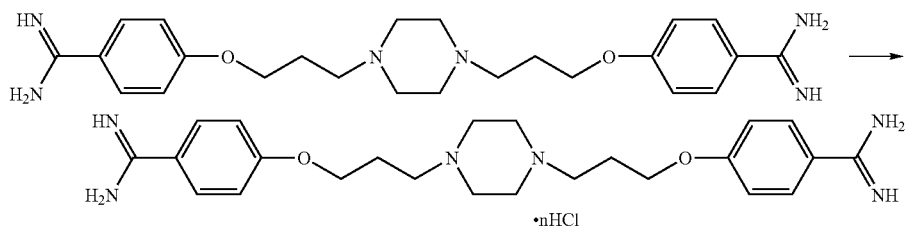

Example 41

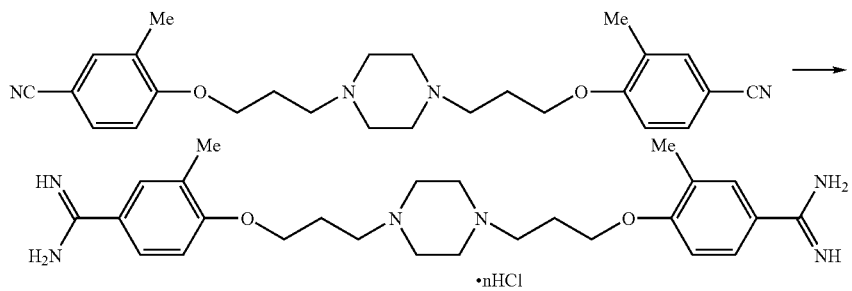

The following compound was obtained in the same manner as Example 40.

4-{3-[4-(3-{4-[amino(imino)methyl]-2-methylphenoxy}propyl)-1-piperazinyl]propoxy}-3-methylbenzamidine Hydrochloride $^1$H-NMR (d$_6$-DMSO) δ: 2.10-2.40 (10H, m), 3.00-4.00 (12H, m), 4.22 (4H, t, J=5.6 Hz), 7.17 (2H, d, J=8.3 Hz), 7.70-7.80 (4H, m), 9.06 (4H, s), 9.24 (4H, s), 12.10-12.80 (2H, br)

Example 42

The following compound was obtained in the same manner as Example 40.

4-{3-[4-(3-{4-[amino(imino)methyl]-2-fluorophenoxy}propyl)-1-piperazinyl]propoxy}-3-fluorobenzamidine Hydrochloride $^1$H-NMR(D$_2$O) δ: 2.41-2.47 (4H, m), 3.63 (4H, t, J=7.4 Hz), 3.65-4.00 (8H, m), 4.40 (4H, t, J=5.4 Hz), 7.32-7.36 (2H, m), 7.65-7.68 (4H, m)

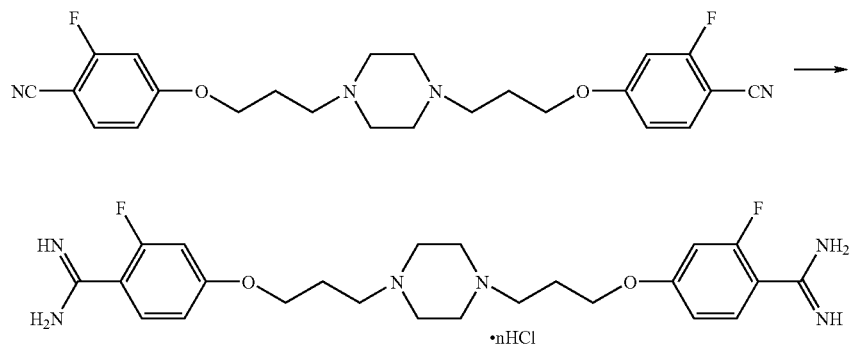

The following compound was obtained in the same manner as Example 40.

4-{3-[4-(3-{4-[amino(imino)methyl]-3-fluorophenoxy}propyl)-1-piperazinyl]propoxy}-2-fluorobenzamidine Hydrochloride $^1$H-NMR (d$_6$-DMSO+D$_2$O) δ: 2.16-2.30 (4H, m), 3.35 (4H, t, J=7.7 Hz), 3.58 (8H, brs), 4.00-4.40 (4H, m), 6.99-7.09 (4H, m), 7.66 (2H, t, J=8.5 Hz)

Example 43

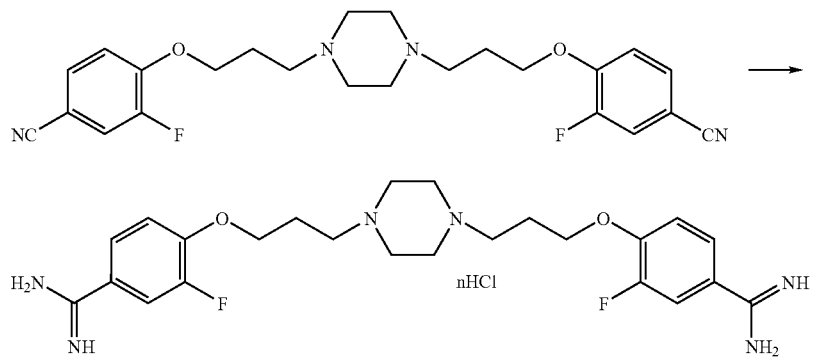

Example 44

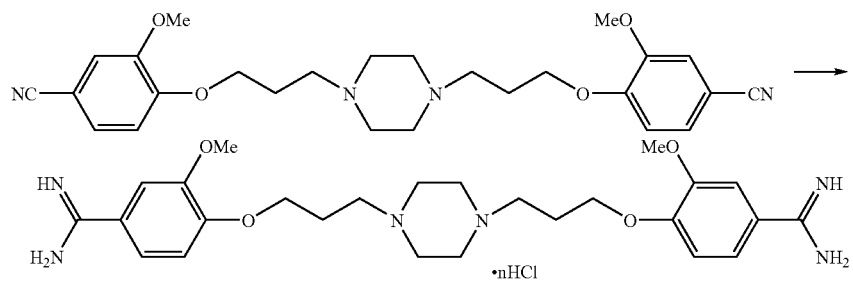

The following compound was obtained in the same manner as Example 40.

4-{3-[4-(3-{4-[amino(imino)methyl]-2-methoxyphenoxy}propyl)-1-piperazinyl]propoxy}-3-methoxybenzamidine Hydrochloride $^1$H-NMR (d$_6$-DMSO) δ: 2.10-2.40 (4H, m), 3.10-4.00 (14H, m), 3.88 (6H, s), 4.20 (4H, t, J=5.9 Hz), 7.20 (2H, d, J=8.3 Hz), 7.51 (2H, s), 7.51-7.53 (2H, m), 9.01 (4H, s), 9.29 (4H, s)

The following compound was obtained in the same manner as Example 40.

4'-{3-[4-(3-{4-[amino(imino)methyl]phenoxy}propyl)-1-piperazinyl]propoxy}[1,1'-biphenyl]-4-amidine Hydrochloride $^1$H-NMR (d$_6$-DMSO) δ: 2.20-2.30 (4H, m), 3.20-3.90 (14H, m), 4.17 (2H, t, J=5.8 Hz), 4.23 (2H, t, J=5.8 Hz), 7.11 (2H, d, J=8.8 Hz), 7.18 (2H, d, J=9.2 Hz), 7.77 (2H, d, J=8.8 Hz), 7.89-7.97 (6H, m), 9.16 (2H, s), 9.31-9.33 (4H, m), 9.49 (2H, s)

Example 45

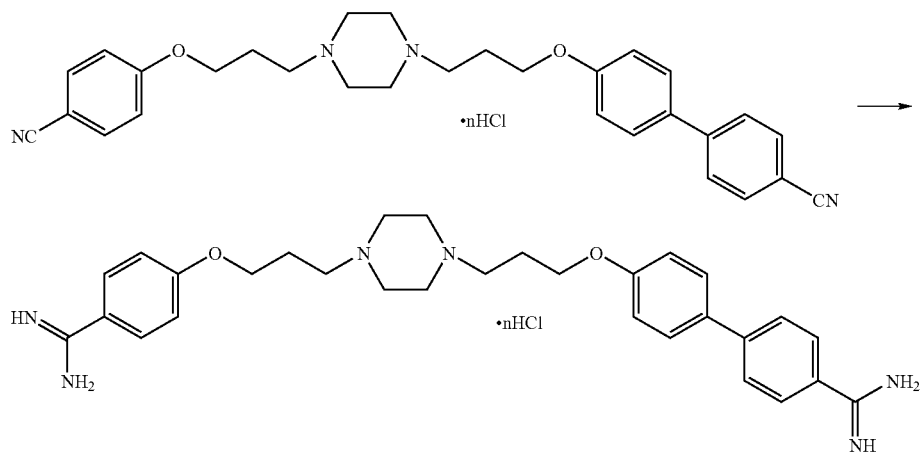

Example 46

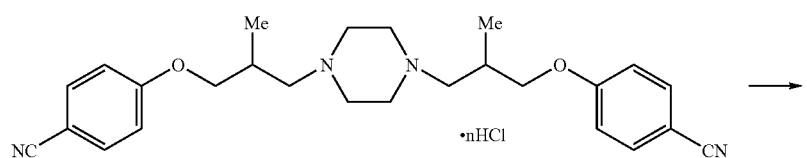

-continued

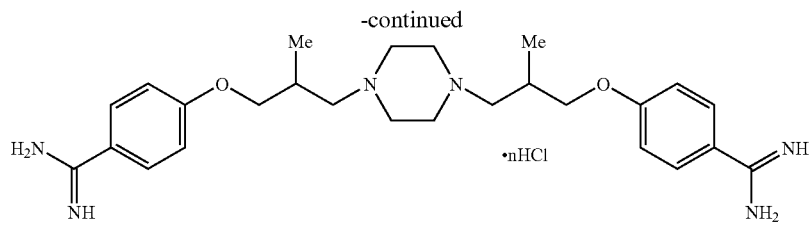

The following compound was obtained in the same manner as Example 40.

4-{3-[4-(3-{4-[amino(imino)methyl]phenoxy}-2-methylpropyl)-1-piperazinyl]-2-methylpropoxy}benzamidine Hydrochloride $^1$H-NMR(D$_2$O) δ: 1.20 (6H, d, J=6.8 Hz), 2.66-2.70 (2H, m), 3.31-3.36 (2H, m), 3.47-3.52 (2H, m), 3.55-4.00 (8H, m), 4.09-4.13 (2H, m), 4.21-4.25 (2H, m), 7.19 (4H, d, J=8.8 Hz), 7.81 (4H, J=8.8 Hz)

Example 47

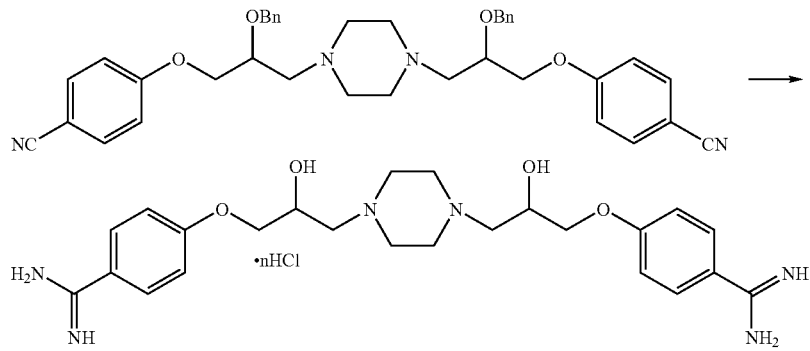

70 ml of ethanol was added to 1.00 g of 4-(2-(benzyloxy)-3-{4-[2-(benzyloxy)-3-(4-cyanophenoxy)propyl]-1-piperazinyl}propoxy)benzonitrile. While cooled by ice, hydrogen chloride gas was introduced into the mixture, until it became saturated, followed by stirring at room temperature for 18 hours. Thereafter, 20 ml of ethanol was further added to the reaction mixture. While cooled by ice, hydrogen chloride gas was introduced into the mixture again, until it became saturated, followed by stirring at room temperature for 20 hours. The reaction mixture was concentrated under a reduced pressure to obtain 1.35 g of a pale yellow solid. 1.24 g of the obtained solid was suspended in 120 ml of ethanol, and 2.20 g of ammonium acetate was then added thereto at room temperature, followed by stirring for 4 hours under heated to reflux. The reaction mixture was cooled to room temperature, and it was then concentrated under a reduced pressure. The obtained residue was dissolved in methanol, and a 2 mol/L hydrogen chloride ethanol solution was then added to the solution. The solvent was removed under a reduced pressure, and the obtained yellow solid was purified by silica gel chromatography [YMC-GEL, ODS-AM 120-S50, eluent; a 10% acetonitrile aqueous solution] to obtain a colorless oil product. 15 ml of 6 mol/L hydrochloric acid was added to the obtained oil product, followed by stirring at 85° C. to 90° C. for 7 hours. The reaction mixture was concentrated under a reduced pressure. The obtained solid was filtrated with isopropanol to obtain 0.42 g of a white solid, 4-{3-[4-(3-{4-[amino(imino)methyl]phenoxy}-2-hydroxypropyl)-1-piperazinyl]-2-hydroxypropoxy}benzamidine hydrochloride.

$^1$H-NMR(D$_2$O) δ: 3.50-3.70 (4H, m), 3.80-4.00 (8H, m), 4.21-4.31 (4H, m), 4.55-4.65 (2H, m), 7.10-7.30 (4H, m), 7.70-7.90 (4H, m)

Example 48

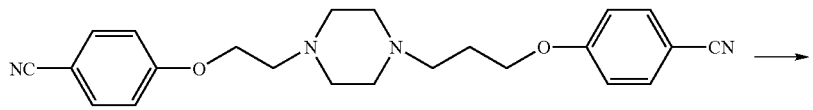

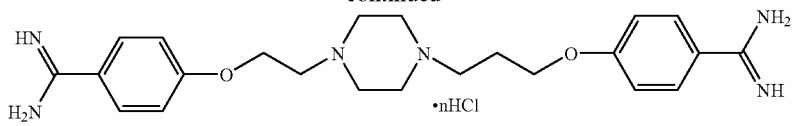

The following compound was obtained in the same manner as Example 40. 4-{3-[4-(2-{4-[amino(imino)methyl]phenoxy}ethyl)-1-piperazinyl]propoxy}benzamidine Hydrochloride $^{1}$H-NMR (d$_6$-DMSO) δ: 2.20-2.30 (2H, brm), 3.20-3.90 (14H, m), 4.22 (2H, t, J=6.0 Hz), 4.53 (2H, brs), 7.16-7.25 (4H, m), 7.87-7.92 (4H, m), 9.10 (2H, s), 9.13 (2H, s), 9.30 (2H, s), 9.32 (2H, s)

Example 49

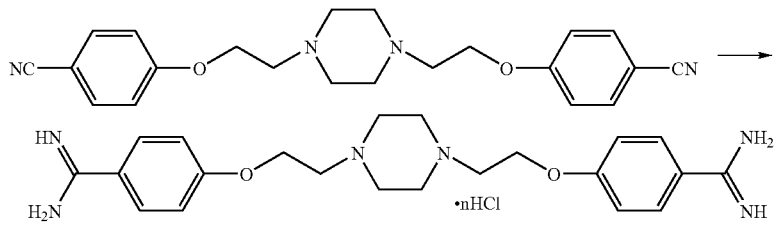

The following compound was obtained in the same manner as Example 40.

4-{2-[4-(2-{4-[amino(imino)methyl]phenoxy}ethyl)-1-piperazinyl]ethoxy}benzamidine Hydrochloride $^{1}$H-NMR (d$_6$-DMSO) δ: 3.20-3.90 (14H, m), 4.40-4.60 (4H, m), 7.23 (4H, d, J=8.8 Hz), 7.89 (4H, d, J=8.8 Hz), 9.06 (4H, s), 9.29 (4H, s)

Example 50

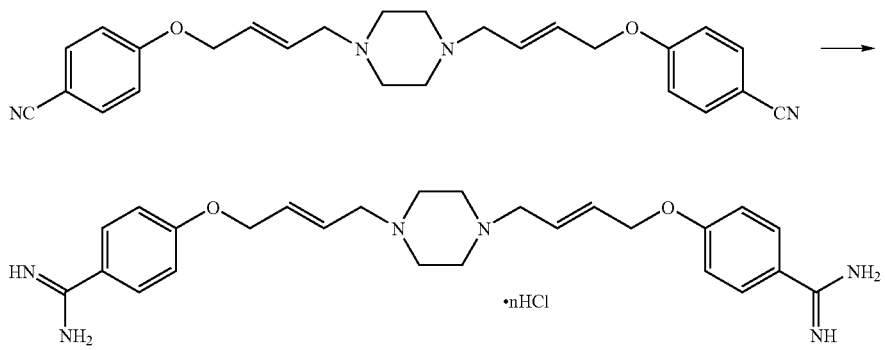

The following compound was obtained in the same manner as Example 40.

4-({(E)-4-[4-((E)-4-{4-[amino(imino)methyl]phenoxy}-2-butenyl)-1-piperazinyl]-2-butenyl}oxy)benzamidine Hydrochloride ¹H-NMR (d₆-DMSO): 3.10-4.00 (14H, m), 4.76 (4H, d, J=4.4 Hz), 5.94-6.03 (2H, m), 6.10-6.30 (2H, m), 7.19 (4H, d, J=9.0 Hz), 7.87 (4H, d, J=9.0 Hz), 9.04 (4H, s), 9.27 (4H, s)

Example 51

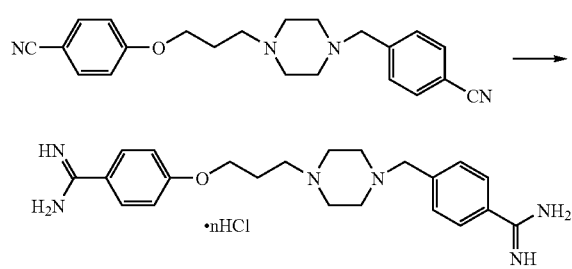

The following compound was obtained in the same manner as Example 40.

4-[3-(4-{4-[amino(imino)methyl]benzyl}-1-piperazinyl)propoxy]benzamidine Hydrochloride ¹H-NMR (d₆-DMSO) δ: 2.10-2.30 (2H, m), 3.10-4.90 (16H, m), 7.46 (2H, d, J=8.8 Hz), 7.91 (2H, d, J=8.8 Hz), 7.90-8.10 (4H, m), 9.14 (2H, s), 9.33 (2H, s), 9.42 (2H, s), 9.58 (2H, s)

Example 52

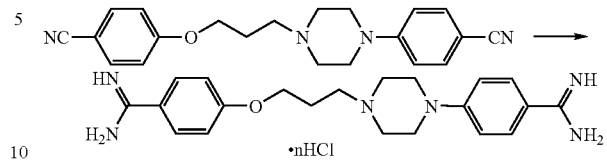

The following compound was obtained in the same manner as Example 40.

4-[4-(3-{4-[amino(imino)methyl]phenoxy}propyl)-1-piperazinyl]benzamidine Hydrochloride ¹H-NMR (d₆-DMSO) δ: 2.20-2.40 (2H, m), 3.00-3.50 (8H, m), 3.50-3.70 (2H, m), 4.10-4.20 (2H, m), 4.22 (2H, t, J=6.6 Hz), 7.16-7.20 (4H, m), 7.82 (2H, d, J=8.9 Hz), 7.86 (2H, d, J=8.9 Hz), 8.77 (2H, s), 8.93 (2H, s), 9.09 (2H, s), 9.22 (2H, s)

Example 53

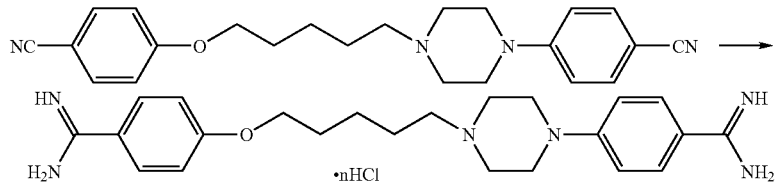

The following compound was obtained in the same manner as Example 40.

4-[4-(5-{4-[amino(imino)methyl]phenoxy}pentyl)-1-piperazinyl]benzamidine Hydrochloride ¹H-NMR (d₆-DMSO) δ: 1.42-1.54 (2H, m), 1.74-1.90 (4H, m), 3.00-3.20 (4H, m), 3.20-3.50 (4H, m), 3.50-3.70 (2H, m), 4.06-4.16 (4H, m), 7.16 (2H, d, J=9.1 Hz), 7.17 (2H, d, J=9.1 Hz), 7.82 (2H, d, J=9.1 Hz), 7.85 (2H, d, J=9.1 Hz), 8.85 (2H, s), 8.99 (2H, s), 9.11 (2H, s), 9.24 (2H, s)

Example 54

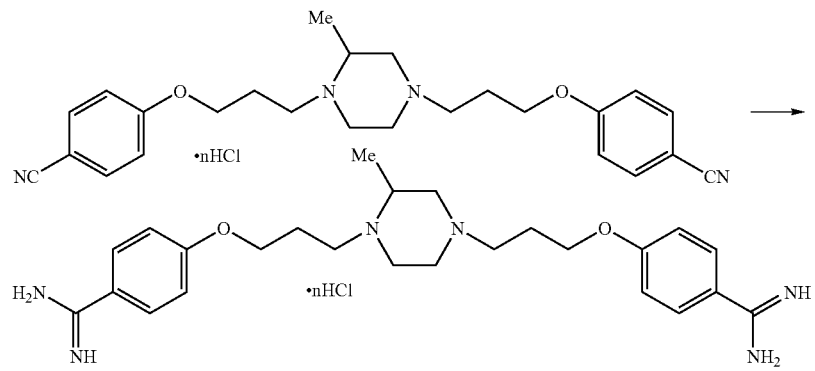

The following compound was obtained in the same manner as Example 40.

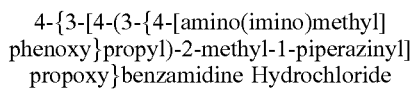

¹H-NMR(D₂O) δ: 2.20-2.50 (4H, m), 3.33-3.60 (5H, m), 3.72-4.04 (6H, m), 4.20-4.40 (4H, m), 7.17-7.20 (4H, m), 7.86 (4H, d, J=8.4 Hz)

Example 55

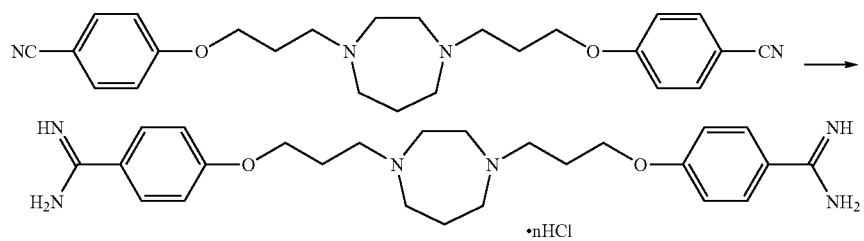

The following compound was obtained in the same manner as Example 40.

4-{3-[4-(3-{4-[amino(imino)methyl]phenoxy}propyl)-1,4-diazepan-1-yl]propoxy}benzamidine Hydrochloride ¹H-NMR (d₆-DMSO) δ: 2.10-2.40 (6H, m), 3.20-4.00 (14H, m), 4.21 (4H, t, J=5.9 Hz), 7.17 (4H, d, J=8.8 Hz), 7.86 (4H, d, J=8.8 Hz), 8.96 (4H, s), 9.23 (4H, s)

Example 56

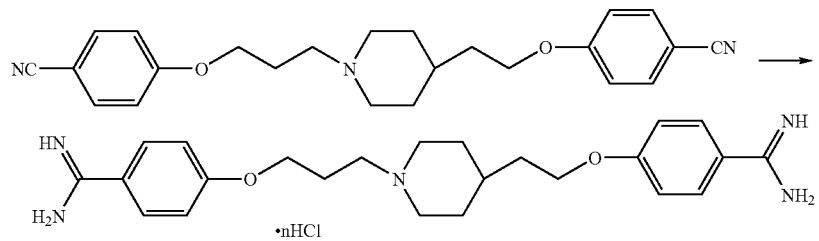

The following compound was obtained in the same manner as Example 40.

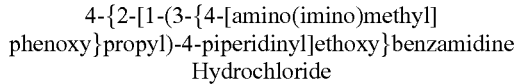

¹H-NMR (d₆-DMSO) δ: 1.60-1.80 (3H, m), 1.80-2.00 (2H, m), 2.10-2.30 (2H, m), 2.80-3.00 (2H, m), 3.10-3.40 (5H, m), 3.40-3.60 (2H, m), 4.10-4.21 (4H, m), 7.16 (4H, d, J=8.8 Hz), 7.85 (2H, d, J=8.8 Hz), 7.86 (2H, d, J=8.8 Hz), 8.99-9.00 (4H, m), 9.24-9.25 (4H, m)

Example 57

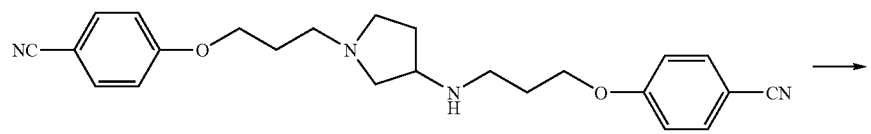

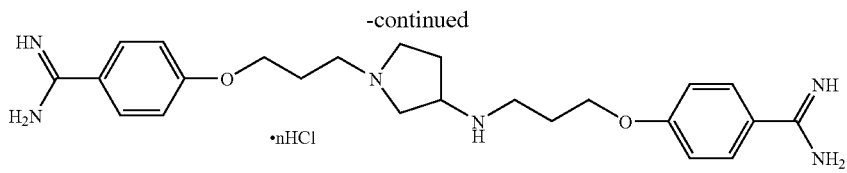

The following compound was obtained in the same manner as Example 40.

4-(3-{3-[(3-{4-[amino (imino)methyl] phenoxy}propyl)amino]-1-pyrrolidinyl}propoxy) benzamidine Hydrochloride $^1$H-NMR (d$_6$-DMSO) δ: 2.10-2.70 (6H, m), 3.00-4.10 (10H, m), 4.21-4.26 (4H, m), 7.18 (4H, d, J=8.8 Hz), 7.86 (4H, d, J=8.8 Hz), 8.96 (4H, brs), 9.24 (4H, brs), 9.80-10.02 (2H, br)

Example 58

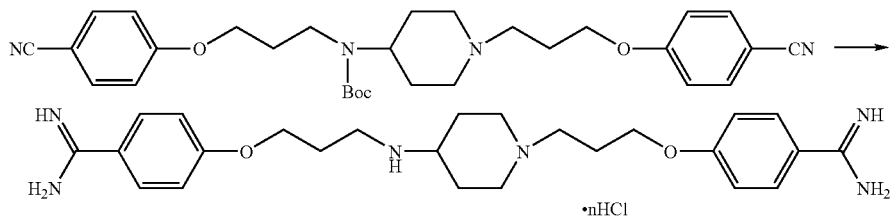

The following compound was obtained in the same manner as Example 40.

4-(3-{[1-(3-{4-[amino(imino)methyl] phenoxy}propyl)-4-piperidinyl]amino}propoxy) benzamidine Hydrochloride $^1$H-NMR (d$_6$-DMSO) δ: 2.00-2.40 (8H, m), 2.90-3.70 (10H, m), 4.10-4.30 (4H, m), 7.16 (2H, d, J=8.8 Hz), 7.17 (2H, d, J=8.8 Hz), 7.88 (4H, d, J=8.8 Hz), 9.05 (4H, s), 9.28 (4H, s), 9.60-9.80 (2H, m)

Example 59

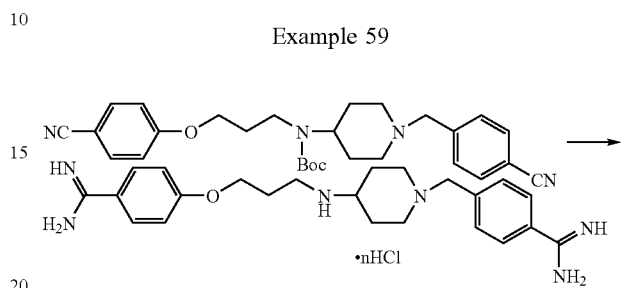

The following compound was obtained in the same manner as Example 40.

4-{3-[(1-{4-[amino(imino)methyl]benzyl}-4-piperidinyl)amino]propoxy}benzamidine Hydrochloride $^1$H-NMR (d$_6$-DMSO) δ: 2.00-2.40 (6H, m), 2.90-3.70 (7H, m), 4.22 (2H, t, J=6.1 Hz), 4.30-4.50 (2H, m), 7.16 (2H, d, J=8.7 Hz), 7.80-8.00 (1H, m), 7.87 (2H, d, J=8.7 Hz), 7.90 (2H, d, J=8.7 Hz), 7.95 (2H, d, J=8.7 Hz), 9.03 (2H, s), 9.20-9.40 (4H, m), 9.40-9.80 (4H, m)

Example 60

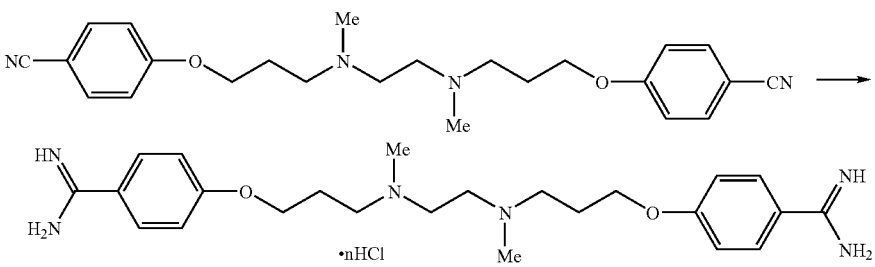

The following compound was obtained in the same manner as Example 40.

4-{3-[{2-[(3-{4-[amino(imino)methyl]phenoxy}propyl)(methyl)amino]ethyl}(methyl)amino]propoxy}benzamidine Hydrochloride ¹H-NMR (d₆-DMSO) δ: 2.10-2.30 (4H, m), 2.85 (6H, s), 3.20-3.90 (8H, m), 4.22 (4H, t, J=6.0 Hz), 7.17 (4H, d, J=9.0 Hz), 7.91 (4H, d, J=9.0 Hz), 9.17 (4H, s), 9.37 (4H, s), 11.7 (2H, brs)

Example 61

The following compound was obtained in the same manner as Example 40.

Ethyl 6-{(3-{4-[amino(imino)methyl]phenoxy}propyl)[1-(3-{4-[amino(imino)methyl]phenoxy}propyl)-4-piperidinyl]amino}hexanoate Hydrochloride ¹H-NMR (d₆-DMSO) δ: 1.18 (3H, t, J=7.1 Hz), 1.25-1.40 (2H, m), 1.45-1.65 (2H, m), 1.70-1.90 (2H, m), 2.10-2.40 (10H, m), 3.00-3.90 (11H, m), 4.06 (2H, q, J=7.1 Hz), 4.10-4.30 (4H, m), 7.16-7.21 (4H, m), 7.86 (4H, d, J=8.8 Hz), 8.94 (4H, s), 9.23 (4H, s), 11.05 (1H, s), 11.20 (1H, s)

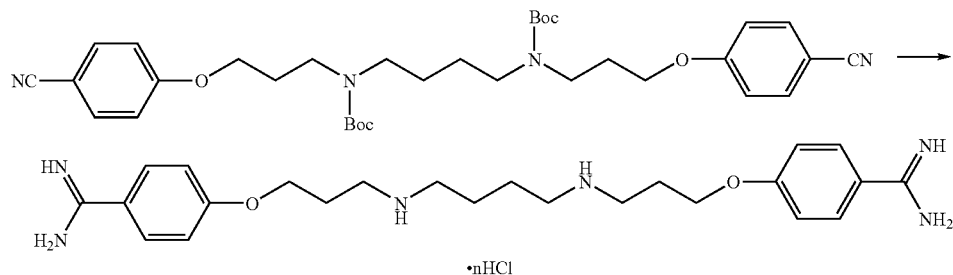

The following compound was obtained in the same manner as Example 40.

4-[3-({4-[(3-{4-[amino(imino)methyl]phenoxy}propyl)amino]butyl}amino)propoxy]benzamidine Hydrochloride ¹H-NMR (d₆-DMSO) δ: 1.60-1.80 (4H, m), 2.10-2.30 (4H, m), 2.80-3.20 (8H, m), 4.22 (4H, t, J=6.1 Hz), 7.17 (4H, d, J=9.0 Hz), 7.86 (4H, d, J=9.0 Hz), 8.97 (4H, s), 9.00-9.60 (2H, br), 9.25 (6H, s)

Example 62

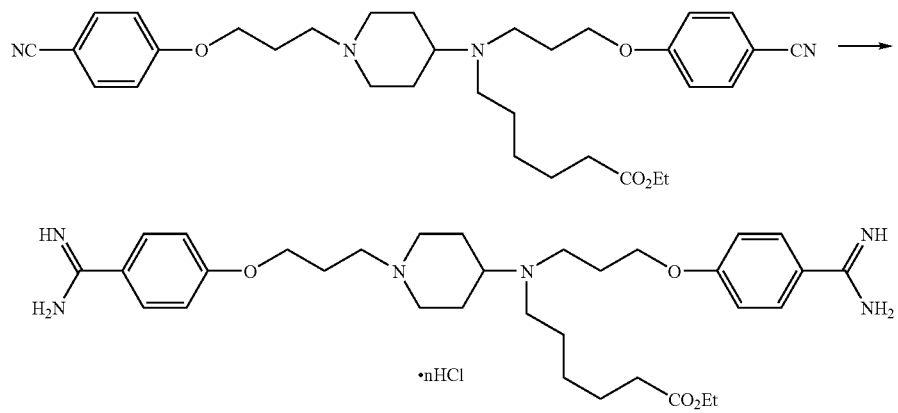

Example 63

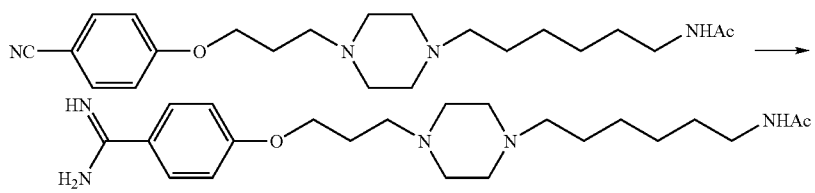

The following compound was obtained in the same manner as Example 40.

N-{6-[4-(3-{4-[amino(imino)methyl]phenoxy}propyl)-1-piperazinyl]hexyl}acetamide $^1$H-NMR (CDCl$_3$) δ: 1.25-1.42 (4H, m), 1.44-1.54 (4H, m), 1.90-2.10 (2H, m), 1.97 (3H, s), 2.10-2.80 (15H, m), 3.21-3.26 (2H, m), 4.05 (2H, t, J=6.3 Hz), 5.30-5.50 (1H, brs), 6.92 (2H, d, J=8.7 Hz), 7.55 (2H, d, J=8.7 Hz)

Example 64

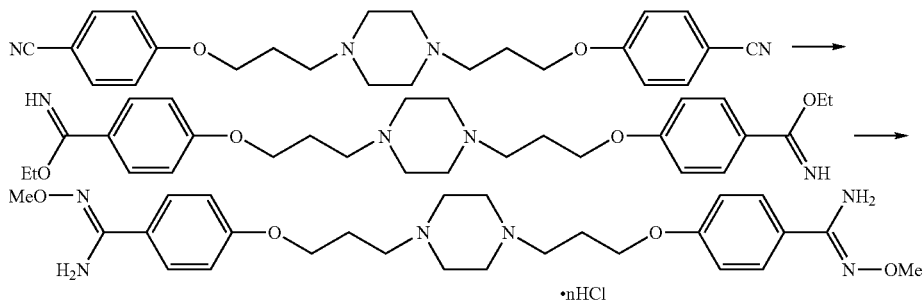

0.81 g of 4-(3-{4-[3-(4-cyanophenoxy)propyl]-1-piperazinyl}propoxy)benzonitrile was dissolved in 20 ml of chloroform, and 180 ml of ethanol was then added thereto. While cooled by ice, hydrogen chloride gas was blown into the solution. The solution was reacted at room temperature for 24 hours. Thereafter, the solvent was removed under a reduced pressure. The obtained residue and 0.84 g of methoxyamine hydrochloride were suspended in 30 ml of ethanol. While cooled by ice, 4.2 ml of triethylamine was added to the suspension, followed by stirring for 5 hours. The solvent was removed under a reduced pressure. 30 ml of chloroform and 30 ml of a 1 mol/L sodium hydroxide aqueous solution were added to the obtained residue, so that the organic layer was separated. The separated organic layer was dried over anhydrous sodium sulfate and then concentrated under a reduced pressure. The obtained residue was purified by silica gel column chromatography [eluent; chloroform:methanol=20:1] to obtain 0.59 g of a pale brown solid. 0.50 g of the obtained solid was dissolved in 10 ml of chloroform, and 2 ml of a 2 mol/L hydrogen chloride ethanol solution was added thereto. The solvent was removed under a reduced pressure, and the obtained residue was filtrated with ethanol to obtain 0.51 g of a white solid, 4-{3-[4-(3-{4-[amino(methoxyimino)methyl]phenoxy}propyl)-1-piperazinyl]propoxy}-N'-methoxybenzamidine hydrochloride.

$^1$H-NMR (d$_6$-DMSO) δ: 2.20-2.40 (4H, m), 3.25-4.00 (14H, m), 3.86 (6H, s), 4.21 (4H, t, J=6.0 Hz), 7.15 (4H, d, J=9.0 Hz), 7.82 (4H, d, J=9.0 Hz), 8.75-9.50 (4H, br), 12.00-13.00 (2H, br)

Example 65

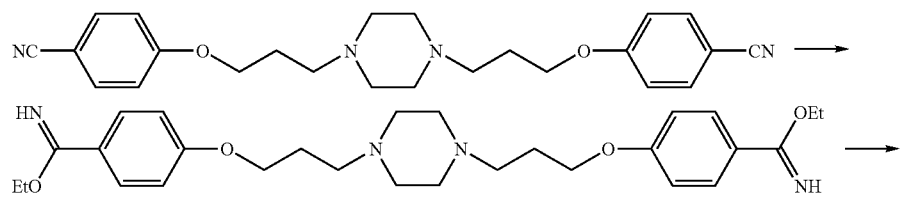

-continued

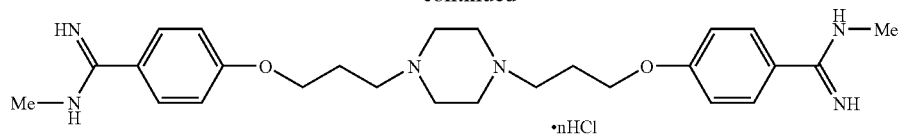

The following compound was obtained in the same manner as Example 64.

4-{3-[4-(3-{4-[imino(methylamino)methyl]phenoxy}propyl)-1-piperazinyl]propoxy}-N-methyl-benzamidine Hydrochloride $^1$H-NMR (d$_6$-DMSO+D$_2$O) δ: 2.20-2.30 (4H, m), 3.00 (6H, s), 3.30-3.40 (4H, m), 3.90-4.00 (8H, m), 4.19 (4H, t, J=6.0 Hz), 7.16 (4H, d, J=9.2 Hz), 7.75 (4H, d, J=9.2 Hz)

Example 66

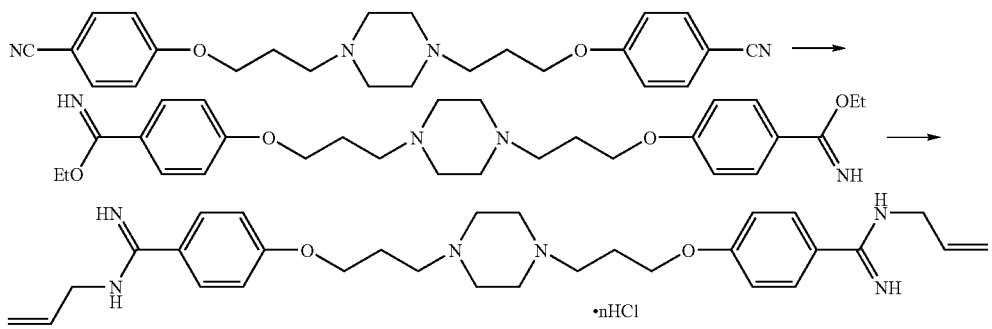

The following compound was obtained in the same manner as Example 64.

N-allyl-4-{3-[4-(3-{4-[(allylamino)(imino)methyl]phenoxy}propyl)-1-piperazinyl]propoxy}benzamidine Hydrochloride $^1$H-NMR (d$_6$-DMSO) δ: 2.20-2.30 (4H, m), 3.30-4.00 (14H, m), 4.00-4.30 (8H, m), 5.23-5.33 (4H, m), 5.89-5.98 (2H, m), 7.16 (4H, d, J=8.2 Hz), 7.85 (4H, d, J=8.2 Hz), 9.07 (2H, s), 9.55 (2H, s), 10.05 (2H, s)

Example 67

5.9 ml of water and 23.7 ml of ethanol were added to 2.06 g of hydroxylamine hydrochloride and 0.60 g of 4-(3-{4-[3-(4-cyanophenoxy)propyl]-1-piperazinyl}propoxy)benzonitrile. Then, 4.14 ml of triethylamine was added thereto, and the mixture was subject to heating to reflux for 1 hour. After cooling to room temperature, a precipitate was filtrated, and 2 mol/L hydrochloric acid and ethanol were added thereto and dissolved therein. The solvent was removed under reduced pressure. The obtained residue was purified by silica gel chromatography [YMC-GEL, ODS-AM 120-S50, eluent; water] to obtain 0.44 g of a white solid, 4-{3-[4-(3-{4-[amino(hydroxyimino)methyl]phenoxy}propyl)-1-piperazinyl]propoxy}-N'-hydroxybenzamidine hydrochloride.

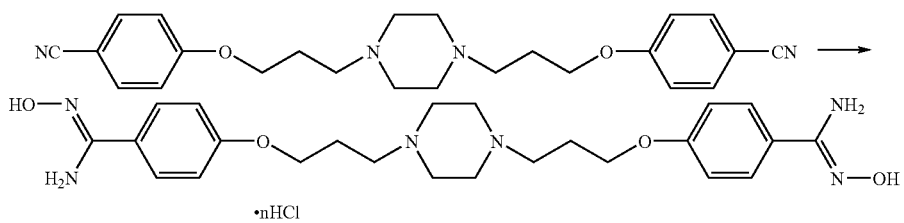

¹H-NMR (d₆-DMSO+D₂O) δ: 2.20-2.30 (4H, m), 3.30-3.50 (4H, m), 3.50-3.90 (8H, m), 4.20 (4H, t, J=5.6 Hz), 7.18 (4H, d, J=9.2 Hz), 7.71 (4H, d, J=9.2 Hz)

Example 68

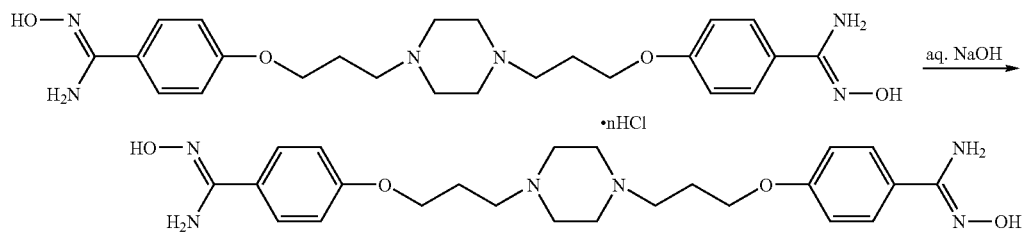

0.54 g of 4-{3-[4-(3-{4-[amino(hydroxyimino)methyl]phenoxy}propyl)-1-piperazinyl]propoxy}-N'-hydroxybenzamidine hydrochloride was dissolved in 20 ml of water, and the solution was then adjusted to pH 12 with a 5 mol/L sodium hydroxide aqueous solution. A precipitate was filtrated, and it was washed with water and ethanol to obtain 0.42 g of a white solid, 4-{3-[4-(3-{4-[amino(hydroxyimino)methyl]phenoxy}propyl)-1-piperazinyl]propoxy}-N'-hydroxybenzamidine.

¹H-NMR (d₆-DMSO) δ: 1.80-2.00 (4H, m), 2.20-2.80 (12H, m), 4.02 (4H, t, J=6.3 Hz), 5.71 (4H, s), 6.91 (4H, d, J=8.7 Hz), 7.59 (4H, d, J=8.7 Hz), 9.45 (2H, s)

Example 69

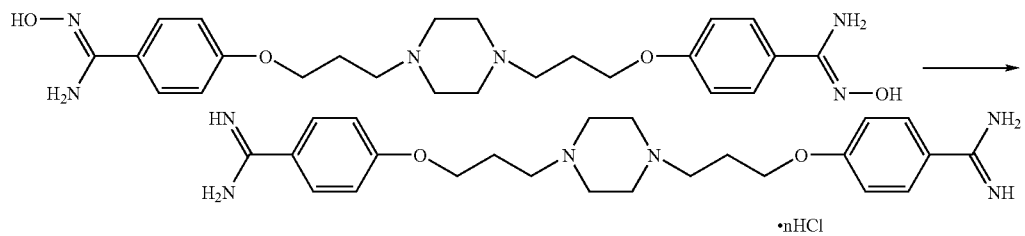

0.12 g of 4-{3-[4-(3-{4-[amino(hydroxyimino)methyl]phenoxy}propyl)-1-piperazinyl]propoxy}-N'-hydroxybenzamidine was dissolved in 2.0 ml of acetic acid, and 0.08 ml of acetic anhydride was then added to the solution at room temperature, followed by stirring for 1 hour. 1 hour later, 0.08 g of 5% palladium-carbon was added to the reaction mixture, and the mixture was stirred under a hydrogen atmosphere at room temperature under atmospheric pressure for 1.5 hours. After completion of the reaction, the catalyst was removed by filtration, and the solvent was removed under a reduced pressure. The obtained residue was dissolved in methanol, and 3 ml of a 2.6 mol/L hydrogen chloride ethanol solution was added thereto. Thereafter, the solvent was removed under a reduced pressure. Isopropanol was added to the obtained residue, and a precipitate was filtrated to obtain 0.11 g of a pale brown solid, 4-{3-[4-(3-{4-[amino(imino)methyl]phenoxy}propyl)-1-piperazinyl]propoxy}benzamidine hydrochloride.

Data of physicochemical properties of this compound was consistent with data of the compound obtained in Example 40-2.

Example 70

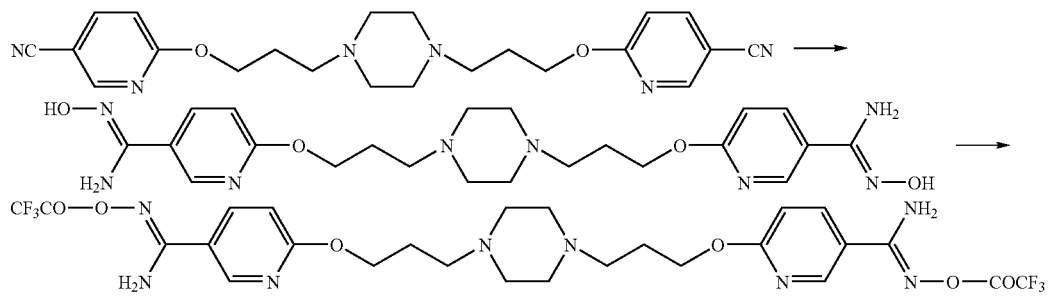

0.30 g of 6-[3-(4-{3-[(5-cyano-2-pyridinyl)oxy]propyl}-1-piperazinyl)propoxy]nicotinonitrile was suspended in 7.4 ml of ethanol. 0.21 ml of triethylamine and 0.10 g of hydroxylamine hydrochloride were successively added to the suspension, followed by heating to reflux for 2 hours. Thereafter, 0.01 g of hydroxylamine hydrochloride and 0.02 ml of triethylamine were successively added to the reaction solution, followed by heating to reflux for 3.5 hours. After cooling, a solid was filtered, and it was then washed with 10 ml of ethanol to obtain 0.25 g of a pale brown solid. 0.20 g of the obtained pale brown solid was dissolved in 2.0 ml of trifluoroacetic acid, and 0.15 ml of trifluoroacetic anhydride was added to the solution, followed by stirring for 0.7 hour. 0.15 ml of trifluoroacetic anhydride was further added to the reaction solution, and the mixture was stirred for 1.3 hours. 0.29 ml of triethylamine and 1.5 ml of trifluoroacetic anhydride were added to the reaction solution, followed by stirring for 62.5 hours. The solvent was removed under a reduced pressure. 10 ml of water, 10 ml of a saturated sodium bicarbonate solution, and 20 ml of ethyl acetate were added to the obtained residue, so that the organic layer was separated. The separated organic layer was washed twice with 10 ml of a saturated sodium bicarbonate solution, and then dried over anhydrous magnesium sulfate. The solvent was then removed under a reduced pressure. The obtained residue was purified by silica gel column chromatography [eluent; n-hexane:ethyl acetate=1:1] to obtain 0.14 g of a white solid, (6-{3-[4-(3-{[5-(amino{[(2,2,2-trifluoroacetyl)oxy]imino}methyl)-2-pyridinyl]oxy}propyl)-1-piperazinyl]propoxy}-3-pyridinyl){[(2,2,2-trifluoroacetyl)oxy]imino}methylamine.

IR(KBr)cm$^{-1}$: 1610

Example 71

0.13 g of (6-{3-[4-(3-{[5-(amino{[(2,2,2-trifluoroacetyl)oxy]imino}methyl)-2-pyridinyl]oxy}propyl)-1-piperazinyl]propoxy}-3-pyridinyl){[(2,2,2-trifluoroacetyl)oxy]imino}methylamine was dissolved in 5.0 ml of methanol, 2.0 ml of ethyl acetate, and 0.12 ml of trifluoroacetic acid. 26 mg of 5% palladium-carbon was added to the solution, and the mixture was stirred under a hydrogen atmosphere at room temperature under atmospheric pressure for 7.5 hours. 50 ml of methanol was added to the reaction solution followed by filtration, and the filtrate was then concentrated under a reduced pressure. 5 ml of a 2 mol/L hydrogen chloride methanol solution was added to the obtained residue, and the mixture was concentrated under a reduced pressure. Thereafter, 5 ml of ethanol was added thereto, and the solvent was removed under a reduced pressure. Ethanol was added to the obtained residue, and the mixture was filtrated to obtain 0.12 g of a white solid, 6-(3-{4-[3-({5-[amino(imino)methyl]-2-pyridinyl}oxy)propyl]-1-piperazinyl}propoxy)-3-pyridinecarboximidamide hydrochloride.

$^{1}$H-NMR (d$_{6}$-DMSO) δ: 2.20-2.30 (4H, m), 3.20-3.60 (8H, m), 3.70-3.91 (4H, br), 4.45 (4H, t, J=6.0 Hz), 7.06 (2H, d, J=8.8 Hz), 8.19 (2H, dd, J=2.6, 8.8 Hz), 8.73 (2H, d, J=2.6 Hz), 9.22 (4H, s), 9.50 (4H, s), 11.80-12.60 (2H, br)

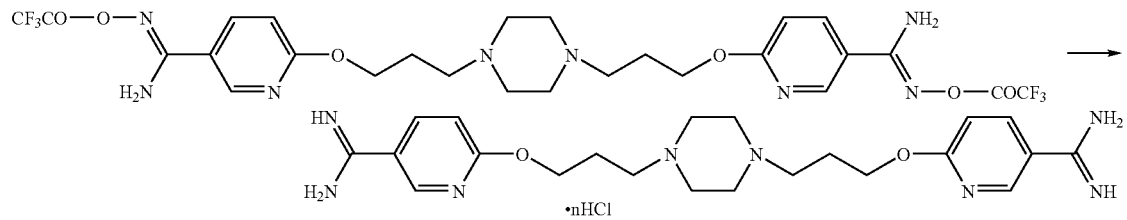

Example 72

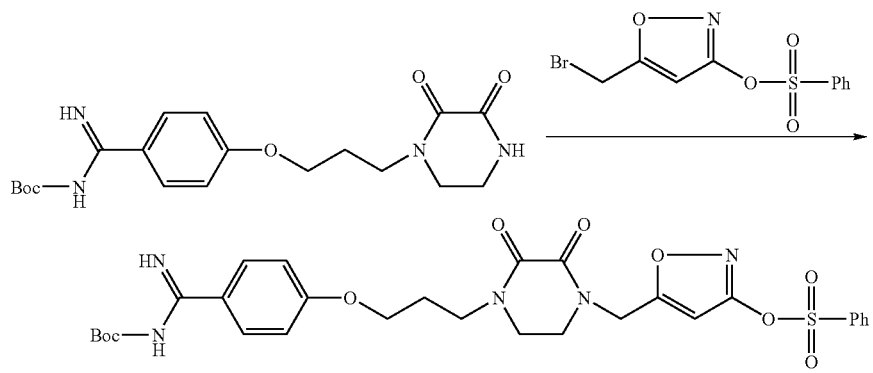

191

The following compound was obtained in the same manner as Example 11.

5-{[4-(3-{4-[[(tert-butoxycarbonyl)amino](imino)methyl]phenoxy}propyl)-2,3-dioxo-1-piperazinyl]methyl}-3-isoxazolyl benzenesulfonate $^1$H-NMR (CDCl$_3$) δ: 1.57 (11H, s), 2.10-2.20 (2H, m), 3.50-3.70 (6H, m), 4.07 (2H, t, J=5.7 Hz), 4.69 (2H, s), 6.30 (1H, s), 6.88 (2H, d, J=8.8 Hz), 7.50-7.70 (2H, m), 7.70-7.80 (1H, m), 7.83 (2H, d, J=8.8 Hz), 7.90-8.00 (2H, m)

Example 73

192

The following compound was obtained in the same manner as Example 24.

4-[3-({2-[(6-{4-[amino(imino)methyl]phenoxy}hexyl)amino]ethyl}amino)propoxy]benzamidine Hydrochloride $^1$H-NMR (d$_6$-DMSO) δ: 1.35-1.50 (4H, m), 1.64-1.80 (4H, m), 2.10-2.30 (2H, m), 2.87-2.90 (2H, m), 3.07-3.20 (2H, m), 3.27-3.50 (4H, m), 4.10 (2H, t, J=5.6 Hz), 4.20-

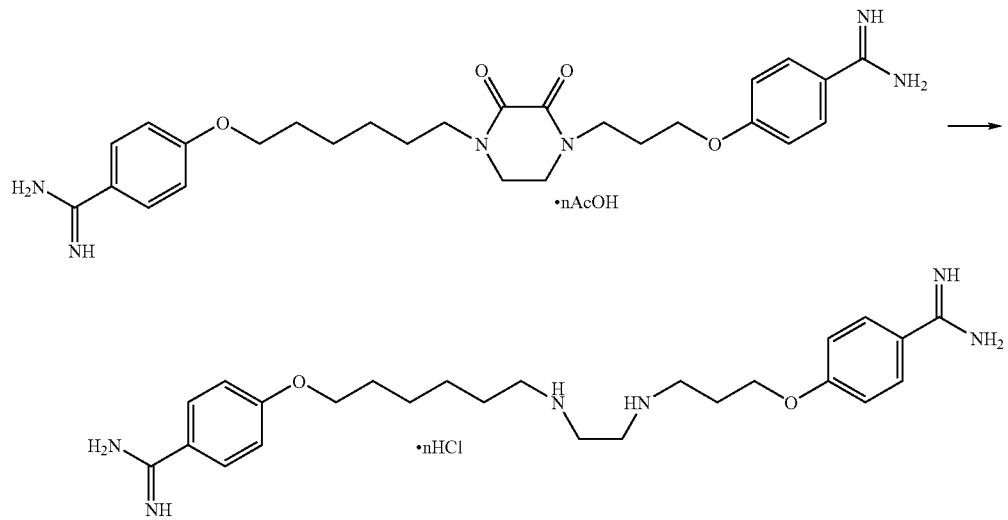

4.30 (2H, m), 7.13-7.21 (4H, m), 7.83-7.93 (4H, m), 9.00-9.20 (4H, m), 9.20-9.40 (4H, m), 9.50-10.00 (4H, m)

Example 74

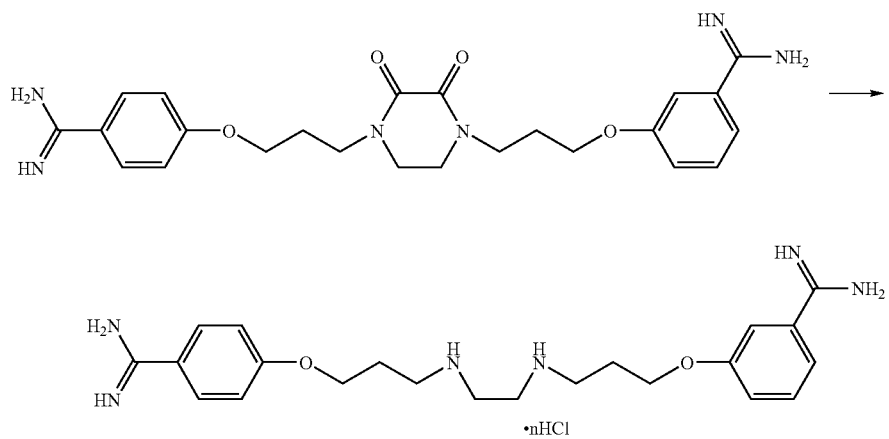

The following compound was obtained in the same manner as Example 24.

3-[3-({2-[(3-{4-[amino(imino)methyl]phenoxy}propyl)amino]ethyl}amino)propoxy]benzamidine Hydrochloride ¹H-NMR (d₆-DMSO) δ: 2.10-2.30 (4H, m), 3.10-3.20 (4H, m), 3.30-3.50 (4H, m), 4.20-4.30 (4H, m), 7.18 (2H, d, J=8.2 Hz), 7.32 (1H, d, J=7.6 Hz), 7.45 (1H, d, J=7.6 Hz), 7.49 (1H, s), 7.54 (1H, t, J=7.6 Hz), 7.89 (2H, d, J=8.2 Hz), 9.12 (2H, s), 9.32 (4H, s), 9.50 (2H, s), 9.60-10.20 (4H, m)

The following compound was obtained in the same manner as Example 24.

4-[3-({2-[(3-{4-[amino(imino)methyl]phenoxy}-2-hydroxypropyl)amino]ethyl}amino)-2-hydroxypropoxy]benzamidine Hydrochloride ¹H-NMR (d₆-DMSO+D₂O) δ: 3.00-3.20 (2H, m), 3.20-3.40 (2H, m), 3.40-3.50 (4H, m), 4.00-4.20 (4H, m), 4.20-4.40 (2H, m), 7.10-7.30 (4H, m), 7.80-8.00 (4H, m)

Example 75

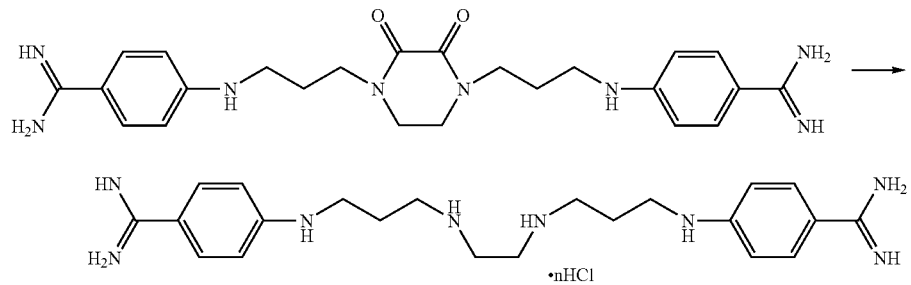

The following compound was obtained in the same manner as Example 24.

4-{[3-({2-[(3-{4-[amino(imino)methyl]anilino}propyl)amino]ethyl}amino)propyl]amino}benzamidine Hydrochloride ¹H-NMR (d₆-DMSO) δ: 1.90-2.00 (4H, m), 3.00-3.10 (4H, m), 3.27 (4H, t, J=6.8 Hz), 3.34 (4H, brs), 3.50-3.90 (2H, br), 6.72 (4H, d, J=8.9 Hz), 6.80-7.20 (2H, br), 7.69 (4H, d, J=8.9 Hz), 8.62 (4H, s), 8.89 (4H, s), 9.75 (4H, brs)

Example 76

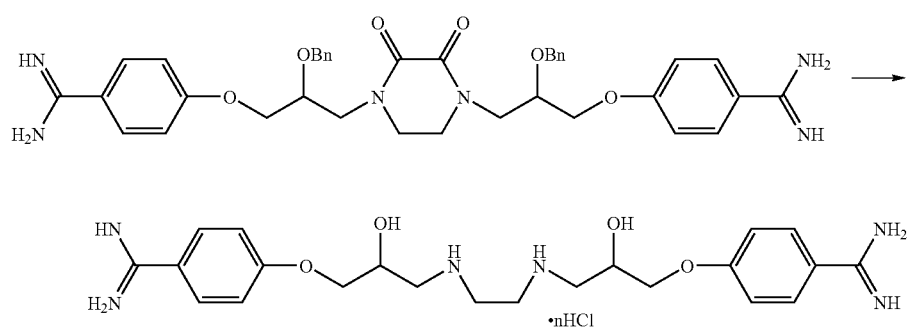

Example 77

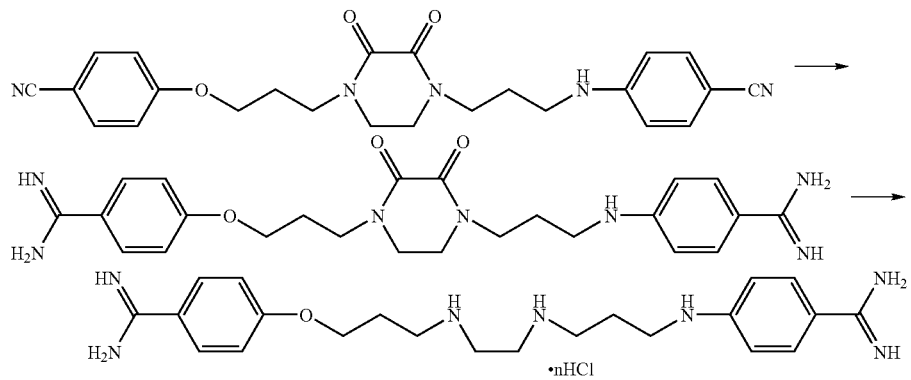

The following compound was obtained in the same manner as Examples 18 and 24.

4-{[3-({2-[(3-{4-[amino(imino)methyl]phenoxy}propyl)amino]ethyl}amino)propyl]amino}benzamidine Hydrochloride $^1$H-NMR (d$_6$-DMSO+D$_2$O) δ: 1.90-2.00 (2H, m), 2.10-2.30 (2H, m), 3.00-3.20 (4H, m), 3.24-3.30 (2H, m), 3.36 (4H, s), 4.25 (2H, t, J=6.0 Hz), 6.73 (2H, d, J=8.4 Hz), 7.18 (2H, d, J=8.8 Hz), 7.71 (2H, d, J=8.4 Hz), 7.89 (2H, d, J=8.8 Hz)

The following compound was obtained in the same manner as Example 24.

N-(3-{4-[amino(imino)methyl]phenoxy}propyl)-N-{2-[(3-{4-[amino(imino)methyl]phenoxy}propyl)amino]ethyl}-β-alanine Hydrochloride $^1$H-NMR(D$_2$O) δ: 2.30-2.47 (4H, m), 3.04-3.12 (2H, m), 3.43-3.52 (2H, m), 3.59-3.87 (8H, m), 4.25-4.35 (4H, m), 7.15-7.23 (4H, m), 7.74-7.81 (4H, m)

Example 78

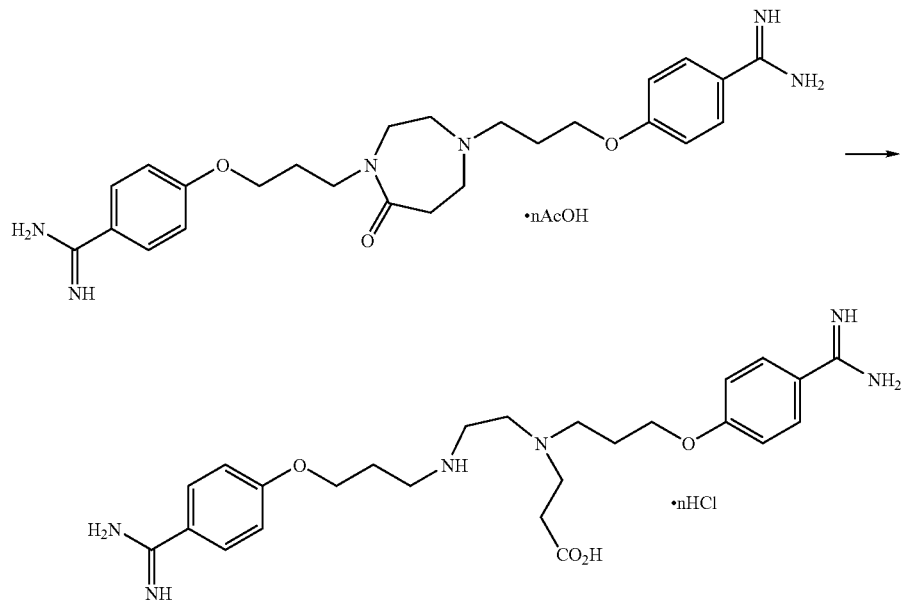

Example 79

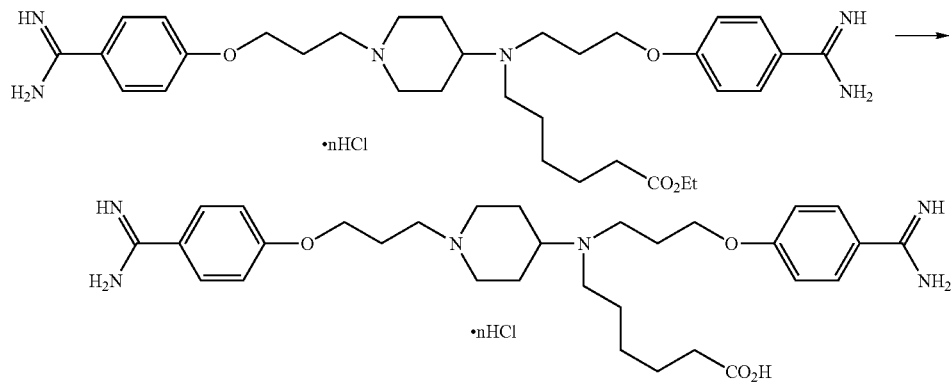

The following compound was obtained in the same manner as Example 24.

6-{(3-{4-[amino(imino)methyl]phenoxy}propyl)[1-(3-{4-[amino(imino)methyl]phenoxy}propyl)-4-piperidinyl]amino}hexanoic Acid Hydrochloride $^1$H-NMR (d$_6$-DMSO) δ: 1.20-1.40 (2H, m), 1.45-1.70 (2H, m), 1.70-1.90 (2H, m), 2.10-2.40 (10H, m), 3.00-3.80 (13H, m), 4.10-4.30 (4H, m), 7.10-7.30 (4H, m), 7.85 (4H, d, J=8.8 Hz), 8.89 (4H, s), 9.21 (4H, s)

Example 80

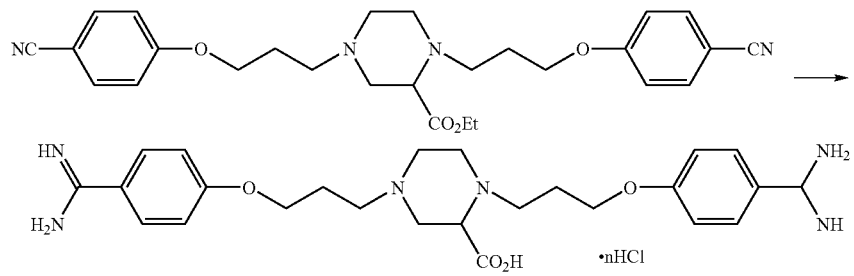

0.54 g of ethyl 1,4-bis[3-(4-cyanophenoxy)propyl]-2-piperazinecarboxylate was suspended in 11.3 ml of ethanol. While cooled by ice, hydrogen chloride gas was blown into the suspension. The suspension was reacted at room temperature for 13.5 hours, and thereafter, the solvent was removed under a reduced pressure. The obtained residue was dissolved in 11.3 ml of ethanol, and 0.78 g of ammonium acetate was added to the solution, followed by heating to reflux for 2 hours. After cooling to room temperature, insoluble products were removed by filtration, and the filtrate was then concentrated under a reduced pressure. The obtained residue was dissolved in 22.6 ml of 2 mol/L hydrochloric acid, followed by heating to reflux for 4 hours. Thereafter, 11.3 ml of 6 mol/L hydrochloric acid was further added thereto, followed by heating to reflux for 2 hours. Thereafter, the reaction mixture was cooled to room temperature, and the solvent was then removed under a reduced pressure. The obtained residue was purified by silica gel chromatography [YMC-GEL, ODS-AM 120-S50, eluent; water] to obtain 0.29 g of a white solid, 1,4-bis(3-{4-[amino(imino)methyl]phenoxy}propyl)-2-piperazine carboxylic acid hydrochloride.

$^1$H-NMR(D$_2$O) δ: 2.19-2.30 (4H, m), 3.10-3.30 (6H, m), 3.37-3.50 (2H, m), 3.50-3.85 (3H, m), 4.26 (4H, t, J=5.6 Hz), 7.15-7.18 (4H, m), 7.76-7.80 (4H, m)

Example 81

-continued

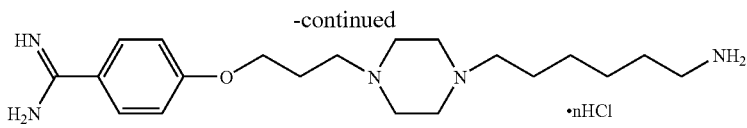

0.59 g of N-{6-[4-(3-{4-[amino(imino)methyl]phenoxy}propyl)-1-piperazinyl]hexyl}acetamide was dissolved in 20 ml of 6 mol/L hydrochloric acid, followed by heating to reflux for 5 hours. After cooling to room temperature, the solvent was removed under a reduced pressure. The obtained solid was purified by silica gel chromatography [YMC-GEL, ODS-AM 120-S50, eluent; water] to obtain 0.33 g of a white solid, 4-{3-[4-(6-aminohexyl)-1-piperazinyl]propoxy}benzamidine hydrochloride.

$^1$H-NMR (d$_6$-DMSO+D$_2$O) δ: 1.20-1.40 (4H, m), 1.50-1.80 (4H, m), 2.10-2.30 (2H, m), 2.70-2.90 (2H, m), 3.00-3.90 (12H, m), 4.20 (2H, t, J=5.9 Hz), 7.17 (2H, d, J=8.3 Hz), 7.84 (2H, d, J=8.3 Hz)

Example 82

5.6 ml of 6 mol/L hydrochloric acid was added to 0.14 g of 5-{[4-(3-{4-[[(tert-butoxycarbonyl)amino](imino)methyl]phenoxy}propyl)-2,3-dioxo-1-piperazinyl]methyl}-3-isoxazolyl benzenesulfonate, and the mixture was subject to heating to reflux for 50 minutes. After cooling to room temperature, the solvent was removed under a reduced pressure. Ethanol was added to the obtained residue, and a precipitate was filtrated to obtain 0.06 g of a white solid, 4-{3-[(2-{[(3-hydroxy-5-isoxazolyl)methyl]amino}ethyl)amino]propoxy}benzamidine hydrochloride.

$^1$H-NMR (d$_6$-DMSO+CF$_3$CO$_2$D) δ: 2.05-2.20 (2H, m), 3.15 (2H, t, J=7.2 Hz), 3.36 (4H, s), 4.22 (2H, t, J=6.0 Hz), 4.38 (2H, s), 6.34 (1H, s), 7.17 (2H, d, J=9.0 Hz), 7.84 (2H, d, J=9.0 Hz)

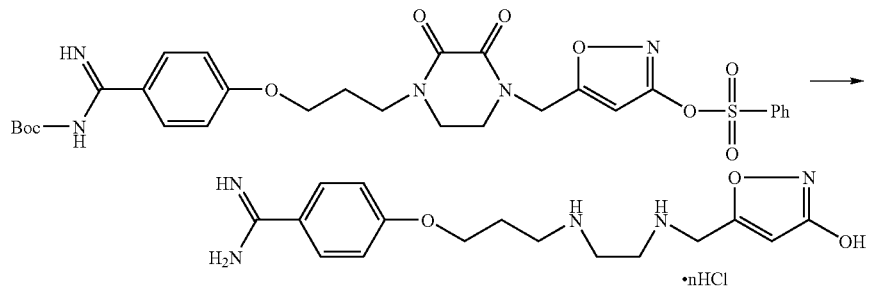

Example 83

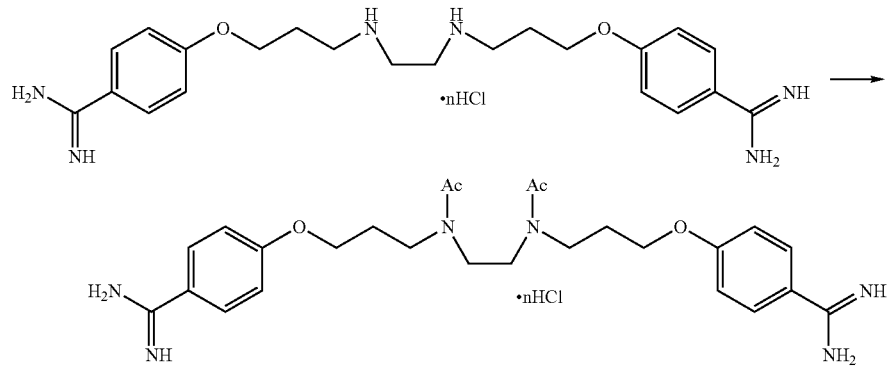

0.55 g of 4-[3-({2-[(3-{4-[amino(imino)methyl]phenoxy}propyl)amino]ethyl}amino)propoxy]benzamidine hydrochloride was suspended in 10 ml of dimethyl sulfoxide, and then, 0.66 g of triethylamine and 0.22 g of acetic anhydride were added to the suspension at room temperature. The mixture was stirred at the same above temperature for 5.5 hours. Water and chloroform were added to the reaction solution, and then, a sodium hydroxide aqueous solution was added thereto, so that the mixture was converted into alkaline. The aqueous layer was then separated. The aqueous layer was converted into acidic by adding a hydrogen chloride ethanol solution, and they were then concentrated under a reduced pressure. The obtained residue was purified by silica gel chromatography [YMC-GEL, ODS-AM 120-S50, eluent; 5% acetonitrile aqueous solution] to obtain 0.30 g of a colorless amorphous solid, N-{2-[acetyl(3-{4-[amino(imino)methyl]phenoxy}propyl)amino]ethyl}-N-(3-{4-[amino(imino)methyl]phenoxy}propyl)acetamide hydrochloride.

$^1$H-NMR (d$_6$-DMSO) δ: 1.90-2.10 (10H, m), 3.30-3.50 (8H, m), 4.00-4.20 (4H, m), 7.12-7.18 (4H, m), 7.84-7.87 (4H, m), 9.02 (4H, s), 9.25 (4H, s)

Example 84

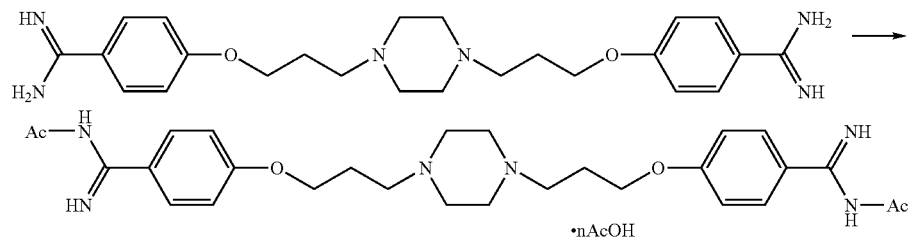

0.31 g of 4-{3-[4-(3-{4-[amino(imino)methyl]phenoxy}propyl)-1-piperazinyl]propoxy}benzamidine was suspended in 2.0 ml of dimethyl sulfoxide, and then, 0.26 ml of acetic anhydride was added to the suspension at room temperature, followed by stirring for 4 hours. A precipitate was filtrated, and it was then washed with dimethyl sulfoxide and with ethanol to obtain 0.21 g of a white solid, N-[(4-{3-[4-(3-{4-[(acetylamino)(imino)methyl]phenoxy}propyl)-1-piperazinyl]propoxy}phenyl)(imino)methyl]acetamide acetate.

$^1$H-NMR (d$_6$-DMSO+D$_2$O) δ: 1.80-2.00 (4H, m), 2.07 (12H, s), 2.30-2.50 (12H, m), 4.07 (4H, t, J=6.3 Hz), 7.02 (4H, d, J=8.8 Hz), 7.71 (4H, d, J=8.8 Hz)

Example 85

Example 85-1

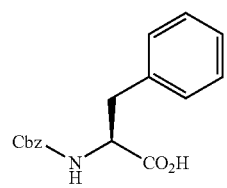

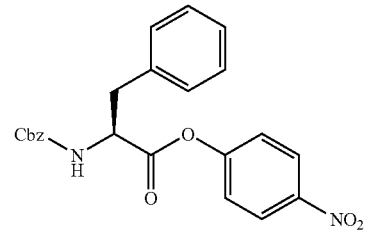

5.99 g of N-benzyloxycarbonyl-(S)-phenylalanine and 3.34 g of 4-nitrophenol were dissolved in 50 ml of chloroform. 10 ml of a chloroform solution containing 4.54 g of N,N'-dicyclohexylcarbodiimide was added dropwise to the solution at a temperature of 25° C. or lower, and the mixture was stirred at room temperature for 4 hours. A precipitate was removed by filtration, and the filtrate was concentrated under a reduced pressure. 50 ml of ethyl acetate was added to the obtained residue, and insoluble products were removed by filtration. Thereafter, the filtrate was washed with a 1 mol/L sodium hydroxide aqueous solution 3 times, and then with a saturated aqueous solution of sodium chloride once. Organic layer was dried over anhydrous magnesium sulfate, and then concentrated under a reduced pressure. Isopropanol was added to the obtained residue, and a precipitate was filtrated to obtain 3.69 g of a pale yellow solid, N-benzyloxycarbonyl-(S)-phenylalanine 4-nitrophenyl ester.

$^1$H-NMR (CDCl$_3$) δ: 3.20-3.30 (2H, m), 4.86-4.91 (1H, m), 5.13 (2H, s), 5.27 (1H, d, J=7.6 Hz), 7.10-7.38 (12H, m), 8.24 (2H, d, J=8.8 Hz)

Example 85-2

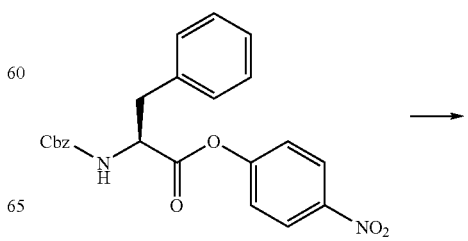

-continued

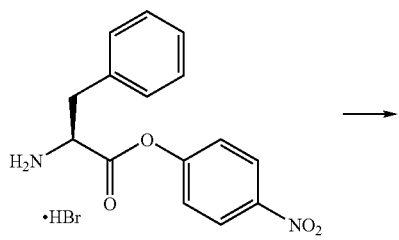

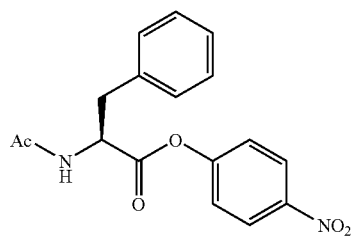

16.0 ml of a 30% hydrogen bromide-acetic acid solution was added to 3.36 g of N-benzyloxycarbonyl-(S)-phenylalanine 4-nitrophenyl ester at room temperature, and the mixture was stirred for 4 hours. 40 ml of diethyl ether was added to the reaction solution, and a precipitate was filtrated to obtain 2.72 g of a white solid, N-(S)-phenylalanine=4-nitrophenyl ester hydrobromide. 1.47 g of N-(S)-phenylalanine 4-nitrophenyl ester hydrobromide was dissolved in 5.0 ml of N,N-dimethylformamide. While cooled by ice, 0.40 ml of acetic anhydride and 0.62 ml of triethylamine were successively added dropwise to the solution, and then the mixture was stirred at room temperature for 0.5 hour. 30 ml of chloroform and 2 mol/L hydrochloric acid were added to the reaction solution, so that the organic layer was separated. The separated organic layer was washed with a saturated sodium bicarbonate solution and with a saturated aqueous solution of sodium chloride, and then dried over anhydrous magnesium sulfate. The obtained solution was concentrated under reduced pressure. Thus, 1.23 g of a white solid, N-acetyl-(S)-phenylalanine 4-nitrophenyl ester was obtained.

$^1$H-NMR (CDCl$_3$) δ: 2.05 (3H, s), 3.23 (1H, dd, J=6.6, 14.0 Hz), 3.29 (1H, dd, J=6.6, 14.0 Hz), 5.07 (1H, dt, J=7.3, 6.6 Hz), 5.95 (1H, d, J=7.3 Hz), 7.13-7.23 (4H, m), 7.32-7.40 (3H, m), 8.23-8.27 (2H, m)

Example 85-3

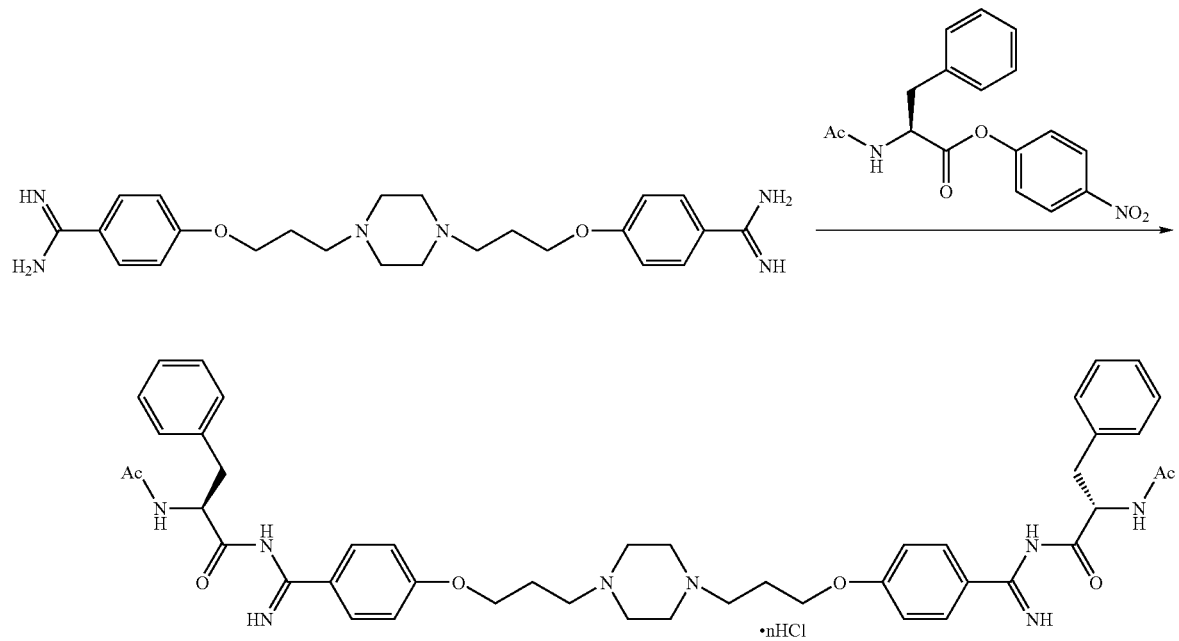

0.35 g of 4-{3-[4-(3-{4-[amino(imino)methyl]phenoxy}propyl)-1-piperazinyl]propoxy}benzamidine was suspended in 4.0 ml of N,N-dimethylformamide, and 0.58 g of N-acetyl-(S)-phenylalanine 4-nitrophenyl ester was added to the suspension at room temperature, followed by stirring for 12 hours. Ethyl acetate and water were added to the reaction mixture, and the obtained mixture was then adjusted to pH 12 with 5 mol/L sodium hydroxide aqueous solution. Thereafter, the organic layer was separated. The separated organic layer was washed with a 5 mol/L sodium hydroxide aqueous solution and with a saturated saline solution, and then concentrated under a reduced pressure. The obtained residue was dissolved in 10 ml of isopropanol, and carbon dioxide gas was blown into the solution. A precipitate was filtrated to obtain 0.30 g of a pale yellow solid. 0.25 g of the obtained solid was dissolved in 5 ml of ethanol, and 0.50 ml of a 2.5 mol/L hydrogen chloride ethanol solution was added to the solution at room temperature. Thereafter, the mixture was concentrated under a reduced pressure to obtain 0.27 g of a pale yellow solid, (2S)-2-(acetylamino)-N-[(4-{3-[4-(3-{4-[{[(2S)-2-(acetylamino)-3-phenylpropanoyl]amino}(imino)methyl]phenoxy}propyl)-1-piperazinyl]propoxy}phenyl)(imino)methyl]-3-phenylpropanamide hydrochloride.

$^1$H-NMR (d$_6$-DMSO) δ: 1.85 (6H, s), 2.20-2.30 (4H, m), 2.95 (2H, dd, J=9.6, 13.7 Hz), 3.20 (2H, dd, J=5.5, 13.7 Hz), 3.25-3.90 (12H, m), 4.20-4.30 (4H, m), 4.80-5.00 (2H, m), 7.18-7.40 (14H, m), 7.23 (4H, d, J=8.5 Hz), 8.68 (2H, d, J=5.4 Hz), 10.87 (2H, brs), 11.30-11.70 (2H, br), 12.00-12.80 (2H, br)

Example 86

The following compond was obtained in the same manner as Examples 18 and 19.

4-(3-{2,3-dioxo-4-[4-(4-piperidinyl)butyl]-1-piperazinyl}propoxy)benzamidine Acetate $^1$H-NMR (d$_6$-DMSO) δ: 1.05-1.13 (2H, m), 1.15-1.44 (5H, m), 1.35 (1H, brs), 1.44-1.51 (2H, m), 1.60-1.70 (2H, m), 1.79 (3H, s), 1.96-2.04 (2H, m), 2.50-2.60 (2H, m), 2.95-3.70 (15H, m), 4.10 (2H, t, J=6.0 Hz), 7.12 (2H, d, J=8.8 Hz), 7.80 (2H, d, J=8.8 Hz)

Example 87

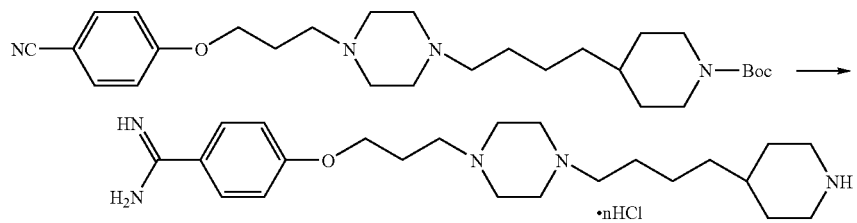

The following compond was obtained in the same manner as Example 40.

4-(3-{4-[4-(4-piperidinyl)butyl]-1-piperazinyl}propoxy)benzamidine Hydrochloride $^1$H-NMR (d$_6$-DMSO) δ: 1.20-1.40 (6H, m), 1.51 (1H, brs), 1.64-1.84 (4H, m), 2.20-2.30 (2H, m), 2.72-2.88 (2H, m), 3.00-3.90 (16H, m), 4.18-4.23 (2H, m), 7.17 (2H, d, J=8.7 Hz), 7.88 (2H, d, J=8.7 Hz), 8.81 (1H, s), 8.96-9.14 (3H, m), 9.29 (2H, s)

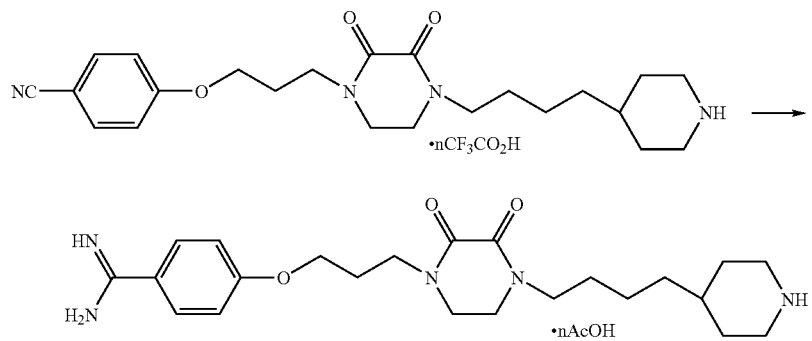

Example 88

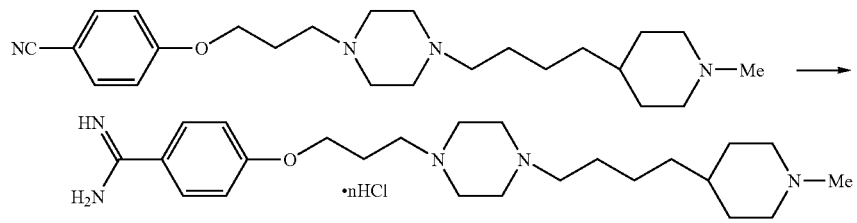

The following compond was obtained in the same manner as Example 40.

4-(3-{4-[4-(1-methyl-4-piperidinyl)butyl]-1-piperazinyl}propoxy)benzamidine Hydrochloride $^1$H-NMR (d$_6$-DMSO) δ: 1.21-1.45 (7H, m), 1.66-1.84 (4H, m), 2.20-2.29 (2H, m), 2.67 (3H, d, J=4.8 Hz), 2.80-2.92 (2H, m), 3.00-3.20 (2H, m), 3.20-3.90 (15H, m), 4.22 (2H, t, J=6.4 Hz), 7.17 (2H, d, J=8.8 Hz), 7.89 (2H, d, J=8.8 Hz), 9.12 (2H, s), 9.32 (2H, s)

Example 89

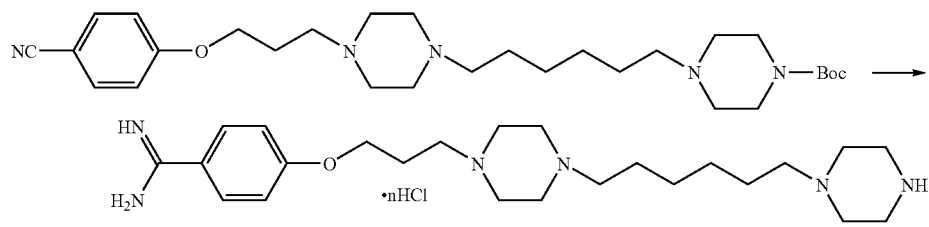

The following compond was obtained in the same manner as Example 40.

4-(3-{4-[6-(1-piperazinyl)hexyl]-1-piperazinyl}propoxy)benzamidine Hydrochloride $^1$H-NMR (d$_6$-DMSO) δ: 1.26-1.42 (4H, m), 1.62-1.82 (4H, m), 2.14-2.30 (2H, m), 2.80-4.10 (25H, m), 4.14-4.26 (2H, m), 7.17 (2H, d, J=9.0 Hz), 7.86 (2H, d, J=9.0 Hz), 8.95 (2H, s), 9.23 (2H, s), 9.50-9.90 (2H, m)

Example 90

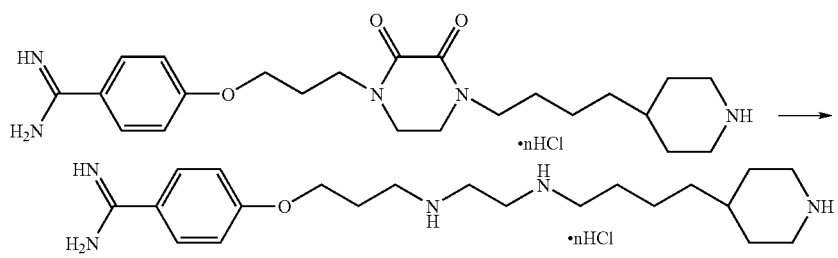

The following compond was obtained in the same manner as Example 11.

4-{3-[(2-{[4-(4-piperidinyl)butyl]amino}ethyl)amino]propoxy}benzamidine hydrochloride $^1$H-NMR (d$_6$-DMSO) δ: 1.24-1.35 (6H, m), 1.50-1.80 (5H, m), 2.12-2.23 (2H, m), 2.70-3.00 (4H, m), 3.00-3.80

(8H, m), 4.10-4.30 (2H, br), 7.18 (2H, d, J=7.4 Hz), 7.88 (2H, d, J=7.4 Hz), 8.70-8.90 (1H, m), 8.90-9.20 (3H, m), 9.30 (2H, s), 9.40-10.20 (4H, m)

Example 91

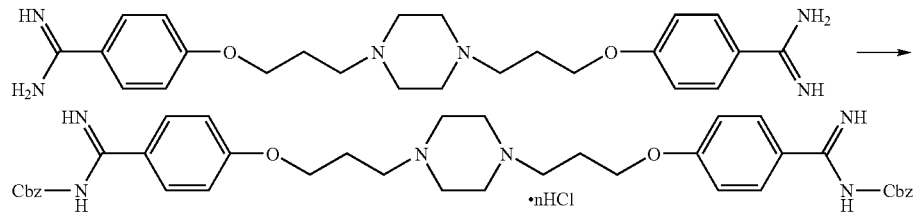

0.44 g of 4-{3-[4-(3-{4-[amino(imino)methyl] phenoxy}propyl)-1-piperazinyl]propoxy}benzamidine was suspended in 5.0 ml of dimethyl sulfoxide, and 0.66 g of benzyl 4-nitrophenyl carbonate was added to the suspension at room temperature, followed by stirring for 27 hours. 20 ml of chloroform, 50 ml of water, and 4 ml of a 1 mol/L sodium hydroxide aqueous solution were added to the reaction solution, so that the organic layer was separated. The aqueous layer was extracted twice with 20 ml of chloroform. The obtained organic layer was combined. The thus obtained layer was dried with anhydrous sodium sulfate, and then concentrated under a reduced pressure. The obtained solid was filtrated with ethyl acetate, and the product was then purified by silica gel column chromatography [eluent; chloroform:methanol=20:1] to obtain 0.43 g of a solid. Chloroform and ethanol were added to 0.24 g of the obtained solid to dissolve it, and then, 1 ml of a 2.2 mol/L hydrogen chloride ethanol solution was added thereto at room temperature, followed by concentration under a reduced pressure. The obtained solid was filtrated with diethyl ether, and the solid was dissolved in methanol. Isopropanol was added to the solution, and a precipitate was filtrated to obtain 0.25 g of a white solid, benzyl (4-{3-[4-(3-{4-[{[(benzyloxy)carbonyl]amino}(imino)methyl]phenoxy}propyl)-1-piperazinyl]propoxy}phenyl)(imino)methylcarbamate.

$^1$H-NMR (d$_6$-DMSO) δ: 2.22-2.32 (4H, m), 3.20-3.90 (12H, m), 4.23 (4H, t, J=6.0 Hz), 5.36 (4H, s), 7.16 (4H, d, J=8.8 Hz), 7.36-7.54 (10H, m), 7.86 (4H, d, J=8.8 Hz), 10.40 (2H, s), 11.20-11.60 (2H, br), 12.20-12.80 (2H, br)

INDUSTRIAL APPLICABILITY

A novel arylamidine derivative represented by general formula [1], or a salt thereof, has a strong antifungal activity, and it is useful for preventing or treating fungous diseases of humans and animals.

The invention claimed is:

1. An arylamidine compound or a salt thereof represented by the following general formula:

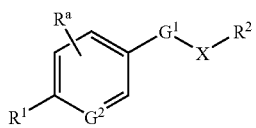

wherein X represents an unsubstituted or substituted lower alkylene group;

$G^1$ represents an oxygen atom;
$G^2$ represents a carbon atom;
$R^a$ represents at least one group selected from the group consisting of a hydrogen atom, a halogen atom, and unsubstituted or substituted alkyl, cycloalkyl and alkoxy groups;
$R^1$ represents an unprotected or protected or unsubstituted or substituted amidino group; and
$R^2$ represents a group represented by formula (3):

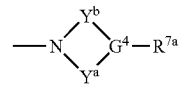

wherein $Y^a$ represents an unsubstituted or substituted $C_{2-4}$ lower alkylene group; and
$Y^b$ represents an unsubstituted or substituted $C_{1-4}$ lower alkylene group;
$G^4$ represents a carbon atom or a nitrogen atom;
$R^{7a}$ represents an alkyl group substituted by at least one group selected from the group consisting of a cyano group, a nitro group, a halogen atom, a sulfo group, a phosphoryl group, an unprotected or protected hydroxyl group, an unprotected or protected amino group, carbamoyl group, hydroxycarbamoyl group, aminosulfonyl group, cyclic amino group, lower alkylamino group, a lower alkenyl group, a lower alkoxy group, a heterocyclic group, a cycloalkyl group, a lower alkylidene group, a mercapto group, an amidinophenylaryloxy group, an aryloxy group, a lower alkylthio group, a lower alkylsulfinyl group, a lower alkylsulfonyl group, a lower alkylcarbamoyl group, a lower alkylsulfonylamino group, a lower alkylaminosulfonyl group, a carboxyl lower alkenyl group, a hydroxyl heterocyclic group, a lower alkyl heterocyclic group, a lower alkoxy-lower alkoxy group, and a lower alkoxyimino group, or an unsubstituted or substituted phenyl, cycloalkyl or alkenyl group, or a group represented by the following formula:

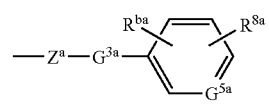

wherein $Z^a$ represents an unsubstituted or substituted lower alkylene or alkenylene group;

$G^{3a}$ represents an oxygen atom, a sulfur atom, an imino group, or a direct bond;

$G^{5a}$ represents a carbon atom or a nitrogen atom;

$R^{ba}$ represents at least one group selected from the group consisting of a hydrogen atom, a halogen atom, and unsubstituted or substituted alkyl, cycloalkyl and alkoxy groups; and $R^{8a}$ represents an unprotected or protected or unsubstituted or substituted amidino group which is bonded at the para or meta position of the position connected to $G^{3a}$, wherein the substituent of lower alkylene group for X, $C_{2-4}$ lower alkylene group for $Y^a$ and each of lower alkylene and alkenylene group for $Z^a$ represent at least one group selected from the group consisting of a cyano group, a nitro group, a halogen atom, unprotected or protected amino, hydroxyl and carboxyl groups, a carbamoyl group, a hydroxycarbamoyl group, a lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group and a lower alkoxycarbonyl group;

the substituent of each of alkyl, cycloalkyl and alkoxy group for $R^a$, each of phenyl, cycloalkyl and alkenyl group for $R^{7a}$ and each of alkyl cycloalkyl and alkoxy group for $R^{ba}$ represent at least one group selected from the group consisting of a cyano group, a nitro group, a halogen atom, a sulfo group, a phosphoryl group, unprotected or protected carboxyl, hydroxyl and amino groups, a carbamoyl group, a hydroxycarbamoyl group, an aminosulfonyl group, a hydroxy lower alkyl group, an amino lower alkyl group, a cyclic amino group, a lower alkylamino group, a lower alkylamino-lower alkyl group, a lower alkyl group, a lower alkenyl group, a lower alkoxy group, a lower alkoxycarbonyl group, an acyl group, an aryl group, a heterocyclic group, a cycloalkyl group, an aralkyl group, a lower alkylidene group, a mercapto group, a lower alkylthio group, a lower alkylsulfinyl group, a lower alkylsulfonyl group, a lower alkylcarbamoyl group, a lower alkylsulfonylamino group, a lower alkylaminosulfonyl group, a carboxyl lower alkyl group, a carboxyl lower alkenyl group, a hydroxyl heterocyclic group, a lower alkyl heterocyclic group, a lower alkoxy-lower alkoxy group, a halogeno lower alkyl group, a lower alkoxy-lower alkyl group, a lower alkoxycarbonyl-lower alkyl group and a lower alkoxyimino group;

the substituent of amidino group for each of $R^1$ and $R^{8a}$ represent at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group and an aralkyl group;

the substituent of $C_{1-4}$ lower alkylene group for $Y^b$ represent at least one group selected from the group consisting of a cyano group, a nitro group, a halogen atom, unprotected or protected amino and carboxyl groups, a carbamoyl group, a hydroxycarbamoyl group, an unprotected or protected hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group and a keto group;

the protecting group of amidino group represent one group selected from the group consisting of acyl groups, alkyloxycarbonyl groups, cycloalkyloxycarbonyl groups, aralkyloxycarbonyl groups, aryloxycarbonyl groups, alkylthiocarbonyl groups, aralkyl groups, alkoxyalkyl groups, arylthio groups, alkylsulfonyl or arylsulfonyl groups, dialkylaminoalkylidene groups, aralkylidene groups, nitrogen-containing heterocyclic alkylidene groups, cycloalkylidene groups, oxygen-containing heterocyclic alkyl groups and substituted silyl groups;

the protecting group of hydroxyl group represent acyl groups, alkyl groups, alkenyl groups, aralkyl groups, oxygen- or sulfur-containing heterocyclic groups, alkoxyalkyl groups, alkylsulfonyl or arylsulfonyl groups or substituted silyl groups;

the protecting group of amino group represent acyl groups, alkyloxycarbonyl groups, aralkyloxycarbonyl groups, aryloxycarbonyl groups, aralkyl groups, alkoxyalkyl groups, arylthio groups, alkylsulfonyl or arylsulfonyl groups, dialkylaminoalkylidene groups, aralkylidene groups, nitrogen-containing heterocyclic alkylidene groups, cycloalkylidene groups, diaryl- or diaralkylphosphoryl groups, oxygen-containing heterocyclic alkyl groups or substituted silyl groups;

the protecting group of carboxyl group represent alkyl groups, aryl groups, aralkyl groups, acylalkyl groups, oxygen-containing heterocyclic groups, halogenoalkyl groups, alkylsilylalkyl groups, acyloxyalkyl groups, nitrogen-containing heterocyclic alkyl groups, cycloalkyl groups, alkoxyalkyl groups, aralkoxyalkyl groups, lower alkylthioalkyl groups, arylthioalkyl groups, alkenyl groups or substituted silyl groups.

2. The arylamidine compound or a salt thereof according to claim 1, wherein $R^a$ represents at least one group selected from the group consisting of a hydrogen atom and a halogen atom.

3. The arylamidine compound or a salt thereof according to claim 1, wherein $R^a$ represents a hydrogen atom.

4. The arylamidine compound or a salt thereof according to claim 1, wherein $R^a$ represents a group represented by formula (3):

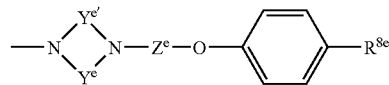

wherein $Y^e$ and $Y^{e'}$, independently represents an unsubstituted or substituted $C_{2-4}$ lower alkylene group;

$Z^e$ represents an unsubstituted or substituted lower alkylene or alkenylene group; and $R^{8e}$ represents an unprotected or protected or unsubstituted or substituted amidino group, wherein the substituent of $C_{2-4}$ lower alkylene group for $Y^e$ and lower alkylene or alkenylene group for $Z^e$ represent at least one group selected from the group consisting of a cyano group, a nitro group, a halogen atom, unprotected or protected amino, hydroxyl and carboxyl groups, a carbamoyl group, a hydroxycarbamoyl group, a lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group and a lower alkoxycarbonyl group;

the substituent of $C_{2-4}$ lower alkylene group for $Y^{e'}$ represent at least one group selected from the group consisting of a cyano group, a nitro group, a halogen atom, unprotected or protected amino and carboxyl groups, a carbamoyl group, a hydroxycarbamoyl group, an unprotected or protected hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group and a keto group;

the substituent of amidino group for $R^{8e}$ represent at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group and an aralkyl group;

the protecting group of each of amino, hydroxyl, carboxyl and amidino group is defined as in claim 1.

5. The arylamidine compound or a salt thereof according to claim 1, wherein $R^2$ represents a group represented by the following formula:

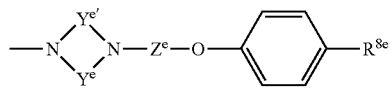

wherein each of $Y^e$ and $Y^{e'}$, independently represents an unsubstituted or substituted $C_{2-4}$ lower alkylene group;

$Z^e$ represents an unsubstituted or substituted lower alkylene or alkenylene group; and $R^{8e}$ represents an unprotected or protected or unsubstituted or substituted amidino group, wherein the substituent of $C_{2-4}$ lower alkylene group for $Y^e$ and lower alkylene or alkenylene group for $Z^e$ represent at least one group selected from the group consisting of a cyano group, a nitro group, a halogen atom, unprotected or protected amino, hydroxyl and carboxyl groups, a carbamoyl group, a hydroxycarbamoyl group, a lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group and a lower alkoxycarbonyl group;

the substituent of $C_{2-4}$ lower alkylene group for $Y^{e'}$ represent at least one group selected from the group consisting of a cyano group, a nitro group, a halogen atom, unprotected or protected amino and carboxyl groups, a carbamoyl group, a hydroxycarbamoyl group, an unprotected or protected hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group and a keto group;

the substituent of amidino group for $R^{8e}$ represent at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group and an aralkyl group;

the protecting group of amidino group is defined as in claim 1.

6. The arylamidine compound or a salt thereof according to claim 1, wherein $R^a$ represents a hydrogen atom; and $R^2$ represents a group represented by formula (3):

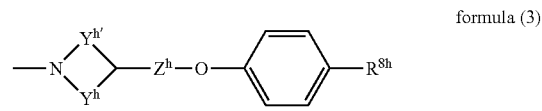

formula (3)

wherein $Y^h$ and $Y^{h'}$ independently represents an unsubstituted or substituted $C_{2-4}$ lower alkylene group;

$Z^h$ represents an unsubstituted or substituted lower alkylene or alkenylene group; and $R^{8h}$ represents an unprotected or protected or unsubstituted or substituted amidino group, wherein the substituent of $C_{2-4}$ lower alkylene group for $Y^h$ and lower alkylene or alkenylene group for $Z^h$ represent at least one group selected from the group consisting of a cyano group, a nitro group, a halogen atom, unprotected or protected amino, hydroxyl and carboxyl groups, a carbamoyl group, a hydroxycarbamoyl group, a lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group and a lower alkoxycarbonyl group;

the substituent of $C_{2-4}$ lower alkylene group for $Y^{h'}$ represent at least one group selected from the group consisting of a cyano group, a nitro group, a halogen atom, unprotected or protected amino and carboxyl groups, a carbamoyl group, a hydroxycarbamoyl group, an unprotected or protected hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group and a keto group;

the substituent of amidino group for $R^{8h}$ represent at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group and an aralkyl group;

the protecting group of each of amino, carboxyl, hydroxyl and amidino group is defined as in claim 1.

7. The arylamidine compound or a salt thereof according to claim 1, wherein $R^2$ represents a group represented by the following formula:

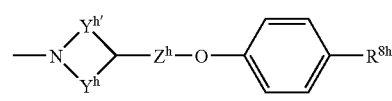

wherein each of $Y^h$ and $Y^{h'}$ which may be the same or different, represents an unsubstituted or substituted $C_{2-4}$ lower alkylene group;

$Z^h$ represents an unsubstituted or substituted lower alkylene or alkenylene group; and $R^{8h}$ represents an unprotected or protected or unsubstituted or substituted amidino group, wherein the substituent of $C_{2-4}$ lower alkylene group for $Y^h$ and lower alkylene or alkenylene group for $Z^h$ represent at least one group selected from the group consisting of a cyano group, a nitro group, a halogen atom, unprotected or protected amino, hydroxyl and carboxyl groups, a carbamoyl group, a hydroxycarbamoyl group, a lower alkylamino group, a lower alkoxycarbonyl group, an acyl group, an aryl group, a heterocyclic group, a cycloalkyl group, a lower alkenyl group, a lower alkylsulfonylcarbamoyl group, a lower alkylcarbamoyl group, a lower alkoxy group and a lower alkoxycarbonyl group;

the substituent of $C_{2-4}$ lower alkylene group for $Y^{h'}$ represent at least one group selected from the group consisting of a cyano group, a nitro group, a halogen atom, unprotected or protected amino and carboxyl groups, a carbamoyl group, a hydroxycarbamoyl group, an unprotected or protected hydroxyl group, a lower alkylamino group, a lower alkoxycarbonyl group, an acyl group, an aryl group, a heterocyclic group, a cycloalkyl group, a lower alkylsulfonylcarbamoyl group, a lower alkylcarbamoyl group, a lower alkoxy group, a lower alkoxycarbonyl group and a keto group;

the substituent of amidino group for $R^{8h}$ represent at least one group selected from the group consisting of an unprotected or protected hydroxyl group, a lower alkyl group, a lower alkenyl group, a lower alkoxy group, a lower alkoxycarbonyl group, an acyl group, an aryl group, a heterocyclic group, a cycloalkyl group and an aralkyl group;

the protecting group of amidino group is defined as in claim 1.

8. The arylamidine compound or a salt thereof according to claim 1, wherein the arylamidine compound is 4-{3-[4-(3-{4-[amino(imino)methyl]phenoxy}propyl)-1-piperazinyl]propoxy}benzamidine.

9. The arylamidine compound or a salt thereof according to claim 1, wherein the arylamidine compound is 4-{2-[1-(3-{4-[amino(imino)methyl]phenoxy}propyl)-4-piperidinyl]ethoxy}benzamidine.

10. An antifungal agent comprising, as an active ingredient, the arylamidine compound or a salt thereof according to claim 1.

* * * * *

UNITED STATES PATENT AND TRADEMARK OFFICE
CERTIFICATE OF CORRECTION

PATENT NO. : 7,291,617 B2                                                                 Page 1 of 1
APPLICATION NO. : 10/506422
DATED : November 6, 2007
INVENTOR(S) : Hayashi et al.

It is certified that error appears in the above-identified patent and that said Letters Patent is hereby corrected as shown below:

On the title page, Item (30), the Foreign Application Priority Data has been omitted. Item (30) should read:

Item -- (30) Foreign Application Priority Data

March 6, 2002      (JP).....................2002-60618 --

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,291,617 B2
APPLICATION NO. : 10/506422
DATED : November 6, 2007
INVENTOR(S) : Kazuya Hayashi et al.

Page 1 of 1

It is certified that error appears in the above-identified patent and that said Letters Patent is hereby corrected as shown below:

Column 210, line 26, "formula (3):" should read --the following formula:--.

Column 212, line 43, "$R^{a}$" should read --$R^2$--,
line 44, "formula (3):" should read --the following formula:--,
line 52, "$Y^e$ and $Y^{e}$" should read --$Y^e$ and $Y^{e'}$--.

Column 214, line 9, "formula (3):" should read --the following formula:--, line 12, " 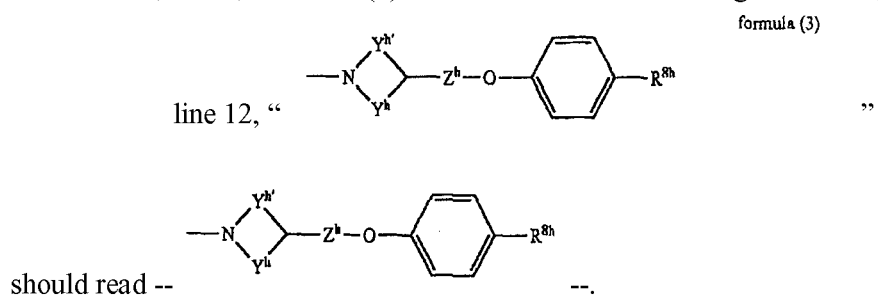 "

should read -- 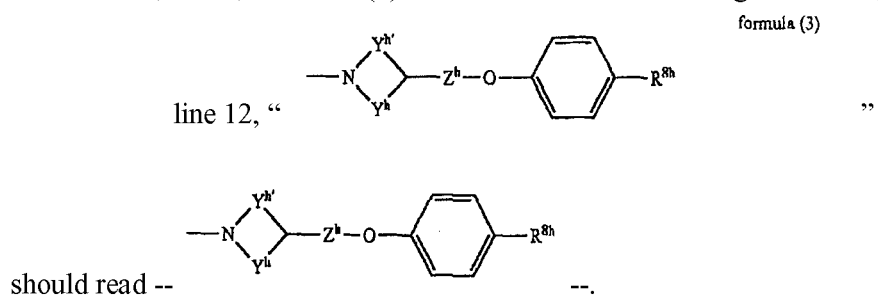 --.

Signed and Sealed this
Twelfth Day of April, 2011

David J. Kappos
*Director of the United States Patent and Trademark Office*